US012521041B2

(12) United States Patent
DiPalma et al.

(10) Patent No.: US 12,521,041 B2
(45) Date of Patent: Jan. 13, 2026

(54) SYSTEMS, DEVICES, AND METHODS FOR ANALYTE SENSOR INSERTION

(71) Applicant: ABBOTT DIABETES CARE INC., Alameda, CA (US)

(72) Inventors: Vincent M. DiPalma, Oakland, CA (US); Phillip W. Carter, Oakland, CA (US); Udo Hoss, San Ramon, CA (US); Peter G. Robinson, Alamo, CA (US); Andrew H. Naegeli, Walnut Creek, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 16/433,931

(22) Filed: Jun. 6, 2019

(65) Prior Publication Data

US 2020/0196919 A1 Jun. 25, 2020

Related U.S. Application Data

(60) Provisional application No. 62/784,074, filed on Dec. 21, 2018.

(51) Int. Cl.
*A61B 5/145* (2006.01)
*A61B 5/1486* (2006.01)

(52) U.S. Cl.
CPC ...... *A61B 5/14503* (2013.01); *A61B 5/14546* (2013.01); *A61B 5/14865* (2013.01); *A61B 5/14532* (2013.01)

(58) Field of Classification Search
CPC ............ A61B 5/14532; A61B 5/14546; A61B 5/150282; A61B 5/150274; A61B 5/150297; A61B 5/150374; A61B 5/150381; A61B 5/150389; A61B 5/150396; A61B 5/150427; A61B 5/150442; A61B 5/150458; A61B 5/150503; A61B 5/150511; A61B 5/6848; A61B 2560/063; A61B 5/14503;
(Continued)

(56) References Cited

U.S. PATENT DOCUMENTS 2,402,306 A 6/1946 Turkel
2,752,918 A 7/1956 Uytenbogaart
(Continued)

FOREIGN PATENT DOCUMENTS

AU 2003259741 2/2004
CA 2291105 12/1998
(Continued)

OTHER PUBLICATIONS

WO, PCT/US19/35843 ISR and Written Opinion, dated Sep. 18, 2019.

(Continued)

*Primary Examiner* — Tse W Chen
*Assistant Examiner* — Alice Ling Zou
(74) *Attorney, Agent, or Firm* — ONE LLP

(57) ABSTRACT

Systems, devices and methods are provided for inserting at least a portion of an in vivo analyte sensor for sensing an analyte level in a bodily fluid of a subject. In various embodiments, applicators and components thereof are designed to reduce trauma to tissue of a sensor insertion site and to increase the likelihood of a successful sensor insertion. Some embodiments ensure structural integrity of a sensor.

28 Claims, 146 Drawing Sheets

(58) Field of Classification Search
CPC . A61B 5/14865; A61B 5/1459; A61B 5/1473; A61B 5/150206; A61B 5/150412; A61B 5/150473; A61B 5/6849; A61B 17/34; A61B 17/3417; A61B 2017/3454–346; A61B 17/3468; A61M 2005/1585; A61M 5/3286; A61M 5/32; A61M 5/158; B21G 1/006; B21G 1/12; B21G 1/08
See application file for complete search history.

(56) References Cited

U.S. PATENT DOCUMENTS 3,123,790 A 3/1964 Tyler
3,132,123 A 5/1964 Harris, Jr. et al.
3,173,200 A 3/1965 Dunmire et al.
3,211,001 A 10/1965 Petit
3,260,656 A 7/1966 Ross, Jr.
3,517,670 A 6/1970 Speelman
3,522,807 A 8/1970 Millenbach
3,581,062 A 5/1971 Aston
3,653,841 A 4/1972 Klein
3,670,727 A 6/1972 Reiterman
3,719,564 A 3/1973 Lilly, Jr. et al.
3,776,832 A 12/1973 Oswin et al.
3,837,339 A 9/1974 Aisenberg et al.
3,926,760 A 12/1975 Allen et al.
3,949,388 A 4/1976 Fuller
3,960,497 A 6/1976 Acord et al.
3,972,320 A 8/1976 Kalman
3,979,274 A 9/1976 Newman
4,008,717 A 2/1977 Kowarski
4,016,866 A 4/1977 Lawton
4,033,330 A 7/1977 Willis et al.
4,036,749 A 7/1977 Anderson
4,055,175 A 10/1977 Clemens et al.
4,059,406 A 11/1977 Fleet
4,076,596 A 2/1978 Connery et al.
4,098,574 A 7/1978 Dappen
4,100,048 A 7/1978 Pompei et al.
4,120,292 A 10/1978 LeBlanc, Jr. et al.
4,129,128 A 12/1978 McFarlane
4,151,845 A 5/1979 Clemens
4,168,205 A 9/1979 Danninger et al.
4,172,770 A 10/1979 Semersky et al.
4,178,916 A 12/1979 McNamara
4,203,446 A 5/1980 Hofert et al.
4,206,755 A 6/1980 Klein
4,224,125 A 9/1980 Nakamura et al.
4,240,438 A 12/1980 Updike et al.
4,240,889 A 12/1980 Yoda et al.
4,245,634 A 1/1981 Albisser et al.
4,247,297 A 1/1981 Berti et al.
4,294,258 A 10/1981 Bernard
4,305,401 A 12/1981 Reissmueller et al.
4,308,981 A 1/1982 Miura
4,327,725 A 5/1982 Cortese et al.
4,340,458 A 7/1982 Lerner et al.
4,344,438 A 8/1982 Schultz
4,349,728 A 9/1982 Phillips et al.
4,352,960 A 10/1982 Dormer et al.
4,353,888 A 10/1982 Sefton
4,356,074 A 10/1982 Johnson
4,365,637 A 12/1982 Johnson
4,366,033 A 12/1982 Richter et al.
4,373,527 A 2/1983 Fischell
4,375,399 A 3/1983 Havas et al.
4,384,586 A 5/1983 Christiansen
4,390,621 A 6/1983 Bauer
4,392,849 A 7/1983 Petre et al.
4,401,122 A 8/1983 Clark, Jr.
4,404,066 A 9/1983 Johnson
4,418,148 A 11/1983 Oberhardt
4,425,920 A 1/1984 Bourland et al.
4,427,004 A 1/1984 Miller et al.
4,427,770 A 1/1984 Chen et al.
4,431,004 A 2/1984 Bessman et al.
4,436,094 A 3/1984 Cerami
4,440,175 A 4/1984 Wilkins
4,441,968 A 4/1984 Emmer et al.
4,450,842 A 5/1984 Zick et al.
4,458,686 A 7/1984 Clark, Jr.
4,461,691 A 7/1984 Frank
4,464,170 A 8/1984 Clemens et al.
4,469,110 A 9/1984 Slama
4,477,314 A 10/1984 Richter et al.
4,478,976 A 10/1984 Goertz et al.
4,484,987 A 11/1984 Gough
4,494,950 A 1/1985 Fischell
4,509,531 A 4/1985 Ward
4,522,690 A 6/1985 Venkatasetty
4,524,114 A 6/1985 Samuels et al.
4,526,661 A 7/1985 Steckhan et al.
4,527,240 A 7/1985 Kvitash
4,534,356 A 8/1985 Papadakis
4,538,616 A 9/1985 Rogoff
4,543,955 A 10/1985 Schroeppel
4,545,382 A 10/1985 Higgins et al.
4,552,840 A 11/1985 Riffer
4,553,541 A 11/1985 Burns
4,560,534 A 12/1985 Kung et al.
4,571,292 A 2/1986 Liu et al.
4,573,994 A 3/1986 Fischell et al.
4,581,336 A 4/1986 Malloy et al.
4,592,745 A 6/1986 Rex et al.
4,595,011 A 6/1986 Phillips
4,619,754 A 10/1986 Niki et al.
4,619,793 A 10/1986 Lee
4,622,966 A 11/1986 Beard
4,627,445 A 12/1986 Garcia et al.
4,627,842 A 12/1986 Katz
4,627,908 A 12/1986 Miller
4,633,878 A 1/1987 Bombardieri
4,637,403 A 1/1987 Garcia et al.
4,639,062 A 1/1987 Taniguchi et al.
4,650,547 A 3/1987 Gough
4,654,197 A 3/1987 Lilja et al.
4,655,880 A 4/1987 Liu
4,655,885 A 4/1987 Hill et al.
4,663,824 A 5/1987 Kenmochi
4,665,906 A 5/1987 Jervis
4,671,288 A 6/1987 Gough
4,675,346 A 6/1987 Lin et al.
4,679,562 A 7/1987 Luksha
4,680,268 A 7/1987 Clark, Jr.
4,682,602 A 7/1987 Prohaska
4,684,245 A 8/1987 Goldring
4,684,537 A 8/1987 Graetzel et al.
4,685,463 A 8/1987 Williams
4,685,466 A 8/1987 Rau
4,690,675 A 9/1987 Katz
4,698,057 A 10/1987 Joishy
4,703,324 A 10/1987 White
4,703,756 A 11/1987 Gough et al.
4,711,245 A 12/1987 Higgins et al.
4,711,247 A 12/1987 Fishman
4,717,673 A 1/1988 Wrighton et al.
4,721,601 A 1/1988 Wrighton et al.
4,721,677 A 1/1988 Clark, Jr.
4,726,378 A 2/1988 Kaplan
4,726,716 A 2/1988 McGuire
4,729,672 A 3/1988 Takagi
4,731,726 A 3/1988 Allen, III
4,749,985 A 6/1988 Corsberg
4,755,173 A 7/1988 Konopka
4,757,022 A 7/1988 Shults et al.
4,758,323 A 7/1988 Davis et al.
4,759,371 A 7/1988 Franetzki
4,759,828 A 7/1988 Young et al.
4,764,416 A 8/1988 Ueyama et al.
4,776,944 A 10/1988 Janata et al.
4,777,953 A 10/1988 Ash et al.
4,779,618 A 10/1988 Mund et al.
4,781,683 A 11/1988 Wozniak et al.
4,781,798 A 11/1988 Gough

(56) References Cited

U.S. PATENT DOCUMENTS

| | | | |
|---|---|---|---|
| 4,784,736 | A | 11/1988 | Lonsdale et al. |
| 4,785,868 | A | 11/1988 | Koenig, Jr. |
| 4,795,707 | A | 1/1989 | Niiyama et al. |
| 4,796,634 | A | 1/1989 | Huntsman et al. |
| 4,805,624 | A | 2/1989 | Yao et al. |
| 4,813,424 | A | 3/1989 | Wilkins |
| 4,815,469 | A | 3/1989 | Cohen et al. |
| 4,817,603 | A | 4/1989 | Turner et al. |
| 4,818,994 | A | 4/1989 | Orth et al. |
| 4,820,399 | A | 4/1989 | Senda et al. |
| 4,822,337 | A | 4/1989 | Newhouse et al. |
| 4,830,959 | A | 5/1989 | McNeil et al. |
| 4,832,797 | A | 5/1989 | Vadgama et al. |
| RE32,947 | E | 6/1989 | Dormer et al. |
| 4,840,893 | A | 6/1989 | Hill et al. |
| 4,847,785 | A | 7/1989 | Stephens |
| 4,848,351 | A | 7/1989 | Finch |
| 4,852,025 | A | 7/1989 | Herpichböhm |
| 4,854,322 | A | 8/1989 | Ash et al. |
| 4,856,648 | A | 8/1989 | Krueger |
| 4,865,038 | A | 9/1989 | Rich et al. |
| 4,871,351 | A | 10/1989 | Feingold |
| 4,871,440 | A | 10/1989 | Nagata et al. |
| 4,874,500 | A | 10/1989 | Madou et al. |
| 4,890,620 | A | 1/1990 | Gough |
| 4,894,137 | A | 1/1990 | Takizawa et al. |
| 4,895,147 | A | 1/1990 | Bodicky et al. |
| 4,897,162 | A | 1/1990 | Lewandowski et al. |
| 4,897,173 | A | 1/1990 | Nankai et al. |
| 4,909,908 | A | 3/1990 | Ross et al. |
| 4,911,794 | A | 3/1990 | Parce et al. |
| 4,917,800 | A | 4/1990 | Lonsdale et al. |
| 4,919,141 | A | 4/1990 | Zier et al. |
| 4,919,767 | A | 4/1990 | Vadgama et al. |
| 4,921,199 | A | 5/1990 | Villaveces |
| 4,923,586 | A | 5/1990 | Katayama et al. |
| 4,925,268 | A | 5/1990 | Lyer et al. |
| 4,927,516 | A | 5/1990 | Yamaguchi et al. |
| 4,934,369 | A | 6/1990 | Maxwell |
| 4,935,105 | A | 6/1990 | Churchouse |
| 4,935,345 | A | 6/1990 | Guibeau et al. |
| 4,938,860 | A | 7/1990 | Wogoman |
| 4,944,299 | A | 7/1990 | Silvian |
| 4,950,378 | A | 8/1990 | Nagara |
| 4,953,552 | A | 9/1990 | DeMarzo |
| 4,954,129 | A | 9/1990 | Giuliani et al. |
| 4,969,468 | A | 11/1990 | Byers et al. |
| 4,970,145 | A | 11/1990 | Bennetto et al. |
| 4,974,929 | A | 12/1990 | Curry |
| 4,985,142 | A | 1/1991 | Laycock et al. |
| 4,986,271 | A | 1/1991 | Wilkins |
| 4,988,341 | A | 1/1991 | Columbus et al. |
| 4,994,167 | A | 2/1991 | Shults et al. |
| 4,995,402 | A | 2/1991 | Smith et al. |
| 5,000,180 | A | 3/1991 | Kuypers et al. |
| 5,001,054 | A | 3/1991 | Wagner |
| 5,002,054 | A | 3/1991 | Ash et al. |
| 5,006,110 | A | 4/1991 | Garrison et al. |
| 5,013,161 | A | 5/1991 | Zaragoza et al. |
| 5,019,974 | A | 5/1991 | Beckers |
| 5,035,860 | A | 7/1991 | Kleingeld et al. |
| 5,036,860 | A | 8/1991 | Leigh et al. |
| 5,047,044 | A | 9/1991 | Smith et al. |
| 5,050,612 | A | 9/1991 | Matsumura |
| 5,051,688 | A | 9/1991 | Murase et al. |
| 5,055,171 | A | 10/1991 | Peck |
| 5,058,592 | A | 10/1991 | Whisler |
| 5,067,957 | A | 11/1991 | Jervis |
| 5,068,536 | A | 11/1991 | Rosenthal |
| 5,070,535 | A | 12/1991 | Hochmair et al. |
| 5,082,550 | A | 1/1992 | Rishpon et al. |
| 5,082,786 | A | 1/1992 | Nakamoto |
| 5,086,246 | A | 2/1992 | Dymond et al. |
| 5,089,112 | A | 2/1992 | Skotheim et al. |
| 5,095,904 | A | 3/1992 | Seligman et al. |
| 5,101,814 | A | 4/1992 | Palti |
| 5,106,365 | A | 4/1992 | Hernandez |
| 5,108,564 | A | 4/1992 | Szuminsky et al. |
| 5,108,889 | A | 4/1992 | Smith et al. |
| 5,109,850 | A | 5/1992 | Blanco et al. |
| 5,120,420 | A | 6/1992 | Nankai et al. |
| 5,122,925 | A | 6/1992 | Inpyn |
| 5,124,661 | A | 6/1992 | Zelin et al. |
| 5,126,034 | A | 6/1992 | Carter et al. |
| 5,133,856 | A | 7/1992 | Yamaguchi et al. |
| 5,135,003 | A | 8/1992 | Souma |
| 5,135,004 | A | 8/1992 | Adams et al. |
| 5,140,985 | A | 8/1992 | Schroeder et al. |
| 5,141,868 | A | 8/1992 | Shanks et al. |
| 5,161,532 | A | 11/1992 | Joseph |
| 5,162,407 | A | 11/1992 | Turner |
| 5,165,407 | A | 11/1992 | Wilson et al. |
| 5,173,165 | A | 12/1992 | Schmid et al. |
| 5,174,291 | A | 12/1992 | Schoonen et al. |
| 5,190,041 | A | 3/1993 | Palti |
| 5,190,546 | A | 3/1993 | Jervis |
| 5,192,416 | A | 3/1993 | Wang et al. |
| 5,193,545 | A | 3/1993 | Marsoner et al. |
| 5,198,367 | A | 3/1993 | Aizawa et al. |
| 5,202,261 | A | 4/1993 | Musho et al. |
| 5,204,264 | A | 4/1993 | Kaminer et al. |
| 5,205,297 | A | 4/1993 | Montecalvo et al. |
| 5,205,920 | A | 4/1993 | Oyama et al. |
| 5,208,154 | A | 5/1993 | Weaver et al. |
| 5,209,229 | A | 5/1993 | Gilli |
| 5,217,595 | A | 6/1993 | Smith et al. |
| 5,228,449 | A | 7/1993 | Christ et al. |
| 5,229,282 | A | 7/1993 | Yoshioka et al. |
| 5,231,988 | A | 8/1993 | Wernicke et al. |
| 5,234,835 | A | 8/1993 | Nestor et al. |
| 5,238,729 | A | 8/1993 | Debe |
| 5,243,696 | A | 9/1993 | Carr et al. |
| 5,245,314 | A | 9/1993 | Kah et al. |
| 5,246,867 | A | 9/1993 | Lakowicz et al. |
| 5,250,439 | A | 10/1993 | Musho et al. |
| 5,251,126 | A | 10/1993 | Kahn et al. |
| 5,262,035 | A | 11/1993 | Gregg et al. |
| 5,262,305 | A | 11/1993 | Heller et al. |
| 5,264,103 | A | 11/1993 | Yoshioka et al. |
| 5,264,104 | A | 11/1993 | Gregg et al. |
| 5,264,105 | A | 11/1993 | Gregg et al. |
| 5,264,106 | A | 11/1993 | McAleer et al. |
| 5,271,815 | A | 12/1993 | Wong |
| 5,279,294 | A | 1/1994 | Anderson |
| 5,284,156 | A | 2/1994 | Schramm et al. |
| 5,285,792 | A | 2/1994 | Sjoquist et al. |
| 5,286,362 | A | 2/1994 | Hoenes et al. |
| 5,286,364 | A | 2/1994 | Yacynych et al. |
| 5,288,636 | A | 2/1994 | Pollmann et al. |
| 5,289,497 | A | 2/1994 | Jackobson et al. |
| 5,293,546 | A | 3/1994 | Tadros et al. |
| 5,293,877 | A | 3/1994 | O'Hara et al. |
| 5,299,571 | A | 4/1994 | Mastrototaro |
| 5,305,008 | A | 4/1994 | Turner et al. |
| 5,320,098 | A | 6/1994 | Davidson |
| 5,320,715 | A | 6/1994 | Berg |
| 5,320,725 | A | 6/1994 | Gregg et al. |
| 5,322,063 | A | 6/1994 | Allen et al. |
| 5,333,615 | A | 8/1994 | Craelius et al. |
| 5,337,747 | A | 8/1994 | Neftel |
| 5,340,722 | A | 8/1994 | Wolfbeis et al. |
| 5,342,789 | A | 8/1994 | Chick et al. |
| 5,352,348 | A | 10/1994 | Young et al. |
| 5,356,420 | A | 10/1994 | Czernecki et al. |
| 5,356,786 | A | 10/1994 | Heller et al. |
| 5,360,404 | A | 11/1994 | Novacek et al. |
| 5,368,028 | A | 11/1994 | Palti |
| 5,372,133 | A | 12/1994 | Hogen Esch |
| 5,372,427 | A | 12/1994 | Padovani et al. |
| 5,376,251 | A | 12/1994 | Kaneko et al. |
| 5,378,628 | A | 1/1995 | Gratzel et al. |
| 5,379,238 | A | 1/1995 | Stark |
| 5,384,547 | A | 1/1995 | Lynk et al. |
| 5,387,327 | A | 2/1995 | Khan |

(56) References Cited

U.S. PATENT DOCUMENTS

| | | | | |
|---|---|---|---|---|
| 5,390,670 | A | | 2/1995 | Centa et al. |
| 5,390,671 | A | | 2/1995 | Lord et al. |
| 5,391,250 | A | | 2/1995 | Cheney, II et al. |
| 5,394,877 | A | | 3/1995 | Orr et al. |
| 5,395,504 | A | | 3/1995 | Saurer et al. |
| 5,400,782 | A | | 3/1995 | Beaubiah |
| 5,400,794 | A | | 3/1995 | Gorman |
| 5,402,780 | A | | 4/1995 | Faasse, Jr. |
| 5,407,431 | A | | 4/1995 | Botich et al. |
| 5,408,999 | A | | 4/1995 | Singh et al. |
| 5,410,326 | A | | 4/1995 | Goldstein |
| 5,411,647 | A | | 5/1995 | Johnson et al. |
| 5,425,361 | A | | 6/1995 | Fenzlein et al. |
| 5,425,868 | A | | 6/1995 | Pedersen |
| 5,431,160 | A | | 7/1995 | Wilkins |
| 5,431,921 | A | | 7/1995 | Thombre |
| 5,437,999 | A | | 8/1995 | Diebold et al. |
| 5,438,983 | A | | 8/1995 | Falcone |
| 5,462,051 | A | | 10/1995 | Oka et al. |
| 5,462,645 | A | | 10/1995 | Albery et al. |
| 5,469,846 | A | | 11/1995 | Khan |
| 5,472,317 | A | | 12/1995 | Field et al. |
| 5,482,473 | A | | 1/1996 | Lord et al. |
| 5,484,403 | A | | 1/1996 | Yoakum et al. |
| 5,489,414 | A | | 2/1996 | Schreiber et al. |
| 5,491,474 | A | | 2/1996 | Suni et al. |
| 5,494,562 | A | | 2/1996 | Maley et al. |
| 5,496,453 | A | | 3/1996 | Uenoyama et al. |
| 5,497,772 | A | | 3/1996 | Schulman et al. |
| 5,499,243 | A | | 3/1996 | Hall |
| 5,507,288 | A | | 4/1996 | Bocker et al. |
| 5,509,410 | A | | 4/1996 | Hill et al. |
| 5,514,718 | A | | 5/1996 | Lewis et al. |
| 5,516,832 | A | | 5/1996 | Kennan et al. |
| 5,527,288 | A | | 6/1996 | Gross et al. |
| 5,531,878 | A | | 7/1996 | Vadgama et al. |
| 5,532,686 | A | | 7/1996 | Urbas et al. |
| 5,533,977 | A | | 7/1996 | Metcalf et al. |
| 5,536,259 | A | | 7/1996 | Utterberg |
| 5,543,326 | A | | 8/1996 | Heller et al. |
| 5,544,196 | A | | 8/1996 | Tiedmann, Jr. et al. |
| 5,545,191 | A | | 8/1996 | Mann et al. |
| 5,549,568 | A | | 8/1996 | Sheilds |
| 5,551,427 | A | | 9/1996 | Altman |
| 5,555,190 | A | | 9/1996 | Derby et al. |
| 5,558,638 | A | | 9/1996 | Evers et al. |
| 5,560,357 | A | | 10/1996 | Faupei et al. |
| 5,562,713 | A | | 10/1996 | Silvian |
| 5,564,434 | A | | 10/1996 | Halperin et al. |
| 5,565,085 | A | | 10/1996 | Ikeda et al. |
| 5,567,302 | A | | 10/1996 | Song et al. |
| 5,568,806 | A | | 10/1996 | Cheney, II et al. |
| 5,569,186 | A | | 10/1996 | Lord et al. |
| 5,571,022 | A | | 11/1996 | Schaarschmidt |
| 5,575,563 | A | | 11/1996 | Chiu et al. |
| 5,581,206 | A | | 12/1996 | Chevallier et al. |
| 5,582,184 | A | | 12/1996 | Erickson et al. |
| 5,582,697 | A | | 12/1996 | Ikeda et al. |
| 5,582,698 | A | | 12/1996 | Flaherty et al. |
| 5,584,813 | A | | 12/1996 | Livingston et al. |
| 5,586,553 | A | | 12/1996 | Halli et al. |
| 5,589,326 | A | | 12/1996 | Deng et al. |
| 5,593,852 | A | | 1/1997 | Heller et al. |
| 5,596,150 | A | | 1/1997 | Arndt et al. |
| 5,597,378 | A | | 1/1997 | Jervis |
| 5,600,301 | A | | 2/1997 | Robinson, III |
| 5,601,435 | A | | 2/1997 | Quy |
| 5,609,575 | A | | 3/1997 | Larson et al. |
| 5,613,978 | A | | 3/1997 | Harding |
| 5,617,851 | A | | 4/1997 | Lipkovker |
| 5,623,933 | A | | 4/1997 | Amano et al. |
| 5,626,566 | A | | 5/1997 | Petersen et al. |
| 5,628,310 | A | | 5/1997 | Rao et al. |
| 5,628,324 | A | | 5/1997 | Sarbach |
| 5,628,890 | A | | 5/1997 | Carter et al. |
| 5,632,557 | A | | 5/1997 | Simons |
| 5,634,468 | A | | 6/1997 | Platt et al. |
| 5,636,640 | A | | 6/1997 | Staehlin |
| 5,638,832 | A | | 6/1997 | Singer et al. |
| 5,640,954 | A | | 6/1997 | Pfeiffer et al. |
| 5,651,869 | A | | 7/1997 | Yoshioka et al. |
| 5,653,239 | A | | 8/1997 | Pompei et al. |
| 5,659,454 | A | | 8/1997 | Vermesse |
| 5,660,163 | A | | 8/1997 | Schulman et al. |
| 5,665,071 | A | | 9/1997 | Wyrick |
| 5,665,222 | A | | 9/1997 | Heller et al. |
| 5,669,543 | A | * | 9/1997 | Ueno ...................... B65C 7/003 112/222 |
| 5,669,890 | A | * | 9/1997 | Grimm ............... A61M 5/3286 604/272 |
| 5,670,031 | A | | 9/1997 | Hintsche et al. |
| 5,673,322 | A | | 9/1997 | Pepe et al. |
| 5,680,858 | A | | 10/1997 | Hansen et al. |
| 5,682,233 | A | | 10/1997 | Brinda |
| 5,695,623 | A | | 12/1997 | Michel et al. |
| 5,707,502 | A | | 1/1998 | McCaffrey et al. |
| 5,708,247 | A | | 1/1998 | McAleer et al. |
| 5,711,001 | A | | 1/1998 | Bussan et al. |
| 5,711,297 | A | | 1/1998 | Iliff et al. |
| 5,711,861 | A | | 1/1998 | Ward et al. |
| 5,711,862 | A | | 1/1998 | Sakoda et al. |
| 5,724,030 | A | | 3/1998 | Urbas et al. |
| 5,726,646 | A | | 3/1998 | Bane et al. |
| 5,733,044 | A | | 3/1998 | Rose et al. |
| 5,733,259 | A | | 3/1998 | Valcke et al. |
| 5,733,262 | A | | 3/1998 | Paul |
| 5,733,313 | A | | 3/1998 | Barreras, Sr. et al. |
| 5,735,285 | A | | 4/1998 | Albert et al. |
| 5,738,220 | A | | 4/1998 | Geszler |
| 5,741,211 | A | | 4/1998 | Renirie et al. |
| 5,743,262 | A | | 4/1998 | Lepper, Jr. et al. |
| 5,746,217 | A | | 5/1998 | Erickson et al. |
| 5,746,697 | A | | 5/1998 | Swedlow et al. |
| 5,748,103 | A | | 5/1998 | Flach et al. |
| 5,749,656 | A | | 5/1998 | Boehm et al. |
| 5,749,907 | A | | 5/1998 | Mann |
| 5,758,290 | A | | 5/1998 | Nealon et al. |
| 5,766,131 | A | | 6/1998 | Kondo et al. |
| 5,770,028 | A | | 6/1998 | Maley et al. |
| 5,771,001 | A | | 6/1998 | Cobb |
| 5,771,891 | A | | 6/1998 | Gozani |
| 5,772,586 | A | | 6/1998 | Heinonen et al. |
| 5,778,879 | A | | 7/1998 | Ota et al. |
| 5,779,665 | A | | 7/1998 | Mastrototaro et al. |
| 5,786,439 | A | | 7/1998 | Van Antwerp et al. |
| 5,791,344 | A | | 8/1998 | Schulman et al. |
| 5,798,961 | A | | 8/1998 | Heyden et al. |
| 5,800,420 | A | | 9/1998 | Gross et al. |
| 5,804,047 | A | | 9/1998 | Karube et al. |
| 5,807,375 | A | | 9/1998 | Gross et al. |
| 5,814,020 | A | | 9/1998 | Gross |
| 5,820,551 | A | | 10/1998 | Hill et al. |
| 5,820,570 | A | | 10/1998 | Erickson et al. |
| 5,820,622 | A | | 10/1998 | Gross et al. |
| 5,822,715 | A | | 10/1998 | Worthington et al. |
| 5,823,802 | A | | 10/1998 | Bartley |
| 5,827,184 | A | | 10/1998 | Netherly et al. |
| 5,830,064 | A | | 11/1998 | Bradish et al. |
| 5,833,603 | A | | 11/1998 | Kovacs et al. |
| 5,840,020 | A | | 11/1998 | Heinonen et al. |
| 5,842,983 | A | | 12/1998 | Abel et al. |
| 5,851,197 | A | | 12/1998 | Marano et al. |
| 5,856,758 | A | | 1/1999 | Joffe et al. |
| 5,858,001 | A | | 1/1999 | Tsals et al. |
| 5,865,804 | A | | 2/1999 | Bachynsky |
| 5,871,494 | A | | 2/1999 | Simons et al. |
| 5,875,186 | A | | 2/1999 | Belanger et al. |
| 5,879,311 | A | | 3/1999 | Duchon et al. |
| 5,885,211 | A | | 3/1999 | Eppstein et al. |
| 5,891,049 | A | | 4/1999 | Cyrus et al. |
| 5,899,855 | A | | 5/1999 | Brown |
| 5,899,856 | A | | 5/1999 | Schoendorfer et al. |
| 5,914,026 | A | | 6/1999 | Blubaugh, Jr. et al. |
| 5,918,603 | A | | 7/1999 | Brown |

(56) References Cited

U.S. PATENT DOCUMENTS

| | | | |
|---|---|---|---|
| 5,919,141 | A | 7/1999 | Money et al. |
| 5,921,963 | A | 7/1999 | Erez et al. |
| 5,924,979 | A | 7/1999 | Sedlow et al. |
| 5,925,021 | A | 7/1999 | Castellano et al. |
| 5,931,814 | A | 8/1999 | Gross et al. |
| 5,931,868 | A | 8/1999 | Gross |
| 5,935,224 | A | 8/1999 | Svancarek et al. |
| 5,938,679 | A | 8/1999 | Freeman et al. |
| 5,942,979 | A | 8/1999 | Luppino |
| 5,948,006 | A | 9/1999 | Mann |
| 5,951,492 | A | 9/1999 | Douglas et al. |
| 5,951,521 | A | 9/1999 | Mastrototaro et al. |
| 5,951,582 | A | 9/1999 | Thorne et al. |
| 5,954,643 | A | 9/1999 | Antwerp |
| 5,954,685 | A | 9/1999 | Tierny |
| 5,957,854 | A | 9/1999 | Besson et al. |
| 5,961,451 | A | 10/1999 | Reber et al. |
| 5,964,718 | A | 10/1999 | Duchon et al. |
| 5,964,993 | A | 10/1999 | Blubaugh, Jr. et al. |
| 5,965,380 | A | 10/1999 | Heller et al. |
| 5,971,922 | A | 10/1999 | Arita et al. |
| 5,971,941 | A | 10/1999 | Simons et al. |
| 5,972,199 | A | 10/1999 | Heller et al. |
| 5,987,353 | A | 11/1999 | Khatchatrian et al. |
| 5,993,411 | A | 11/1999 | Choi |
| 5,995,860 | A | 11/1999 | Sun et al. |
| 5,997,501 | A | 12/1999 | Gross et al. |
| 6,001,067 | A | 12/1999 | Shults et al. |
| 6,004,278 | A | 12/1999 | Botich et al. |
| 6,017,335 | A | 1/2000 | Burnham |
| 6,022,315 | A | 2/2000 | Iliff |
| 6,022,368 | A | 2/2000 | Gavronsky et al. |
| 6,024,699 | A | 2/2000 | Surwit et al. |
| 6,026,321 | A | 2/2000 | Miyata et al. |
| 6,027,459 | A | 2/2000 | Shain et al. |
| 6,028,413 | A | 2/2000 | Brockmann |
| 6,032,064 | A | 2/2000 | Devlin et al. |
| 6,036,924 | A | 3/2000 | Simons et al. |
| 6,048,352 | A | 4/2000 | Douglas et al. |
| 6,049,727 | A | 4/2000 | Crothall |
| 6,052,565 | A | 4/2000 | Ishikura et al. |
| 6,054,194 | A | 4/2000 | Kane |
| 6,056,718 | A | 5/2000 | Funderburk et al. |
| 6,059,946 | A | 5/2000 | Yukawa et al. |
| 6,066,243 | A | 5/2000 | Anderson et al. |
| 6,068,399 | A | 5/2000 | Tseng |
| 6,071,294 | A | 6/2000 | Simons et al. |
| 6,071,391 | A | 6/2000 | Gotoh et al. |
| 6,083,710 | A | 7/2000 | Heller et al. |
| 6,085,342 | A | 7/2000 | Marholev et al. |
| 6,088,605 | A | 7/2000 | Griffith et al. |
| 6,088,608 | A | 7/2000 | Schulman et al. |
| 6,091,975 | A | 7/2000 | Daddona et al. |
| 6,091,976 | A | 7/2000 | Pfeiffer et al. |
| 6,091,987 | A | 7/2000 | Thompson |
| 6,093,172 | A | 7/2000 | Funderburk et al. |
| 6,096,364 | A | 8/2000 | Bok et al. |
| 6,097,480 | A | 8/2000 | Kaplan |
| 6,099,484 | A | 8/2000 | Douglas et al. |
| 6,102,896 | A | 8/2000 | Roser |
| 6,103,033 | A | 8/2000 | Say et al. |
| 6,106,484 | A | 8/2000 | Terwilliger |
| 6,117,290 | A | 9/2000 | Say et al. |
| 6,119,028 | A | 9/2000 | Schulman et al. |
| 6,120,676 | A | 9/2000 | Heller et al. |
| 6,121,009 | A | 9/2000 | Heller et al. |
| 6,121,611 | A | 9/2000 | Lindsay et al. |
| 6,122,351 | A | 9/2000 | Schlueter, Jr. et al. |
| 6,129,666 | A | 10/2000 | DeLuca et al. |
| 6,130,623 | A | 10/2000 | MacLellan et al. |
| 6,132,449 | A | 10/2000 | Lum et al. |
| 6,134,461 | A | 10/2000 | Say et al. |
| 6,141,573 | A | 10/2000 | Kurnik et al. |
| 6,143,164 | A | 11/2000 | Heller et al. |
| 6,144,837 | A | 11/2000 | Quy |
| 6,144,871 | A | 11/2000 | Saito et al. |
| 6,144,922 | A | 11/2000 | Douglas et al. |
| 6,157,850 | A | 12/2000 | Diab et al. |
| 6,159,147 | A | 12/2000 | Lichter et al. |
| 6,159,181 | A | 12/2000 | Crossman et al. |
| 6,161,095 | A | 12/2000 | Brown |
| 6,162,611 | A | 12/2000 | Heller et al. |
| 6,168,606 | B1 | 1/2001 | Levin et al. |
| 6,175,752 | B1 | 1/2001 | Say et al. |
| 6,186,982 | B1 | 2/2001 | Gross et al. |
| 6,192,891 | B1 | 2/2001 | Gravel et al. |
| 6,197,040 | B1 | 3/2001 | LeVaughn et al. |
| 6,198,946 | B1 | 3/2001 | Shin et al. |
| 6,200,265 | B1 | 3/2001 | Walsh et al. |
| 6,203,495 | B1 | 3/2001 | Bardy et al. |
| 6,212,416 | B1 | 4/2001 | Ward et al. |
| 6,213,972 | B1 | 4/2001 | Butterfield et al. |
| 6,219,574 | B1 | 4/2001 | Cormier et al. |
| 6,223,283 | B1 | 4/2001 | Chaiken et al. |
| 6,231,531 | B1 | 5/2001 | Lum et al. |
| 6,233,471 | B1 | 5/2001 | Berner et al. |
| 6,237,394 | B1 | 5/2001 | Harris et al. |
| 6,248,067 | B1 | 6/2001 | Causey et al. |
| 6,254,536 | B1 | 7/2001 | DeVito |
| 6,254,586 | B1 | 7/2001 | Mann et al. |
| 6,264,810 | B1 | 7/2001 | Stol et al. |
| 6,270,455 | B1 | 8/2001 | Brown |
| 6,275,717 | B1 | 8/2001 | Gross et al. |
| 6,283,761 | B1 | 9/2001 | Joao |
| 6,283,982 | B1 | 9/2001 | Levaughn et al. |
| 6,284,478 | B1 | 9/2001 | Heller et al. |
| 6,291,200 | B1 | 9/2001 | LeJeune et al. |
| 6,293,925 | B1 | 9/2001 | Safabash et al. |
| 6,294,997 | B1 | 9/2001 | Paratore et al. |
| 6,295,506 | B1 | 9/2001 | Heinonen et al. |
| 6,298,255 | B1 | 10/2001 | Cordero et al. |
| 6,299,347 | B1 | 10/2001 | Pompei |
| 6,299,757 | B1 | 10/2001 | Feldman et al. |
| 6,302,866 | B1 | 10/2001 | Marggi |
| 6,304,766 | B1 | 10/2001 | Colvin, Jr. |
| 6,306,104 | B1 | 10/2001 | Cunningham et al. |
| 6,306,141 | B1 | 10/2001 | Jervis |
| 6,309,884 | B1 | 10/2001 | Cooper et al. |
| 6,314,317 | B1 | 11/2001 | Willis |
| 6,329,161 | B1 | 12/2001 | Heller et al. |
| 6,331,244 | B1 | 12/2001 | Lewis et al. |
| 6,336,269 | B1 | 1/2002 | Eldridge et al. |
| 6,338,790 | B1 | 1/2002 | Feldman et al. |
| 6,341,232 | B1 | 1/2002 | Conn et al. |
| 6,348,640 | B1 | 2/2002 | Navot et al. |
| 6,359,270 | B1 | 3/2002 | Bridson |
| 6,359,444 | B1 | 3/2002 | Grimes |
| 6,360,888 | B1 | 3/2002 | McIvor et al. |
| 6,364,890 | B1 | 4/2002 | Lum et al. |
| 6,366,794 | B1 | 4/2002 | Moussy et al. |
| 6,368,141 | B1 | 4/2002 | Van Antwerp et al. |
| 6,368,274 | B1 | 4/2002 | Van Antwerp et al. |
| 6,368,339 | B1 | 4/2002 | Amplatz |
| 6,377,828 | B1 | 4/2002 | Chaiken et al. |
| 6,377,829 | B1 | 4/2002 | Al-Ali |
| 6,377,894 | B1 | 4/2002 | Deweese et al. |
| 6,379,301 | B1 | 4/2002 | Worthington et al. |
| 6,387,048 | B1 | 5/2002 | Schulman et al. |
| 6,400,974 | B1 | 6/2002 | Lesho |
| 6,405,066 | B1 | 6/2002 | Essenpreis et al. |
| 6,409,740 | B1 | 6/2002 | Kuhr et al. |
| 6,413,393 | B1 | 7/2002 | Van Antwerp et al. |
| 6,416,471 | B1 | 7/2002 | Kumar et al. |
| 6,418,332 | B1 | 7/2002 | Mastrototaro et al. |
| 6,418,346 | B1 | 7/2002 | Nelson et al. |
| 6,424,847 | B1 | 7/2002 | Mastrototaro et al. |
| 6,427,088 | B1 | 7/2002 | Bowman, IV et al. |
| 6,433,743 | B1 | 8/2002 | Massy et al. |
| 6,435,017 | B1 | 8/2002 | Nowicki, Jr. et al. |
| 6,437,679 | B1 | 8/2002 | Roques |
| 6,438,414 | B1 | 8/2002 | Conn et al. |
| 6,440,068 | B1 | 8/2002 | Brown et al. |
| 6,442,413 | B1 | 8/2002 | Silver |
| 6,445,374 | B2 | 9/2002 | Albert et al. |

(56) References Cited

U.S. PATENT DOCUMENTS 6,451,025 B1 9/2002 Jervis
6,458,109 B1 10/2002 Henley et al.
6,461,496 B1 10/2002 Feldman et al.
6,471,689 B1 10/2002 Joseph et al.
6,472,220 B1 10/2002 Simons et al.
6,478,736 B1 11/2002 Mault
6,482,176 B1 11/2002 Wich
6,484,045 B1 11/2002 Holker et al.
6,484,046 B1 11/2002 Say et al.
6,493,069 B1 12/2002 Nagashimada et al.
6,494,830 B1 12/2002 Wessel
6,496,729 B2 12/2002 Thompson
6,497,655 B1 12/2002 Linberg et al.
6,503,381 B1 1/2003 Gotoh et al.
6,510,344 B1 1/2003 Halpern
6,514,460 B1 2/2003 Fendrock
6,514,689 B2 2/2003 Han et al.
6,514,718 B2 2/2003 Heller et al.
6,520,326 B2 2/2003 McIvor et al.
6,522,927 B1 2/2003 Bishay et al.
6,533,805 B1 3/2003 Jervis
6,537,242 B1 3/2003 Palmer
6,540,891 B1 4/2003 Stewart et al.
6,544,212 B2 4/2003 Galley et al.
6,546,268 B1 4/2003 Ishikawa et al.
6,549,796 B2 4/2003 Sohrab
6,551,494 B1 4/2003 Heller et al.
6,551,496 B1 4/2003 Moles et al.
6,554,795 B2 4/2003 Bagaoisan et al.
6,554,798 B1 4/2003 Mann et al.
6,558,320 B1 5/2003 Causey, III et al.
6,558,321 B1 5/2003 Burd et al.
6,558,351 B1 5/2003 Steil et al.
6,560,471 B1 5/2003 Heller et al.
6,561,975 B1 5/2003 Pool et al.
6,561,978 B1 5/2003 Conn et al.
6,562,001 B2 5/2003 Lebel et al.
6,564,105 B2 5/2003 Starkweather et al.
6,565,509 B1 5/2003 Say et al.
6,571,128 B2 5/2003 Lebel et al.
6,572,542 B1 6/2003 Houben et al.
6,572,566 B2 6/2003 Effenhauser
6,574,490 B2 6/2003 Abbink et al.
6,574,510 B2 6/2003 Von Arx et al.
6,575,895 B1 6/2003 Blair
6,576,101 B1 6/2003 Heller et al.
6,577,899 B2 6/2003 Lebel et al.
6,579,231 B1 6/2003 Phipps
6,579,690 B1 6/2003 Bonnecaze et al.
6,584,335 B1 6/2003 Haar et al.
6,585,644 B2 7/2003 Lebel et al.
6,589,229 B1 7/2003 Connelly et al.
6,591,125 B1 7/2003 Buse et al.
6,591,745 B2 7/2003 Feldman et al.
6,595,919 B2 7/2003 Berner et al.
6,600,997 B2 7/2003 Deweese et al.
6,602,268 B2 8/2003 Kuhr et al.
6,603,995 B1 8/2003 Carter
6,604,050 B2 8/2003 Trippel et al.
6,605,200 B1 8/2003 Mao et al.
6,605,201 B1 8/2003 Mao et al.
6,607,509 B2 8/2003 Bobroff et al.
6,607,543 B2 8/2003 Purcell et al.
6,608,562 B1 8/2003 Kimura et al.
6,610,012 B2 8/2003 Mault
6,611,206 B2 8/2003 Eshelman et al.
6,613,015 B2 9/2003 Sandstrom et al.
6,616,819 B1 9/2003 Liamos et al.
6,618,934 B1 9/2003 Feldman et al.
6,627,154 B1 9/2003 Goodman et al.
6,631,281 B1 10/2003 Kastle
6,633,772 B2 10/2003 Ford et al.
6,635,014 B2 10/2003 Starkweather et al.
6,635,167 B1 10/2003 Batman et al.
6,637,611 B2 10/2003 Luch
6,641,533 B2 11/2003 Causey, III et al.
6,645,359 B1 11/2003 Bhullar et al.
6,648,821 B2 11/2003 Lebel et al.
6,650,471 B2 11/2003 Doi
6,654,625 B1 11/2003 Say et al.
6,656,114 B1 12/2003 Poulson et al.
6,658,396 B1 12/2003 Tang et al.
6,659,948 B2 12/2003 Lebel et al.
6,662,439 B1 12/2003 Bhullar
6,666,849 B1 12/2003 Marshall et al.
6,668,196 B1 12/2003 Villegas et al.
6,671,534 B2 12/2003 Putz
6,675,030 B2 1/2004 Ciurczak et al.
6,676,290 B1 1/2004 Lu
6,676,816 B2 1/2004 Mao et al.
6,682,546 B2 1/2004 Amplatz
6,687,546 B2 2/2004 Lebel et al.
6,689,056 B1 2/2004 Kilcoyne et al.
6,694,191 B2 2/2004 Starkweather et al.
6,695,860 B1 2/2004 Ward et al.
6,698,269 B2 3/2004 Baber et al.
6,699,188 B2 3/2004 Wessel
6,702,857 B2 3/2004 Brauker et al.
6,706,159 B2 3/2004 Moerman et al.
6,721,582 B2 4/2004 Trepagnier et al.
6,730,025 B1 5/2004 Platt
6,730,072 B2 5/2004 Shawgo et al.
6,730,200 B1 5/2004 Stewart et al.
6,731,976 B2 5/2004 Penn et al.
6,733,446 B2 5/2004 Lebel et al.
6,735,183 B2 5/2004 O'Toole et al.
6,735,479 B2 5/2004 Fabian et al.
6,736,957 B1 5/2004 Forrow et al.
6,740,075 B2 5/2004 Lebel et al.
6,741,877 B1 5/2004 Shults et al.
6,743,635 B2 6/2004 Neel et al.
6,746,582 B2 6/2004 Heller et al.
6,748,445 B1 6/2004 Darcey et al.
6,749,740 B2 6/2004 Liamos et al.
6,758,810 B2 7/2004 Lebel et al.
6,758,835 B2 7/2004 Close et al.
6,764,581 B1 7/2004 Forrow et al.
6,767,440 B1 7/2004 Bhullar et al.
6,770,030 B1 8/2004 Schaupp et al.
6,773,671 B1 8/2004 Lewis et al.
6,781,522 B2 8/2004 Sleva et al.
6,790,178 B1 9/2004 Mault et al.
6,804,558 B2 10/2004 Haller et al.
6,804,561 B2 10/2004 Stover
6,809,653 B1 10/2004 Mann et al.
6,810,290 B2 10/2004 Lebel et al.
6,811,533 B2 11/2004 Lebel et al.
6,811,534 B2 11/2004 Bowman, IV et al.
6,813,519 B2 11/2004 Lebel et al.
6,814,844 B2 11/2004 Bhullar et al.
6,830,551 B1 12/2004 Uchigaki et al.
6,837,858 B2 1/2005 Cunningham et al.
6,837,885 B2 1/2005 Koblish et al.
6,837,988 B2 1/2005 Leong et al.
6,849,052 B2 2/2005 Uchigaki et al.
6,850,790 B2 2/2005 Berner et al.
6,850,859 B1 2/2005 Schuh
6,854,882 B2 2/2005 Chen
6,862,465 B2 3/2005 Shults et al.
6,873,268 B2 3/2005 Lebel et al.
6,878,112 B2 4/2005 Linberg et al.
6,881,551 B2 4/2005 Heller et al.
6,892,085 B2 5/2005 McIvor et al.
6,893,545 B2 5/2005 Gotoh et al.
6,895,263 B2 5/2005 Shin et al.
6,895,265 B2 5/2005 Silver
6,923,763 B1 8/2005 Kovatchev et al.
6,923,764 B2 8/2005 Aceti et al.
6,925,393 B1 8/2005 Kalatz et al.
6,931,327 B2 8/2005 Goode, Jr. et al.
6,932,892 B2 8/2005 Chen
6,932,894 B2 8/2005 Mao et al.
6,936,006 B2 8/2005 Sabra
6,937,222 B2 8/2005 Numao

(56) References Cited

U.S. PATENT DOCUMENTS

| | | | |
|---|---|---|---|
| 6,940,403 | B2 | 9/2005 | Kail, IV |
| 6,941,163 | B2 | 9/2005 | Ford et al. |
| 6,942,518 | B2 | 9/2005 | Liamos et al. |
| 6,950,708 | B2 | 9/2005 | Bowman IV et al. |
| 6,954,662 | B2 | 10/2005 | Freger et al. |
| 6,958,705 | B2 | 10/2005 | Lebel et al. |
| 6,959,211 | B2 | 10/2005 | Rule et al. |
| 6,968,294 | B2 | 11/2005 | Gutta et al. |
| 6,971,274 | B2 | 12/2005 | Olin |
| 6,971,999 | B2 | 12/2005 | Py et al. |
| 6,973,706 | B2 | 12/2005 | Say et al. |
| 6,974,437 | B2 | 12/2005 | Lebel et al. |
| 6,975,893 | B2 | 12/2005 | Say et al. |
| 6,983,867 | B1 | 1/2006 | Fugere |
| 6,990,366 | B2 | 1/2006 | Say et al. |
| 6,997,907 | B2 | 2/2006 | Safabash et al. |
| 6,998,247 | B2 | 2/2006 | Monfre et al. |
| 6,999,854 | B2 | 2/2006 | Roth |
| 7,003,336 | B2 | 2/2006 | Holker et al. |
| 7,003,340 | B2 | 2/2006 | Say et al. |
| 7,003,341 | B2 | 2/2006 | Say et al. |
| 7,005,857 | B2 | 2/2006 | Stiene et al. |
| 7,009,511 | B2 | 3/2006 | Mazar et al. |
| 7,010,356 | B2 | 3/2006 | Jog et al. |
| 7,015,817 | B2 | 3/2006 | Copley et al. |
| 7,016,713 | B2 | 3/2006 | Gardner et al. |
| 7,020,508 | B2 | 3/2006 | Stivoric et al. |
| 7,022,072 | B2 | 4/2006 | Fox et al. |
| 7,022,219 | B2 | 4/2006 | Mansouri et al. |
| 7,024,236 | B2 | 4/2006 | Ford et al. |
| 7,024,245 | B2 | 4/2006 | Lebel et al. |
| 7,025,743 | B2 | 4/2006 | Mann et al. |
| 7,025,774 | B2 | 4/2006 | Freeman et al. |
| 7,027,848 | B2 | 4/2006 | Robinson et al. |
| 7,027,859 | B1 | 4/2006 | McNichols et al. |
| 7,027,931 | B1 | 4/2006 | Jones et al. |
| 7,029,444 | B2 | 4/2006 | Shin et al. |
| 7,041,057 | B1 | 5/2006 | Faupel et al. |
| 7,041,068 | B2 | 5/2006 | Freeman et al. |
| 7,041,468 | B2 | 5/2006 | Drucker et al. |
| 7,043,305 | B2 | 5/2006 | Kenknight et al. |
| 7,046,153 | B2 | 5/2006 | Oja et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,073,246 | B2 | 7/2006 | Bhullar et al. |
| 7,074,307 | B2 | 7/2006 | Simpson et al. |
| 7,081,195 | B2 | 7/2006 | Simpson et al. |
| 7,082,334 | B2 | 7/2006 | Boute et al. |
| 7,097,637 | B2 | 8/2006 | Triplett et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,118,667 | B2 | 10/2006 | Lee |
| 7,120,483 | B2 | 10/2006 | Russel et al. |
| 7,123,950 | B2 | 10/2006 | Mannheimer |
| 7,124,027 | B1 | 10/2006 | Ernst et al. |
| 7,125,382 | B2 | 10/2006 | Zhou et al. |
| 7,131,984 | B2 | 11/2006 | Sato et al. |
| 7,134,999 | B2 | 11/2006 | Brauker et al. |
| 7,136,689 | B2 | 11/2006 | Shults et al. |
| 7,144,384 | B2 | 12/2006 | Gorman et al. |
| 7,146,202 | B2 | 12/2006 | Ward et al. |
| 7,154,398 | B2 | 12/2006 | Chen et al. |
| 7,155,290 | B2 | 12/2006 | Von Arx et al. |
| 7,167,818 | B2 | 1/2007 | Brown |
| 7,169,600 | B2 | 1/2007 | Hoss et al. |
| 7,171,274 | B2 | 1/2007 | Starkweather et al. |
| 7,174,199 | B2 | 2/2007 | Berner et al. |
| 7,179,226 | B2 | 2/2007 | Crothall et al. |
| 7,183,102 | B2 | 2/2007 | Monfre et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,207,974 | B2 | 4/2007 | Safabash et al. |
| 7,220,387 | B2 | 5/2007 | Flaherty et al. |
| 7,223,276 | B2 | 5/2007 | List et al. |
| 7,225,535 | B2 | 6/2007 | Feldman et al. |
| 7,226,442 | B2 | 6/2007 | Sheppard et al. |
| 7,226,978 | B2 | 6/2007 | Tapsak et al. |
| 7,228,162 | B2 | 6/2007 | Ward et al. |
| 7,228,182 | B2 | 6/2007 | Healy et al. |
| 7,237,712 | B2 | 7/2007 | DeRocco et al. |
| 7,267,665 | B2 | 9/2007 | Steil et al. |
| 7,276,029 | B2 | 10/2007 | Goode, Jr. et al. |
| 7,276,146 | B2 | 10/2007 | Wilsey |
| 7,276,147 | B2 | 10/2007 | Wilsey |
| 7,278,983 | B2 | 10/2007 | Ireland et al. |
| 7,286,894 | B1 | 10/2007 | Grant et al. |
| 7,287,318 | B2 | 10/2007 | Bhullar et al. |
| 7,291,497 | B2 | 11/2007 | Holmes et al. |
| 7,295,867 | B2 | 11/2007 | Berner et al. |
| 7,297,151 | B2 | 11/2007 | Boecker et al. |
| 7,299,082 | B2 | 11/2007 | Feldman et al. |
| 7,310,544 | B2 | 12/2007 | Brister et al. |
| 7,318,816 | B2 | 1/2008 | Bobroff et al. |
| 7,324,012 | B2 | 1/2008 | Mann et al. |
| 7,324,850 | B2 | 1/2008 | Persen et al. |
| 7,329,239 | B2 | 2/2008 | Safabash et al. |
| 7,335,294 | B2 | 2/2008 | Heller et al. |
| 7,340,287 | B2 | 3/2008 | Mason et al. |
| 7,340,309 | B2 | 3/2008 | Miazga et al. |
| 7,344,500 | B2 | 3/2008 | Talbot et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,381,184 | B2 | 6/2008 | Funderburk et al. |
| 7,384,397 | B2 | 6/2008 | Zhang et al. |
| 7,386,937 | B2 | 6/2008 | Bhullar et al. |
| 7,387,010 | B2 | 6/2008 | Sunshine et al. |
| 7,399,277 | B2 | 7/2008 | Saidara et al. |
| 7,400,111 | B2 | 7/2008 | Batman et al. |
| 7,401,111 | B1 | 7/2008 | Batman et al. |
| 7,402,153 | B2 | 7/2008 | Steil et al. |
| 7,404,796 | B2 | 7/2008 | Ginsberg |
| 7,407,493 | B2 | 8/2008 | Cane |
| 7,408,132 | B2 | 8/2008 | Wambsganss et al. |
| 7,416,541 | B2 | 8/2008 | Yuzhakov et al. |
| 7,419,573 | B2 | 9/2008 | Gundel |
| 7,424,318 | B2 | 9/2008 | Brister et al. |
| 7,429,255 | B2 | 9/2008 | Thompson |
| 7,433,727 | B2 | 10/2008 | Ward |
| 7,448,996 | B2 | 11/2008 | Khanuja et al. |
| 7,455,663 | B2 | 11/2008 | Bikovsky |
| 7,460,898 | B2 | 12/2008 | Brister et al. |
| 7,462,264 | B2 | 12/2008 | Heller et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,476,827 | B1 | 1/2009 | Bhullar et al. |
| 7,481,819 | B2 | 1/2009 | Koeppel et al. |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,519,408 | B2 | 4/2009 | Rasdal et al. |
| 7,545,272 | B2 | 6/2009 | Goodnow et al. |
| 7,547,281 | B2 | 6/2009 | Hayes et al. |
| 7,565,197 | B2 | 7/2009 | Haubrich et al. |
| 7,568,619 | B2 | 8/2009 | Todd et al. |
| 7,569,030 | B2 | 8/2009 | Lebel et al. |
| 7,574,266 | B2 | 8/2009 | Dudding et al. |
| 7,582,059 | B2 | 9/2009 | Funderburk et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,604,592 | B2 | 10/2009 | Freeman et al. |

(56) References Cited

U.S. PATENT DOCUMENTS

| | | | |
|---|---|---|---|
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,048 | B2 | 12/2009 | Dobbles et al. |
| 7,643,798 | B2 | 1/2010 | Ljung |
| 7,651,596 | B2 | 1/2010 | Petisce et al. |
| 7,651,845 | B2 | 1/2010 | Doyle, III et al. |
| 7,653,425 | B2 | 1/2010 | Hayter et al. |
| 7,654,956 | B2 | 2/2010 | Brister et al. |
| 7,657,297 | B2 | 2/2010 | Simpson et al. |
| 7,659,823 | B1 | 2/2010 | Killian et al. |
| 7,660,615 | B2 | 2/2010 | VanAntwerp et al. |
| 7,666,149 | B2 | 2/2010 | Simons et al. |
| 7,668,596 | B2 | 2/2010 | Von Arx et al. |
| 7,682,338 | B2 | 3/2010 | Griffin |
| 7,697,967 | B2 | 4/2010 | Stafford |
| 7,699,775 | B2 | 4/2010 | Desai et al. |
| 7,699,807 | B2 | 4/2010 | Faust et al. |
| 7,701,052 | B2 | 4/2010 | Borland et al. |
| 7,711,402 | B2 | 5/2010 | Shults et al. |
| 7,713,574 | B2 | 5/2010 | Brister et al. |
| 7,715,893 | B2 | 5/2010 | Kamath et al. |
| 7,727,147 | B1 | 6/2010 | Osorio et al. |
| 7,729,737 | B2 | 6/2010 | Ward |
| 7,731,657 | B2 | 6/2010 | Stafford |
| 7,731,691 | B2 | 6/2010 | Cote et al. |
| 7,736,310 | B2 | 6/2010 | Taub et al. |
| 7,736,344 | B2 | 6/2010 | Moberg et al. |
| 7,741,734 | B2 | 6/2010 | Joannopoulos et al. |
| 7,763,042 | B2 | 7/2010 | Lio et al. |
| 7,766,829 | B2 | 8/2010 | Sloan et al. |
| 7,768,387 | B2 | 8/2010 | Fennell et al. |
| 7,771,352 | B2 | 8/2010 | Shults et al. |
| 7,774,145 | B2 | 8/2010 | Brauker et al. |
| 7,775,444 | B2 | 8/2010 | DeRocco et al. |
| 7,778,680 | B2 | 8/2010 | Goode, Jr. et al. |
| 7,779,332 | B2 | 8/2010 | Karr et al. |
| 7,780,827 | B1 | 8/2010 | Bhullar et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,811,231 | B2 | 10/2010 | Jin et al. |
| 7,813,809 | B2 | 10/2010 | Strother et al. |
| 7,822,454 | B1 | 10/2010 | Alden et al. |
| 7,826,981 | B2 | 11/2010 | Goode, Jr. et al. |
| 7,831,310 | B2 | 11/2010 | Lebel et al. |
| 7,833,151 | B2 | 11/2010 | Khait et al. |
| 7,833,170 | B2 | 11/2010 | Matsumoto et al. |
| 7,837,633 | B2 | 11/2010 | Conway et al. |
| 7,842,046 | B1 | 11/2010 | Nakao |
| 7,850,652 | B2 | 12/2010 | Liniger et al. |
| 7,860,574 | B2 | 12/2010 | Von Arx et al. |
| 7,866,026 | B1 | 1/2011 | Wang et al. |
| 7,867,244 | B2 | 1/2011 | Lathrop et al. |
| 7,873,299 | B2 | 1/2011 | Berner et al. |
| 7,882,611 | B2 | 2/2011 | Shah et al. |
| 7,883,464 | B2 | 2/2011 | Stafford |
| 7,883,473 | B2 | 2/2011 | LeVaughn et al. |
| 7,885,697 | B2 | 2/2011 | Brister et al. |
| 7,889,069 | B2 | 2/2011 | Fifolt et al. |
| 7,896,844 | B2 | 3/2011 | Thalmann et al. |
| 7,899,511 | B2 | 3/2011 | Shults et al. |
| 7,899,545 | B2 | 3/2011 | John |
| 7,905,833 | B2 | 3/2011 | Brister et al. |
| 7,912,655 | B2 | 3/2011 | Power et al. |
| 7,912,674 | B2 | 3/2011 | Killoren Clark et al. |
| 7,914,450 | B2 | 3/2011 | Goode, Jr. et al. |
| 7,914,460 | B2 | 3/2011 | Melker et al. |
| 7,916,013 | B2 | 3/2011 | Stevenson |
| 7,920,906 | B2 | 4/2011 | Goode, Jr. et al. |
| 7,920,907 | B2 | 4/2011 | McGarraugh et al. |
| 7,938,797 | B2 | 5/2011 | Estes |
| 7,941,200 | B2 | 5/2011 | Weinart et al. |
| 7,946,984 | B2 | 5/2011 | Brister et al. |
| 7,946,985 | B2 | 5/2011 | Mastrototaro et al. |
| 7,955,258 | B2 | 6/2011 | Goscha et al. |
| 7,955,297 | B2 | 6/2011 | Radmer et al. |
| 7,970,448 | B2 | 6/2011 | Shults et al. |
| 7,970,449 | B2 | 6/2011 | Ward |
| 7,972,296 | B2 | 7/2011 | Braig et al. |
| 7,974,672 | B2 | 7/2011 | Shults et al. |
| 7,976,467 | B2 | 7/2011 | Young et al. |
| 7,978,063 | B2 | 7/2011 | Baldus et al. |
| 7,985,203 | B2 | 7/2011 | Haueter et al. |
| 7,985,222 | B2 | 7/2011 | Gall et al. |
| 7,996,158 | B2 | 8/2011 | Hayter et al. |
| 7,999,674 | B2 | 8/2011 | Kamen |
| 8,000,918 | B2 | 8/2011 | Fjield et al. |
| 8,005,524 | B2 | 8/2011 | Brauker et al. |
| 8,010,174 | B2 | 8/2011 | Goode, Jr. et al. |
| 8,010,256 | B2 | 8/2011 | Oowada |
| 8,016,774 | B2 | 9/2011 | Freeman et al. |
| 8,028,837 | B2 | 10/2011 | Gerstle et al. |
| 8,029,441 | B2 | 10/2011 | Mazza et al. |
| 8,029,442 | B2 | 10/2011 | Funderburk et al. |
| 8,072,310 | B1 | 12/2011 | Everhart |
| 8,090,445 | B2 | 1/2012 | Ginggen |
| 8,093,991 | B2 | 1/2012 | Stevenson et al. |
| 8,094,009 | B2 | 1/2012 | Allen et al. |
| 8,098,159 | B2 | 1/2012 | Batra et al. |
| 8,098,160 | B2 | 1/2012 | Howarth et al. |
| 8,098,161 | B2 | 1/2012 | Lavedas |
| 8,098,201 | B2 | 1/2012 | Choi et al. |
| 8,098,208 | B2 | 1/2012 | Ficker et al. |
| 8,102,021 | B2 | 1/2012 | Degani |
| 8,102,154 | B2 | 1/2012 | Bishop et al. |
| 8,102,263 | B2 | 1/2012 | Yeo et al. |
| 8,102,789 | B2 | 1/2012 | Rosar et al. |
| 8,103,241 | B2 | 1/2012 | Young et al. |
| 8,103,325 | B2 | 1/2012 | Swedlow et al. |
| 8,103,471 | B2 | 1/2012 | Hayter |
| 8,111,042 | B2 | 2/2012 | Bennett |
| 8,112,240 | B2 | 2/2012 | Fennell |
| 8,115,488 | B2 | 2/2012 | McDowell |
| 8,116,681 | B2 | 2/2012 | Baarman |
| 8,116,683 | B2 | 2/2012 | Baarman |
| 8,117,481 | B2 | 2/2012 | Anselmi et al. |
| 8,120,493 | B2 | 2/2012 | Burr |
| 8,124,452 | B2 | 2/2012 | Sheats |
| 8,130,093 | B2 | 3/2012 | Mazar et al. |
| 8,131,351 | B2 | 3/2012 | Kalgren et al. |
| 8,131,365 | B2 | 3/2012 | Zhang et al. |
| 8,131,565 | B2 | 3/2012 | Docks et al. |
| 8,132,037 | B2 | 3/2012 | Fehr et al. |
| 8,135,352 | B2 | 3/2012 | Langsweirdt et al. |
| 8,136,735 | B2 | 3/2012 | Arai et al. |
| 8,138,925 | B2 | 3/2012 | Downie et al. |
| 8,140,160 | B2 | 3/2012 | Pless et al. |
| 8,140,169 | B2 | 3/2012 | Olson et al. |
| 8,140,299 | B2 | 3/2012 | Siess |
| 8,140,312 | B2 | 3/2012 | Hayter et al. |
| 8,150,321 | B2 | 4/2012 | Winter et al. |
| 8,150,516 | B2 | 4/2012 | Levine et al. |
| 8,160,670 | B2 | 4/2012 | Quyang et al. |
| 8,160,900 | B2 | 4/2012 | Taub et al. |
| 8,172,805 | B2 | 5/2012 | Mogensen et al. |
| 8,175,673 | B2 | 5/2012 | Say et al. |
| 8,179,266 | B2 | 5/2012 | Hermle |
| 8,180,423 | B2 | 5/2012 | Mang et al. |
| 8,192,394 | B2 | 6/2012 | Estes et al. |
| 8,216,138 | B1 | 7/2012 | McGaraugh et al. |
| 8,221,332 | B2 | 7/2012 | Robbins et al. |
| 8,224,410 | B2 | 7/2012 | Hadvary et al. |
| 8,239,166 | B2 | 8/2012 | Hayter et al. |
| 8,255,026 | B1 | 8/2012 | Al-Ali |
| 8,260,558 | B2 | 9/2012 | Hayter et al. |
| 8,262,618 | B2 | 9/2012 | Scheurer |
| 8,282,549 | B2 | 10/2012 | Brauker et al. |
| 8,333,714 | B2 | 12/2012 | Stafford |
| 8,346,335 | B2 | 1/2013 | Harper et al. |

(56) References Cited

U.S. PATENT DOCUMENTS

| | | | |
|---|---|---|---|
| 8,346,337 | B2 | 1/2013 | Heller et al. |
| 8,373,544 | B2 | 2/2013 | Pitt-Plady |
| 8,374,668 | B1 | 2/2013 | Hayter et al. |
| 8,376,945 | B2 | 2/2013 | Hayter et al. |
| 8,377,271 | B2 | 2/2013 | Mao et al. |
| 8,382,671 | B2 | 2/2013 | Anthony et al. |
| 8,398,664 | B2 | 3/2013 | Lamps et al. |
| 8,409,093 | B2 | 4/2013 | Bugler |
| 8,409,145 | B2 | 4/2013 | Raymond et al. |
| 8,439,838 | B2 | 5/2013 | Mogensen et al. |
| 8,444,560 | B2 | 5/2013 | Hayter et al. |
| 8,461,985 | B2 | 6/2013 | Fennell et al. |
| 8,469,986 | B2 | 6/2013 | Schraga |
| 8,512,243 | B2 | 8/2013 | Stafford |
| 8,515,518 | B2 | 8/2013 | Ouyang et al. |
| 8,515,519 | B2 | 8/2013 | Brister et al. |
| 8,538,512 | B1 | 9/2013 | Bibian et al. |
| 8,545,403 | B2 | 10/2013 | Peyser et al. |
| 8,560,038 | B2 | 10/2013 | Hayter et al. |
| 8,562,567 | B2 | 10/2013 | Gundberg |
| 8,571,808 | B2 | 10/2013 | Hayter |
| 8,583,205 | B2 | 11/2013 | Budiman et al. |
| 8,585,591 | B2 | 11/2013 | Sloan et al. |
| 8,597,570 | B2 | 12/2013 | Terashima et al. |
| 8,600,681 | B2 | 12/2013 | Hayter et al. |
| 8,602,991 | B2 | 12/2013 | Stafford |
| 8,612,163 | B2 | 12/2013 | Hayter et al. |
| 8,615,282 | B2 | 12/2013 | Brister et al. |
| 8,617,069 | B2 | 12/2013 | Bernstein et al. |
| 8,617,071 | B2 | 12/2013 | Say et al. |
| 8,622,903 | B2 | 1/2014 | Jin et al. |
| 8,628,498 | B2 | 1/2014 | Safabach et al. |
| 8,641,674 | B2 | 2/2014 | Bobroff et al. |
| 8,652,043 | B2 | 2/2014 | Drucker et al. |
| 8,682,408 | B2 | 3/2014 | Boock et al. |
| 8,682,615 | B2 | 3/2014 | Hayter et al. |
| 8,684,930 | B2 | 4/2014 | Feldman et al. |
| 8,692,655 | B2 | 4/2014 | Zimman et al. |
| 8,710,993 | B2 | 4/2014 | Hayter et al. |
| 8,747,363 | B2 | 6/2014 | Nielsen et al. |
| 8,771,183 | B2 | 7/2014 | Sloan |
| 8,797,163 | B2 | 8/2014 | Finkenzeller |
| 8,808,515 | B2 | 8/2014 | Feldman et al. |
| 8,834,366 | B2 | 9/2014 | Hayter et al. |
| 8,845,536 | B2 | 9/2014 | Brauker et al. |
| 8,870,822 | B2 | 10/2014 | Thalmann et al. |
| 8,880,138 | B2 | 11/2014 | Cho |
| 8,945,056 | B2 | 2/2015 | Lio et al. |
| 8,961,413 | B2 | 2/2015 | Teller et al. |
| 9,007,781 | B2 | 4/2015 | Moein et al. |
| 9,014,774 | B2 | 4/2015 | Mao et al. |
| 9,031,630 | B2 | 5/2015 | Hoss et al. |
| 9,060,719 | B2 | 6/2015 | Hayter et al. |
| 9,060,805 | B2 | 6/2015 | Goodnow et al. |
| 9,066,697 | B2 | 6/2015 | Peyser et al. |
| 9,101,302 | B2 | 8/2015 | Mace et al. |
| 9,186,098 | B2 | 11/2015 | Lee et al. |
| 9,215,992 | B2 | 12/2015 | Donnay et al. |
| 9,241,631 | B2 | 1/2016 | Valdes et al. |
| 9,259,175 | B2 | 2/2016 | Stafford |
| 9,265,453 | B2 | 2/2016 | Curry et al. |
| 9,289,179 | B2 | 3/2016 | Hayter et al. |
| 9,295,786 | B2 | 3/2016 | Gottlieb et al. |
| 9,357,951 | B2 | 6/2016 | Simpson et al. |
| 9,398,872 | B2 | 7/2016 | Hayter et al. |
| 9,402,544 | B2 | 8/2016 | Yee et al. |
| 9,439,586 | B2 | 9/2016 | Bugler |
| 9,451,910 | B2 | 9/2016 | Brister et al. |
| 9,474,479 | B2 | 10/2016 | Pusey et al. |
| 9,480,421 | B2 | 11/2016 | Stafford |
| 9,483,608 | B2 | 11/2016 | Hayter et al. |
| 9,504,471 | B2 | 11/2016 | Vaitekunas et al. |
| 9,558,325 | B2 | 1/2017 | Hayter et al. |
| 9,566,384 | B2 | 2/2017 | Gyrn et al. |
| 9,636,068 | B2 | 5/2017 | Yee et al. |
| 9,668,682 | B2 | 6/2017 | Brister et al. |
| 9,743,876 | B2 | 8/2017 | Gelfand et al. |
| 9,808,574 | B2 | 11/2017 | Yodfat et al. |
| 9,814,414 | B2 | 11/2017 | Brister et al. |
| 9,951,485 | B2 | 4/2018 | Tichell Fortea et al. |
| 10,213,139 | B2 | 2/2019 | Rao et al. |
| 10,292,632 | B2 | 5/2019 | Lee et al. |
| 10,342,489 | B2 | 7/2019 | Stafford |
| 10,820,842 | B2 | 11/2020 | Harper |
| 10,827,954 | B2 | 11/2020 | Hoss et al. |
| 10,874,338 | B2 | 12/2020 | Stafford |
| 10,881,340 | B2 | 1/2021 | Curry et al. |
| 10,881,341 | B1 | 1/2021 | Curry et al. |
| 10,945,647 | B2 | 3/2021 | Mazza et al. |
| 10,945,649 | B2 | 3/2021 | Lee et al. |
| 10,952,653 | B2 | 3/2021 | Harper |
| 10,959,654 | B2 | 3/2021 | Curry et al. |
| 10,966,644 | B2 | 4/2021 | Stafford |
| 10,973,443 | B2 | 4/2021 | Funderburk et al. |
| 10,980,461 | B2 | 4/2021 | Bohm et al. |
| 11,000,213 | B2 | 5/2021 | Kamath et al. |
| 11,000,216 | B2 | 5/2021 | Curry et al. |
| 11,006,870 | B2 | 5/2021 | Yee et al. |
| 11,006,871 | B2 | 5/2021 | Yee et al. |
| 11,013,440 | B2 | 5/2021 | Lee et al. |
| 11,051,724 | B2 | 7/2021 | Pace et al. |
| 11,064,917 | B2 | 7/2021 | Simpson et al. |
| 11,116,430 | B2 | 9/2021 | Funderburk et al. |
| 11,141,084 | B2 | 10/2021 | Funderburk et al. |
| 11,166,656 | B2 | 11/2021 | Yee et al. |
| 11,179,068 | B2 | 11/2021 | Pace et al. |
| 11,197,625 | B1 | 12/2021 | Schleicher et al. |
| 11,202,591 | B2 | 12/2021 | Yee et al. |
| 11,213,229 | B2 | 1/2022 | Yee et al. |
| 11,246,519 | B2 | 2/2022 | Donnay et al. |
| 11,266,335 | B2 | 3/2022 | Donnay et al. |
| 11,298,056 | B2 | 4/2022 | Harper |
| 11,298,058 | B2 | 4/2022 | Stafford |
| 11,510,625 | B2 | 11/2022 | Gray et al. |
| 2001/0016682 | A1 | 8/2001 | Berner et al. |
| 2001/0034479 | A1 | 10/2001 | Ring et al. |
| 2001/0037060 | A1 | 11/2001 | Thompson et al. |
| 2001/0037366 | A1 | 11/2001 | Webb et al. |
| 2001/0039387 | A1 | 11/2001 | Rutynowski et al. |
| 2001/0044608 | A1 | 11/2001 | Odell et al. |
| 2001/0047127 | A1 | 11/2001 | New et al. |
| 2001/0056262 | A1 | 12/2001 | Cabiri et al. |
| 2002/0002344 | A1 | 1/2002 | Douglas et al. |
| 2002/0010390 | A1 | 1/2002 | Guice et al. |
| 2002/0013522 | A1 | 1/2002 | Lav et al. |
| 2002/0013538 | A1 | 1/2002 | Teller |
| 2002/0016534 | A1 | 2/2002 | Trepagnier et al. |
| 2002/0016568 | A1 | 2/2002 | Lebel et al. |
| 2002/0019022 | A1 | 2/2002 | Dunn et al. |
| 2002/0019584 | A1 | 2/2002 | Schulze et al. |
| 2002/0019606 | A1 | 2/2002 | Lebel et al. |
| 2002/0022855 | A1 | 2/2002 | Bobroff et al. |
| 2002/0023852 | A1 | 2/2002 | McIvor et al. |
| 2002/0029058 | A1 | 3/2002 | LeVaughn et al. |
| 2002/0032386 | A1 | 3/2002 | Sackner et al. |
| 2002/0039026 | A1 | 4/2002 | Stroth et al. |
| 2002/0042090 | A1 | 4/2002 | Heller et al. |
| 2002/0045808 | A1 | 4/2002 | Ford et al. |
| 2002/0049482 | A1 | 4/2002 | Fabian et al. |
| 2002/0050250 | A1 | 5/2002 | Peterson et al. |
| 2002/0055711 | A1 | 5/2002 | Lavi et al. |
| 2002/0057993 | A1 | 5/2002 | Maisey et al. |
| 2002/0065454 | A1 | 5/2002 | Lebel et al. |
| 2002/0066764 | A1 | 6/2002 | Perry et al. |
| 2002/0072720 | A1 | 6/2002 | Hague et al. |
| 2002/0072784 | A1 | 6/2002 | Sheppard et al. |
| 2002/0074162 | A1 | 6/2002 | Su et al. |
| 2002/0076966 | A1 | 6/2002 | Carron et al. |
| 2002/0077599 | A1 | 6/2002 | Wojcik |
| 2002/0082487 | A1 | 6/2002 | Kollias et al. |
| 2002/0084196 | A1 | 7/2002 | Liamos et al. |
| 2002/0091796 | A1 | 7/2002 | Higginson et al. |
| 2002/0093969 | A1 | 7/2002 | Lin et al. |
| 2002/0095076 | A1 | 7/2002 | Krausman et al. |

(56) References Cited

U.S. PATENT DOCUMENTS

2002/0103499 A1 8/2002 Perez et al.
2002/0106709 A1 8/2002 Potts et al.
2002/0111832 A1 8/2002 Judge
2002/0117639 A1 8/2002 Paolini et al.
2002/0118528 A1 8/2002 Su et al.
2002/0119711 A1 8/2002 VanAntwerp et al.
2002/0120186 A1 8/2002 Keimel
2002/0124017 A1 9/2002 Mault
2002/0128594 A1 9/2002 Das et al.
2002/0130042 A1 9/2002 Moerman et al.
2002/0133066 A1 9/2002 Miller et al.
2002/0147135 A1 10/2002 Schnell
2002/0150959 A1 10/2002 Lejeune et al.
2002/0151770 A1 10/2002 Noll et al.
2002/0151796 A1 10/2002 Koulik
2002/0151816 A1 10/2002 Rich et al.
2002/0154050 A1 10/2002 Krupp et al.
2002/0161288 A1 10/2002 Shin et al.
2002/0161290 A1 10/2002 Chance
2002/0161338 A1 10/2002 Peterson
2002/0164836 A1 11/2002 Ho
2002/0165462 A1 11/2002 Westbrook et al.
2002/0169369 A1 11/2002 Ward et al.
2002/0169439 A1 11/2002 Flaherty et al.
2002/0169635 A1 11/2002 Shillingburg
2002/0183604 A1 12/2002 Gowda et al.
2002/0185128 A1 12/2002 Theobald
2002/0185130 A1 12/2002 Wright et al.
2002/0188748 A1 12/2002 Blackwell et al.
2002/0197522 A1 12/2002 Lawrence et al.
2002/0198444 A1 12/2002 Ughigaki et al.
2002/0198543 A1 12/2002 Burdulis et al.
2003/0004403 A1 1/2003 Drinan et al.
2003/0020477 A1 1/2003 Goldstein
2003/0023189 A1 1/2003 Kuo
2003/0023317 A1 1/2003 Brauker et al.
2003/0023461 A1 1/2003 Quintanilla et al.
2003/0028089 A1 2/2003 Galley et al.
2003/0028184 A1 2/2003 Lebel et al.
2003/0032077 A1 2/2003 Itoh et al.
2003/0032867 A1 2/2003 Crothall et al.
2003/0032874 A1 2/2003 Rhodes et al.
2003/0042137 A1 3/2003 Mao et al.
2003/0050546 A1 3/2003 Desai et al.
2003/0054428 A1 3/2003 Monfre et al.
2003/0055380 A1 3/2003 Flaherty
2003/0060692 A1 3/2003 Ruchti et al.
2003/0060753 A1 3/2003 Starkweather et al.
2003/0065308 A1 4/2003 Lebel et al.
2003/0069509 A1 4/2003 Matzinger et al.
2003/0069510 A1 4/2003 Semler
2003/0076792 A1 4/2003 Theimer
2003/0077642 A1 4/2003 Fritsch et al.
2003/0078481 A1 4/2003 Mclvor et al.
2003/0078560 A1 4/2003 Miller et al.
2003/0083686 A1 5/2003 Freeman et al.
2003/0088166 A1 5/2003 Say et al.
2003/0097092 A1 5/2003 Flaherty
2003/0100040 A1 5/2003 Bonnecaze et al.
2003/0100821 A1 5/2003 Heller et al.
2003/0109775 A1 6/2003 O'Neil et al.
2003/0114897 A1 6/2003 Von Arx et al.
2003/0114898 A1 6/2003 Von Arx et al.
2003/0119457 A1 6/2003 Standke
2003/0125612 A1 7/2003 Fox et al.
2003/0130616 A1 7/2003 Steil et al.
2003/0134347 A1 7/2003 Heller et al.
2003/0135127 A1 7/2003 Sackner et al.
2003/0135333 A1 7/2003 Aceti et al.
2003/0144579 A1 7/2003 Buss
2003/0144581 A1 7/2003 Conn et al.
2003/0144608 A1 7/2003 Kojima et al.
2003/0153900 A1 8/2003 Aceti et al.
2003/0155656 A1 8/2003 Chiu et al.
2003/0168338 A1 9/2003 Gao et al.
2003/0176933 A1 9/2003 Lebel et al.
2003/0187338 A1 10/2003 Say et al.
2003/0188427 A1 10/2003 Say et al.
2003/0199744 A1 10/2003 Buse et al.
2003/0199790 A1 10/2003 Boecker et al.
2003/0199910 A1 10/2003 Boecker et al.
2003/0204290 A1 10/2003 Sadler et al.
2003/0208113 A1 11/2003 Mault et al.
2003/0208114 A1 11/2003 Ackerman
2003/0212317 A1 11/2003 Kovatchev et al.
2003/0212379 A1 11/2003 Bylund et al.
2003/0212579 A1 11/2003 Brown et al.
2003/0216621 A1 11/2003 Alpert et al.
2003/0216630 A1 11/2003 Jersey-Willuhn et al.
2003/0217966 A1 11/2003 Tapsak et al.
2003/0225361 A1 12/2003 Sabra
2003/0225373 A1 12/2003 Bobroff et al.
2003/0236489 A1 12/2003 Jacobson et al.
2004/0002682 A1 1/2004 Kovelman et al.
2004/0010207 A1 1/2004 Flaherty et al.
2004/0011671 A1 1/2004 Shults et al.
2004/0015131 A1 1/2004 Flaherty et al.
2004/0017300 A1 1/2004 Kotzin et al.
2004/0030226 A1 2/2004 Quy
2004/0030531 A1 2/2004 Miller et al.
2004/0030581 A1 2/2004 Levin et al.
2004/0034289 A1 2/2004 Teller et al.
2004/0039255 A1 2/2004 Simonsen et al.
2004/0039298 A1 2/2004 Abreu
2004/0040840 A1 3/2004 Mao et al.
2004/0045879 A1 3/2004 Shults et al.
2004/0054263 A1 3/2004 Moerman et al.
2004/0060818 A1 4/2004 Feldman et al.
2004/0061232 A1 4/2004 Shah et al.
2004/0063435 A1 4/2004 Sakamoto et al.
2004/0064068 A1 4/2004 DeNuzzio et al.
2004/0064133 A1 4/2004 Miller et al.
2004/0073266 A1 4/2004 Haefner et al.
2004/0078215 A1 4/2004 Dahlin et al.
2004/0096959 A1 5/2004 Steine et al.
2004/0100376 A1 5/2004 Lye et al.
2004/0105411 A1 6/2004 Boatwright et al.
2004/0106858 A1 6/2004 Say et al.
2004/0106859 A1 6/2004 Say et al.
2004/0106860 A1 6/2004 Say et al.
2004/0111017 A1 6/2004 Say et al.
2004/0116847 A1 6/2004 Wall
2004/0116865 A1 6/2004 Bengtsson
2004/0116866 A1 6/2004 Gorman et al.
2004/0117204 A1 6/2004 Mazar et al.
2004/0119169 A1 6/2004 Hanawa
2004/0122353 A1 6/2004 Shahmirian et al.
2004/0122489 A1 6/2004 Mazar et al.
2004/0133089 A1 7/2004 Kilcoyne et al.
2004/0133164 A1 7/2004 Funderburk et al.
2004/0133390 A1 7/2004 Osorio et al.
2004/0135571 A1 7/2004 Uutela et al.
2004/0135684 A1 7/2004 Steinthal et al.
2004/0138544 A1 7/2004 Ward et al.
2004/0138588 A1 7/2004 Saikley et al.
2004/0138688 A1 7/2004 Giraud
2004/0140211 A1 7/2004 Broy et al.
2004/0142403 A1 7/2004 Hetzel et al.
2004/0146909 A1 7/2004 Duong et al.
2004/0147872 A1 7/2004 Thompson
2004/0147996 A1 7/2004 Miazga et al.
2004/0152366 A1 8/2004 Schultz et al.
2004/0152622 A1 8/2004 Keith et al.
2004/0158207 A1 8/2004 Hunn et al.
2004/0162521 A1 8/2004 Bengtsson et al.
2004/0162678 A1 8/2004 Hetzel et al.
2004/0167801 A1 8/2004 Say et al.
2004/0171910 A1 9/2004 Moore-Steele
2004/0171921 A1 9/2004 Say et al.
2004/0176672 A1 9/2004 Silver et al.
2004/0186362 A1 9/2004 Brauker et al.
2004/0186365 A1 9/2004 Jin et al.
2004/0193020 A1 9/2004 Chiba et al.
2004/0193025 A1 9/2004 Steil et al.

(56) References Cited

U.S. PATENT DOCUMENTS

| | | | |
|---|---|---|---|
| 2004/0193090 | A1 | 9/2004 | Lebel et al. |
| 2004/0197846 | A1 | 10/2004 | Hockersmith et al. |
| 2004/0199056 | A1 | 10/2004 | Husemann et al. |
| 2004/0199059 | A1 | 10/2004 | Brauker et al. |
| 2004/0204673 | A1 | 10/2004 | Flaherty |
| 2004/0204687 | A1 | 10/2004 | Mogensen et al. |
| 2004/0204744 | A1 | 10/2004 | Penner et al. |
| 2004/0204868 | A1 | 10/2004 | Maynard et al. |
| 2004/0206625 | A1 | 10/2004 | Bhullar et al. |
| 2004/0206916 | A1 | 10/2004 | Colvin, Jr. et al. |
| 2004/0210122 | A1 | 10/2004 | Sleburg |
| 2004/0221057 | A1 | 11/2004 | Darcey et al. |
| 2004/0223876 | A1 | 11/2004 | Kirollos et al. |
| 2004/0223985 | A1 | 11/2004 | Dunfield et al. |
| 2004/0225199 | A1 | 11/2004 | Evanyk et al. |
| 2004/0225262 | A1 | 11/2004 | Fathallah et al. |
| 2004/0225338 | A1 | 11/2004 | Lebel et al. |
| 2004/0236200 | A1 | 11/2004 | Say et al. |
| 2004/0236251 | A1 | 11/2004 | Roe et al. |
| 2004/0240426 | A1 | 12/2004 | Wu et al. |
| 2004/0249253 | A1 | 12/2004 | Racchini et al. |
| 2004/0249999 | A1 | 12/2004 | Connolly et al. |
| 2004/0254433 | A1 | 12/2004 | Bandis et al. |
| 2004/0254434 | A1 | 12/2004 | Goodnow et al. |
| 2004/0258564 | A1 | 12/2004 | Charlton |
| 2004/0260224 | A1 | 12/2004 | Binder et al. |
| 2004/0267300 | A1 | 12/2004 | Mace |
| 2005/0001024 | A1 | 1/2005 | Kusaka et al. |
| 2005/0003470 | A1 | 1/2005 | Nelson et al. |
| 2005/0004439 | A1 | 1/2005 | Shin et al. |
| 2005/0004494 | A1 | 1/2005 | Perez et al. |
| 2005/0006122 | A1 | 1/2005 | Burnette |
| 2005/0010269 | A1 | 1/2005 | Lebel et al. |
| 2005/0017864 | A1 | 1/2005 | Tsoukalis |
| 2005/0027177 | A1 | 2/2005 | Shi et al. |
| 2005/0027180 | A1 | 2/2005 | Goode et al. |
| 2005/0027181 | A1 | 2/2005 | Goode et al. |
| 2005/0027462 | A1 | 2/2005 | Goode et al. |
| 2005/0027463 | A1 | 2/2005 | Goode et al. |
| 2005/0031689 | A1 | 2/2005 | Shults et al. |
| 2005/0033132 | A1 | 2/2005 | Shults et al. |
| 2005/0038332 | A1 | 2/2005 | Saidara et al. |
| 2005/0038465 | A1 | 2/2005 | Shraga |
| 2005/0038680 | A1 | 2/2005 | McMahon |
| 2005/0043598 | A1 | 2/2005 | Goode et al. |
| 2005/0049179 | A1 | 3/2005 | Davidson et al. |
| 2005/0051427 | A1 | 3/2005 | Brauker et al. |
| 2005/0051440 | A1 | 3/2005 | Simpson et al. |
| 2005/0056552 | A1 | 3/2005 | Simpson et al. |
| 2005/0065464 | A1 | 3/2005 | Talbot et al. |
| 2005/0070774 | A1 | 3/2005 | Addison et al. |
| 2005/0070819 | A1 | 3/2005 | Poux et al. |
| 2005/0085872 | A1 | 4/2005 | Yanagihara et al. |
| 2005/0090607 | A1 | 4/2005 | Tapsak et al. |
| 2005/0090850 | A1 | 4/2005 | Thoes et al. |
| 2005/0096511 | A1 | 5/2005 | Fox et al. |
| 2005/0096512 | A1 | 5/2005 | Fox et al. |
| 2005/0096516 | A1 | 5/2005 | Soykan et al. |
| 2005/0096520 | A1 | 5/2005 | Maekawa et al. |
| 2005/0096587 | A1 | 5/2005 | Santini et al. |
| 2005/0101912 | A1 | 5/2005 | Faust et al. |
| 2005/0101932 | A1 | 5/2005 | Cote et al. |
| 2005/0103624 | A1 | 5/2005 | Bhullar et al. |
| 2005/0104457 | A1 | 5/2005 | Jordan et al. |
| 2005/0106713 | A1 | 5/2005 | Phan et al. |
| 2005/0112169 | A1 | 5/2005 | Brauker et al. |
| 2005/0112544 | A1 | 5/2005 | Xu et al. |
| 2005/0113648 | A1 | 5/2005 | Yang et al. |
| 2005/0113653 | A1 | 5/2005 | Fox et al. |
| 2005/0113886 | A1 | 5/2005 | Fischell et al. |
| 2005/0114068 | A1 | 5/2005 | Chey et al. |
| 2005/0115832 | A1 | 6/2005 | Simpson et al. |
| 2005/0116683 | A1 | 6/2005 | Cheng et al. |
| 2005/0121322 | A1 | 6/2005 | Say et al. |
| 2005/0131346 | A1 | 6/2005 | Douglas |
| 2005/0131347 | A1 | 6/2005 | Marano-Ford et al. |
| 2005/0134731 | A1 | 6/2005 | Lee et al. |
| 2005/0137488 | A1 | 6/2005 | Henry et al. |
| 2005/0137530 | A1 | 6/2005 | Campbell et al. |
| 2005/0143635 | A1 | 6/2005 | Kamath et al. |
| 2005/0149066 | A1 | 7/2005 | Stafford |
| 2005/0151976 | A1 | 7/2005 | Toma |
| 2005/0154271 | A1 | 7/2005 | Rasdal et al. |
| 2005/0154410 | A1 | 7/2005 | Conway et al. |
| 2005/0159678 | A1 | 7/2005 | Taniike et al. |
| 2005/0161346 | A1 | 7/2005 | Simpson et al. |
| 2005/0165404 | A1 | 7/2005 | Miller |
| 2005/0171442 | A1 | 8/2005 | Shirasaki et al. |
| 2005/0173245 | A1 | 8/2005 | Feldman et al. |
| 2005/0176136 | A1 | 8/2005 | Burd et al. |
| 2005/0177398 | A1 | 8/2005 | Watanabe et al. |
| 2005/0181010 | A1 | 8/2005 | Hunter et al. |
| 2005/0182306 | A1 | 8/2005 | Sloan |
| 2005/0182358 | A1 | 8/2005 | Heit et al. |
| 2005/0187442 | A1 | 8/2005 | Cho et al. |
| 2005/0187720 | A1 | 8/2005 | Goode, Jr. et al. |
| 2005/0192494 | A1 | 9/2005 | Ginsberg |
| 2005/0192557 | A1 | 9/2005 | Brauker et al. |
| 2005/0195930 | A1 | 9/2005 | Spital et al. |
| 2005/0197554 | A1 | 9/2005 | Polcha |
| 2005/0197793 | A1 | 9/2005 | Baker, Jr. |
| 2005/0199494 | A1 | 9/2005 | Say et al. |
| 2005/0203360 | A1 | 9/2005 | Brauker et al. |
| 2005/0204134 | A1 | 9/2005 | Von Arx et al. |
| 2005/0214892 | A1 | 9/2005 | Kovatchev et al. |
| 2005/0215871 | A1 | 9/2005 | Feldman et al. |
| 2005/0221504 | A1 | 10/2005 | Petruno et al. |
| 2005/0222518 | A1 | 10/2005 | Dib |
| 2005/0222599 | A1 | 10/2005 | Czemecki et al. |
| 2005/0236277 | A9 | 10/2005 | Imran et al. |
| 2005/0236361 | A1 | 10/2005 | Ufer et al. |
| 2005/0239154 | A1 | 10/2005 | Feldman et al. |
| 2005/0239156 | A1 | 10/2005 | Drucker et al. |
| 2005/0241957 | A1 | 11/2005 | Mao et al. |
| 2005/0245795 | A1 | 11/2005 | Goode, Jr. et al. |
| 2005/0245799 | A1 | 11/2005 | Brauker et al. |
| 2005/0245839 | A1 | 11/2005 | Stivoric et al. |
| 2005/0245844 | A1 | 11/2005 | Mace et al. |
| 2005/0245904 | A1 | 11/2005 | Estes et al. |
| 2005/0247319 | A1 | 11/2005 | Berger |
| 2005/0251033 | A1 | 11/2005 | Scarantino et al. |
| 2005/0261563 | A1 | 11/2005 | Zhou et al. |
| 2005/0267325 | A1 | 12/2005 | Bouchier et al. |
| 2005/0267327 | A1 | 12/2005 | Lizuka et al. |
| 2005/0269214 | A1 | 12/2005 | Lee |
| 2005/0277164 | A1 | 12/2005 | Drucker et al. |
| 2005/0277912 | A1 | 12/2005 | John |
| 2005/0281234 | A1 | 12/2005 | Kawamura et al. |
| 2005/0283114 | A1 | 12/2005 | Bresina et al. |
| 2005/0283208 | A1 | 12/2005 | Von Arx et al. |
| 2005/0283209 | A1 | 12/2005 | Katoozi et al. |
| 2005/0284758 | A1 | 12/2005 | Funke et al. |
| 2005/0287620 | A1 | 12/2005 | Heller et al. |
| 2006/0001538 | A1 | 1/2006 | Kraft et al. |
| 2006/0001551 | A1 | 1/2006 | Kraft et al. |
| 2006/0004270 | A1 | 1/2006 | Bedard et al. |
| 2006/0004272 | A1 | 1/2006 | Shah et al. |
| 2006/0004303 | A1 | 1/2006 | Weidenhaupt et al. |
| 2006/0006141 | A1 | 1/2006 | Ufer et al. |
| 2006/0009727 | A1 | 1/2006 | O'Mahony et al. |
| 2006/0010098 | A1 | 1/2006 | Goodnow et al. |
| 2006/0012464 | A1 | 1/2006 | Nitzan et al. |
| 2006/0015020 | A1 | 1/2006 | Neale et al. |
| 2006/0015024 | A1 | 1/2006 | Brister et al. |
| 2006/0016700 | A1 | 1/2006 | Brister et al. |
| 2006/0019327 | A1 | 1/2006 | Brister et al. |
| 2006/0020186 | A1 | 1/2006 | Brister et al. |
| 2006/0020187 | A1 | 1/2006 | Brister et al. |
| 2006/0020188 | A1 | 1/2006 | Kamath et al. |
| 2006/0020189 | A1 | 1/2006 | Brister et al. |
| 2006/0020190 | A1 | 1/2006 | Kamath et al. |
| 2006/0020191 | A1 | 1/2006 | Brister et al. |
| 2006/0020192 | A1 | 1/2006 | Brister et al. |
| 2006/0020300 | A1 | 1/2006 | Nghiem et al. |

(56) References Cited

U.S. PATENT DOCUMENTS

2006/0025662 A1 2/2006 Buse et al.
2006/0025663 A1 2/2006 Talbot et al.
2006/0029177 A1 2/2006 Cranford, Jr. et al.
2006/0030789 A1 2/2006 Allen
2006/0031094 A1 2/2006 Cohen et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0040402 A1 2/2006 Brauker et al.
2006/0040793 A1 2/2006 Martens et al.
2006/0041276 A1 2/2006 Chan
2006/0042080 A1 3/2006 Say et al.
2006/0047220 A1 3/2006 Sakata et al.
2006/0049359 A1 3/2006 Busta et al.
2006/0058588 A1 3/2006 Zdeblick
2006/0064035 A1 3/2006 Wang et al.
2006/0068208 A1 3/2006 Tapsak et al.
2006/0079740 A1 4/2006 Silver et al.
2006/0081469 A1 4/2006 Lee
2006/0086624 A1 4/2006 Tapsak et al.
2006/0091006 A1 5/2006 Wang et al.
2006/0094944 A1 5/2006 Chuang
2006/0095014 A1 5/2006 Ethelfeld
2006/0116607 A1 6/2006 Nakamura et al.
2006/0129173 A1 6/2006 Wilkinson
2006/0129733 A1 6/2006 Solbelman
2006/0135908 A1 6/2006 Liniger et al.
2006/0142651 A1 6/2006 Brister et al.
2006/0154642 A1 7/2006 Scannell
2006/0155180 A1 7/2006 Brister et al.
2006/0155210 A1 7/2006 Beckman et al.
2006/0155317 A1 7/2006 List
2006/0161194 A1 7/2006 Freeman et al.
2006/0161664 A1 7/2006 Motoyama
2006/0166629 A1 7/2006 Reggiardo
2006/0173260 A1 8/2006 Gaoni et al.
2006/0173406 A1 8/2006 Hayes et al.
2006/0173444 A1 8/2006 Choy et al.
2006/0181695 A1 8/2006 Sage, Jr.
2006/0183984 A1 8/2006 Dobbles et al.
2006/0183985 A1 8/2006 Brister et al.
2006/0189851 A1 8/2006 Tvig et al.
2006/0189863 A1 8/2006 Peyser et al.
2006/0189939 A1 8/2006 Gonnelli et al.
2006/0193375 A1 8/2006 Lee et al.
2006/0195029 A1 8/2006 Shults et al.
2006/0195133 A1 8/2006 Freeman et al.
2006/0200020 A1 9/2006 Brister et al.
2006/0200022 A1 9/2006 Brauker et al.
2006/0200181 A1 9/2006 Fukuzawa et al.
2006/0200970 A1 9/2006 Brister et al.
2006/0200981 A1 9/2006 Bhullar et al.
2006/0200982 A1 9/2006 Bhullar et al.
2006/0202805 A1 9/2006 Schulman et al.
2006/0202859 A1 9/2006 Mastrototaro et al.
2006/0211921 A1 9/2006 Brauker et al.
2006/0220839 A1 10/2006 Fifolt et al.
2006/0222566 A1 10/2006 Brauker et al.
2006/0222866 A1 10/2006 Nakamura et al.
2006/0224108 A1 10/2006 Brauker et al.
2006/0224109 A1 10/2006 Steil et al.
2006/0224141 A1 10/2006 Rush et al.
2006/0224171 A1 10/2006 Sakata et al.
2006/0226985 A1 10/2006 Goodnow et al.
2006/0229512 A1 10/2006 Petisce et al.
2006/0233839 A1 10/2006 Jacquet
2006/0247508 A1 11/2006 Fennell
2006/0247710 A1 11/2006 Goetz et al.
2006/0247895 A1 11/2006 Liamos et al.
2006/0248398 A1 11/2006 Neel et al.
2006/0253085 A1 11/2006 Geismar et al.
2006/0253086 A1 11/2006 Moberg et al.
2006/0258929 A1 11/2006 Goode, Jr. et al.
2006/0258939 A1 11/2006 Pesach et al.
2006/0258959 A1 11/2006 Sode
2006/0264785 A1 11/2006 Dring et al.
2006/0264888 A1 11/2006 Moberg et al.
2006/0270922 A1 11/2006 Brauker et al.
2006/0270923 A1 11/2006 Brauker et al.
2006/0271013 A1 11/2006 Triplett et al.
2006/0272652 A1 12/2006 Stocker et al.
2006/0273759 A1 12/2006 Reggiardo
2006/0276714 A1 12/2006 Holt et al.
2006/0276724 A1 12/2006 Freeman et al.
2006/0276771 A1 12/2006 Galley et al.
2006/0281985 A1 12/2006 Ward et al.
2006/0282042 A1 12/2006 Walters et al.
2006/0287591 A1 12/2006 Ocvirk et al.
2006/0287691 A1 12/2006 Drew
2006/0290496 A1 12/2006 Peeters et al.
2006/0293607 A1 12/2006 Alt et al.
2007/0007133 A1 1/2007 Mang et al.
2007/0010950 A1 1/2007 Abensour et al.
2007/0016129 A1 1/2007 Liniger et al.
2007/0016381 A1 1/2007 Kamath et al.
2007/0017983 A1 1/2007 Frank et al.
2007/0027381 A1 2/2007 Stafford
2007/0027384 A1 2/2007 Brister et al.
2007/0027385 A1 2/2007 Brister et al.
2007/0027507 A1 2/2007 Burdett et al.
2007/0030154 A1 2/2007 Aiki et al.
2007/0032706 A1 2/2007 Kamath et al.
2007/0032717 A1 2/2007 Brister et al.
2007/0032718 A1 2/2007 Shults et al.
2007/0033074 A1 2/2007 Nitzan et al.
2007/0038044 A1 2/2007 Dobbles et al.
2007/0045902 A1 3/2007 Brauker et al.
2007/0049865 A1 3/2007 Radmer et al.
2007/0055799 A1 3/2007 Koehler et al.
2007/0056858 A1 3/2007 Chen et al.
2007/0059196 A1 3/2007 Brister et al.
2007/0060801 A1 3/2007 Neinast
2007/0060814 A1* 3/2007 Stafford ............... A61B 5/0002
600/365
2007/0060869 A1 3/2007 Tolle et al.
2007/0066873 A1 3/2007 Kamath et al.
2007/0068807 A1 3/2007 Feldman et al.
2007/0071681 A1 3/2007 Gadkar et al.
2007/0073129 A1 3/2007 Shah et al.
2007/0078320 A1 4/2007 Stafford
2007/0078321 A1 4/2007 Mazza et al.
2007/0078322 A1 4/2007 Stafford
2007/0078323 A1 4/2007 Reggiardo et al.
2007/0088377 A1 4/2007 Levaughn et al.
2007/0090511 A1 4/2007 Borland et al.
2007/0093704 A1 4/2007 Brister et al.
2007/0093754 A1 4/2007 Mogensen et al.
2007/0093786 A1 4/2007 Goldsmith et al.
2007/0095661 A1 5/2007 Wang et al.
2007/0100218 A1 5/2007 Sweitzer et al.
2007/0100222 A1 5/2007 Mastrototaro et al.
2007/0106133 A1 5/2007 Satchwell et al.
2007/0106135 A1 5/2007 Sloan et al.
2007/0108048 A1 5/2007 Wang et al.
2007/0110124 A1 5/2007 Shiraki et al.
2007/0111196 A1 5/2007 Alarcon et al.
2007/0123819 A1 5/2007 Mernoe et al.
2007/0124002 A1 5/2007 Estes et al.
2007/0129621 A1 6/2007 Kellogg et al.
2007/0135696 A1 6/2007 Ward
2007/0135774 A1 6/2007 Turner et al.
2007/0149873 A1 6/2007 Say et al.
2007/0149875 A1 6/2007 Ouyang et al.
2007/0153705 A1 7/2007 Rosar et al.
2007/0156033 A1 7/2007 Causey, III et al.
2007/0156094 A1 7/2007 Safabash et al.
2007/0163880 A1 7/2007 Woo et al.
2007/0168224 A1 7/2007 Letzt et al.
2007/0173706 A1 7/2007 Neinast et al.
2007/0173709 A1 7/2007 Petisce et al.

(56) References Cited

U.S. PATENT DOCUMENTS

2007/0173710 A1 7/2007 Petisce et al.
2007/0173741 A1 7/2007 Deshmukh et al.
2007/0173761 A1 7/2007 Kanderian, Jr. et al.
2007/0179349 A1 8/2007 Hoyme et al.
2007/0179352 A1 8/2007 Randlov et al.
2007/0179406 A1 8/2007 DeNuzzio et al.
2007/0191701 A1 8/2007 Feldman et al.
2007/0191702 A1 8/2007 Yodfat et al.
2007/0197889 A1 8/2007 Brister et al.
2007/0199818 A1 8/2007 Petyt et al.
2007/0202562 A1 8/2007 Curry et al.
2007/0203407 A1 8/2007 Hoss et al.
2007/0203539 A1 8/2007 Stone et al.
2007/0203966 A1 8/2007 Brauker et al.
2007/0208244 A1 9/2007 Brauker et al.
2007/0208245 A1 9/2007 Brauker et al.
2007/0208246 A1 9/2007 Brauker et al.
2007/0213611 A1 9/2007 Simpson et al.
2007/0219480 A1 9/2007 Kamen et al.
2007/0219496 A1 9/2007 Kamen et al.
2007/0222609 A1 9/2007 Duron et al.
2007/0227911 A1 10/2007 Wang et al.
2007/0228071 A1 10/2007 Kamen et al.
2007/0231846 A1 10/2007 Cosentino et al.
2007/0232877 A1 10/2007 He
2007/0232878 A1 10/2007 Kovatchev et al.
2007/0232879 A1 10/2007 Brister et al.
2007/0232880 A1 10/2007 Siddiqui et al.
2007/0233013 A1 10/2007 Schoenberg et al.
2007/0235331 A1 10/2007 Simpson et al.
2007/0244368 A1 10/2007 Bayloff et al.
2007/0244379 A1 10/2007 Boock et al.
2007/0244383 A1 10/2007 Talbot et al.
2007/0244398 A1 10/2007 Lo et al.
2007/0249922 A1 10/2007 Peyser et al.
2007/0253021 A1 11/2007 Mehta et al.
2007/0255116 A1 11/2007 Mehta et al.
2007/0255125 A1 11/2007 Moberg et al.
2007/0255302 A1 11/2007 Koeppel et al.
2007/0255321 A1 11/2007 Gerber et al.
2007/0255348 A1 11/2007 Holtzclaw
2007/0255531 A1 11/2007 Drew
2007/0258395 A1 11/2007 Jollota et al.
2007/0270672 A1 11/2007 Hayter
2007/0282299 A1 12/2007 Hellwig
2007/0285238 A1 12/2007 Batra
2008/0004512 A1 1/2008 Funderbunk et al.
2008/0004515 A1 1/2008 Jennewine et al.
2008/0004573 A1 1/2008 Kaufmann et al.
2008/0004601 A1 1/2008 Jennewine et al.
2008/0004904 A1 1/2008 Tran
2008/0009304 A1 1/2008 Fry
2008/0009692 A1 1/2008 Stafford
2008/0009805 A1 1/2008 Ethelfeld
2008/0017522 A1 1/2008 Heller et al.
2008/0018433 A1 1/2008 Pitt-Pladdy
2008/0021543 A1 1/2008 Shrivastava
2008/0021666 A1 1/2008 Goode, Jr. et al.
2008/0027296 A1 1/2008 Hadvary et al.
2008/0027474 A1 1/2008 Curry et al.
2008/0029391 A1 2/2008 Mao et al.
2008/0030369 A1 2/2008 Mann et al.
2008/0031941 A1 2/2008 Pettersson
2008/0033254 A1 2/2008 Kamath et al.
2008/0033268 A1 2/2008 Stafford
2008/0033273 A1 2/2008 Zhou et al.
2008/0033318 A1 2/2008 Mace et al.
2008/0039702 A1 2/2008 Hayter et al.
2008/0045824 A1 2/2008 Tapsak et al.
2008/0046038 A1 2/2008 Hill et al.
2008/0055070 A1 3/2008 Bange et al.
2008/0057484 A1 3/2008 Miyata et al.
2008/0058625 A1 3/2008 McGarraugh et al.
2008/0058626 A1 3/2008 Miyata et al.
2008/0058678 A1 3/2008 Miyata et al.
2008/0058773 A1 3/2008 John
2008/0058830 A1 3/2008 Cole et al.
2008/0059227 A1 3/2008 Clapp
2008/0060955 A1 3/2008 Goodnow
2008/0061961 A1 3/2008 John
2008/0062055 A1 3/2008 Cunningham et al.
2008/0064437 A1 3/2008 Chambers et al.
2008/0064937 A1 3/2008 McGarraugh et al.
2008/0064941 A1 3/2008 Funderbunk et al.
2008/0064943 A1 3/2008 Talbot et al.
2008/0064944 A1 3/2008 VanAntwerp et al.
2008/0065646 A1 3/2008 Zhang et al.
2008/0066305 A1 3/2008 Wang et al.
2008/0067627 A1 3/2008 Boeck et al.
2008/0071156 A1 3/2008 Brister et al.
2008/0071157 A1 3/2008 McGarraugh et al.
2008/0071158 A1 3/2008 McGarraugh et al.
2008/0071328 A1 3/2008 Haubrich et al.
2008/0071580 A1 3/2008 Marcus
2008/0081977 A1 4/2008 Hayter et al.
2008/0083617 A1 4/2008 Simpson et al.
2008/0086042 A1 4/2008 Brister et al.
2008/0086044 A1 4/2008 Brister et al.
2008/0086273 A1 4/2008 Shults et al.
2008/0092638 A1 4/2008 Brenneman et al.
2008/0092911 A1 4/2008 Schulman et al.
2008/0097246 A1 4/2008 Stafford
2008/0097289 A1 4/2008 Steil et al.
2008/0097908 A1 4/2008 Dicks et al.
2008/0099332 A1 5/2008 Scott et al.
2008/0102441 A1 5/2008 Chen et al.
2008/0108942 A1 5/2008 Brister et al.
2008/0112848 A1 5/2008 Huffstodt et al.
2008/0114228 A1 5/2008 McCluskey et al.
2008/0114280 A1 5/2008 Stafford
2008/0119705 A1 5/2008 Patel et al.
2008/0119707 A1 5/2008 Stafford
2008/0119710 A1 5/2008 Reggiardo et al.
2008/0125636 A1 5/2008 Ward et al.
2008/0127052 A1 5/2008 Rostoker
2008/0129486 A1 6/2008 Jeckelmann et al.
2008/0133059 A1 6/2008 Trippel et al.
2008/0133702 A1 6/2008 Sharma et al.
2008/0139910 A1 6/2008 Mastrototaro et al.
2008/0146904 A1 6/2008 Hunn
2008/0148873 A1 6/2008 Wang
2008/0154205 A1 6/2008 Wojcik
2008/0154286 A1 6/2008 Abbott et al.
2008/0154513 A1 6/2008 Kovatchev et al.
2008/0161664 A1 7/2008 Mastrototaro et al.
2008/0161666 A1 7/2008 Feldman et al.
2008/0167543 A1 7/2008 Say et al.
2008/0167572 A1 7/2008 Stivoric et al.
2008/0167578 A1 7/2008 Bryer et al.
2008/0172205 A1 7/2008 Breton et al.
2008/0177149 A1 7/2008 Weinart et al.
2008/0177165 A1 7/2008 Blomquist et al.
2008/0179187 A1 7/2008 Ouyang
2008/0182537 A1 7/2008 Manku et al.
2008/0183060 A1 7/2008 Steil et al.
2008/0183061 A1 7/2008 Goode, Jr. et al.
2008/0183399 A1 7/2008 Goode, Jr. et al.
2008/0188731 A1 8/2008 Brister et al.
2008/0188796 A1 8/2008 Steil et al.
2008/0189051 A1 8/2008 Goode, Jr. et al.
2008/0194926 A1 8/2008 Goh et al.
2008/0194934 A1 8/2008 Ray et al.
2008/0194935 A1 8/2008 Brister et al.
2008/0194936 A1 8/2008 Goode, Jr. et al.
2008/0194937 A1 8/2008 Goode, Jr. et al.
2008/0194938 A1 8/2008 Brister et al.
2008/0195049 A1 8/2008 Thalmann et al.
2008/0195232 A1 8/2008 Carr-Brendel et al.
2008/0195967 A1 8/2008 Goode, Jr. et al.
2008/0197024 A1 8/2008 Simpson et al.
2008/0200788 A1 8/2008 Brister et al.
2008/0200789 A1 8/2008 Brister et al.
2008/0200791 A1 8/2008 Simpson et al.
2008/0200897 A1 8/2008 Hoss et al.

(56) References Cited

U.S. PATENT DOCUMENTS

| | | | |
|---|---|---|---|
| 2008/0201325 | A1 | 8/2008 | Doniger et al. |
| 2008/0208025 | A1 | 8/2008 | Shults et al. |
| 2008/0208026 | A1 | 8/2008 | Noujaim et al. |
| 2008/0208113 | A1 | 8/2008 | Daminao et al. |
| 2008/0214481 | A1 | 9/2008 | Challoner et al. |
| 2008/0214900 | A1 | 9/2008 | Fennell et al. |
| 2008/0214910 | A1 | 9/2008 | Buck |
| 2008/0214915 | A1 | 9/2008 | Brister et al. |
| 2008/0214918 | A1 | 9/2008 | Brister et al. |
| 2008/0215035 | A1 | 9/2008 | Yodfat et al. |
| 2008/0228051 | A1 | 9/2008 | Shults et al. |
| 2008/0228054 | A1 | 9/2008 | Shults et al. |
| 2008/0234561 | A1 | 9/2008 | Roesicke et al. |
| 2008/0234992 | A1 | 9/2008 | Ray et al. |
| 2008/0235469 | A1 | 9/2008 | Drew |
| 2008/0242961 | A1 | 10/2008 | Brister et al. |
| 2008/0242962 | A1 | 10/2008 | Roesicke et al. |
| 2008/0242963 | A1 | 10/2008 | Essenpreis et al. |
| 2008/0243051 | A1 | 10/2008 | DeStefano |
| 2008/0252459 | A1 | 10/2008 | Butler et al. |
| 2008/0254544 | A1 | 10/2008 | Modzelewski et al. |
| 2008/0255434 | A1 | 10/2008 | Hayter et al. |
| 2008/0255437 | A1 | 10/2008 | Hayter |
| 2008/0255438 | A1 | 10/2008 | Saidara et al. |
| 2008/0255440 | A1 | 10/2008 | Eilerson et al. |
| 2008/0255808 | A1 | 10/2008 | Hayter |
| 2008/0256048 | A1 | 10/2008 | Hayter |
| 2008/0262300 | A1 | 10/2008 | Reynolds et al. |
| 2008/0262469 | A1 | 10/2008 | Brister et al. |
| 2008/0267823 | A1 | 10/2008 | Wang et al. |
| 2008/0269584 | A1 | 10/2008 | Shekalim |
| 2008/0269673 | A1 | 10/2008 | Butoi et al. |
| 2008/0269683 | A1 | 10/2008 | Bikovsky |
| 2008/0269687 | A1 | 10/2008 | Chong et al. |
| 2008/0269714 | A1 | 10/2008 | Mastrototaro et al. |
| 2008/0275313 | A1 | 11/2008 | Brister et al. |
| 2008/0275327 | A1 | 11/2008 | Faarbaek et al. |
| 2008/0278333 | A1 | 11/2008 | Fennell et al. |
| 2008/0281178 | A1 | 11/2008 | Chuang et al. |
| 2008/0281179 | A1 | 11/2008 | Fennell et al. |
| 2008/0283396 | A1 | 11/2008 | Wang et al. |
| 2008/0287755 | A1 | 11/2008 | Sass et al. |
| 2008/0287761 | A1 | 11/2008 | Hayter |
| 2008/0287762 | A1 | 11/2008 | Hayter |
| 2008/0287763 | A1 | 11/2008 | Hayter |
| 2008/0287764 | A1 | 11/2008 | Rasdal et al. |
| 2008/0287765 | A1 | 11/2008 | Rasdal et al. |
| 2008/0287766 | A1 | 11/2008 | Rasdal et al. |
| 2008/0288180 | A1 | 11/2008 | Hayter |
| 2008/0288204 | A1 | 11/2008 | Hayter et al. |
| 2008/0294024 | A1 | 11/2008 | Cosentino et al. |
| 2008/0294096 | A1 | 11/2008 | Uber et al. |
| 2008/0296155 | A1 | 12/2008 | Shults et al. |
| 2008/0300476 | A1 | 12/2008 | Stafford |
| 2008/0300572 | A1 | 12/2008 | Rankers et al. |
| 2008/0306368 | A1 | 12/2008 | Goode, Jr. et al. |
| 2008/0306434 | A1 | 12/2008 | Dobbles et al. |
| 2008/0306435 | A1 | 12/2008 | Kamath et al. |
| 2008/0306444 | A1 | 12/2008 | Brister et al. |
| 2008/0308523 | A1 | 12/2008 | Krulevitch et al. |
| 2008/0312518 | A1 | 12/2008 | Jina et al. |
| 2008/0312601 | A1 | 12/2008 | Cane |
| 2008/0312841 | A1 | 12/2008 | Hayter |
| 2008/0312842 | A1 | 12/2008 | Hayter |
| 2008/0312844 | A1 | 12/2008 | Hayter et al. |
| 2008/0312845 | A1 | 12/2008 | Hayter et al. |
| 2008/0312859 | A1 | 12/2008 | Skyggebjerg et al. |
| 2008/0319085 | A1 | 12/2008 | Wright et al. |
| 2008/0319295 | A1 | 12/2008 | Bernstein et al. |
| 2008/0319296 | A1 | 12/2008 | Bernstein et al. |
| 2008/0319414 | A1 | 12/2008 | Yodfat et al. |
| 2008/0319416 | A1 | 12/2008 | Yodfat et al. |
| 2009/0005659 | A1 | 1/2009 | Kollias et al. |
| 2009/0005665 | A1 | 1/2009 | Hayter et al. |
| 2009/0005666 | A1 | 1/2009 | Shin et al. |
| 2009/0005729 | A1 | 1/2009 | Hendrixson et al. |
| 2009/0006034 | A1 | 1/2009 | Hayter et al. |
| 2009/0006061 | A1 | 1/2009 | Thukral et al. |
| 2009/0006133 | A1 | 1/2009 | Weinart et al. |
| 2009/0012376 | A1 | 1/2009 | Agus |
| 2009/0012377 | A1 | 1/2009 | Jennewine et al. |
| 2009/0012379 | A1 | 1/2009 | Goode, Jr. et al. |
| 2009/0018424 | A1 | 1/2009 | Kamath et al. |
| 2009/0018425 | A1 | 1/2009 | Ouyang et al. |
| 2009/0020502 | A1 | 1/2009 | Bhullar et al. |
| 2009/0028824 | A1 | 1/2009 | Chiang et al. |
| 2009/0030293 | A1 | 1/2009 | Cooper et al. |
| 2009/0030294 | A1 | 1/2009 | Petisce et al. |
| 2009/0033482 | A1 | 2/2009 | Hayter et al. |
| 2009/0036747 | A1 | 2/2009 | Hayter et al. |
| 2009/0036758 | A1 | 2/2009 | Brauker et al. |
| 2009/0036760 | A1 | 2/2009 | Hayter |
| 2009/0036763 | A1 | 2/2009 | Brauker et al. |
| 2009/0036915 | A1 | 2/2009 | Karbowniczek et al. |
| 2009/0040022 | A1 | 2/2009 | Finkenzeller |
| 2009/0043181 | A1 | 2/2009 | Brauker et al. |
| 2009/0043182 | A1 | 2/2009 | Brauker et al. |
| 2009/0043525 | A1 | 2/2009 | Brauker et al. |
| 2009/0043541 | A1 | 2/2009 | Brauker et al. |
| 2009/0043542 | A1 | 2/2009 | Brauker et al. |
| 2009/0045055 | A1 | 2/2009 | Rhodes et al. |
| 2009/0048499 | A1 | 2/2009 | Glejbol |
| 2009/0048503 | A1 | 2/2009 | Dalal et al. |
| 2009/0048563 | A1 | 2/2009 | Ethelfeld et al. |
| 2009/0054737 | A1 | 2/2009 | Magar et al. |
| 2009/0054745 | A1 | 2/2009 | Jennewine et al. |
| 2009/0054747 | A1 | 2/2009 | Fennell |
| 2009/0054748 | A1 | 2/2009 | Feldman et al. |
| 2009/0054753 | A1 | 2/2009 | Robinson et al. |
| 2009/0054866 | A1 | 2/2009 | Teisen-Simony et al. |
| 2009/0055149 | A1 | 2/2009 | Hayter et al. |
| 2009/0058635 | A1 | 3/2009 | LaLonde et al. |
| 2009/0062633 | A1 | 3/2009 | Brauker et al. |
| 2009/0062635 | A1 | 3/2009 | Brauker et al. |
| 2009/0062767 | A1 | 3/2009 | Van Antwerp et al. |
| 2009/0063187 | A1 | 3/2009 | Johnson et al. |
| 2009/0063402 | A1 | 3/2009 | Hayter |
| 2009/0069658 | A1 | 3/2009 | Say et al. |
| 2009/0069750 | A1 | 3/2009 | Schraga |
| 2009/0076356 | A1 | 3/2009 | Simpson et al. |
| 2009/0076359 | A1 | 3/2009 | Peyser |
| 2009/0076360 | A1 | 3/2009 | Brister et al. |
| 2009/0076361 | A1 | 3/2009 | Kamath et al. |
| 2009/0082693 | A1 | 3/2009 | Stafford |
| 2009/0085768 | A1 | 4/2009 | Patel et al. |
| 2009/0085873 | A1 | 4/2009 | Betts et al. |
| 2009/0088614 | A1 | 4/2009 | Taub |
| 2009/0088787 | A1 | 4/2009 | Koike et al. |
| 2009/0093687 | A1 | 4/2009 | Telfort et al. |
| 2009/0099436 | A1 | 4/2009 | Brister et al. |
| 2009/0099521 | A1 | 4/2009 | Gravesen et al. |
| 2009/0102678 | A1 | 4/2009 | Mazza et al. |
| 2009/0105554 | A1 | 4/2009 | Stahmann et al. |
| 2009/0105560 | A1 | 4/2009 | Solomon |
| 2009/0105568 | A1 | 4/2009 | Bugler |
| 2009/0105569 | A1 | 4/2009 | Stafford |
| 2009/0105570 | A1 | 4/2009 | Sloan et al. |
| 2009/0105571 | A1 | 4/2009 | Fennell et al. |
| 2009/0105636 | A1 | 4/2009 | Hayter et al. |
| 2009/0108992 | A1 | 4/2009 | Shafer |
| 2009/0112123 | A1 | 4/2009 | Freeman et al. |
| 2009/0112478 | A1 | 4/2009 | Mueller, Jr. et al. |
| 2009/0118592 | A1 | 5/2009 | Klitgaard |
| 2009/0124877 | A1 | 5/2009 | Goode, Jr. et al. |
| 2009/0124878 | A1 | 5/2009 | Goode, Jr. et al. |
| 2009/0124879 | A1 | 5/2009 | Brister et al. |
| 2009/0124964 | A1 | 5/2009 | Leach et al. |
| 2009/0124979 | A1 | 5/2009 | Raymond et al. |
| 2009/0131768 | A1 | 5/2009 | Simpson et al. |
| 2009/0131769 | A1 | 5/2009 | Leach et al. |
| 2009/0131776 | A1 | 5/2009 | Simpson et al. |
| 2009/0131777 | A1 | 5/2009 | Simpson et al. |
| 2009/0131860 | A1 | 5/2009 | Nielsen |
| 2009/0137886 | A1 | 5/2009 | Shariati et al. |

(56) References Cited

U.S. PATENT DOCUMENTS

2009/0137887 A1 5/2009 Shariati et al.
2009/0143659 A1 6/2009 Li et al.
2009/0143660 A1 6/2009 Brister et al.
2009/0149728 A1 6/2009 Van Antwerp et al.
2009/0150186 A1 6/2009 Cohen et al.
2009/0150454 A1 6/2009 Gejdos et al.
2009/0156919 A1 6/2009 Brister et al.
2009/0156924 A1 6/2009 Shariati et al.
2009/0163790 A1 6/2009 Brister et al.
2009/0163791 A1 6/2009 Brister et al.
2009/0163855 A1 6/2009 Shin et al.
2009/0164190 A1 6/2009 Hayter
2009/0164239 A1 6/2009 Hayter et al.
2009/0164251 A1 6/2009 Hayter
2009/0171182 A1 7/2009 Stafford
2009/0177068 A1 7/2009 Stivoric et al.
2009/0178459 A1 7/2009 Li et al.
2009/0182217 A1 7/2009 Li et al.
2009/0189738 A1 7/2009 Hermle
2009/0192366 A1 7/2009 Mensinger et al.
2009/0192380 A1 7/2009 Shariati et al.
2009/0192722 A1 7/2009 Shariati et al.
2009/0192724 A1 7/2009 Brauker et al.
2009/0192745 A1 7/2009 Kamath et al.
2009/0192751 A1 7/2009 Kamath et al.
2009/0198118 A1 8/2009 Hayter et al.
2009/0198186 A1 8/2009 Mernoe et al.
2009/0198215 A1 8/2009 Chong et al.
2009/0203981 A1 8/2009 Brauker et al.
2009/0204340 A1 8/2009 Feldman et al.
2009/0204341 A1 8/2009 Brauker et al.
2009/0210249 A1 8/2009 Rasch-Menges et al.
2009/0212766 A1 8/2009 Olson et al.
2009/0216100 A1 8/2009 Ebner et al.
2009/0216103 A1 8/2009 Brister et al.
2009/0216215 A1 8/2009 Thalmann et al.
2009/0234200 A1 9/2009 Husheer
2009/0240120 A1 9/2009 Mensinger et al.
2009/0240121 A1 9/2009 Bickoff
2009/0240128 A1 9/2009 Mensinger et al.
2009/0240193 A1 9/2009 Mensinger et al.
2009/0242399 A1 10/2009 Kamath et al.
2009/0242425 A1 10/2009 Kamath et al.
2009/0247855 A1 10/2009 Boock et al.
2009/0247856 A1 10/2009 Boock et al.
2009/0247857 A1 10/2009 Harper et al.
2009/0247931 A1 10/2009 Damgaard-Sorenson
2009/0253973 A1 10/2009 Bashan et al.
2009/0259118 A1 10/2009 Feldman et al.
2009/0259201 A1 10/2009 Hwang et al.
2009/0259202 A1 10/2009 Leeflang et al.
2009/0267765 A1 10/2009 Greene et al.
2009/0270765 A1 10/2009 Ghesquire et al.
2009/0277242 A1 11/2009 Crane et al.
2009/0281406 A1 11/2009 McGarraugh et al.
2009/0287073 A1 11/2009 Boock et al.
2009/0287074 A1 11/2009 Shults et al.
2009/0289796 A1 11/2009 Blumberg
2009/0292184 A1 11/2009 Funderburk et al.
2009/0292185 A1 11/2009 Funderburk et al.
2009/0294277 A1 12/2009 Thomas et al.
2009/0298182 A1 12/2009 Schulat et al.
2009/0299152 A1 12/2009 Taub et al.
2009/0299155 A1 12/2009 Yang et al.
2009/0299156 A1 12/2009 Simpson et al.
2009/0299162 A1 12/2009 Brauker et al.
2009/0299167 A1 12/2009 Seymour
2009/0299276 A1 12/2009 Brauker et al.
2009/0299301 A1 12/2009 Gottleib et al.
2010/0004597 A1 1/2010 Gryn et al.
2010/0010324 A1 1/2010 Brauker et al.
2010/0010329 A1 1/2010 Taub et al.
2010/0010331 A1 1/2010 Brauker et al.
2010/0010332 A1 1/2010 Brauker et al.
2010/0014626 A1 1/2010 Fennell et al.
2010/0016687 A1 1/2010 Brauker et al.
2010/0016698 A1 1/2010 Rasdal et al.
2010/0022855 A1 1/2010 Brauker et al.
2010/0022863 A1 1/2010 Mogensen et al.
2010/0022988 A1 1/2010 Wochner et al.
2010/0025238 A1 2/2010 Gottlieb et al.
2010/0030038 A1 2/2010 Brauker et al.
2010/0030053 A1 2/2010 Goode, Jr. et al.
2010/0030111 A1 2/2010 Perriere
2010/0030484 A1 2/2010 Brauker et al.
2010/0030485 A1 2/2010 Brauker et al.
2010/0036215 A1 2/2010 Goode, Jr. et al.
2010/0036216 A1 2/2010 Goode, Jr. et al.
2010/0036222 A1 2/2010 Goode, Jr. et al.
2010/0036223 A1 2/2010 Goode, Jr. et al.
2010/0036225 A1 2/2010 Goode, Jr. et al.
2010/0036281 A1 2/2010 Doi
2010/0041971 A1 2/2010 Goode, Jr. et al.
2010/0045465 A1 2/2010 Brauker et al.
2010/0049014 A1 2/2010 Funderburk et al.
2010/0049024 A1 2/2010 Saint et al.
2010/0049129 A1 2/2010 Yokoi et al.
2010/0057040 A1 3/2010 Hayter
2010/0057041 A1 3/2010 Hayter
2010/0057042 A1 3/2010 Hayter
2010/0057044 A1 3/2010 Hayter
2010/0057057 A1 3/2010 Hayter et al.
2010/0063373 A1 3/2010 Kamath et al.
2010/0069728 A1 3/2010 Funderburk et al.
2010/0076283 A1 3/2010 Simpson et al.
2010/0076379 A1 3/2010 Matusch
2010/0081905 A1 4/2010 Bommakanti et al.
2010/0081906 A1 4/2010 Hayter et al.
2010/0081908 A1 4/2010 Dobbles et al.
2010/0081910 A1 4/2010 Brister et al.
2010/0081953 A1 4/2010 Syeda-Mahmood et al.
2010/0087724 A1 4/2010 Brauker et al.
2010/0094251 A1 4/2010 Estes et al.
2010/0096259 A1 4/2010 Zhang et al.
2010/0099970 A1 4/2010 Shults et al.
2010/0099971 A1 4/2010 Shults et al.
2010/0100113 A1 4/2010 Lio et al.
2010/0105999 A1 4/2010 Dixon et al.
2010/0106088 A1 4/2010 Yodfat et al.
2010/0113897 A1 5/2010 Brenneman et al.
2010/0119693 A1 5/2010 Tapsak et al.
2010/0119881 A1 5/2010 Patel et al.
2010/0121167 A1 5/2010 McGarraugh et al.
2010/0121169 A1 5/2010 Petisce et al.
2010/0137695 A1 6/2010 Yodfat et al.
2010/0141656 A1 6/2010 Krieftewirth
2010/0145229 A1 6/2010 Perez et al.
2010/0145377 A1 6/2010 Lai et al.
2010/0146300 A1 6/2010 Brown
2010/0152548 A1 6/2010 Koski
2010/0152554 A1 6/2010 Steine et al.
2010/0152674 A1 6/2010 Kavazov et al.
2010/0160757 A1 6/2010 Weinart et al.
2010/0160759 A1 6/2010 Celentano et al.
2010/0160760 A1 6/2010 Shults et al.
2010/0161269 A1 6/2010 Kamath et al.
2010/0168538 A1 7/2010 Keenan et al.
2010/0168540 A1 7/2010 Kamath et al.
2010/0168541 A1 7/2010 Kamath et al.
2010/0168542 A1 7/2010 Kamath et al.
2010/0168543 A1 7/2010 Kamath et al.
2010/0168544 A1 7/2010 Kamath et al.
2010/0168545 A1 7/2010 Kamath et al.
2010/0168546 A1 7/2010 Kamath et al.
2010/0168547 A1 7/2010 Kamath et al.
2010/0168660 A1 7/2010 Galley et al.
2010/0168677 A1 7/2010 Gabriel et al.
2010/0174157 A1 7/2010 Brister et al.
2010/0174158 A1 7/2010 Kamath et al.
2010/0174163 A1 7/2010 Brister et al.
2010/0174164 A1 7/2010 Brister et al.
2010/0174165 A1 7/2010 Brister et al.
2010/0174166 A1 7/2010 Brister et al.
2010/0174167 A1 7/2010 Kamath et al.

(56) References Cited

U.S. PATENT DOCUMENTS

| | | | |
|---|---|---|---|
| 2010/0174168 | A1 | 7/2010 | Goode, Jr. et al. |
| 2010/0174266 | A1 | 7/2010 | Estes |
| 2010/0179399 | A1 | 7/2010 | Goode, Jr. et al. |
| 2010/0179400 | A1 | 7/2010 | Brauker et al. |
| 2010/0179401 | A1 | 7/2010 | Rasdal et al. |
| 2010/0179402 | A1 | 7/2010 | Goode, Jr. et al. |
| 2010/0179404 | A1 | 7/2010 | Kamath et al. |
| 2010/0179405 | A1 | 7/2010 | Goode, Jr. et al. |
| 2010/0179407 | A1 | 7/2010 | Goode, Jr. et al. |
| 2010/0179408 | A1 | 7/2010 | Kamath et al. |
| 2010/0179409 | A1 | 7/2010 | Kamath et al. |
| 2010/0185065 | A1 | 7/2010 | Goode, Jr. et al. |
| 2010/0185069 | A1 | 7/2010 | Brister et al. |
| 2010/0185070 | A1 | 7/2010 | Brister et al. |
| 2010/0185071 | A1 | 7/2010 | Simpson et al. |
| 2010/0185072 | A1 | 7/2010 | Goode, Jr. et al. |
| 2010/0185073 | A1 | 7/2010 | Goode, Jr. et al. |
| 2010/0185074 | A1 | 7/2010 | Goode, Jr. et al. |
| 2010/0185075 | A1 | 7/2010 | Brister et al. |
| 2010/0185175 | A1 | 7/2010 | Kamen et al. |
| 2010/0190435 | A1 | 7/2010 | Cook et al. |
| 2010/0191082 | A1 | 7/2010 | Brister et al. |
| 2010/0191087 | A1 | 7/2010 | Talbot et al. |
| 2010/0191472 | A1 | 7/2010 | Doniger et al. |
| 2010/0198033 | A1 | 8/2010 | Krulevitch et al. |
| 2010/0198034 | A1 | 8/2010 | Thomas et al. |
| 2010/0198035 | A1 | 8/2010 | Kamath et al. |
| 2010/0198036 | A1 | 8/2010 | Kamath et al. |
| 2010/0198042 | A1 | 8/2010 | Sloan et al. |
| 2010/0198142 | A1 | 8/2010 | Sloan et al. |
| 2010/0198314 | A1 | 8/2010 | Wei |
| 2010/0204557 | A1 | 8/2010 | Kiaie et al. |
| 2010/0204653 | A1 | 8/2010 | Gryn et al. |
| 2010/0212583 | A1 | 8/2010 | Brister et al. |
| 2010/0213057 | A1 | 8/2010 | Feldman et al. |
| 2010/0213080 | A1 | 8/2010 | Celentano et al. |
| 2010/0214104 | A1 | 8/2010 | Goode, Jr. et al. |
| 2010/0217105 | A1 | 8/2010 | Yodfat et al. |
| 2010/0217557 | A1 | 8/2010 | Kamath et al. |
| 2010/0223013 | A1 | 9/2010 | Kamath et al. |
| 2010/0223022 | A1 | 9/2010 | Kamath et al. |
| 2010/0223023 | A1 | 9/2010 | Kamath et al. |
| 2010/0228109 | A1 | 9/2010 | Kamath et al. |
| 2010/0228111 | A1 | 9/2010 | Friman et al. |
| 2010/0228497 | A1 | 9/2010 | Kamath et al. |
| 2010/0230285 | A1 | 9/2010 | Hoss et al. |
| 2010/0235439 | A1 | 9/2010 | Goodnow et al. |
| 2010/0240975 | A1 | 9/2010 | Goode, Jr. et al. |
| 2010/0240976 | A1 | 9/2010 | Goode, Jr. et al. |
| 2010/0256471 | A1 | 10/2010 | Say et al. |
| 2010/0259543 | A1 | 10/2010 | Tarassenko et al. |
| 2010/0261987 | A1 | 10/2010 | Kamath et al. |
| 2010/0262183 | A1 | 10/2010 | Abbott et al. |
| 2010/0262201 | A1 | 10/2010 | He et al. |
| 2010/0267161 | A1 | 10/2010 | Wu et al. |
| 2010/0274107 | A1 | 10/2010 | Boock et al. |
| 2010/0274111 | A1 | 10/2010 | Say et al. |
| 2010/0274515 | A1 | 10/2010 | Hoss et al. |
| 2010/0275108 | A1 | 10/2010 | Sloan et al. |
| 2010/0280341 | A1 | 11/2010 | Boock et al. |
| 2010/0286496 | A1 | 11/2010 | Simpson et al. |
| 2010/0298684 | A1 | 11/2010 | Leach et al. |
| 2010/0312176 | A1 | 12/2010 | Lauer et al. |
| 2010/0313105 | A1 | 12/2010 | Nekoomaram et al. |
| 2010/0317952 | A1 | 12/2010 | Budiman et al. |
| 2010/0324392 | A1 | 12/2010 | Yee et al. |
| 2010/0324403 | A1 | 12/2010 | Brister et al. |
| 2010/0325868 | A1 | 12/2010 | Wang et al. |
| 2010/0326842 | A1 | 12/2010 | Mazza et al. |
| 2010/0331642 | A1 | 12/2010 | Bruce et al. |
| 2010/0331644 | A1 | 12/2010 | Neale et al. |
| 2010/0331647 | A1 | 12/2010 | Shah et al. |
| 2010/0331648 | A1 | 12/2010 | Kamath et al. |
| 2010/0331651 | A1 | 12/2010 | Groll |
| 2010/0331653 | A1 | 12/2010 | Stafford |
| 2010/0331656 | A1 | 12/2010 | Mensinger et al. |
| 2010/0331657 | A1 | 12/2010 | Mensinger et al. |
| 2011/0004085 | A1 | 1/2011 | Mensinger et al. |
| 2011/0004276 | A1 | 1/2011 | Blair et al. |
| 2011/0009727 | A1 | 1/2011 | Mensinger et al. |
| 2011/0015509 | A1 | 1/2011 | Peyser |
| 2011/0016691 | A1 | 1/2011 | Alden et al. |
| 2011/0021889 | A1 | 1/2011 | Hoss et al. |
| 2011/0022411 | A1 | 1/2011 | Hjelm et al. |
| 2011/0024043 | A1 | 2/2011 | Boock et al. |
| 2011/0024307 | A1 | 2/2011 | Simpson et al. |
| 2011/0027127 | A1 | 2/2011 | Simpson et al. |
| 2011/0027453 | A1 | 2/2011 | Boock et al. |
| 2011/0027458 | A1 | 2/2011 | Boock et al. |
| 2011/0028815 | A1 | 2/2011 | Simpson et al. |
| 2011/0028816 | A1 | 2/2011 | Simpson et al. |
| 2011/0031986 | A1 | 2/2011 | Bhat et al. |
| 2011/0040163 | A1 | 2/2011 | Telson et al. |
| 2011/0040256 | A1 | 2/2011 | Bobroff et al. |
| 2011/0040263 | A1 | 2/2011 | Hordum et al. |
| 2011/0046456 | A1 | 2/2011 | Hordum et al. |
| 2011/0046467 | A1 | 2/2011 | Simpson et al. |
| 2011/0046977 | A1 | 2/2011 | Goodnow et al. |
| 2011/0054275 | A1 | 3/2011 | Stafford |
| 2011/0054282 | A1 | 3/2011 | Nekoomaram et al. |
| 2011/0060196 | A1 | 3/2011 | Stafford |
| 2011/0060530 | A1 | 3/2011 | Fennell |
| 2011/0070633 | A1 | 3/2011 | Matsumoto et al. |
| 2011/0073475 | A1 | 3/2011 | Kastanos et al. |
| 2011/0077469 | A1 | 3/2011 | Blocker et al. |
| 2011/0077490 | A1 | 3/2011 | Simpson et al. |
| 2011/0077494 | A1 | 3/2011 | Doniger et al. |
| 2011/0077659 | A1 | 3/2011 | Mandecki et al. |
| 2011/0081726 | A1 | 4/2011 | Berman et al. |
| 2011/0082484 | A1 | 4/2011 | Saravia et al. |
| 2011/0087196 | A1 | 4/2011 | Hunn et al. |
| 2011/0097090 | A1 | 4/2011 | Cao |
| 2011/0106126 | A1 | 5/2011 | Love et al. |
| 2011/0112696 | A1 | 5/2011 | Yodfat et al. |
| 2011/0118579 | A1 | 5/2011 | Goode, Jr. et al. |
| 2011/0118580 | A1 | 5/2011 | Goode, Jr. et al. |
| 2011/0123971 | A1 | 5/2011 | Berkowitz et al. |
| 2011/0124992 | A1 | 5/2011 | Brauker et al. |
| 2011/0124997 | A1 | 5/2011 | Goode, Jr. et al. |
| 2011/0125040 | A1 | 5/2011 | Crawford et al. |
| 2011/0125410 | A1 | 5/2011 | Goode, Jr. et al. |
| 2011/0130970 | A1 | 6/2011 | Goode, Jr. et al. |
| 2011/0130971 | A1 | 6/2011 | Goode, Jr. et al. |
| 2011/0130998 | A1 | 6/2011 | Goode, Jr. et al. |
| 2011/0137257 | A1 | 6/2011 | Gyrn et al. |
| 2011/0137571 | A1 | 6/2011 | Power et al. |
| 2011/0144465 | A1 | 6/2011 | Shults et al. |
| 2011/0148905 | A1 | 6/2011 | Simmons et al. |
| 2011/0152637 | A1 | 6/2011 | Kateraas et al. |
| 2011/0172510 | A1 | 7/2011 | Chickering, III et al. |
| 2011/0178378 | A1 | 7/2011 | Brister et al. |
| 2011/0178461 | A1 | 7/2011 | Chong et al. |
| 2011/0184258 | A1 | 7/2011 | Stafford |
| 2011/0184482 | A1 | 7/2011 | Eberman et al. |
| 2011/0184752 | A1 | 7/2011 | Ray et al. |
| 2011/0190603 | A1 | 8/2011 | Stafford |
| 2011/0190614 | A1 | 8/2011 | Brister et al. |
| 2011/0191044 | A1 | 8/2011 | Stafford |
| 2011/0193704 | A1 | 8/2011 | Harper et al. |
| 2011/0201910 | A1 | 8/2011 | Rasdal et al. |
| 2011/0201911 | A1 | 8/2011 | Johnson et al. |
| 2011/0208027 | A1 | 8/2011 | Wagner et al. |
| 2011/0213225 | A1 | 9/2011 | Bernstein et al. |
| 2011/0218414 | A1 | 9/2011 | Kamath et al. |
| 2011/0218490 | A1 | 9/2011 | Ocvirk et al. |
| 2011/0230741 | A1 | 9/2011 | Liang et al. |
| 2011/0231107 | A1 | 9/2011 | Brauker et al. |
| 2011/0231140 | A1 | 9/2011 | Goode, Jr. et al. |
| 2011/0231141 | A1 | 9/2011 | Goode, Jr. et al. |
| 2011/0231142 | A1 | 9/2011 | Goode, Jr. et al. |
| 2011/0253533 | A1 | 10/2011 | Shults et al. |
| 2011/0257495 | A1 | 10/2011 | Hoss et al. |
| 2011/0257521 | A1 | 10/2011 | Fraden |
| 2011/0257895 | A1 | 10/2011 | Brauker et al. |

(56) References Cited

U.S. PATENT DOCUMENTS

2011/0263958 A1 10/2011 Brauker et al.
2011/0263959 A1 10/2011 Young et al.
2011/0264378 A1 10/2011 Breton et al.
2011/0270062 A1 11/2011 Goode, Jr. et al.
2011/0270158 A1 11/2011 Brauker et al.
2011/0275919 A1 11/2011 Petisce et al.
2011/0282327 A1 11/2011 Kellogg et al.
2011/0287528 A1 11/2011 Fern et al.
2011/0288574 A1 11/2011 Curry et al.
2011/0289497 A1 11/2011 Kiaie et al.
2011/0290645 A1 12/2011 Brister et al.
2011/0313543 A1 12/2011 Brauker et al.
2011/0319729 A1 12/2011 Donnay et al.
2011/0319733 A1 12/2011 Stafford
2011/0319738 A1 12/2011 Woodruff et al.
2011/0319739 A1 12/2011 Kamath et al.
2011/0320130 A1 12/2011 Valdes et al.
2012/0010642 A1 1/2012 Lee et al.
2012/0035445 A1 2/2012 Boock et al.
2012/0040101 A1 2/2012 Tapsak et al.
2012/0046534 A1 2/2012 Simpson et al.
2012/0078071 A1 3/2012 Bohm et al.
2012/0088995 A1 4/2012 Fennell et al.
2012/0095406 A1 4/2012 Gyrn et al.
2012/0108934 A1 5/2012 Valdes et al.
2012/0108983 A1 5/2012 Banet et al.
2012/0116322 A1* 5/2012 Brink ................. A61B 10/0233 604/264
2012/0123385 A1 5/2012 Edwards et al.
2012/0143135 A1 6/2012 Cole et al.
2012/0165626 A1 6/2012 Irina et al.
2012/0165640 A1 6/2012 Galley et al.
2012/0173200 A1 7/2012 Breton et al.
2012/0179113 A1 7/2012 Yokota et al.
2012/0184909 A1 7/2012 Gyrn et al.
2012/0190989 A1 7/2012 Kaiser et al.
2012/0197098 A1 8/2012 Donnay et al.
2012/0197222 A1 8/2012 Donnay et al.
2012/0245447 A1 9/2012 Karan et al.
2012/0265042 A1 10/2012 Neinast et al.
2012/0296327 A1 11/2012 Hutchins et al.
2012/0303043 A1 11/2012 Donnay et al.
2013/0035575 A1 2/2013 Mayou et al.
2013/0047981 A1 2/2013 Bacon
2013/0109940 A1 5/2013 Yang et al.
2013/0111248 A1 5/2013 Ghesquiere et al.
2013/0150691 A1 6/2013 Pace et al.
2013/0184547 A1 7/2013 Taub et al.
2013/0199312 A1 8/2013 Wilmer et al.
2013/0225959 A1 8/2013 Bugler
2013/0235166 A1 9/2013 Jones et al.
2013/0253289 A1 9/2013 Hadvary et al.
2013/0267811 A1* 10/2013 Pryor .................. A61B 5/6833 600/365
2013/0317323 A1 11/2013 Fujiwara et al.
2014/0031655 A1 1/2014 Stafford
2014/0121480 A1 5/2014 Budiman et al.
2014/0148667 A1 5/2014 Boock et al.
2014/0171771 A1 6/2014 Feldman et al.
2014/0188053 A1 7/2014 Lundquist
2014/0228760 A1 8/2014 Ethelfeld
2014/0275907 A1 9/2014 Feldman et al.
2015/0005601 A1 1/2015 Hoss et al.
2015/0018643 A1 1/2015 Cole et al.
2015/0025338 A1 1/2015 Lee et al.
2015/0073238 A1 3/2015 Matsumoto et al.
2015/0105644 A1 4/2015 Yang et al.
2015/0141776 A1 5/2015 Hadvary et al.
2015/0164545 A1 6/2015 Gyrn
2015/0173661 A1 6/2015 Myles
2015/0241407 A1 8/2015 Ou et al.
2015/0326072 A1 11/2015 Petras et al.
2016/0058342 A1 3/2016 Maiz-Aguinaga et al.
2016/0058470 A1 3/2016 Peterson et al.
2016/0058474 A1 3/2016 Peterson et al.
2016/0128615 A1 5/2016 Curry et al.
2016/0157759 A1 6/2016 Yang
2016/0256106 A1 9/2016 Krasnow et al.
2016/0331283 A1 11/2016 Rao et al.
2016/0331284 A1 11/2016 Pace
2016/0338733 A1 11/2016 Shah et al.
2016/0338734 A1* 11/2016 Shah .................. A61B 5/14503
2016/0354555 A1 12/2016 Gibson et al.
2017/0112531 A1 4/2017 Schoonmaker et al.
2017/0112533 A1 4/2017 Schoonmaker et al.
2017/0112534 A1 4/2017 Schoonmaker et al.
2017/0127985 A1 5/2017 Thompson et al.
2017/0128011 A1* 5/2017 Frey ................... A61B 5/14532
2017/0188908 A1 7/2017 Hoss et al.
2017/0188910 A1 7/2017 Halac et al.
2017/0188912 A1 7/2017 Halac et al.
2017/0216536 A1* 8/2017 Scott ..................... A61M 5/158
2017/0265791 A1 9/2017 Pace et al.
2017/0290533 A1 10/2017 Antonio et al.
2017/0290534 A1 10/2017 Antonio et al.
2017/0290535 A1 10/2017 Rao et al.
2017/0290546 A1 10/2017 Antonio et al.
2017/0319137 A1 11/2017 Tsubouchi et al.
2017/0367630 A1 12/2017 Arita et al.
2017/0368268 A1 12/2017 Chopra
2018/0116572 A1 5/2018 Simpson et al.
2018/0125464 A1 5/2018 Kolb et al.
2018/0235520 A1 8/2018 Rao et al.
2018/0360493 A1 12/2018 Baker et al.
2018/0368771 A1 12/2018 Gray et al.
2019/0133501 A1 5/2019 Rao et al.
2019/0133638 A1 5/2019 Il et al.
2019/0298240 A1 10/2019 Lee et al.
2020/0077928 A1 3/2020 Brister et al.
2020/0100712 A1 4/2020 Stafford
2020/0113494 A1* 4/2020 Akiyama ............ B21C 37/0815
2020/0178899 A1 6/2020 Chae et al.
2020/0196919 A1 6/2020 Rao et al.
2020/0397356 A1 12/2020 Yee et al.
2021/0030969 A1 2/2021 Huang et al.
2021/0113124 A1 4/2021 Yee et al.
2021/0161437 A1 6/2021 Thomas et al.
2021/0177315 A1 6/2021 Thomas et al.
2021/0204841 A1 7/2021 Thomas et al.
2021/0204843 A1 7/2021 Mazza et al.
2021/0378592 A1 12/2021 Rodriguez et al.
2022/0007973 A1 1/2022 Rao et al.
2022/0079475 A1 3/2022 Cole et al.
2022/0125480 A1 4/2022 Rao et al.
2024/0293615 A1 9/2024 Lanigan

FOREIGN PATENT DOCUMENTS

CA 2468577 6/2003
CA 2495648 2/2004
CA 2143172 7/2005
CA 2498682 9/2005
CA 2555749 9/2005
CA 2632709 6/2007
CA 2396613 3/2008
CA 2678336 5/2008
CA 2615575 6/2008
CA 2626349 9/2008
CA 2701374 4/2009
CA 2413148 8/2010
CA 2728831 7/2011
CA 2766693 A1 9/2011
CA 2617965 10/2011
CA 2766685 A1 12/2011
CA 3050721 7/2018
CN 1202872 5/2005
CN 101163440 4/2008
CN 101268932 9/2008
CN 101296650 10/2008
CN 201370857 12/2009
DE 44 01 400 7/1995
DE 201 10 059 8/2002
DE 101 17 285 11/2002
DE 10 2008 053 216 5/2010

(56) References Cited

FOREIGN PATENT DOCUMENTS

| | | | |
|---|---|---|---|
| EP | 0 010 375 | | 4/1980 |
| EP | 0 026 995 | | 4/1981 |
| EP | 0 048 090 | | 3/1982 |
| EP | 0 078 636 | | 5/1983 |
| EP | 0 096 288 | | 12/1983 |
| EP | 0 098 592 | | 1/1984 |
| EP | 0 125 139 | | 11/1984 |
| EP | 0127 958 | | 12/1984 |
| EP | 0 136 362 | | 4/1985 |
| EP | 0 170 375 | | 2/1986 |
| EP | 0 177 743 | | 4/1986 |
| EP | 0 080 304 | | 5/1986 |
| EP | 0 184 909 | | 6/1986 |
| EP | 0 206 218 | | 12/1986 |
| EP | 0 230 472 | | 8/1987 |
| EP | 0 241 309 | | 10/1987 |
| EP | 0 245 073 | | 11/1987 |
| EP | 0 255 291 | | 2/1988 |
| EP | 0 278 647 | | 8/1988 |
| EP | 0 319 277 | A1 | 6/1989 |
| EP | 0 320 109 | | 6/1989 |
| EP | 0 353 328 | | 2/1990 |
| EP | 0 359 831 | | 3/1990 |
| EP | 0 368 209 | | 5/1990 |
| EP | 0 390 390 | | 10/1990 |
| EP | 0 396 788 | | 11/1990 |
| EP | 0 400 918 | | 12/1990 |
| EP | 0 453 283 | | 10/1991 |
| EP | 0 470 290 | | 2/1992 |
| EP | 0 567 725 | | 11/1993 |
| EP | 0 286 118 | | 1/1995 |
| EP | 0 680 727 | | 11/1995 |
| EP | 0 724 859 | | 8/1996 |
| EP | 0 805 574 | | 11/1997 |
| EP | 1 897 488 | | 12/1999 |
| EP | 0 973 289 | | 1/2000 |
| EP | 0 678 308 | | 5/2000 |
| EP | 1 048 264 | | 11/2000 |
| EP | 1 177 802 | | 2/2002 |
| EP | 0 729 366 | | 7/2002 |
| EP | 1 292 218 | | 3/2003 |
| EP | 1 077 634 | | 7/2003 |
| EP | 1 092 390 | | 7/2004 |
| EP | 1 568 309 | | 8/2005 |
| EP | 1 630 898 | | 3/2006 |
| EP | 1 666 091 | | 6/2006 |
| EP | 1 669 020 | | 6/2006 |
| EP | 1 703 697 | | 9/2006 |
| EP | 1 704 889 | | 9/2006 |
| EP | 1 704 893 | | 9/2006 |
| EP | 1 729 128 | | 12/2006 |
| EP | 0 987 982 | | 1/2007 |
| EP | 1 956 371 | | 8/2008 |
| EP | 2 031 534 | | 3/2009 |
| EP | 2 060 284 | | 5/2009 |
| EP | 1 897 487 | | 11/2009 |
| EP | 1 897 492 | | 11/2009 |
| EP | 2 113 864 | | 11/2009 |
| EP | 1 681 992 | | 4/2010 |
| EP | 2 201 969 | | 6/2010 |
| EP | 1 448 489 | | 8/2010 |
| EP | 1 971 396 | | 8/2010 |
| EP | 1 725 163 | | 12/2010 |
| EP | 2 260 757 | | 12/2010 |
| EP | 1 413 245 | | 6/2011 |
| EP | 2 327 362 | | 6/2011 |
| EP | 2 327 984 | | 6/2011 |
| EP | 2 335 587 | | 6/2011 |
| EP | 2 153 382 | | 2/2012 |
| EP | 2 284 773 | | 2/2012 |
| EP | 1 789 116 | B1 | 5/2013 |
| EP | 3 251 597 | B1 | 11/2019 |
| EP | 3 632 314 | | 4/2020 |
| EP | 3 632 315 | A1 | 4/2020 |
| EP | 3 851 045 | A1 | 7/2021 |
| EP | 3 730 044 | B1 | 12/2021 |
| EP | 3 730 045 | B1 | 3/2022 |
| EP | 3 766 408 | B1 | 4/2022 |
| EP | 3 928 688 | B1 | 6/2022 |
| EP | 4 111 949 | B1 | 7/2023 |
| EP | 4 344 633 | | 4/2024 |
| EP | 4 203 819 | | 7/2024 |
| GB | 1 394 171 | | 5/1975 |
| GB | 1 599 241 | | 9/1981 |
| GB | 2 073 891 | | 10/1981 |
| GB | 2 067 764 | | 1/1984 |
| GB | 2 154 003 | | 8/1985 |
| GB | 2 204 408 | | 11/1988 |
| GB | 2 254 436 | | 10/1992 |
| GB | 2 409 951 | | 7/2005 |
| JP | 54-041191 | | 4/1979 |
| JP | 55-010581 | | 1/1980 |
| JP | 55-010583 | | 1/1980 |
| JP | 55-010584 | | 1/1980 |
| JP | 55-012406 | | 1/1980 |
| JP | 56-163447 | | 10/1981 |
| JP | 57-070448 | | 4/1982 |
| JP | 60-173457 | | 9/1985 |
| JP | 60-173458 | | 9/1985 |
| JP | 60-173459 | | 9/1985 |
| JP | 62-085855 | | 4/1987 |
| JP | 62-114747 | | 5/1987 |
| JP | 63-058149 | | 3/1988 |
| JP | 63-128252 | | 5/1988 |
| JP | 63-139246 | | 6/1988 |
| JP | 63-294799 | | 12/1988 |
| JP | 63-317757 | | 12/1988 |
| JP | 63-317758 | | 12/1988 |
| JP | 01-114746 | | 5/1989 |
| JP | 01-114747 | | 5/1989 |
| JP | 01-124060 | | 5/1989 |
| JP | 01-134244 | | 5/1989 |
| JP | 01-156658 | | 6/1989 |
| JP | 02-062958 | | 3/1990 |
| JP | 02-120655 | | 5/1990 |
| JP | 02-287145 | | 11/1990 |
| JP | 02-310457 | | 12/1990 |
| JP | 03-020752 | | 1/1991 |
| JP | 03-026956 | | 2/1991 |
| JP | 03-028752 | | 2/1991 |
| JP | 03-500940 | | 2/1991 |
| JP | 03-194458 | | 8/1991 |
| JP | 03-202764 | | 9/1991 |
| JP | 05-072171 | | 3/1993 |
| JP | 05-196595 | | 8/1993 |
| JP | 06-190050 | | 7/1994 |
| JP | 07-055757 | | 3/1995 |
| JP | 07-072585 | | 3/1995 |
| JP | 07-182462 | | 7/1995 |
| JP | 07-311196 | | 11/1995 |
| JP | 08-285814 | | 11/1996 |
| JP | 08-285815 | | 11/1996 |
| JP | 09-021778 | | 1/1997 |
| JP | 09-101280 | | 4/1997 |
| JP | 09-285459 | | 4/1997 |
| JP | 10-170471 | | 6/1998 |
| JP | 10-305016 | | 11/1998 |
| JP | 11-506629 | | 6/1999 |
| JP | 11-225359 | | 8/1999 |
| JP | 2003-144417 | | 5/2003 |
| JP | 2004-033438 | | 2/2004 |
| JP | 2004-214014 | | 7/2004 |
| JP | 2004-520103 | | 7/2004 |
| JP | 2004-520898 | | 7/2004 |
| JP | 2004-358016 | A | 12/2004 |
| JP | 2006-021031 | | 1/2006 |
| JP | 2006-280464 | | 10/2006 |
| JP | 2006-527036 | | 11/2006 |
| JP | 2007-510499 | | 4/2007 |
| JP | 2007-152037 | | 6/2007 |
| JP | 2008-506468 | | 3/2008 |
| KR | 10-2017-0068694 | | 6/2017 |
| SU | 1281988 | | 1/1987 |
| WO | WO 89/05119 | | 6/1989 |

(56) References Cited

FOREIGN PATENT DOCUMENTS

WO WO 89/08713 9/1989
WO WO 90/05300 5/1990
WO WO 90/05910 5/1990
WO WO 91/01680 2/1991
WO WO 91/04704 4/1991
WO WO 91/15993 10/1991
WO WO 92/13271 8/1992
WO WO 94/20602 9/1994
WO WO 95/28878 2/1995
WO WO 96/25089 8/1996
WO WO 96/35370 11/1996
WO WO 96/39977 12/1996
WO WO 97/02847 1/1997
WO WO 97/19344 5/1997
WO WO 97/21457 6/1997
WO WO 97/33513 9/1997
WO WO 97/42882 11/1997
WO WO 97/42883 11/1997
WO WO 97/42886 11/1997
WO WO 97/42888 11/1997
WO WO 97/43962 11/1997
WO WO 98/04902 2/1998
WO WO 98/35053 8/1998
WO WO 98/56293 12/1998
WO WO 99/27849 6/1999
WO WO 99/28736 6/1999
WO WO 99/33504 7/1999
WO WO 99/56613 11/1999
WO WO-0040159 A1 * 7/2000 ....... A61B 17/06109
WO WO 00/49940 8/2000
WO WO 00/59370 10/2000
WO WO 00/60350 10/2000
WO WO 00/74753 12/2000
WO WO 00/78992 12/2000
WO WO 01/17875 A1 3/2001
WO WO 01/52727 A1 7/2001
WO WO 01/52935 7/2001
WO WO 01/54753 8/2001
WO WO 01/58348 8/2001
WO WO 02/15778 2/2002
WO WO 02/16905 2/2002
WO WO 02/50534 6/2002
WO WO 02/058537 8/2002
WO WO 02/100457 12/2002
WO WO 03/026728 4/2003
WO WO 03/028784 4/2003
WO WO 03/056319 7/2003
WO WO 03/057027 7/2003
WO WO 03/072164 9/2003
WO WO 03/073936 9/2003
WO WO 03/076893 9/2003
WO WO 03/082091 10/2003
WO WO 03/085372 10/2003
WO WO 2004/006982 1/2004
WO WO 2004/015539 2/2004
WO WO 2004/028337 4/2004
WO WO 2004/030726 4/2004
WO WO 2004/034024 4/2004
WO WO 2004/047445 6/2004
WO WO 2004/049237 6/2004
WO WO 2004/054445 7/2004
WO WO 2004/060436 7/2004
WO WO 2004/061420 7/2004
WO WO 2004/090503 10/2004
WO WO 2004/098405 11/2004
WO WO 2004/098682 A2 11/2004
WO WO 2004/098683 11/2004
WO WO 2004/098684 11/2004
WO WO 2004/098685 11/2004
WO WO 2004/107971 12/2004
WO WO 2004/112602 12/2004
WO WO 2005/011779 A1 2/2005
WO WO 2005/018450 3/2005
WO WO 2005/037184 4/2005
WO WO 2005/041766 5/2005
WO WO 2005/045744 5/2005
WO WO 2005/046780 5/2005
WO WO-2005044116 A2 * 5/2005 ......... A61B 17/3415
WO WO 2005/051170 6/2005
WO WO 2005/057175 6/2005
WO WO 2005/065538 7/2005
WO WO 2005/084534 9/2005
WO WO 2005/089103 9/2005
WO WO 2005/092177 10/2005
WO WO 2005/121785 12/2005
WO WO 2005/123186 12/2005
WO WO 2006/001024 1/2006
WO WO 2006/015922 2/2006
WO WO 2006/017358 2/2006
WO WO 2006/020212 2/2006
WO WO 2006/024671 3/2006
WO WO 2006/026741 3/2006
WO WO 2006/036145 4/2006
WO WO 2006/040083 4/2006
WO WO 2006/042811 4/2006
WO WO 2006/061354 6/2006
WO WO 2006/064397 6/2006
WO WO 2006/072035 7/2006
WO WO 2006/079114 7/2006
WO WO 2006/086423 8/2006
WO WO 2006/094513 9/2006
WO WO 2006/108809 10/2006
WO WO 2006/110742 10/2006
WO WO 2006/114297 11/2006
WO WO 2006/118947 11/2006
WO WO 2006/121921 11/2006
WO WO 2006/124099 11/2006
WO WO 2007/002189 1/2007
WO WO 2007/007459 1/2007
WO WO 2007/016399 2/2007
WO WO 2007/019289 2/2007
WO WO 2007/027788 3/2007
WO WO 2007/041069 4/2007
WO WO 2007/041070 4/2007
WO WO 2007/041248 4/2007
WO WO 2007/053832 5/2007
WO WO 2007/056638 5/2007
WO WO 2007/065285 6/2007
WO WO 2007/089738 8/2007
WO WO 2007/092618 8/2007
WO WO 2007/097754 8/2007
WO WO 2007/101223 9/2007
WO WO 2007/120363 10/2007
WO WO 2007/126444 11/2007
WO WO 2007/140783 12/2007
WO WO 2007/143225 12/2007
WO WO 2007/149319 12/2007
WO WO 2008/001366 1/2008
WO WO 2008/014792 2/2008
WO WO 2008/021913 2/2008
WO WO 2008/031106 3/2008
WO WO 2008/031110 3/2008
WO WO 2008/039944 4/2008
WO WO 2008/042760 4/2008
WO WO 2008/048452 4/2008
WO WO 2008/051920 5/2008
WO WO 2008/051924 5/2008
WO WO 2008/052374 5/2008
WO WO 2008/062099 5/2008
WO WO 2008/065646 6/2008
WO WO 2008/073813 6/2008
WO WO 2008/086541 7/2008
WO WO 2008/103620 8/2008
WO WO 2008/114223 9/2008
WO WO 2008/115409 9/2008
WO WO 2008/128210 10/2008
WO WO 2008/129532 10/2008
WO WO 2008/130896 10/2008
WO WO 2008/130897 10/2008
WO WO 2008/130898 10/2008
WO WO 2008/133702 11/2008
WO WO 2008/138006 11/2008
WO WO 2008/143943 11/2008
WO WO 2008/144445 11/2008

(56) References Cited

FOREIGN PATENT DOCUMENTS

| | | | | |
|---|---|---|---|---|
| WO | WO 2008/147921 | | 12/2008 | |
| WO | WO 2008/150917 | | 12/2008 | |
| WO | WO 2008/153693 | | 12/2008 | |
| WO | WO 2008/155377 | | 12/2008 | |
| WO | WO 2008/157821 | | 12/2008 | |
| WO | WO 2009/007287 | | 1/2009 | |
| WO | WO 2009/010396 | | 1/2009 | |
| WO | WO 2009/016635 | | 2/2009 | |
| WO | WO 2009/016638 | | 2/2009 | |
| WO | WO 2009/018058 | | 2/2009 | |
| WO | WO 2006/032653 | | 3/2009 | |
| WO | WO 2009/035773 | | 3/2009 | |
| WO | WO 2009/039013 | | 3/2009 | |
| WO | WO 2009/062674 | | 5/2009 | |
| WO | WO 2009/062675 | | 5/2009 | |
| WO | WO 2009/066288 | A1 | 5/2009 | |
| WO | WO 2009/068661 | | 6/2009 | |
| WO | WO 2009/086216 | | 7/2009 | |
| WO | WO 2009/097594 | | 8/2009 | |
| WO | WO 2010/062898 | | 6/2010 | |
| WO | WO 2010/077329 | | 7/2010 | |
| WO | WO 2010/091005 | | 8/2010 | |
| WO | WO 2010/099507 | | 9/2010 | |
| WO | WO 2010/112521 | | 10/2010 | |
| WO | WO 2010/141922 | | 12/2010 | |
| WO | WO 2011/000528 | | 1/2011 | |
| WO | WO 2011/002815 | | 1/2011 | |
| WO | WO 2011/015659 | | 2/2011 | |
| WO | WO 2011/022418 | | 2/2011 | |
| WO | WO 2011/025549 | | 3/2011 | |
| WO | WO 2011/104616 | | 9/2011 | |
| WO | WO 2011/119896 | | 9/2011 | |
| WO | WO 2011/119898 | A1 | 9/2011 | |
| WO | WO 2012/103429 | | 8/2012 | |
| WO | WO 2013/090215 | | 6/2013 | |
| WO | WO 2016/183493 | | 11/2016 | |
| WO | WO 2017/027749 | | 2/2017 | |
| WO | WO 2017/116915 | | 7/2017 | |
| WO | WO 2017/134227 | | 8/2017 | |
| WO | WO 2018/136898 | | 7/2018 | |
| WO | WO-2018166963 | A1 * | 9/2018 | ......... A61B 17/3468 |
| WO | WO 2019/005627 | A1 | 1/2019 | |
| WO | WO 2019/236850 | | 12/2019 | |
| WO | WO 2019/236859 | | 12/2019 | |
| WO | WO 2019/236876 | | 12/2019 | |
| WO | WO 2022/046416 | A1 | 3/2022 | |
| WO | WO 2022/060677 | | 3/2022 | |

OTHER PUBLICATIONS

AU 2008265541 Examiner's Report, Oct. 15, 2012.
AU 2008265541 Examiner's Report, Nov. 29, 2013.
AU 2011269796 Examiner's Report, Apr. 3, 2014.
AU 2016201703 Examiner's Report, Mar. 22, 2017.
AU 2017254903 Examiner's Report, Dec. 11, 2018.
AU 2018200899 Examiner's Report, Dec. 6, 2018.
CA 2,765,712 Examiner's Report, Apr. 10, 2017.
CA 2,765,712 Examiner's Report, Mar. 27, 2018.
CN 201080027344.1 Office Action, May 5, 2014.
CN 201080027344.1 Office Action, Feb. 6, 2015.
CN 2018080006480.2 Office Action, May 6, 2013.
CN 201080006480.2 Office Action, Dec. 11, 2013.
CN 20180006481.7 Office Action, Dec. 2, 2014.
CN 201180002616.7 Office Action, Apr. 2014.
CN 201180002617.1 Office Action, Jul. 3, 2014.
CN 20160144860.1 Office Action, Mar. 23, 2018.
CN 20160144860.1 Office Action, Dec. 10, 2018.
CN 20160144860.1 Office Action, May 23, 2019.
EP 10739015.5 Extended Search Report, May 10, 2013.
EP 10739031.2 Extended Search Report, May 7, 2013.
EP 10739031.2 Examination Report, Oct. 28, 2016.
EP 10739031.2 Notice of Opposition, Dec. 20, 2018.
EP 10739031.2 Reply to Notice of Opposition, May 21, 2019.
EP 10739031.2 Reply to Notice of Opposition Reply, Aug. 8, 2019.
EP 10739031.2 Summons to Attend Oral Proceedings, Sep. 17, 2019.
EP 10739031.2 Written Submissions, Dec. 3, 2019.
EP 10739031.2 Response to Written Submissions, Jan. 24, 2020.
EP 10739031.2 Summons to Attend Oral Proceedings, May 20, 2020.
EP 10739031.2 Written Submissions, Nov. 20, 2020.
EP 10739031.2 Response to Written Submissions, Jan. 7, 2021.
EP 10739031.2 Decision and Grounds for Revoking Patent, Jun. 9, 2021.
EP 10739031.2 Grounds of Appeal, Oct. 19, 2021.
EP 10739031.2 Response to Grounds of Appeal, Mar. 1, 2022.
EP 10812438.9 Extended European Search Report, Dec. 10, 2013.
EP 11760268.0 Communication from Board of Appeals, Mar. 31, 2022.
EP 11760268.0 Response to Written Submissions, Jan. 14, 2020.
EP 11760268.0 Response to Notice of Appeal, Sep. 15, 2019.
EP 11760268.0 Statement of Grounds of Appeal, Apr. 23, 2019.
EP 11760268.0 Grounds of Appeal, Apr. 18, 2019.
EP 11760268.0 Notice of Appeal ADC, Feb. 25, 2019.
EP 11760268.0 Notice of Appeal Dexcom, Feb. 22, 2019.
EP 11760268.0 Interlocutory Decision, Dec. 13, 2018.
EP 11760268.0 Response to Summons to Attend Oral Proceedings, Sep. 13, 2018.
EP 11760268.0 Letter Regarding the Opposition Procedure, Sep. 12, 2018.
EP 11760268.0 Summons to Attend Oral Proceedings, Mar. 22, 2018.
EP 11760268.0 Comments on Reply to Notice of Opposition, Dec. 27, 2017.
EP 11760268.0 Reply to Notice of Opposition, Sep. 4, 2017.
EP 11760268.0 Notice of Opposition, Mar. 29, 2017.
EP 11760268.0 Extended Search Report, Apr. 14, 2014.
EP 13000105.0 Examination Report, Oct. 18, 2016.
EP 13000105.0 Minutes of the Oral Proceedings, Oct. 18, 2016.
EP 13000105.0 Opposition, Jan. 4, 2019.
EP 15184320.8 Examination Report, Apr. 18, 2017.
EP 16176370.1 Extended Search Report, Dec. 7, 2016.
EP 16793637.6 Extended Search Report, Oct. 9, 2018.
EP 17182379.2 Extended Search Report, Feb. 21, 2018.
EP 17201183.5 Extended Search Report, May 7, 2018.
EP 17201183.5 Examination Report, May 7, 2019.
EP 18192278.2 Extended Search Report, Mar. 13, 2019.
EP 18208224.8 Extended Search Report, Oct. 11, 2019.
EP 18741791.0 Extended Search Report, Sep. 23, 2020.
EP 19151577.4 Extended Search Report, Aug. 16, 2019.
EP 19184881.1 Extended Search Report, Nov. 21, 2019.
EP 20177703.4 Extended Search Report, Sep. 25, 2020.
EP 20177712.5 Extended Search Report, Sep. 30, 2020.
EP 20195922.8 Extended Search Report, Dec. 16, 2020.
EP 21152231.3 Extended Search Report, May 11, 2021.
EP 21192910.4 Extended Search Report, Mar. 31, 2022.
JP 2012-526736 Office Action, Apr. 15, 2014.
JP 2012-526736 Office Action, Dec. 16, 2014.
JP 2013-501503 Office Action, Mar. 3, 2015.
JP 2015-159805 Office Action, Aug. 9, 2016.
JP 2016-44196 Office Action, Apr. 11, 2017.
NL 2009963 Search Report, Aug. 12, 2013.
US Petition For Inter Partes Review Of U.S. Pat. No. 10,945,649, IPR No. 2022-00605, Feb. 15, 2022.
US Petition For Inter Partes Review Of U.S. Pat. No. 11,013,440, IPR No. 2022-00637, Feb. 8, 2022.
WO PCT/US2010/002401 ISR and Written Opinion, Nov. 12, 2010.
WO PCT/US2010/022860 ISR and Written Opinion, Mar. 23, 2010.
WO PCT/US2010/022928 ISR and Written Opinion, Mar. 21, 2010.
WO PCT/US2010/047381 ISR and Written Opinion, Oct. 15, 2010.
WO PCT/US2010/050772 ISR and Written Opinion, Dec. 3, 2010.
WO PCT/US2010/050888 ISR and Written Opinion, Nov. 29, 2010.
WO PCT/US2010/051861 ISR and Written Opinion, Nov. 30, 2010.
WO PCT/US2011/029883 ISR and Written Opinion, Oct. 4, 2012.
WO PCT/US2012/068839 ISR and Written Opinion, Feb. 22, 2013.

(56) References Cited

OTHER PUBLICATIONS

WO PCT/US2016/032485 ISR and Written Opinion, Sep. 12, 2016.
WO PCT/US2018/014745 ISR and Written Opinion, Jun. 4, 2018.
WO PCT/US2021/040541 ISR and Written Opinion, Dec. 20, 2021.
WO PCT/US2021/045576 ISR and Written Opinion, Jan. 27, 2022.
WO PCT/US2021/048086 ISR and Written Opinion, Feb. 28, 2022.
WO PCT/US2021/050672 Isr and Written Opinion, Jan. 5, 2022.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Alcock, S J, et al., "Continuous analyte monitoring to aid clinical practice," IEEE Engineering in Medicine & BioloXY Magazine, 13:319-25 (1994).
Ambade, V. N., et al., "Methods for Estimation of Blood Glucose: A Comparative Evaluation", Medical Journal Armed Forces India, 1998, vol. 54, No. 2, pp. 131-133.
Application Note AN048, Antenna Part No. FR05-S1-N-0-102, Company Reach Xtend™ Bluetooth®, 802.11b/g WLAN Chip Antenna, 2008, pp. 1-13.
Application Note AVR2023—AT86RF231 PCB reference design for antenna diversity, Atmel Corporation, 2008, pp. 1-15.
Application Note nRF9E5 RF and antenna layout, Nordic Semiconductor, 2006, pp. 1-13.
Armour et al., "Application of Chronic Intravascular Blood Glucose Sensor in Dogs," Diabetes, vol. 39, pp. 1519-1526, Dec. 1990.
ASTM International, Designation D2240-05, 2010, pp. 1-13.
Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1071.
Benkič, K., et al., "Using RSSI value for distance estimation in Wireless sensor networks based on ZigBee", 15th International Conference on Systems, Signals and Image Processing, Bratislava, Slovakia, 2008, pp. 1-4.
Bennion, N., et al., "Alternate Site Glucose Testing: A Crossover Design", Diabetes Technology & Therapeutics, vol. 4, No. 1, 2002, pp. 25-33.
Bindra, D.S., et al., "Design and in Vitro Studies of a Needle-Type Glucose Sensor for Subcutaneous Monitoring," Anal. Chem., 63(17): 1692-1696 (Sep. 1, 1991).
Biosensors: Fundamentals and Applications, Turner et al., Eds., 1987, pp. 1-786.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.
"Bluetooth Antenna Design", National Semiconductor Application Note, 2005, pp. 1-16.
Bluetooth Core Specification 4.0, Jun. 30, 2010, Master Table of Contents & Compliance Requirements, pp. 1-89.
Bobbioni-Harsch, E et al., "Lifespan of subcutaneous glucose sensors and their performances during dynamic glycaemia changes in rats," J. Biomed. Eng. 15:457-463 (1993).
Bonnett, A. H., et al., "Squirrel-Cage Rotor Options for AC Induction Motors", IEEE Transactions on Industry Applications, 2001, vol. 37, No. 4, pp. 1197-1209.
Brooks, S. L., et al., "Development of an On-Line Glucose Sensor for Fermentation Monitoring", Biosensors, vol. 3, 1987/88, pp. 45-56.
Callaway, Jr., E. H., "Wireless Sensor Networks: Architectures and Protocols", 2004,.
Chapter 8, Antennas and the Definition of RF Performance, pp. 201-202.
Cass, A.E.G et al., "Ferrocene-Mediated Enzyme Electrode for Amperometric Determination of Glucose," Anal. Chem., 56(4):667-671 (Apr. 1984).
Claremont, D. J., et al., "Biosensors for Continuous In Vivo Glucose Monitoring", Proceedings of the Annual International Conference of the IEEE Engineering in Medicine and Biology Society, vol. 10, 1988.
Clark Jr., L. C., et al., "Electrode Systems for Continuous Monitoring in Cardiovascular Surgery", Annals New York Academy of Sciences, 1962, pp. 29-45.
Clark Jr., L. C., et al., "Long-term Stability of Electroenzymatic Glucose Sensors Implanted in Mice", American Society of Artificial Internal Organs Transactions, vol. XXXIV, 1988, pp. 259-265.
Clarke, W., et al., "Statistical Tools to Analyze Continuous Glucose Monitor Data", Diabetes Technology & Therapeutics, 2009, vol. 11, Suppl. 1, pp. S-45-S-54.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Csoregi, E., et al., "Design, Characterization, and One-Point in Vivo Calibration of a Subcutaneously Implanted Glucose Electrode", Analytical Chemistry, vol. 66 No. 19, 1994, pp. 3131-3138.
In Vivo Glucose Sensing, Cunningham et al., Eds., 2010, Chemical Analysis, vol. 174, pp. 1-466.
IPR2022-00605 (Ex. 1003) Declaration of Gary D. Fletcher, Ph.D dated Feb. 15, 2022, pp. 1-122.
IPR2022-00605 (Ex. 1003) Corrected Declaration of Gary D. Fletcher, Ph.D dated Feb. 18, 2022, pp. 1-124.
IPR2022-00637 (Ex. 1035) Second Declaration of Gary D. Fletcher, Ph.D dated Feb. 28, 2022, pp. 1-136.
Decuir, J., "Bluetooth 4.0: Low Energy", IEEE Scv Consultants' Network of Silicon Valley, 2012, pp. 1-68.
Dehez, B., et al., "Development of a Spherical Induction Motor With Two Degrees of Freedom", IEEE Transactions on Magnetics, 2006, vol. 42, No. 8, pp. 2077-2089.
Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.
DexCom™ STS™ Continuous Glucose Monitoring System User's Guide, 2006, pp. 1-57.
Dexcom STS®-7 Continuous Glucose Monitoring System User's Guide, 2007, pp. 1-74.
Diem, P., et al., "Clinical Performance of a Continuous Viscometric Affinity Sensor for Glucose", Diabetes Technology & Therapeutics, vol. 6, 2004, pp. 790-799.
ECMA International Standard ECMA-340, Near Field Communication Interface and Protocol (NFCIP-1), 2nd Edition, 2004, pp. 1-65.
El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, vol. 1, No. 2, 2007, pp. 181-192.
Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.
Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
File History of U.S. Pat. No. 10,292,632.
File History of U.S. Pat. No. 10,945,649.
File History of U.S. Pat. No. 11,013,440.
U.S. Appl. No. 12/250,760.
Frenzel, L. E., "Printed-Circuit-Board Antennas", retrieved from https://www.electronicdesign.com/technologies/boards/article/21751417/printedcircuitboard-antennasprint/3266, Electronic Design, 2005, pp. 1-4.
Fujipoly Silver ZEBRAR Connector Data Sheet FSDS 01-34, Version 5, 2006, pp. 1-7.
Garg, S., et al., "Improvement in Glycemic Excursions with a Transcutaneous, Real-Time Continuous Glucose Sensor", Diabetes Care, vol. 29, No. 1, 2006, pp. 44-50.

(56) References Cited

OTHER PUBLICATIONS

Gilligan, B. J., et al., "Evaluation of a Subcutaneous Glucose Sensor out to 3 Months in a Dog Model", Diabetes Care, 1994, vol. 17, No. 8, pp. 882-887.
Gonzalez, O. L., et al., "Low-Cost Wireless Sensors—Designer Reference Manual", Freescale Semiconductor, 2007, pp. 1-146.
Gregg, B. A. et al., "Cross-Linked Redox Gels Containing Glucose Oxidase for Amperometric Biosensor Applications," Analytical Chemistry, 62(3):258-263 (Feb. 1, 1990).
Guerra, S., et al., "A Dynamic Risk Measure from Continuous Glucose Monitoring Data",.
Diabetes Technology & Therapeutics, 2011, vol. 13, No. 8, pp. 843-852.
Güler, N. F., et al., "Theory and Applications of Biotelemetry", Journal of Medical Systems, 2002, vol. 26, No. 2, pp. 159-178.
Gunasingham, et al., "Electrochemically Modulated Optrode for Glucose", Biosensors & Bioelectronics, vol. 7, 1992, pp. 353-359.
Hao, Y., "Wireless body sensor networks for health-monitoring applications", Physiol. Meas., 2008, vol. 29, R27-R56.
Harrison, Dj, et al., "Characterization of Perfluorosulfonic Acid Polymer Coated Enzyme Electrodes and a Miniaturized Integrated Potentiostat for Glucose Analysis in Whole Blood," Anal. Chem., 60 (19):2002-2007 (Oct. 1, 1988).
Heftman, G., "Chip Antenna Reduces Cell-Phone Dimensions", Microwaves & RF, 1999, p. 182.
Heise, T., et al., "Hypoglycemia Warning Signal and Glucose Sensors: Requirements and Concepts", Diabetes Technology & Therapeutics, 2003, vol. 5, No. 4, pp. 563-571.
Heller, A., "Electrical Connection of Enzyme Redox Centers to Electrodes," J. Phys. Chern., 96 (9):3579-3587 (1992).
Heller, A., "Electrical Wiring of Redox Enzymes," Acc. Chem. Res., 23(5):129-134 (1990).
Heller, A., "Implanted Electrochemical Glucose Sensors for the Management of Diabetes", Annnu. Rev. Biomed. Eng., 1999, vol. 1, pp. 153-175.
Huang, Y., et al., "Antennas from Theory to Practice", 2008, Chapter 8, Antenna Diversity, pp. 322-325.
Ikeda, T., et al., "Artificial Pancreas—Investigation of the Stability of Glucose Sensors Using a Telemetry System" (English language translation of abstract), Jpn. J. Artif. Organs, vol. 19, No. 2, 1990, 889-892.
"In Vitro Diagnostic Products for Human Use", Federal Register, 1974, vol. 39, No. 126, pp. 24136-24147.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.
James, Jr., et al., "Handbook of Microstrip Antennas", 1969, pp. 1038-1047.
Johnson, K., et al., "In vivo evaluation of an electroenzymatic glucose sensor implanted in subcutaneous tissue," Biosensors and Bioelectronics. 1992, vol. 7, pp. 709-714.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, p. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142, 548, 549.
Klonoff, D. C., "A Review of Continuous Glucose Monitoring Technology", Diabetes Technology & Therapeutics, 2005, vol. 7, No. 5, pp. 770-775.
Kondepati, V., et al., "Recent Progress in Analytical Instrumentation for Glycemic Control in Diabetic and Critically Ill Patients", Analytical Bioanalytical Chemistry, vol. 388, 2007, pp. 545-563.
Koudelka, M., et al., "In-Vivo Behaviour of Hypodermically Implanted Microfabricated Glucose Sensors", Biosensors & Bioelectronics, vol. 6, 1991, pp. 31-36.
Lager, W., et al., "Implantable Electrocatalytic Glucose Sensor", Hormone Metabolic Research, vol. 26, 1994, pp. 526-530.
Leon, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.
Lo, B., et al., "Key Technical Challenges and Current Implementations of Body Sensor Networks", Body Sensor Networks, 2005, pp. 1-5.
Lodwig, V., et al., "Continuous Glucose Monitoring with Glucose Sensors: Calibration and Assessment Criteria", Diabetes Technology & Therapeutics, vol. 5, No. 4, 2003, pp. 573-587.
Lortz, J., et al., "What is Bluetooth? We Explain The Newest Short-Range Connectivity Technology", Smart Computing Learning Series, Wireless Computing, vol. 8, Issue 5, 2002, pp. 72-74.
Loy, M., et al., "ISM—Band and Short Range Device Antennas", Texas Instruments Application Report, 2005, pp. 1-38.
Maidan, R. et al., "Elimination of Electroaxidizable Interferant-Produced Currents in Amperometric Biosensors," Analytical Chemistry, 64(23):2889-2896 (Dec. 1, 1992).
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
Mastrototaro, J.J., et al., "An Electroenzymatic Glucose Sensor Fabricated on a Flexible Substrate," Sensors and Biosensors B Chemical, B5: 139-144 (1991).
McGarraugh, G., et al., "Glucose Measurements Using Blood Extracted from the Forearm and the Finger", TheraSense, Inc., 2001, 16 Pages.
McGarraugh, G., et al., "Physiological Influences on Off-Finger Glucose Testing", Diabetes Technology & Therapeutics, vol. 3, No. 3, 2001, pp. 367-376.
McKean, B., et al., "A Telemetry-Instrumentation System for Chronically Implanted Glucose and Oxygen Sensors," IEEE Transactions on Biomedical Engineering, vol. 35, No. 7, (Jul. 1988), pp. 526-532.
IPR2022-00605 (Ex. 1027) The Merriam-Webster Dictionary, Merriam Webster, Incorporated (2005), pp. 66, 403, and 415.
Microchip Technology Inc., MRF24J40MA Data Sheet, 2008, pp. 1-30.
Minimed Technologies, "Tape Tips and Other Infusion Site Information", 1995.
Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.
Moatti-Sirat, D., et al., "Reduction of Acetaminophen Interference in Glucose Sensors by a Composite Nafion Membrane: Demonstration in Rats and Man", Diabetologia, vol. 37, 1994, pp. 610-616.
Moatti-Sirat, D., et al., "Towards continuous glucose monitoring: in vivo evaluation of a miniaturized glucose sensor implanted for several days in rat subcutaneous tissue," Diabetolocia, 35(3) (1 page--Abstract only) (Mar. 1992).
Moore, B., "The Potential Use of Radio Frequency Identification Devices for Active Monitoring of Blood Glucose Levels", Journal of Diabetes Science and Technology, 2009, vol. 3, No. 1, pp. 180-183.
Morak, J., et al., "Design and Evaluation of a Telemonitoring Concept Based on NFC- Enabled Mobile Phones and Sensor Devices", IEEE Transactions on Information Technology in Biomedicine, 2012, vol. 16, No. 1, pp. 17-23.
Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.

(56) References Cited

OTHER PUBLICATIONS

"Murata Puts Antenna on a Chip", Passives, 1999, vol. 44, 1 page.
Ohara, T. J., et al., "Glucose Electrodes Based on Cross-Linked [Os(bpy)2CI]+/2+ Complexed Poly(1-vinylimadazole) Films," Analytical Chemistry, 65(23):3512-3516 (Dec. 1, 1993).
Olievier, C. N., et al., "In Vivo Measurement of Carbon Dioxide Tension with a Miniature Electrodes", Pflugers Archiv: European Journal of Physiology, vol. 373, 1978, pp. 269-272.
Opinion of the Court, Supreme Court of the United States, No. 04-1350, *KSR International co*., Petitioner v. *Teleflex Inc et al*., Apr. 30, 2007.
Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.
Pickup, J., "Developing Glucose Sensors for In Vivo Use", Tibtech, vol. 11, 1993, pp. 285-291.
Pickup, J., et al., "Implantable Glucose Sensors: Choosing the Appropriate Sensing Strategy", Biosensors, vol. 3, 1987/88, pp. 335-346.
Pickup, J. C., et al., "In vivo molecular sensing in diabetes mellitus: an implantable glucose sensor with direct electron transfer," Diabetologia, 32(3):213-217 (1989).
Pickup, J., et al., "Potentially-Implantable, Amperometric Glucose Sensors with Mediated Electron Transfer: Improving the Operating Stability", Biosensors, vol. 4, 1989, pp. 109-119.
Pishko, M. V., et al., "Amperometric Glucose Microelectrodes Prepared Through Immobilization of Glucose Oxidase in Redox Hydrogels," Anal. Chem., 63(20):2268-2272 (Oct. 15, 1991).
Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetolgia, vol. 36, 1993, pp. 658-663.
Poitout, V., et al., "Calibration in Dogs of a Subcutaneous Miniaturized Glucose Sensor Using a Glucose Meter for Blood Glucose Determination", Biosensors & Bioelectronics, vol. 7, 1992, pp. 587-592.
Poitout, V., et al., "In vitro and in vivo evaluation in dogs of a miniaturized glucose sensor," ASAIO Transactions, 37(3) (1 page--Abstract only) (Jul.- Sep. 1991).
Quinn, C. P., et al., "Kinetics of Glucose Delivery to Subcutaneous Tissue in Rats Measured with 0.3-mm Amperometric Microsensors", The American Physiological Society, 1995, E155-E161.
Ratner, B. D., "Reducing Capsular Thickness and Enhancing Angeiogenesis Around Implant Drug Release Systems", Journal of Controlled Release, vol. 78, 2002, pp. 211-218.
Reach, G., et al., "Can Continuous Glucose Monitoring Be Used for the Treatment of Diabetes?," Analytical Chemistry, 64(6):381-386 (Mar. 15, 1992).
Rebrin, K., et al., "Automated Feedback Control of Subcutaneous Glucose Concentration in Diabetic Dogs," Diabetologia, 32(8):573-576 (Aug. 1989).
Repas, R., "Sensor Sense: RFID for smart position sensing", retrieved from https://www/machinedesign/com/automation-iiot/article/21818777/sensor-sense-rfid-for-smart-position-sensing, 2 pages.
Rodriguez, N., et al., "Flexible Communication and Control Protocol for Injectable Neuromuscular Interfaces", IEEE Transactions on Biomedical Circuits and Systems, IEEE, vol. 1, No. 1, 2007, pp. 19-27.
Roe, J. N., et al., "Bloodless Glucose Measurements", Critical Review in Therapeutic Drug Carrier Systems, vol. 15, Issue 3, 1998, pp. 199-241.
IPR2022-00605 (Ex. 1024) "Rotor," Dictionary of Mechanical Engineering, Fourth Ed., G.H.F. Nayler, Society of Automotive Engineers, Inc., 1996, p. 328.
IPR2022-00605 (Ex. 1025) "Rotor," Random House Kernerman Webster's College Dictionary, K Dictionaries Ltd. (2010), available at https://www.thefreedictionary.com/rotor.
IPR2022-00605 (Ex. 1026) "Rotate," Random House Kernerman Webster's College Dictionary, K Dictionaries Ltd. (2010), available at https://www.thefreedictionary.com/rotate.
Sakakida, M., et al., "Ferrocene-mediate needle-type glucose sensor covered with newly designed biocompatible membrane," Sensors and Actuators B, 13-14:319-322 (1993).
Sakakida, M., et al., "Development of ferrocene-mediated needle-type glucose sensor as a measure of true subcutaneous tissue glucose concentrations", Artif Organs Today. 1992, vol. 2, No. 2, pp. 145-458.
Salditt, P., "Trends in Medical Device Design and Manufacturing", SMTA News and Journal of Surface Mount Technology, vol. 17, 2004, pp. 19-24.
Salehi, C., et al., "A Telemetry-Instrumentation System for Long-Term Implantable Glucose and Oxygen Sensors", Analytical Letters, vol. 29, No. 13, 1996, pp. 2289-2308.
Sandham, W., et al., "Blood Glucose Prediction for Diabetes Therapy Using a Recurrent Artificial Neural Network", 9th European Signal Processing Conference, 1998, Rhodes, Greece, pp. 1-4.
IPR2022-00605 (Ex. 1013) Scheduling Order in *Abbott Diabetes Care Inc., et al.* v. *Dexcom, Inc*., 1:21-cv-00977 (D. Del.), dated Dec. 2, 2021.
Scheller, F., et al., "Enzyme Electrodes and Their Application", Philosophical Transactions of The Royal Society of London B, vol. 316, 1987, pp. 85-94.
Schmidt, F. J., et al., "Calibration of a Wearable Glucose Sensor", The International Journal of Artificial Organs, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.
Sharawi, M. S., "Use of low-cost patch antennas in modern wireless technology", IEEE Potentials, 2006, pp. 35-38 and 47.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancrearetomized Dogs with a Wearable Artificial Endocrine Pancreas," Diabetologia, 24(3):179-184 (Mar. 1983).
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device with Needle-type Glucose Sensor: A Useful Tool for Blood Glucose Monitoring in Diabetic Individuals," Diabetes Care, vol. 9, No. 3 (May-Jun. 1986), pp. 298-301.
Shichiri, M., et al., "In vivo characteristics of needle-type glucose sensor—Measurement of subcutaneous glucose concentrations in human volunteers," Horm Metab Res Suppl. 1988, vol. 20, pp. 17-20.
Shichiri, M., et al., "Wearable artificial endocrine pancreas with needle-type glucose sensor," The Lancet, 1982, vol. 2, No. 8308, pp. 1129-1131.
Shults, M., "A Telemetry-Instrumentation System for Monitoring Multiple Subcutaneously Implanted Glucose Sensors," IEEE Transactions on Biomedical Engineering, vol. 41, No. 10 (Oct. 1994), pp. 937-942.
Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.
Sternberg, R., et al., "Study and Development of Multilayer Needle-type Enzyme-based Glucose Microsensors," Biosensors, 4:27-40 (1988).

(56) References Cited

OTHER PUBLICATIONS

Thompson, M., et al., "In Vivo Probes: Problems and Perspectives", Clinical Biochemistry, vol. 19, 1986, pp. 255-261.
Townsend, K., et al., "Getting Started with Bluetooth Low Energy—Chapter 1", 2014, pp. 1-26.
Tung, S., "Layers of Security for Active RFID Tags", RFID Handbook: Applications, Technology, Security, and Privacy, Edited by Ehson, et al., Chapter 33, 2008, pp. 1-28.
Turner, A.P.F., et al., "Diabetes Mellitus: Biosensors for Research and Management", Biosensors, 1:85-115 (1985).
Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous In vivo Monitoring, Chapter 4, 1997, pp. 117-137.
Updike, S. J., et al., "A Subcutaneous Glucose Sensor With Improved Longevity, Dynamic Range, and Stability of Calibration", Diabetes Care, 2000, vol. 23, pp. 208-214.
Velho, G., et al., "In Vitro and In Vivo Stability of Electrode Potentials in Needle-Type Glucose Sensors", Diabetes, vol. 38, No. 2, 1989, pp. 164-171.
Velho, G. et al., "Strategies for calibrating a subcutaneous glucose sensor," Biomed. Biochim. Acta, 48 (11112):957-964 (1989).
Von Woedtke, T., et al., "In Situ Calibration of Implanted Electrochemical Glucose Sensors", Biomedica Biochimica Acta, vol. 48, 1989, pp. 943-952.
Wang, X.H., et al., "Bluetooth: Opening a blue sky for healthcare", Mobile Information Systems, 2006, vol. 2, pp. 151-167.
Waterhouse, R., "Printed Antennas for Wireless Communications," 2007, pp. 116-129 and 284-289.
Wilson, G. S. et al., "Progress toward the Development of an Implantable Sensor for Glucose," Clinical Chemistry, 38(9):1613-1617 (1992).
Wong, KL, "Planar Antennas for Wireless Communications," 2003, Chapter 1, Introduction and Overview, pp. 4-17, 38-45, and 218-221.
Ye, L. et al., "High Current Density "Wired" Quinoprotein Glucose Dehydrogenase Electroade," Anal. Chem., 65(3):238-241 (Feb. 1, 1993).
Z-Carbon Connector, retrieved from http://www.zaxisconnector.com/SS_zc.shtml, 2004, 2 pages.
Z-Silver Connector, retrieved from http://www.zaxisconnector.com/SS_zs.shtml, 2004, 2 pages.
AU 2007309066 Examiner's Report, Jul. 12, 2012.
AU 2007309066 Examiner's Report, Aug. 16, 2013.
AU 2010286917 Examiner's Report, Sep. 8, 2014.
AU 2011230596 Examiner's Report, Feb. 28, 2014.
CN 200780045373.9 Notice of Allowance, May 18, 2011.
CN 200780045373.9 Office Action, Apr. 14, 2010.
EP 06804122.7 Decision to Refuse the Application, Feb. 25, 2013.
EP 06804122.7 Examination Report, Nov. 30, 2011.
EP 06804122.7 Examination Report, Jan. 25, 2011.
EP 06815715.5 Extended Search Report, Oct. 30, 2009.
EP 07842173.2 Examination Report, Mar. 21, 2013.
EP 07842173.2 Extended Search Report, Dec. 29, 2010.
EP 07842180.7 Examination Report, Oct. 23, 2012.
EP 07842180.7 Examination Report, Dec. 14, 2011.
EP 07842180.7 Examination Report, Feb. 23, 2011.
EP 07842180.7 Extended Search Report, Sep. 28, 2009.
EP 21211041.5 Extended Search Report, Mar. 3, 2002.
IL 198329 Office Action, Mar. 5, 2012.
JP 2009-534798 Office Action, Sep. 25, 2012.
MX MX/a/2009/004398 Office Action, Sep. 24, 2012.
US Reexamination U.S. Appl. No. 95/002,162 Request to Review Order Denying Request for Reexamination, Dec. 13, 2012.
US Reexamination U.S. Appl. No. 95/002,162 Order Denying Request for Reexamination, Nov. 13, 2012.
US Request for Reexamination Appl. No. 95/002,162 of U.S. Pat. No. 8,175,673, Sep. 7, 2012.
US Reexamination U.S. Appl. No. 95/002,113 Request to Review Order Denying Request for Reexamination, Dec. 13, 2012.
US Reexamination U.S. Appl. No. 95/002,113 Order Denying Request for Reexamination, Nov. 13, 2012.
US Request for Reexamination U.S. Appl. No. 95/002,113 of U.S. Pat. No. 6,990,366, Aug. 30, 2012.
US Reexamination U.S. Appl. No. 90/011,730 Notice of Intent to Issue Ex Parte Reexamination Certificate, Apr. 5, 2012.
US Reexamination U.S. Appl. No. 90/011,730 Office Action, Jan. 11, 2012.
US Reexamination U.S. Appl. No. 90/011,730 Order Granting Request for Reexamination, Aug. 24, 2011.
US Request for Reexamination U.S. Appl. No. 90/011,730 of U.S. Pat. No. 6,990,366, Jun. 3, 2011.
US Reexamination U.S. Appl. No. 90/010,791 Ex Parte Reexamination Certificate, May 17, 2011.
US Reexamination U.S. Appl. No. 90/010,791 Office Action, Dec. 17, 2010.
US Reexamination U.S. Appl. No. 90/010,791 Office Action, May 28, 2010.
US Reexamination U.S. Appl. No. 90/010,791 Order Granting Request for Reexamination, Feb. 22, 2010.
US Request for Reexamination U.S. Appl. No. 90/010,791 of U.S. Pat. No. 6,990,366, Dec. 22, 2009.
US Reexamination U.S. Appl. No. 90/009,328 Notice of Intent to Issue Ex Parte Reexamination Certificate, Nov. 20, 2009.
US Reexamination U.S. Appl. No. 90/009,328 Office Action, Sep. 30, 2009.
US Reexamination U.S. Appl. No. 90/009,328 Office Action, Aug. 4, 2009.
US Reexamination U.S. Appl. No. 90/009,328 Order Granting Request for Reexamination, Dec. 9, 2008.
US Request for Reexamination U.S. Appl. No. 90/009,328 of U.S. Pat. No. 6,990,366, Nov. 10, 2008.
US Reexamination U.S. Appl. No. 90/009,104 Notice of Intent to Issue Ex Parte Reexamination Certificate, Nov. 20, 2009.
US Reexamination U.S. Appl. No. 90/009,104 Office Action, Sep. 30, 2009.
US Reexamination U.S. Appl. No. 90/009,104 Office Action, Aug. 4, 2009.
US Reexamination U.S. Appl. No. 90/009,104 Office Action, Oct. 16, 2008.
US Reexamination U.S. Appl. No. 90/009,104 Order Granting Request for Reexamination, Jun. 5, 2008.
US Request for Reexamination U.S. Appl. No. 90/009,104 of U.S. Pat. No. 6,990,366, Apr. 8, 2008.
US Reexamination U.S. Appl. No. 90/008,457 Notice of Intent to Issue Ex Parte Reexamination Certificate, Mar. 13, 2008.
US Reexamination U.S. Appl. No. 90/008,457 Order Granting Request for Reexamination, Feb. 23, 2007.
US Request for Reexamination U.S. Appl. No. 90/008,457 of U.S. Pat. No. 6,990,366, Jan. 23, 2007.
US Request for Reexamination U.S. Appl. No. 90/008,172 of U.S. Pat. No. 6,990,366, Aug. 16, 2006.
US Reexamination U.S. Appl. No. 90/007,910 Patent Board Decision, May 17, 2013.
US Reexamination U.S. Appl. No. 90/007,910 Decision on Appeal, Jan. 18, 2011.
US Reexamination U.S. Appl. No. 90/007,910 Advisory Action, Jul. 30, 2009.
US Reexamination U.S. Appl. No. 90/007,910 Advisory Action, Feb. 6, 2009.
US Reexamination U.S. Appl. No. 90/007,910 Examiner's Answer to Appeal Brief, Nov. 19, 2009.
US Reexamination U.S. Appl. No. 90/007,910 Office Action, Oct. 2, 2008.
US Reexamination U.S. Appl. No. 90/007,910 Office Action, Feb. 13, 2008.
US Reexamination U.S. Appl. No. 90/007,910 Order Granting Request for Reexamination, Mar. 27, 2006.
US Request for Reexamination U.S. Appl. No. 90/007,910 of U.S. Pat. No. 6,175,752, Feb. 1, 2006.

(56) References Cited

OTHER PUBLICATIONS

US Reexamination U.S. Appl. No. 90/009,270 Order Denying Request for Reexamination, Dec. 1, 2008.
US Request for Reexamination U.S. Appl. No. 90/009,270 of U.S. Pat. No. 6,175,752, Sep. 8, 2008.
US Reexamination U.S. Appl. No. 90/009,497 Notice of Intent to Issue Reexamination Certificate, Aug. 23, 2010.
US Reexamination U.S. Appl. No. 90/009,497 Order Granting Request, Jul. 30, 2009.
US Request for Reexamination U.S. Appl. No. 90/009,497 of U.S. Pat. No. 6,175,752, Jun. 17, 2009.
WO PCT/US2006/037312 ISR and Written Opinion, Apr. 17, 2007.
WO PCT/US2006/037928 ISR and Written Opinion, Jul. 11, 2008.
WO PCT/US2007/078065 ISR and Written Opinion, Apr. 11, 2008.
WO PCT/US2007/078073 ISR and Written Opinion, Apr. 11, 2008.
WO PCT/US2007/082114 ISR and Written Opinion, May 9, 2008.
WO PCT/US2011/029881 ISR and Written Opinion, May 20, 2011.
WO PCT/US2011/029884 ISR and Written Opinion, Jun. 1, 2011.
WO PCT/US2013/052397 ISR and Written Opinion, Dec. 2, 2013.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.
Anderson, L. B., et al., "Thin-Layer Electrochemistry: Steady-State Methods of Studying Rate Processes", Journal of ElectroAnalytical Chemistry, 1965, vol. 10, pp. 295-305.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Bindra, D.S., et al., "Pulsed Amperometric Detection of Glucose in Biological Fluids at a Surface-Modified Gold Electrode", American Chemical Society, 1989, vol. 61, No. 22, pp. 2566-2570.
Brandt, J., et al., "Covalent Attachment of Proteins to Polysaccharide Carriers by Means of Benzoquinone", Biochimica et Biophysica Acta, 1975, vol. 386, pp. 196-202.
Brownlee, M., et al., "A Glucose-Controlled Insulin-Delivery System: Semisynthetic Insulin Bound to Lectin", Science, 1979, vol. 206, pp. 1190-1191.
Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.
Cass, A.E.G et al., "Ferricinium lon as an Electron Acceptor for Oxido-Reductases", Journal of ElectroAnalytical Chemistry, 1985, vol. 190, pp. 117-127.
Castner, J. F., et al., "Mass Transport and Reaction Kinetic Parameters Determined Electrochemically for Immobilized Glucose Oxidase", Biochemistry, 1984, vol. 23, No. 10, pp. 2203-2210.
Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.
Clark Jr., L. C., et al., "Differential Anodic Enzyme Polarography for the Measurement of Glucose", Oxygen Transport to Tissue: Instrumentation, Methods, and Physiology, 1973, pp. 127-133.
Clarke, W. L., et al., "Evaluating Clinical Accuracy of Systems for Self-Monitoring of Blood Glucose", Diabetes Care, 1987, vol. 10, No. 5, pp. 622-628.
Complaint *Abbott Diabetes Care Inc.* v. *Dexcom, Inc.* U.S. District Court Delaware C.A. No. 05-590 filed Aug. 11, 2005.
Complaint, Amended, *Abbott Diabetes Care Inc.* v. *Dexcom, Inc.* U.S. District Court Delaware C.A. No. 05-590 filed Jun. 27, 2006.
Complaint *Abbott Diabetes Care Inc.* v. *Dexcom, Inc.* U.S. District Court Delaware C.A. No. 06-514 filed Aug. 17, 2006.
Csoregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.
Cullen, M.T., et al., "The Changing Presentations of Diabetic Ketoacidosis During Pregnancy", Amer. J. Perinatol, 1996, vol. 13, No. 7, pp. 449-451 (abstract only).
Davis, G., "Electromechanical Techniques for the Development of Amperometric Biosensors", Biosensors, 1985, vol. 1, pp. 161-178.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.
Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.
Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.
Dicks, J.M., et al., "Ferrocene Modified Polypyrrole with Immobilised Glucose Oxidase and Its Application in Amperometric Glucose Microbiosensors", Annales de Biologie Clinique, 1989, vol. 47, pp. 607-619.
Ellis, C. D., et al., "Selectivity and Directed Charge Transfer through an Electroactive Metallopolymer Film", Journal of the American Chemical Society, 1981, vol. 103, No. 25, pp. 7480-7483.
Engstrom, R. C., "Electrochemical Pretreatment of Glassy Carbon Electrodes", Analytical Chemistry, 1982, vol. 54, No. 13, pp. 2310-2314.
Engstrom, R. C., et al., "Characterization of Electrochemically Pretreated Glassy Carbon Electrodes", Analytical Chemistry, 1984, vol. 56, No. 2, pp. 136-141.
Feldman, B., et al., "Electron Transfer Kinetics at Redox Polymer/Solution Interfaces Using Microelectrodes and Twin Electrode Thin Layer Cells", Journal of ElectroAnalytical Chemistry, 1985, vol. 194, pp. 63-81.
U.S. Appl. No. 60/587,787.
Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.
Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.
Foulds, N. C., et al., "Immobilization of Glucose Oxidase in Ferrocene-Modified Pyrrole Polymers", Analytical Chemistry, 1988, vol. 60, No. 22, pp. 2473-2478.
Freedman, D., et al., Statistics: Second Edition, 1991, Chapter 5, p. 74.
Frew, J. E., et al., "Electron-Transfer Biosensors", Philosophical Transactions of the Royal Society of London, 1987, vol. 316, pp. 95-106.
Gorton, L., et al., "Selective Detection in Flow Analysis Based on the Combination of Immobilized Enzymes and Chemically Modified Electrodes", Analytica Chimica Acta, 1991, vol. 250, pp. 203-248.
Gregg, B. A., et al., "Redox Polymer Films Containing Enzymes. 1. A Redox-Conducting Epoxy Cement: Synthesis, Characterization,

(56) References Cited

OTHER PUBLICATIONS and Electrocatalytic Oxidation of Hydroquinone", Journal of Physical Chemistry, 1991, vol. 95, No. 15, pp. 5970-5975.
Hale, P. D., et al., "A New Class of Amperometric Biosensor Incorporating a Polymeric Electron-Transfer Mediator", Journal of the American Chemical Society, 1989, vol. 111, No. 9, pp. 3482-3484.
Hawkridge, F. M., et al., "Indirect Coulometric Titration of Biological Electron Transport Components", Analytical Chemistry, 1973, vol. 45, No. 7, pp. 1021-1027.
Heller, A., et al., "Amperometric Biosensors Based on Three-Dimensional Hydrogel-Forming Epoxy Networks", Sensors and Actuators B, 1993, vol. 13-14, pp. 180-183.
Hoel, P. G., Elementary Statistics: Fourth Edition, 1976, Chapter 5, pp. 113-114.
Ianniello, R. M., et al., "Immobilized Enzyme Chemically Modified Electrode as an Amperometric Sensor", Analytical Chemistry, 1981, vol. 53, No. 13, pp. 2090-2095.
Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.
Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.
Ikeda, T., et al., "Glucose Oxidase- Immobilized Benzoquinone-Carbon Paste Electrode as a Glucose Sensor", Agricultural and Biological Chemistry, 1985, vol. 49, No. 2, pp. 541-543.
Johnson, J. M., et al., "Potential-Dependent Enzymatic Activity in an Enzyme Thin-Layer Cell", Analytical Chemistry, 1982, vol. 54, No. 8, pp. 1377-1383.
Johnson, K. W., "Reproducible Electrodeposition of Biomolecules for the Fabrication of Miniature Electroenzymatic Biosensors", Sensors and Actuators B, 1991, vol. 5, pp. 85-89.
Jonsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.
Josowicz, M., et al., "Electrochemical Pretreatment of Thin Film Platinum Electrodes", Journal of the Electrochemical Society, 1988, vol. 135, No. 1, pp. 112-115.
Jovanovic, L., "The Role of Continuous Glucose Monitoring in Gestational Diabetes Mellitus", Diabetes Technology & Therapeutics, 2000, vol. 2, Supplement 1, pp. S-67-S-71.
Katakis, I., et al., "L-α-Glycerophosphate and ⌊-Lactate Electrodes Based on the Electrochemical 'Wiring' of Oxidases", Analytical Chemistry, 1992, vol. 64, No. 9, pp. 1008-1013.
Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.
Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine) $_2$Cl] $^{+/2+}$", Journal of the Chemical Society, Faraday Transactions, 1996, vol. 92, No. 20, pp. 4131-4136.
Kulys, J., et al., "Mediatorless Peroxidase Electrode and Preparation of Bienzyme Sensors", Bioelectrochemistry and Bioenergetics, 1990, vol. 24, pp. 305-311.
Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.
Mcneil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.
Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.
Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.
Mougiakakou, S. G., et al., "A Real Time Simulation Model of Glucose-Insulin Metabolism for Type 1 Diabetes Patients", Proceedings of the 2005 IEEE, 2005, pp. 298-301.
Nagy, G., et al., "A New Type of Enzyme Electrode: The Ascorbic Acid Eliminator Electrode", Life Sciences, 1982, vol. 31, No. 23, pp. 2611-2616.
Nakamura, S., et al., "Effect of Periodate Oxidation on the Structure and Properties of Glucose Oxidase", Biochimica et Biophysica Acta., 1976, vol. 445, pp. 294-308.
Narasimham, K., et al., "ρ-Benzoquinone Activation of Metal Oxide Electrodes for Attachment of Enzymes", Enzyme and Microbial Technology, 1985, vol. 7, pp. 283-286.
Ohara, T. J., et al., "Wired' Enzyme Electrodes for Amperometric Determination of Glucose or Lactate in the Presence of Interfering Substances", Analytical Chemistry, 1994, vol. 66, No. 15, pp. 2451-2457.
Ohara, T. J., "Osmium Bipyridyl Redox Polymers Used in Enzyme Electrodes", Platinum Metals Review, 1995, vol. 39, No. 2, pp. 54-62.
Osmonics, Poretics® Polycarbonate Membrane; Product Leaflet; Engineering Purity.
Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.
Palleschi, G., et al., "A Study of Interferences in Glucose Measurements in Blood by Hydrogen Peroxide Based Glucose Probes", Analytical Biochemistry, 1986, vol. 159, pp. 114-121.
Pankratov, I., et al., "Sol-Gel Derived Renewable-Surface Biosensors", Journal of ElectroAnalytical Chemistry, 1995, vol. 393, pp. 35-41.
Parker, R., et al., "Robust Ho Glucose Control in Diabetes Using a Physiological Model", AIChE Journal, 2000, vol. 46, No. 12, 2000, pp. 2537-2549.
Pathak, C., et al., "Rapid Photopolymerization of Immunoprotective Gels in Contact with Cells and Tissue", Journal of the American Chemical Society, 1992, vol. 114, No. 21, pp. 8311-8312.
Pollak, A., et al., "Enzyme Immobilization by Condensation Copolymerization into Cross-Linked Polyacrylamide Gels", Journal of the American Chemical Society, 1980, vol. 102, No. 20, pp. 6324-6336.
Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.
Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.
Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.
Sittampalam, G., et al., "Surface-Modified Electrochemical Detector for Liquid Chromatography", Analytical Chemistry, 1983, vol. 55, No. 9, pp. 1608-1610.
Soegijoko, S., et al., "External Artificial Pancreas: A New Control Unit Using Microprocessor", Hormone and Metabolic Research Supplement Series, 1982, vol. 12, pp. 165-169.
Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.
Sternberg, F., et al., "Calibration Problems of Subcutaneous Glucosensors when Applied "In-Situ" in Man", Hormone and Metabolic Research, 1994, vol. 26, pp. 523-526.

(56) References Cited

OTHER PUBLICATIONS

Sternberg, R., et al., "Covalent Enzyme Coupling on Cellulose Acetate Membranes for Glucose Sensor Development", Analytical Chemistry, 1988, vol. 60, No. 24, pp. 2781-2786.
Suekane, M., et al., "Immobilization of Glucose Isomerase", Zettschrift fur Allgemeine Mikrobiologie, 1982, vol. 22, No. 8, pp. 565-576.
Tajima, S., et al., "Simultaneous Determination of Glucose and 1,5-Anydroglucitol", Chemical Abstracts, 1989, vol. 111, No. 25, p. 394.
Tarasevich, M. R., "Bioelectrocatalysis", Comprehensive Treatise of Electrochemistry, 1985, vol. 10, pp. 231-295.
Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.
Taylor, C., et al., ""Wiring" of Glucose Oxidase Within a Hydrogel Made with Polyvinyl Imidazole Complexed with [(Os-4,4'-dimethoxy-2,2'-bipyridine)CI]$^{+/2+}$", Journal of ElectroAnalytical Chemistry, 1995, vol. 396, pp. 511-515.
Trojanowicz, M., et al., "Enzyme Entrapped Polypyrrole Modified Electrode for Flow-Injection Determination of Glucose", Biosensors & Bioelectronics, 1990, vol. 5, pp. 149-156.
Turner, R.F.B., et al., "A Biocompatible Enzyme Electrode for Continuous in vivo Glucose Monitoring in Whole Blood", Sensors and Actuators B, 1990, vol. 1, pp. 561-564.
Tuzhi, P., et al., "Constant Potential Pretreatment of Carbon Fiber Electrodes for in Vivo Electrochemistry", Analytical Letters, 1991, vol. 24, No. 6, pp. 935-945.
Umana, M., "Protein-Modified Electrochemically Active Biomaterial Surface", U.S. Army Research Office, Analytical and Chemical Sciences Research Triangle Institute, 1988, pp. 1-9.
United States Court of Appeals for the Federal Circuit, No. 06-1402, *Leapfrog Enterprises, Inc.* v. *Fisher-Price, Inc. and Mattel, Inc.*, May 9, 2007.
Urban, G., et al., "Miniaturized Thin-Film Biosensors Using Covalently Immobilized Glucose Oxidase", Biosensors & Bioelectronics, 1991, vol. 6, pp. 555-562.
Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.
Vreeke, M., et al., "Hydrogen Peroxide and B-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.
Wang, D. L., et al., "Miniaturized Flexible Amperometric Lactate Probe", Analytical Chemistry, 1993, vol. 65, No. 8, pp. 1069-1073.
Wang, J., et al., "Activation of Glassy Carbon Electrodes by Alternating Current Electrochemical Treatment", Analytica Chimica Acta, 1985, vol. 167, pp. 325-334.
Wang, J., et al., "Amperometric Biosensing of Organic Peroxides with Peroxidase-Modified Electrodes", Analytica Chimica Acta, 1991, vol. 254, pp. 81-88.
Wang, J., et al., "Screen-Printable Sol-Gel Enzyme-Containing Carbon Inks", Analytical Chemistry, 1996, vol. 68, No. 15, pp. 2705-2708.
Wang, J., et al., "Sol-Gel-Derived Metal-Dispersed Carbon Composite Amperometric Biosensors", Electroanalysis, 1997, vol. 9, No. 1, pp. 52-55.
Williams, D. L., et al., "Electrochemical-Enzymatic Analysis of Blood Glucose and Lactate", Analytical Chemistry, 1970, vol. 42, No. 1, pp. 118-121.
Yabuki, S., et al., "Electro-Conductive Enzyme Membrane", Journal of the Chemical Society, Chemical Communications, 1989, pp. 945-946.
Yang, L., et al., "Determination of Oxidase Enzyme Substrates Using Cross-Flow Thin-Layer Amperometry", Electroanalysis, 1996, vol. 8, No. 8-9, pp. 716-721.
Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.
Yao, T., "A Chemically-Modified Enzyme Membrane Electrode as an Amperometric Glucose Sensor", Analytica Chimica Acta, 1983, vol. 148, pp. 27-33.
Yildiz, A., et al., "Evaluation of an Improved Thin-Layer Electrode", Analytical Chemistry, 1968, vol. 40, No. 7, pp. 1018-1024.
Zamzow, K., et al., "New Wearable Continuous Blood Glucose Monitor (BGM) and Artificial Pancreas (AP)", Diabetes, 1990, vol. 39, pp. 5A-20.
Zhang, Y., et al., "Application of Cell Culture Toxicity Tests to the Development of Implantable Biosensors", Biosensors & Bioelectronics, 1991, vol. 6, pp. 653-661.
Zhang, Y., et al., "Elimination of the Acetaminophen Interference in an Implantable Glucose Sensor", Analytical Chemistry, 1994, vol. 66, No. 7, pp. 1183-1188.
Zhu, J., et al., "Fabrication and Characterization of Glucose Sensors Based on a Microarray $H_2O_2$ electrode", Biosensors & Bioelectronics, 1994, vol. 9, pp. 295-300.
EP 21211041.5 Extended Search Report, Mar. 3, 2022.
US Request for Reexamination U.S. Appl. No. 95/002,162 of U.S. Pat. No. 8,175,673, Sep. 7, 2012.
US Reexamination U.S. Appl. No. 90/009,497 Notice of Intent to Issue Reexamination Certificate, Aug. 13, 2010.
ACCU-CHEK Compact Plus Owner's Booklet, 2008, pp. 1-100.
ACCU-CHEK Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Cleo™ 90 Infusion Set, 510(k) Summary of Safety and Effectiveness, pp. 1-618.
Cleo® 90 Infusion Set Training Guide, 1 page.
Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.
Freestyle Navigator Summary of Safety and Effectiveness Data, 2008, pp. 1-27.
Freestyle Navigator User's Guide, 2008, pp. 1-195.
Guardian® RT Continuous Glucose Monitoring System Ref MMT-7900 User Guide, 2005, pp. 1-128.
Medtronic Guardian® REAL-Time Continuous Glucose Monitoring System User Guide, 2006, pp. 1-181.
Narasimham, K., et al., "p. Benzoquinone Activation of Metal Oxide Electrodes for Attachment of Enzymes", Enzyme and Microbial Technology, 1985, vol. 7, pp. 283-286.
OmniPod Insulet UST400 User Manual, 2011, pp. 1-190.
Parker, R., et al., "Robust H∞ Glucose Control in Diabetes Using a Physiological Model", AIChE Journal, 2000, vol. 46, No. 12, 2000, pp. 2537-2549.
Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.
Zamzow, K., et al., "New Wearable Continuous Blood Glucose Monitor (BGM) and Artificial Pancreas (AP)", Diabetes, 1990, vol. 39, p. 5A-20.
Cox, M., "An Overview of Continuous Glucose Monitoring Systems", Journal of Pediatric Health Care, 2009, vol. 23, No. 5, pp. 344-347.
Darley, J., "Is your user experience as good as your technology?", 2019, retrieved from https://www.massdevice.com/is-your-user-experience-as-good-as-your-technology/, pp. 1-16.
IPR2022-00605 (Ex. 2001) Declaration of Michael Cima, Ph.D dated May 24, 2022, pp. 1-70.
IPR2022-00637 (Ex. 2001) Declaration of Michael Cima, Ph.D dated Jun. 9, 2022, pp. 1-79.
Delve Talks: Jake Leach, Dexcom, retrieved from https://www.delve.com/podcasts/delve- talks-jake-leach-dexcom, pp. 1-9.

(56) References Cited

OTHER PUBLICATIONS

"Dexcom CEO tells investors not to fear new competition from Abbott's Freestyle Libre", 2017, retrieved from https://www.mobihealthnews.com/content/dexcom-ceo-tells-investors-not-fear-new-competition-abbotts-freestyle-libre, pp. 1-3.
Dexcom G5 Mobile System User Guide, 2020, pp. 1-410.
Dexcom G6, Winner Health & Wellness Award, Core77 Design Awards, 2019, retrieved from https://designawards.core77.com/health-wellness/85111/Dexcom-G6, pp. 1-8.
Freestyle Navigator Continuous Glucose Monitor FDA Premarket Approval (PMA), May 2022, pp. 1-6.
Gonzales, W. V., et al., "The Progress of Glucose Monitoring-A Review of Invasive to Minimally and Non-Invasive Techniques, Devices and Sensors", Sensors, 2019, vol. 19, No. 800, pp. 1-45.
Gregg, T. H., "How Continuous Glucose Monitoring is Transforming Diabetes Treatment", Qualcomm Life Connect, 2013, pp. 1-33.
Hirsch, I. B., "Introduction: History of Glucose Monitoring", Clinical Compendia, 2018, vol. 2018, No. 1, 1 page.
Howe, D., "Comparing the Dexcom G6 To the G5", 2018, retrieved from https://beyondtype1.org/comparing-the-dexcom-g6-to-the-g5/, pp. 1-10.
Medtronic Guardian® REAL-Time Continuous Glucose Monitoring System User Guide, 2006, pp. 1-184.
IPR2022-00605 (Ex. 2008) MiniMed® Glucose Sensor, Ref MMT-7002, Instructions for Use, pp. 1-4.
MINIMED Quick-set™ retrieved from https://web.archive.org/web/20010412224824/http://www.minimed.com/patientfam/pf_ipt_pum pinfusion_quickset.shtml, pp. 1-2.
MINIMED Sof-set Micro QRR Sof-set Ultimate QR® retrieved from https://web.archive.org/web/20010412225617/http://www.minimed.com/patientfam/pf_ipt_pum pinfusion_sofset.shtml, pp. 1-2.
IPR2022-00605 (Ex. 2003) "Monitoring Your Blood Sugar", retrieved from https://www.cdc.gov/diabetes/managing/managing-blood-sugar/bloodglucosemonitoring.html, pp. 1-3.
Patton, S. R., et al., "Continuous Glucose Monitoring Versus Self-monitoring of Blood Glucose in Children with Type 1 Diabetes—Are there Pros and Cons for Both?", US Endocrinol 12, vol. 8, No. 1, pp. 27-29.
EP 10739031.2 Response to Response to Grounds of Appeal, Jul. 29, 2022.
EP 11760268.0 Decision of the Oral Proceedings, Sep. 27, 2022.
EP 11760268.0 Minutes of Oral Proceedings, Aug. 11, 2022.
EP 19151577.4 Examination Report, May 27, 2022.
EP 19900891.3 Extended Search Report, Sep. 26, 2002.
EP 20177703.4 Grounds of Opposition, Sep. 28, 2022.
EP 20177703.4 Notice of Opposition, Sep. 28, 2022.
EP 20177703.4 Examination Report, Jun. 25, 2021.
EP 22168031.7 Extended Search Report, Aug. 17, 2022.
EP 22169853.3 Extended Search Report, Sep. 2, 2022.
MY PI2021004760 Examination Report, Mar. 30, 2022.
MY PI2021005830 Examination Report, Sep. 30, 2022.
MY PI2021005830 Examination Report, Aug. 29, 2022.
US Institution Decision, IPR No. 2022-00605, Jul. 27, 2022.
US Patent Owner's Preliminary Sur-Reply, IPR No. 2022-00605, Jun. 28, 2022.
US Petitioner's Preliminary Reply to Patent Owner's Preliminary Response, IPR No. 2022-00605, Jun. 21, 2022.
US Patent Owner's Preliminary Response, IPR No. 2022-00605, May 24, 2022.
US Institution Decision, IPR No. 2022-00637, Jul. 27, 2022.
US Patent Owner's Preliminary Sur-Reply, IPR No. 2022-00637, Jun. 28, 2022.
US Petitioner's Preliminary Reply to Patent Owner's Preliminary Response, IPR No. 2022-00637, Jun. 21, 2022.
US Patent Owner's Preliminary Response, IPR No. 2022-00637, Jun. 9, 2022.
WO PCT/US22/37291 Invitation to Pay Additional Fees, Sep. 29, 2022.
Affidavit of Richard Paragas signed on May 18, 2016, pp. 1-4.
Affidavit of Paul Neale signed on May 18, 2016, pp. 1-2.
Certified U.S. Appl. No. 60/424,099, filed Nov. 5, 2002.
Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.
Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.
De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.
U.S. Appl. No. 10/633,367.
Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.
Kovatchev, B. P., et al., "Evaluating the Accuracy of Continuous Glucose-Monitoring Sensors", Diabetes Care, 2004, vol. 27, No. 8, pp. 1922-1928.
Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.
Medtronic MiniMed Sen-Serter® User Guide, 2006, pp. 1-96.
Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.
Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.
Tsalikian, e., et al., "Accuracy of the GlucoWatch G2® Biographer and the Continuous Glucose Monintoring System During Hypoglycemia: Experience of the Diabetes Research in Children Network", Diabetes Care, 2004, vol. 27, No. 3, pp. 722-726.
Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.
CA 2,872,576 Examiner's Report, Feb. 17, 2015.
CA 2,872,576 Examiner's Report, Feb. 19, 2016.
CA 3,120,335 Examiner's Report, Mar. 31, 2023.
CA 3,182,961 Examiner's Report, Mar. 29, 2023.
CN 201980082748.1 First Office Action, Jan. 10, 2023.
EP 06851063.5 Extended Search Report, Sep. 21, 2009.
EP 07843396.8 Extended Search Report, Dec. 22, 2010.
EP 10739031.2 Response to Response to Response to Grounds of Appeal, Jan. 18, 2023.
EP 13000104.3 Extended Search Report, Mar. 12, 2013.
EP 14179905.6 Summons to Attend Oral Proceedings, Apr. 10, 2017.
EP 14179905.6 Notice of Opposition, May 19, 2016.
EP 14179905.6 Extended Search Report, Dec. 23, 2014.
EP 15002441.2 Extended Search Report, Dec. 18, 2015.
EP 20177703.4 Reply to Opposition, Feb. 22, 2023.
EP 20177712.5 Grounds of Opposition Guide & Partner Patent, Dec. 22, 2022.
EP 20177712.5 Grounds of Opposition Decom, Dec. 22, 2022.
EP 20177712.5 Notice of Opposition Guide & Partner Patent, Dec. 22, 2022.
EP 20177712.5 Notice of Opposition Dexcom, Dec. 22, 2022.
EP 20195922.8 Grounds of Opposition Dexcom, Jan. 26, 2023.
EP 20195922.8 Notice of Opposition Dexcom, Jan. 26, 2023.
JP 2021-531135 Office Action, Feb. 22, 2023.
WO PCT/US2006/062690 ISR and Written Opinion, Jan. 2, 2008.
WO PCT/US2007/079774 ISR and Written Opinion, Apr. 1, 2008.
WO PCT/US2022/037291 ISR and Written Opinion, Nov. 22, 2022.
WO PCT/US2023/010054 Invitation to Pay Additional Fees, Mar. 24, 2023.

(56) References Cited

OTHER PUBLICATIONS

CN 201980082748.1 Second Office Action, Jul. 10, 2023.
EP 20177703.4 Reply to Reply to Notice of Opposition, Jun. 29, 2023.
EP 20177703.4 Notice of Intervention, Jun. 23, 2023.
EP 20177712.5 Notice of Intervention, Jun. 23, 2023.
EP 20177712.5 Reply of Opposition, May 23, 2023.
EP 20195922.8 Reply to Notice of Opposition, Jun. 20, 2023.
EP 20195922.8 Notice of Intervention, Jun. 13, 2023.
MY PI2022007295 Examination Report, Jul. 11, 2023.
US Final Written Decision, IPR No. 2022-00605, Jul. 10, 2023.
WO PCT/US2012/062551 ISR and Written Opinion, Jan. 2, 2013.
WO PCT/US2023/010054 ISR and Written Opinion, May 15, 2023.
Anderson, A. J., "Foundations of Computer Technology", 1994, pp. 55-57.
Kal, S., "Basic Electronics—Devices, Circuits and IT Fundamentals", 2006, Chapter 13, Microcomputers and Microprocessors, p. 412.
"Abbott Receives CE Mark for Freestyle® Libre, A Revolutionary Glucose Monitoring System for People With Diabetes", 2014, 7 pages.
"Alcove", Webster's New College Dictionary, 2001, p. 26.
Boise, M., "Dexcom CEO Kevin Sayer Explains G6", 2018, retrieved from https://beyondtype1.org/dexcom-ceo-kevin-sayer-explains-g6/, 9 pages.
Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.
Certified True Copy of Preliminary Amendment filed on Apr. 20, 2018 for U.S. Pat. No. 10,827,954, 7 pages.
Certified True Copy of Excerpts of the File History of U.S. Pat. No. 10,973,443, 22 pages.
CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.
"Deciding When to Submit a 510(k) for a Change to an Existing Device, Guidance for Industry and Food and Drug Administration Staff", 2017, pp. 1-77.
"Deciding When to Submit a 510(k) for a Software Change to an Existing Device, Guidance for Industry and Food and Drug Administration Staff", 2017, pp. 1-31.
Dexcom CEO—Prime Position in Our Market—Mad Money—CNBC.mp4, Transcript 2023 by Sonix, 2 pages.
DexCom (DXCM) 2017 Q4 Earnings Call Transcript, 2017, retrieved from https://docoh.com/transcript/1093557/2017Q4/DXCM, 11 pages.
DexCom (DXCM) Q1 2018 Results—Earnings Call Transcript, 2018, retrieved from https://seekingalpha.com/article/4168949-dexcom-dxcm-q1-2018-results-earnings-call-transcript, 4 pages.
Dexcom, Inc. NasdaqGS:DXCM Company Conference Presentation, 2019, 10 pages.
Dexcom, Inc. NasdaqGS:DXCM Company Conference Presentation, 2020, 9 pages.
Dexcom, Inc. NasdaqGS:DXCM Company Conference Presentation, 2021, 16 pages.
Dexcom G6 Continuous Glucose Monitoring System User Guide, 2019, pp. 1-27.
Dexcom G6 Start Here Set up Guide, pp. 1-8.
Dexcom G6 Using Your G6 Guide, Mar. 2020, pp. 1-7.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Dexcom Seven® Plus Continuous Glucose Monitoring System User's Guide, 2011, pp. 1-144.
DexCom™ STS™ Continuous Glucose Monitoring System Summary of Safety and Effectiveness Data, 2006, 20 pages.
DexCom™ STS™ Sensor Instructions for Use, 2006, pp. 1-6.
Dexcom STS-7 Continuous Glucose Monitoring System FDA Premarket Approval (PMA), 2007, pp. 1-7.
Dexcom STS®-7 Continuous Glucose Monitoring System Summary of Safety and Effectiveness Data, 2007, 14 pages.
Diglas, J., et al., "Reduced pain perception with Pen Mate™, an automatic needle insertion device for use with an insulin pen", Practical Diabetes International, 1999, vol. 16, No. 2, pp. 39-41.
"Does Dexcom Really Have a Future If It Can't Match Abbott's Scale", 2019, retrieved from https://www.sprucepointcap.com/reports/dxcm_research_thesis_3-21-2019.pdf, p. 46.
Email from John Shaw of Shaw & Keller dated May 16, 2023, 2 pages.
Email chain from Sophie Hood, oldest email dated Jan. 24, 2023, 5 pages.
European Standard, ISO 11607-1, Packaging for terminally sterilized medical devices—Part 1: Requirements for materials, sterile barrier systems and packaging systems, 2006, 32 pages.
European Standard, ISO 13485, Medical deviceS—Quality management systems—Requirement for regulatory purposes, 2003, 69 pages.
European Standard, ISO 15197, In vitro diagnostic test systems—Requirements for blood glucose monitoring systems for self-testing in managing diabetes mellitus, 2003, 43 pages.
Explore The Monroe Street Market Community, retrieved from https://www.monroestreetmarket.com/floor-plans/apartment/B-231 on May 10, 2023, 2 pages.
"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
Food and Drug Administration, HHS, 2009, Code of Federal Regulation § 820.30, Subpart C-Design Controls, pp. 147-148.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
Hemmerich, K. J., et al., "Sterilization Methods Stand the Test of Time", 2004, retrieved from https://www.mddionline.com/sterilization/sterilization-methods-stand-test-time, pp. 1-8.
Hirsch, I. B., "Realistic Expectations and Practical Use of Continuous Glucose Monitoring for the Endocrinologist", The Journal of Clinical Endocrinology & Metabolism, 2009, vol. 94, No. 7, pp. 2232-2238.
Hoss, U., et al., "Continuous glucose monitoring in the tissue: Do we really need to calibrate in-vivo?", Feb. 28, 2009, pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Hughes, M. D., "The Business of Self-Monitoring of Blood Glucose: A Market Profile", Journal of Diabetes Science and Technology, 2009, vol. 3, No. 5, pp. 1219-1223.
IEEE 100 The Authoritative Dictionary of IEEE Standards Terms, Seventh Edition, 2000, 3 pages.
International Standard, ISO 14971, Medical devices—Application of risk management to medical devices, 2007, 90 pages.
"An Interview with Kevin Sayer, President and CEO of Dexcom, About The New G6", 2021, 5 pages.
Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.

(56) References Cited

OTHER PUBLICATIONS

Medtronic MiniMed Guardian RT FDA Premarket Approval (PMA), 2005, pp. 1-6.
Medtronic MiniMed Guardian RT Summary of Safety and Effectiveness Data, 2005, 13 pages.
Medtronic MiniMed Paradigm® REAL-TIME 522 and 722 Insulin Pumps User Guide, 2008, pp. 1-262.
Occupational Safety and Health Admin., Labor, 2003, 29 CFR § 1910.1030 Bloodborne pathogens, pp. 260-273.
Omnipod image, Exhibit 182 of ADC Reply Brief SJ, Daubert, Sep. 22, 2022, 2 pages.
OneTouch® Ultra™ Blood Glucose Monitoring System Owner's Booklet, 2000, 23 pages.
One Touch Ultra2 Blood Glucose Monitoring System Owner's Booklet, 2005, 34 pages.
Order, Federal Communications Commission, 2006, pp. 1-8.
Panteleon, A. E., et al., "The Role of the Independent Variable to Glucose Sensor Calibration", Diabetes Technology & Therapeutics, 2003, vol. 5, No. 3, pp. 401-410.
Parker, S. P., ed., McGraw-Hill Dictionary of Mechanical and Design Engineering, 1984 (excerpted), pp. 1-4.
Program, 2$^{nd}$ International Conference on Advanced Technologies & Treatments for Diabetes, Athens, Greece, 2009, 3 pages.
"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
Shenoi, B. A., ed., Introduction to Digital Signal Processing and Filter Design, 2006, "Introduction", Chapter 1, pp. 1-30.
Smith, S. S., ed., The Scientist and Engineer's Guide to Digital Signal Processing, Second Edition, 1997-1999, "Digital Signal Processors", Chapter 28, pp. 503-534.
"Submission and Review of Sterility Information in Premarket Notification (510(k)) Submissions for Devices Labeled as Sterile, Guidance for Industry and Food and Drug Administration Staff", 2016, pp. 1-11.
Tegnestedt, C., et al., "Levels and sources of sound in the intensive care unit—an observational study of three room types", Acta Anaesthiesiologica Scandinavica, 2013, pp. 1-10.
Watkin, J., "An Introduction to Flash Gluclose Monitoring", 14 pages.
CA 2,617,192 Examiner's Report, Oct. 22, 2012.
CA 2,984,939 Examiner's Report, Nov. 15, 2023.
CA 3,182,961 Examiner's Report, Dec. 6, 2023.
CN 200780039416.2 Second Office Action, Apr. 25, 2012.
CN 200780039416.2 First Office Action, Mar. 30, 2011.
CN 200880005388.7 Second Office Action, May 16, 2012.
CN 200880005388.7 First Office Action, Jul. 25, 2011.
CN 201980082748.1 Final Office Action, Nov. 27, 2023.
EP 06788869.3 Examination Report, Sep. 25, 2012.
EP 06788869.3 Extended Search Report, Mar. 18, 2010.
EP 06813967.4 Extended Search Report, Mar. 4, 2010.
EP 07854298.2 Extended Search Report, Mar. 29, 2010.
EP 08730066.1 Extended Search Report, Oct. 5, 2012.
EP 10739031.2 Communication from Board of Appeals, Feb. 21, 2024.
EP 10739031.2 Summons to Attend Oral Proceedings, Oct. 26, 2023.
EP 18741791.0 Examination Report, Dec. 15, 2023.
EP 20177703.4 Summons to Attend Oral Proceedings, Apr. 29, 2024.
EP 20177703.4 Reply to Reply to Reply to Notice of Opposition ADC, Dec. 18, 2023.
EP 20177703.4 Reply to Notice of Intervention, Nov. 17, 2023.
EP 20177712.5 Response to Written Submissions Dexcom, Feb. 26, 2024.
EP 20177712.5 Written Submissions ADC, Jan. 26, 2024.
EP 20177712.5 Reply to Reply to Reply to Notice of Opposition ADC, Dec. 18, 2023.
EP 20177712.5 Reply to Notice of Intervention, Nov. 17, 2023.
EP 20177712.5 Reply to Reply to Notice of Opposition Dexcom, Sep. 27, 2023.
EP 20177712.5 Reply to Reply to Notice of Opposition Guide & Partner Patent, Aug. 30, 2023.
EP 20195922.8 Written Submissions Decxom, Mar. 15, 2024.
EP 20195922.8 Response to Summons to Attend Oral Proceedings, Feb. 15, 2024.
EP, 20195922.8 Written Submissions Dexcom, Dec. 12, 2023.
EP 20195922.8 Written Submissions ADC, Oct. 23, 2023
EP 20195922.8 Summons to Attend Oral Proceedings, Sep. 21, 2023.
EP 20195922.8 Reply to Notice of Intervention, Aug. 29, 2023.
EP 20195922.8 Reply to Reply to Notice of Opposition, Aug. 21, 2023.
EP 20211041.5 Grounds of Opposition Dexcom, Mar. 28, 2024.
EP 21211041.5 Notice of Opposition Dexcom, Mar. 28, 2024.
EP 23166498.8 Extended Search Report, Nov. 17, 2023.
EP 23190032.5 Extended Search Report, Nov. 17, 2023.
GB Claim No. HP-2021000025 Approveed Judgement, Oct. 18, 2023.
JP 2009-534799 Final Office Action, Feb. 19, 2013.
JP 2009-534799 Office Action, Sep. 27, 2011.
JP 2021-531135 Office Action, Aug. 9, 2023.
MX MX/a/2009/004322 Office Action, Mar. 11, 2013.
MX MX/a/2009/004322 Office Action, Sep. 19, 2012.
MY PI2023005466 Examination Report, Dec. 28, 2023.
RU 2009135048 Office Action, Dec. 20, 2011.
RU 2009119430 Office Action, Jun. 5, 2011.
US Third Declaration of Gary Fletcher, Ph.D., IPR No. 2024-00520.
US Petition For Inter Partes Review Of U.S. Pat. No. 11,266,335, IPR No. 2024-00520, Jan. 31, 2024.
US Patent Owner's Preliminary Response, IPR No. 2023-01409, Jan. 18, 2024.
US Notice of Filing Date Accorded to Petition and Time for Filing Patent Owner Preliminary Response, IPR No. 2023-01409, Oct. 18, 2023.
US Petition For Inter Partes Review Of U.S. Pat. No. 11,202,591, IPR No. 2023-01409, Oct. 11, 2023.
US Patent Owner's Response to Petitioner's Explanation of Material Differences Between Petitions, IPR Nos. 2023-01396 and 2023-01397, Jan. 18, 2024.
US Petitioner's Explanation of Material Differences Between Petitions, IPR No. 2023-01397, Oct. 6, 2023.
US Declaration of Gary D. Fletcher, Ph.D, IPR No. 2023-01396 and IPR No. 2023-01397, Oct. 6, 2023.
US Petition For Inter Partes Review Of U.S. Pat. No. 11,266,335, IPR No. 2023-01397, Oct. 6, 2023.
US Patent Owner's Preliminary Response, IPR No. 2023-01396, Jan. 18, 2024.
US Notice of Filing Date Accorded to Petition and Time for Filing Patent Owner Preliminary Response, IPR No. 2023-01396, Oct. 18, 2023.
US Petitioner's Explanation of Material Differences Between Petitions, IPR No. 2023-01396, Oct. 6, 2023.
US Petition For Inter Partes Review Of U.S. Pat. No. 11,266,335, IPR No. 2023-01396, Oct. 6, 2023.
US Notice of Final Written Decision re Inter Partes Review of the '649 Patent, IPR No. 2022-00605, Jul. 13, 2023.
US Record of Oral Hearing, IPR No. 2022-00605, Apr. 26, 2023.
US Second Declaration by Dr. Michael Cima in Support of Patent Owner's Response, IPR No. 2022-00605, Oct. 19, 2022.
US Patent Owner's Response, IPR No. 2022-00605, Oct. 19, 2022.
US Reexamination U.S. Appl. No. 90/019,329 Order Granting Request for Reexamination of U.S. Pat. No. 11,013,440, Jan. 23, 2024.
US Request for Ex Parte Reexamination Under 35.U.S.C. §§ 302-307 and 37 C.F.R. § 1.510 of U.S. Pat. No. 11,013,440, Dec. 11, 2023.

(56) References Cited

OTHER PUBLICATIONS

US Reexamination U.S. Appl. No. 90/019,331 Order Granting Request for Reexamination of U.S. Pat. No. 11,000,216, Jan. 23, 2024.
US Request for Ex Parte Reexamination Under 35.U.S.C. §§ 302-307 and 37 C.F.R. § 1.510 of U.S. Pat. No. 11,000,216, Dec. 11, 2023.
US Reexamination U.S. Appl. No. 90/019,307 Order Granting Request for Reexamination of U.S. Pat. No. 10,973,443, Dec. 22, 2023.
US Request for Ex Parte Reexamination Under 35.U.S.C. §§ 302-307 and 37 C.F.R. § 1.510 of U.S. Pat. No. 10,973,443, Nov. 27, 2023.
US Reexamination U.S. Appl. No. 90/019,330 Order Granting Request for Reexamination of U.S. Pat. No. 10,959,654, Jan. 23, 2024.
US Request for Ex Parte Reexamination Under 35.U.S.C. §§ 302-307 and 37 C.F.R. § 1.510 of U.S. Pat. No. 10,959,654, Dec. 11, 2023.
WO PCT/US2006/029541 ISR and Written Opinion, Apr. 24, 2007.
WO PCT/US2006/033885 ISR and Written Opinion, Aug. 3, 2007.
WO PCT/US2007/082121 ISR and Written Opinion, May 9, 2008.
WO PCT/US2008/054186 ISR and Written Opinion, Aug. 8, 2008.
WO PCT/US2008/065154 ISR and Written Opinion, Sep. 3, 2008.
WO PCT/US2010/047065 ISR and Written Opinion, Dec. 21, 2010.
WO PCT/US2010/047414 ISR and Written Opinion, Dec. 27, 2010.
WO PCT/US2010/047415 ISR and Written Opinion, Oct. 25, 2010.
CA 2,984,939 Examiner's Report, Aug. 7, 2024.
CA 3,120,335 Examiner's Report, May 27, 2024.
CN 200880005149.1 Notice of Allowance, Jun. 21, 2013.
CN 200880005149.1 Fourth Office Action, Dec. 3, 2012.
CN 200880005149.1 Third Office Action, Feb. 16, 2012.
CN 200880005149.1 Second Office Action, Aug. 17, 2011.
CN 200880005149.1 First Office Action, Jul. 29, 2010.
DE Complaint in Litigation of EP 3300658, Mar. 20, 2024.
EP 10739031.2 Decision of Oral Proceedings, Jun. 11, 2024.
EP 10739031.2 Minutes of Oral Proceedings, May 10, 2024.
EP 17182379.2 Grounds of Opposition, Jul. 12, 2024.
EP 17182379.2 Notice of Opposition, Jul. 12, 2024.
EP 17182379.2 Reply to Examination Report, Apr. 9, 2021.
EP 17182379.2 Reply to Search Report, Oct. 3, 2018.
EP 20177712.5 Response to Summons to Attend Oral Proceedings, Aug. 30, 2024.
20177712.5 Summons to Attend Oral Proceedings.
20195922.8 Grounds of Appeal.
20195922.8 Notice of Appeal.
20195922.8 Written Submissions Dexcom.
20195922.8 Decision Revoking the European Patent.
20195922.8 Minutes of the Oral Proceedings.
21211041.5 Reply to Notice of Opposition.
23166498.8 Examination Report.
24152079.0 Extended Search Report.
24152079.0 Partial Search Report.
MX/a/2021/007294 Office Action.
2009134334 Office Action.
First Expert Opinion of Dr Michael Schoemaker of Litigation of EP 3977921.
Notice of Filing Date Accorded to Petition and Time for Filing Patent Owner Preliminary Response, IPR No. 2024-00860.
Declaration of Dr. Cameron Riviere, Ph.D., IPR No. 2024-00860.
Petition For Inter Partes Review Of U.S. Pat. No. 11,510,625, IPR No. 2024-00860.
Decision Denying Institution of Inter Partes Review, IPR No. 2024-00520.
Patent Owner's Authorized Sur-Reply to Petitioner's Reply to Patent Owner's Preliminary Response, IPR No. 2024-00520.
Petitioner's Authorized Reply to Patent Owner's Preliminary Response, IPR No. 2024-00520.
Patent Owner's Preliminary Response, IPR No. 2024- 00520.
Patent Owner's Exhibit List, IPR2024-00520.
Telephonic Hearing, IPR2024-00520.
Petitioner's Explanation of Material Differences Between the Petition in IPR2024-00520 and Previously Filed Petitions in IPR2023-01396 and IPR2023-01397, IPR No. 2024-00520, Jan. 31, 2024.
US Order, IPR No. 2023-01409, May 30, 2024.
US Notice of Stipulation, IPR No. 2023-01409, May 29, 2024.
US Patent Owner's Objections to Petitioner's Exhibits to the Petition, IPR No. 2023-01409, Apr. 29, 2024.
US Patent Owner's Request for Rehearing by the Director, IPR 2023-01409, Apr. 29, 2024.
US Email of Peter McAndrews, IPR 2023-01409, Apr. 29, 2024.
US Decision Granting Institution of Inter Partes Review, IPR No. 2023-01409, Apr. 15, 2024.
US Scheduling Order, IPR 2023-01409, Apr. 15, 2024.
US Order Conduct of the Proceeding 37 C.F.R. § 42.5, IPR No. 2023-01409.
US Petitioner's Updated Exhibit List, IPR No. 2023-01409, Feb. 5, 2024.
US Telephonic Conference Call, IPR No. 2023-01409, Feb. 2, 2024.
US Patent Owner's Updated Mandatory Notices, IPR No. 2023-01409, Feb. 2, 2024.
US Email of Andrew M. Mason, IPR 2023-01409, Jan. 30, 2024.
US Decision Denying Institution of Inter Partes Review, IPR No. 2023-01397, Apr. 16, 2024.
US Patent Owner's Updated Exhibit List, IPR2023-01397, Mar. 25, 2024.
US Telephonic Hearing, IPR2023-01397, Mar. 13, 2024.
US Petitioner's Updated Mandatory Notices Pursuant to 37 C.F.R. § 42.8(a)(3), IPR No. 2023-01397, Feb. 19, 2024.
US Patent Owner's Updated Mandatory Notices, IPR No. 2023-01397, Feb. 2, 2024.
US Patent Owner's Preliminary Response, IPR No. 2023-01397, Jan. 18, 2024.
US Petitioner's Request for Rehearing of Decision Denying Institution, IPR No. 2023-01396, May 16, 2024.
US Decision Denying Institution of Inter Partes Review, IPR No. 2023-01396, Apr. 16, 2024.
US Patent Owner's Updated Exhibit List, IPR No. 2023-01396, Mar. 25, 2024.
US Telephonic Hearing, IPR2023-01396, Mar. 13, 2024.
US Petitioner's Updated Mandatory Notices Pursuant to 37 C.F.R. § 42.8(a)(3), IPR No. 2023-01396, Feb. 19, 2024.
US Reexamination U.S. Appl. No. 90/019,307 Petition Under 37 CFR § 1.181 to Terminate, Aug. 15, 2024.
US Reexamination U.S. Appl. No. 90/019,307 Decision on Petitions, Aug. 7, 2024.
US Reexamination U.S. Appl. No. 90/019,307 Petition Under 37 CFR § 1.59 to Expunge Application Papers, Aug. 1, 2024.
US Reexamination U.S. Appl. No. 90/019,307 Petition Under 37 CFR § 1.59 to Expunge Application Papers, Jun. 12, 2024.
US Reexamination U.S. Appl. No. 90/019,307 Notification of Concurrent Proceedings, May 15, 2024.
US Reexamination U.S. Appl. No. 90/019,307 Petition Under 37 CFR §§ 1.182 and/or § 1.183 to Allow Filing and Consideration of Response to Patent Owner's Extraordinary Petition to Suspend, Mar. 19, 2024.
US Reexamination U.S. Appl. No. 90/019,307 Petition Under 37 CFR § 1.181 and/or § 1.183 to Suspend, Mar. 1, 2024.
US Reexamination U.S. Appl. No. 90/019,329 Decision on Petition Under 37 C.F.R. § 1.59, Sep. 16, 2024.
US Reexamination U.S. Appl. No. 90/019,329 Petition Under 37 C.F.R. § 1.182 to Seal Document Versions Filed via IDS and Substitute Redacted Document Versions Therfor, Aug. 1, 2024.
US Reexamination U.S. Appl. No. 90/019,329 Petition Under 37 CFR § 1.59 to Expunge Application Papers, Aug. 1, 2024.
US Reexamination U.S. Appl. No. 90/019,329 Ex Parte Reexamination Interview Summary, Jul. 25, 2024.
US Reexamination U.S. Appl. No. 90/019,329 Decision on Petition Under 37 C.F.R. § 1.59, Jul. 22, 2024.
US Reexamination U.S. Appl. No. 90/019,329 Decision Sua Sponte Vacating Notice of Intent to Issue Ex Parte Reexamination Certificate, Jul. 3, 2024.

(56) References Cited

OTHER PUBLICATIONS

US Reexamination U.S. Appl. No. 90/019,329 Petition Under 37 CFR § 1.59 to Expunge Application Papers, Jun. 12, 2024.
US Reexamination U.S. Appl. No. 90/019,329 Notification of Concurrent Proceedings, May 15, 2024.
US Petition Under 37 CFR § 1.181 and/or § 1.182 to Terminate Reexamination U.S. Appl. No. 90/019,329, Apr. 26, 2024.
US Reexamination U.S. Appl. No. 90/019,329 Order Granting Request for Reexamination of U.S. Pat. No. 11,013,440, Jan. 30, 2024.
US Reexamination U.S. Appl. No. 90/019,329 Declaration of Gary D. Fletcher, Ph.D, Dec. 11, 2023.
US Reexamination U.S. Appl. No. 90/019,330 Decision on Petition Under 37 C.F.R. § 1.59, Sep. 16, 2024.
US Reexamination U.S. Appl. No. 90/019,330 Decision Granting Petition and Vacating a Reexamination Certificate, Aug. 26, 2024.
US Reexamination U.S. Appl. No. 90/019,330 Petition Under 37 C.F.R. § 1.182 to Seal Document Versions Filed via IDS and Substitute Redacted Document Versions Therfor, Aug. 1, 2024.
US Reexamination U.S. Appl. No. 90/019,330 Petition Under 37 CFR § 1.59 to Expunge Application Papers, Aug. 1, 2024.
US Ex Parte Reexamination Certificate of U.S. Pat. No. 10,959,654, Aug. 5, 2024.
US Reexamination U.S. Appl. No. 90/019,330 Petition to Withdraw From Issue and Reopen the Proceeding, Jul. 26, 2024.
US Reexamination U.S. Appl. No. 90/019,330 Decision on Petition Under 37 C.F.R. § 1.59, Jul. 16, 2024.
US Reexamination U.S. Appl. No. 90/019,330 Notice of Intent to Issue Ex Parte Reexamination Certificate of U.S. Pat. No. 10,959,654, Jul. 1, 2024.
US Reexamination No. U.S. Appl. No. 90/019,330 Petition Under 37 CFR § 1.59 to Expunge Application Papers, Jun. 12, 2024.
US Reexamination U.S. Appl. No. 90/019,330 Notification of Concurrent Proceedings, May 15, 2024.
US Reexamination U.S. Appl. No. 90/019,330 Declaration of John Mastrototaro, Ph.D, Dec. 11, 2023.
US Reexamination U.S. Appl. No. 90/019,331 Decision on Petition Under 37 C.F.R. § 1.59, Sep. 16, 2024.
US Reexamination U.S. Appl. No. 90/019,331 Decision Granting Petition, Aug. 26, 2024.
US Reexamination U.S. Appl. No. 90/019,331 Petition Under 37 C.F.R. § 1.182 to Seal Document Versions Filed via IDS and Substitute Redacted Document Versions Therfor, Aug. 1, 2024.
US Reexamination U.S. Appl. No. 90/019,331 Petition Under 37 CFR § 1.59 to Expunge Application Papers, Aug. 1, 2024.
US Reexamination U.S. Appl. No. 90/019,331 Petition to Withdraw From Issue and Reopen the Proceeding, Jul. 26, 2024.
US Reexamination U.S. Appl. No. 90/019,331 Decision on Petition Under 37 C.F.R. § 1.59, Jul. 16, 2024.
US Reexamination U.S. Appl. No. 90/019,331 Notice of Intent to Issue Ex Parte Reexamination Certificate, Jul. 10, 2024.
US Reexamination U.S. Appl. No. 90/019,331 Notification of Concurrent Proceedings, May 15, 2024.
WO PCT/US2008/054165 ISR and Written Opinion, Jun. 5, 2008.
WO PCT/US2008/067791 ISR and Written Opinion, Sep. 30, 2008.
WO PCT/US24/11756 ISR and Written Opinion, Jun. 28, 2024.
WO PCT/US24/11756 Invitation to Pay Additional Fees, May 7, 2024.
WO PCT/US24/16127 ISR and Written Opinion, Sep. 11, 2024.
WO PCT/US24/16127 Invitation to Pay Additional Fees, Jun. 4, 2024.
WO PCT/US24/18665 ISR and Written Opinion, Jun. 21, 2024.
"27 Winners Announced at the 19$^{th}$ Annual Medical Design Excellence Awards (MDEA) Award Ceremony", UBM Americas, 2017, 4 pages.
"55 Chosen as Winners in Annual BIG Innovation Awards", 2018, retrieved from https://www.bintelligence.com/posts/55-chosen-as-winners-in-annual-big-innovation-awards, 2 pages.
2017 Good Design Award, retrieved from https://www.g-mark.org/gallery/winners/9dda01a3-803d-11ed-af7e-0242ac130002, 9 pages.
"2019 Top 10 Innovations", The Scientist, retrieved from https://www.the-scientist.com/2019-top-10-innovations-66738, 7 pages.
Abbott 2023 Annual Report, retrieved from https://www.abbottinvestor.com/static-files/6cb09c09-2422-40e0-a24b-6545ffcf5267, pp. 1-82.
Abbott Clinical Trials Competitor and Ecosystem Players, 2020, 28 pages.
"Abbott's Freestyle Libre® Is Named Best Medical Technology In Last 50 Years By The Galien Foundation", 2022, PRNewswire, 1 page.
"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards#:~:text=FDA%20clears%20Abbott's%20FreeStyle%20Libre,high%20or%20low%20without%20scanning, on Jul. 7, 2024, 3 pages.
"Abbott's Freestyle LibreR 3 Receives U.S. FDA Clearance—Features World's Smallest, Thinnest and Most Accurate 14-Day Glucose Sensor", 2022, PRNewswire, 3 pages.
"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.
"Abbott's Freestyle® Libre 14 Day Flash Glucose Monitoring System Now Approved in U.S.", 2018, PRNewswire, 2 pages.
About the Edison Awards retrieved from https://edisonawards.com/about/, 2024, 3 pages.
Ahn, D., "Abbott's Euro approved wearable glucose monitor is different than anything on the market", 2014, retrieved from https://www.imedicalapps.com/2014/09/abbotts-wearable-glucose-monitor/, 6 pages.
"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.
Blum, A., "Freestyle Libre Glucose Monitoring System", Clinical Pharmacology Update, 2018, vol. 36, No. 2, pp. 203-204.
Cather, D. E., "Cgm Frustrations Survey", 2020, 36 pages.
Certified U.S. Appl. No. 61/149,639, filed Feb. 3, 2009.
CES 2022 Innovation Award Honorees, retrieved from https://www.ces.tech/innovation-awards/honorees/2022/best-of/f/freestyle-libre-3-system.aspx, 1 page.
2019 Chicago Innovation Award Winner Abbott Laboratories, retrieved from https://chicagoinnovation.com/winners/abbott-laboratories/, 4 pages.
Continuous Glucose Monitoring Systems Product Reference Guide, Diabetes Health, 2006-2007, pp. 50-51.
Das, S. D., et al., "Review—Electrochemistry and Other Emerging Technologies for Continuous Glucose Monitoring Devices", ECS Sensors Plus, 2022, 19 pages.
Delve Talks: Jake Leach, Dexcom, retrieved from https://www.delve.com/podcasts/delve-talks-jake-leach-dexcom, 2019, pp. 1-9.
Design Concepts Project Status Update, Glucose Sensor Applicator Dexcom (project #2554), 2014, 5 pages.
Dexcom G5 Quick Start Guide, 2020, pp. 1-31.
Dexcom G6 Continuous Glucose Monitoring System User Guide, 2022, 346 pages.
Dexcom G6 Start Here Set up Guide, 2022, pp. 18 pages.
"The Dexcom G7. The most accurate CGM system.[1]" retrieved from https://www.dexcom.com/g7-cgm-system on Jun. 27, 2024, 20 pages.
Dexcom G7 Continuous Glucose Monitoring (CGM) System Section 510(k) Approval, 2022, 10 pages.
Dexcom G7 User Guide, 2024, p. i-186.
Edison Awards Announces 2016 Gold, Silver, and Bronze Awards Winners, Edison Awards, 9 pages.
Edison Best New Product Awards™ 2021 Winners retrieved from https://edisonawards.com/2021-winners/, 19 pages.
Edison Best New Product Awards™ 2022 Winners retrieved from https://edisonawards.com/2022-winners/, 52 pages.
Email from Christopher M Dougherty dated Dec. 17, 2019, 68 pages.

(56) References Cited

OTHER PUBLICATIONS

Englert, K., et al., "Skin and Adhesive Issues With Continuous Glucose Monitors: A Sticky Situation", Journal of Diabetes Science and Technology, 2014, vol. 8, No. 4, pp. 745-751.
U.S. Appl. No. 61/317,243.
U.S. Appl. No. 61/345,562.
U.S. Appl. No. 61/361,374.
U.S. Appl. No. 61/411,262.
U.S. Appl. No. 62/524,247.
Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.
Freestyle Libre Brochure, 2016, 10 pages.
Freestyle Libre Fact Sheet, 2016, retrieved from www.FreeStyleLibre.de, 2 pages.
Freestyle Libre FAQ, 2024, retrieved from https://www.freestyle.abbott/uk-en/support/faq/question-answer.html?q=UKFaqquestion-55#, 2 pages.
"FreeStyle Libre Honored by Prix Galien", 2019, 4 pages.
FreeStyle Libre In-Service Guide, 2021, 28 pages.
FreeStyle Libre 2 Get Started Guide, 2023, pp. 1-28.
Freestyle Libre 2 HCP Pulse Report, 2021, 13 pages.
"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/#:~:text=Beschreibung%20Die%20kontinuierliche%20Glukosemessung%20mit,um%20die%20Glukosewerte%20kontinuierlich%20aufzuzeichnen, 1 page.
FreeStyle Libre 3 Get Started Guide, 2023, pp. 1-20.
FreeStyle Libre 3 User's Manual, 2022-2023, pp. iv-241.
The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.
Gough, D. A., et al., "Development of the Implantable Glucose Sensor: What Are the Prospects and Why Is It Taking So Long?", Diabetes, 1995, vol. 44, pp. 1005-1009.
Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.
Hermanides, J., et al., "Current Application of Continuous Glucose Monitoring in the Treatment of Diabetes", Diabetes Care, 2011, vol. 34, Suppl. 2, pp. S197-S201.
Hovorka, R., "Continuous glucose monitoring and closed-loop systems", Diabetic Medicine, 2005, vol. 23, pp. 1-12.
Insert Molding, 1996, retrieved from https://www.mddionline.com/equipment/insert-molding, 4 pages.
International Diabetes Device 2022 Blue Book, Seagrove Partners, 142 pages.
Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.
Lomas, P., "Dexcom G7 Release: The Most Exciting New Features", 2024, retrieved from https://notjustapatch.com/dexcom-g7-features/, 13 pages.
Lovett, L., "What's next for Dexcom? CEO, CTO talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.
Medtronic Enlite Serter User Guide, 2014, 26 pages.
Medtronic MiniMed iPro2 User Guide, 2010, pp. 1-99.
Meltsner, M A, et al., "Observations on rotating needle insertions using a brachytherapy robot", Phys. Med. Biol., 2007, vol. 52, pp. 6027-6037.
Nichols, S. P., et al., "Biocompatible Materials for Continuous Glucose Monitoring Devices", Chem Rev., 2013, vol. 113, No. 4, pp. 2528-2549.
Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.
"Periphery", Cambridge Dictionary of American English, 2000, p. 631.
"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.
"Real-World Data Show Abbott's Freestyle Libre® Systems And GLP-1 Medicines Work Better Together For People With Type 2 Diabetes", 2024, PRNewswire, 2 pages.
Rice, M. J., et al., "Continuous Measurement of Glucose: Facts and Challenges", Anesthesiology, 2012, vol. 116, No. 1, pp. 199-204.
Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.
Rocchitta, G., et al., "Enzyme Biosensors for Biomedical Applications: Strategies for Safeguarding Analytical Performances in Biological Fields", Sensors, 2016. vol. 16, No. 6, 21 pages.
Sclater, N., et al., eds., Mechanisms and Mechanical Devices Sourcebook, Fourth Edition, 2007, Chapter 12—Shaft Couplings and Connections, pp. 290-307.
"Transcutaneous", Webster's Third New International Dictionary, 2002, pp. 2426.
Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.
Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.
Xu, J., et al., "Anti-Biofouling Strategies for Long-Term Continuous Use of Implantable Sensors", Chemosensors, 2020, vol. 20 No. 3, 29 pages.
AU 2019404908 Examiner's Report, Feb. 17, 2025.
CA 3,050,721 Examiner's Report, Nov. 8, 2024.
EP 17182379.2 Reply to Opposition, Feb. 27, 2025.
EP 19151577.4 Examination Report, Oct. 7, 20240
EP 20177703.4 Response to Withdrawals, Jan. 7, 2025.
EP 20177703.4 Withdrawal of Intervention, Dec. 27, 2024.
EP 20177703.4 Withdrawal of Opposition, Dec. 27, 2024.
EP 20177703.4 Written Submissions Dexcom, Nov. 22, 2024.
EP 20177712.5 Summons to Attend Oral Proceedings, Oct. 1, 2024.
EP 20195922.8 Withdrawal of Intervention, Dec. 27, 2024.
EP 20195922.8 Withdrawal of Opposition, Dec. 27, 2024.
EP 21211041.5 Withdrawal of Opposition, Dec. 27, 2024.
EP 21211041.5 Notice of Appeal, Dec. 17, 2024
EP 21211041.5 Minutes of Oral Proceedings, Dec. 13, 2024.
EP 21211041.5 Response to Summons to Attend Oral Proceedings Dexcom, Nov. 12, 2024.
EP 21211041.5 Response to Summons to Attend Oral Proceedings, Nov. 12, 2024.
EP 21211041.5 Summons to Attend Oral Proceedings, Sep. 23, 2024.
EP 24152079.0 Examination Report, Dec. 2, 2024.
EP 24183336.7 Extended Search Report, Oct. 11, 2024.
EP 24187206.8 Extended Search Report, Oct. 9, 2024.
EP 24194029.5 Extended Search Report, Nov. 18, 2024.
JP 2024-31538 Office Action, Oct. 16, 2024.
MY PI2021003022 Examination Report, Mar. 5, 2025.
MY PI2022002786 Examination Report, Jan. 8, 2025.
UP Second Expert Opinion of Dr Michael Schoemaker in Litigation of EP 3977921, Nov. 8, 2024.
US Decision Denying Institution of Inter Partes Review, IPR No. 2024-00860, Nov. 20, 2024.

(56) References Cited

OTHER PUBLICATIONS

US Patent Owner's Response To Petitioner's Explanation Of Parallel Petitions Challenging U.S. Pat. No. 11,510,325, IPR No. 2024-00860, Aug. 23, 2024.
US Patent Owner Preliminary Response Pursuant to 37 C.F.R. § 42.107, IPR No. 2024-00860, Aug. 23, 2024.
US Declaration of Julia Castellano, IPR No. 2024-00860, Aug. 21, 2024.
US Declaration of Scott E. Davis, IPR No. 2024-00860, Jun. 5, 2024.
US Petitioner's Explanation Of Parallel Petitions Challenging U.S. Pat. No. 11,510,325, IPR No. 2024-00860, May 5, 2024.
US Termination Due to Settlement After Institution of Trial, IPR No. 2023-01409, Jan. 7, 2025.
US Joint Motion to Treat Settlement Agreement as Business Confidential Information. IPR No. 2023-01409, Jan. 3, 2025.
US Joint Motion to Terminate Proceeding Under 35 U.S.C. § 317(a), IPR No. 2023-01409, Jan. 3, 2025.
US Order Setting Oral Argument, IPR No. 2023-01409, Dec. 11, 2024.
US Patent Owner's Sur-Reply, IPR No. 2023-01409, Dec. 10, 2024.
US Deposition of Gary D. Fletcher, Ph.D., IPR No. 2023-01409, Dec. 4, 2024.
US Patent Owner's Request For Oral Argument, IPR No. 2023-01409, Dec. 3, 2024.
US Petitioner's Request For Oral Argument, IPR No. 2023-01409, Dec. 3, 2024.
US Patent Owner's Objections to Petitioner's Exhibits Submitted With Its Reply, IPR No. 2023-01409With Its Reply, IPR No. 2023-01409, Nov. 1, 2024.
US Petitioner's Updated Exhibit List, IPR No. 2023-01409, Oct. 25, 2024.
US Second Declaration of Gary Fletcher, Ph.D., IPR No. 2023-01409, Oct. 25, 2024.
US Petitioner's Reply to Patent Owner's Response, IPR No. 2023-01409, Oct. 25, 2024.
US Deposition of Karl R. Leinsing, MSME, PE, IPR No. 2023-01409, Oct. 17, 2024.
US Conference Call Before The Patent Trial And Appeal Board Before Judge Cynthia Hardman, IPR No. 2023-01409, Oct. 17, 2024.
US Notice of Joint Stipulation to Modify Schedule, IPR No. 2023-01409, Sep. 26, 2024.
US Declaration of Karl R. Leinsing, MSME, PE, IPR No. 2023-01409, Jul. 19, 2024.
US Patent Owner's Response, IPR No. 2023-01409, Jul. 19, 2024.
US Deposition of Gary Fletcher, Ph.D., IPR No. 2023-01409, Jun. 26, 2024.
US Decision Denying Patent Owner's Request on Rehearing of Decision Denying Institution, IPR No. 2023-01396, Aug. 9, 2024.
US Reexamination U.S. Appl. No. 90/019,307 Decision on Petition, Feb. 13, 2025.
US Ex Parte Reexamination Certificate of U.S. Pat. No. 11,013,440, Oct. 30, 2024.
US Reexamination U.S. Appl. No. 90/019,329 Notice of Intent to Issue Ex Parte Reexamination Certificate, Oct. 8, 2024.
US Reexamination U.S. Appl. No. 90/019,329 Statutory disclaimer per Manual of Patent Examining Procedure (MPEP) 1490, Sep. 3, 2024.
US Ex Parte Reexamination Certificate of U.S. Pat. No. 11,000,216, Nov. 14, 2024.
US Reexamination U.S. Appl. No. 90/019,331 Notice of Intent to Issue Ex Parte Reexamination Certificate, Oct. 15, 2024.
US Reexamination U.S. Appl. No. 90/019,331 Petition Under 37 CFR § 1.59 to Expunge Application Papers, Jun. 12, 2024.
US Ex Parte Reexamination Certificate of U.S. Pat. No. 10,959,654, Nov. 5, 2024.
US Reexamination U.S. Appl. No. 90/019,330 Notice of Intent to Issue Ex Parte Reexamination Certificate, Oct. 7, 2024.
Abbott Patent Marking Diabetes, 2024, retrieved from https://www.abbott.com/patents/diabetes-patents.html, 6 pages.
ACCU-CHEK® Softclix Lancet Device retrieved from file:///C:/Users/afredericks/Downloads/softclix-user-manual.pdf, 2007, 2 pages.
Using your ACCU-CHEK® Multiclix Lancet Device, 2005, retrieved from https://www.northcoastmed.com/wp-content/uploads/2023/03/multiclix_userguide.pdf, 2 pages.
"The Advantages of the Cleo® 90 Infusion Set Are Clear", 2019, retrieved from https://web.archive.org/web/20220816002119/https:/smiths-medical.com/-/media/M/Smiths-medical_com//Files/Import-Files/Product-Literature/IN193873GB-092019_LR.pdf, 2 pages.
American National Standard, ANSI/AAMI HE75:2009, Human factors engineering—Design of medical devices, 2010, 465 pages.
Automated Retractable VanishPoint Syringe 510(k) Safety and Effectiveness Summary, 1998, 5 pages.
"Bluetooth rival unveiled by Nokia", 2006, retrieved from news.bbc.co.uk/1/hi/technology/5403564.stm, 2 pages.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Burge, M. R., et al., "Continuous Glucose Monitoring: The Future of Diabetes Management", Diabetes Spectrum, 2008, vol. 21, No. 2, pp. 112-119.
Clancy, N. T., et al., "A new device for assessing changes in skin viscoelasticity using indentation and optical measurement", Skin Research and Technology, 2010, vol. 16, pp. 210-228.
Cleo® 90 Infusion Set 510(k) Premarket Notification, 2004, 1 page.
Dexcom G5 Mobile System User Guide, 2015, pp. 1-260.
Dexcom G6 Continuous Glucose Monitoring (CGM) System Section 510(k) Approval, 2022, 7 pages.
Dexcom STS Continuous Monitors FDA Premarket Approval (PMA), 2006, 2 pages.
U.S. Appl. No. 61/569,287.
Freestyle Navigator Answers to Frequently Asked Questions, 2007, retrieved from https://web.archive.org/web/20080917183534/http:/www.freestylenavigator.com/ab_nav/url/content/en_US/3 0.10. 10:1 O/general_content/General_ContenL0000004.htm, 2 pages.
"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.
International Standard, IEC 62366, Medical devices—Application of usability engineering to medical devices, 2007, 214 pages.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
Medtronic MiniMed Guardian@ REAL-Time Components, 2007, retrieved from https://web.archive.org/20071013095335/http:www.medtronicdiabetes.com/products/guardian/components.html, 2 pages.
Medtronic MiniMed Guardian@ REAL-Time Features, 2007, retrieved from https://web.archive.org/20071025084715/http:/www.medtronicdiabetes.com/products/guardian/features.html, 2 pages.
Medtronic MiniMed One-press Serter User Guide, 2015, 26 pages.
Medtronic MiniMed Paradigm® 512 and 712 Insulin Pumps User Guide, 2005, pp. 1-136.
Microlet® 2 Lancing Device, 2008, retrieved from https://image.tigermedical.com/Manuals/BAY6606-20141216010820833.pdf, 1 page.
Piper, H. G., et al., "Real-Time Continuous Glucose Monitoring in Pediatric Patients During and After Cardiac Surgery", Pediatrics, 2006, vol. 118, No. 3, pp. 1176-1184.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.
Sacks, A. H., et al., "Skin blood flow changes and tissue deformations produced by cylindrical indentors", Journal of Rehabilitation Research and Development, 1985, vol. 22, No. 3, pp. 1-6.

(56) References Cited

OTHER PUBLICATIONS

Schneider, M., et al., "Evaluating the use of the Cleo® 90 infusion set for patients on a palliative care unit", International Journal of Palliative Nursing, 2009, vol. 15, No. 8, pp. 372-376.
CA 3,228,738 Examiner's Report, May 8, 2025.
CN 202211091194.1 Notification of Filing Divisional Application, Mar. 27, 2025.
EP 17182379.2 Reply to Reply to Opposition, May 16, 2025.
EP 19900891.3 Examination Report, May 8, 2025.
EP 20195922.8 Grounds of Appeal, Sep. 6, 2024.
EP 21211041.5 Grounds of Appeal, Apr. 23, 2025.
EP 23190032.5 Examination Report, May 19, 2025.
EP 24201435.5 Extended Search Report, Jan. 27, 2025.
EP 24220160.6 Extended Search Report, Jun. 17, 2025.
JP 2023-516522 Office Action, Mar. 5, 2025.
JP 2023-514023 Office Action, Apr. 16, 2025.
MX MX/a/2021/007294 Second Office Action, Feb. 19, 2025.
US Reexamination U.S. Appl. No. 90/019,307 Office Action, Mar. 18, 2025.
US Reexamination U.S. Appl. No. 90/019,329 Decision on Petition Under 37 C.F.R. § 1.181, Mar. 18, 2025.
WO PCT/US25/13698 ISR and Written Opinion, Jun. 5, 2025.
WO PCT/US25/13698 Invitation to Pay Additional Fees, Apr. 15, 2025.

* cited by examiner

SYSTEMS, DEVICES, AND METHODS FOR ANALYTE SENSOR INSERTION

CROSS-REFERENCE TO RELATED APPLICATIONS

The present application claims priority to and the benefit of U.S. Provisional Patent Application Ser. No. 62/784,074, filed Dec. 21, 2018, which is incorporated by reference herein in its entirety for all purposes.

FIELD

The subject matter described herein relates generally to systems, devices, and methods for using an applicator to insert at least a portion of an analyte sensor in a subject.

BACKGROUND

The detection and/or monitoring of analyte levels, such as glucose, ketones, lactate, oxygen, hemoglobin A1C, or the like, can be vitally important to the health of an individual having diabetes. Patients suffering from diabetes mellitus can experience complications including loss of consciousness, cardiovascular disease, retinopathy, neuropathy, and nephropathy. Diabetics are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device may be worn on the body of an individual who requires analyte monitoring. To increase comfort and convenience for the individual, the sensor control device may have a small form-factor, and can be assembled and applied by the individual with a sensor applicator. The application process includes inserting at least a portion of a sensor that senses a user's analyte level in a bodily fluid located in a layer of the human body, using an applicator or insertion mechanism, such that the sensor comes into contact with a bodily fluid. The sensor control device may also be configured to transmit analyte data to another device, from which the individual or her health care provider ("HCP") can review the data and make therapy decisions.

While current sensors can be convenient for users, they are also susceptible to malfunctions. These malfunctions can be caused by user error, lack of proper training, poor user coordination, overly complicated procedures, physiological responses to the inserted sensor, and other issues. Some prior art systems, for example, may rely too much on the precision assembly and deployment of a sensor control device and an applicator by the individual user. Other prior art systems may utilize sharp insertion and retraction mechanisms that are susceptible to trauma to the surrounding tissue at the sensor insertion site, which can lead to inaccurate analyte level measurements. These challenges and others described herein can lead to improper insertion and/or suboptimal analyte measurements by the sensor, and consequently, a failure to properly monitor the patient's analyte level.

Thus, a need exists for more reliable sensor insertion devices, systems and methods, that are easy to use by the patient and less prone to error.

SUMMARY

Provided herein are example embodiments of systems, devices and methods for the assembly and use of an applicator and a sensor control device of an in vivo analyte monitoring system. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer's bodily fluid. The embodiments provided herein are improvements to prevent or reduce the likelihood that a sensor is improperly inserted or damaged, or elicits an adverse physiological response. Other improvements and advantages are provided as well. The various configurations of these devices are described in detail by way of the embodiments which are only examples.

Other systems, devices, methods, features and advantages of the subject matter described herein will be or will become apparent to one with skill in the art upon examination of the following figures and detailed description. It is intended that all such additional systems, devices, methods, features, and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 20A is a front perspective view of the embodiment, FIG. 20B is a front side view of the embodiment, FIG. 20C is a rear side view of the embodiment, FIG. 20D is a left side view of the embodiment, FIG. 20E is a right side view of the embodiment, FIG. 20F is a top view of the embodiment, and FIG. 20G is a bottom view of the embodiment.

FIG. 21A is a front perspective view of the embodiment, FIG. 21B is a front side view of the embodiment, FIG. 21C is a rear side view of the embodiment, FIG. 21D is a left side view of the embodiment, FIG. 21E is a right side view of the embodiment, FIG. 21F is a top view of the embodiment, and FIG. 21G is a bottom view of the embodiment.

FIG. 22A is a front perspective view of the embodiment, FIG. 22B is a front side view of the embodiment, FIG. 22C is a rear side view of the embodiment, FIG. 22D is a left side view of the embodiment, FIG. 22E is a right side view of the embodiment, FIG. 22F is a top view of the embodiment, and FIG. 22G is a bottom view of the embodiment.

FIG. 23A is a front perspective view of the embodiment, FIG. 23B is a front side view of the embodiment, FIG. 23C is a rear side view of the embodiment, FIG. 23D is a left side view of the embodiment, FIG. 23E is a right side view of the embodiment, FIG. 23F is a top view of the embodiment, and FIG. 23G is a bottom view of the embodiment.

FIG. 24A is a front perspective view of the embodiment, FIG. 24B is a front side view of the embodiment, FIG. 24C is a rear side view of the embodiment, FIG. 24D is a left side view of the embodiment, FIG. 24E is a right side view of the embodiment, FIG. 24F is a top view of the embodiment, and FIG. 24G is a bottom view of the embodiment.

FIG. 25A is a front perspective view of the embodiment, FIG. 25B is a front side view of the embodiment, FIG. 25C is a rear side view of the embodiment, FIG. 25D is a left side view of the embodiment, FIG. 25E is a right side view of the embodiment, FIG. 25F is a top view of the embodiment, and FIG. 25G is a bottom view of the embodiment.

FIG. 26A is a front perspective view of the embodiment, FIG. 26B is a front side view of the embodiment, FIG. 26C is a rear side view of the embodiment, FIG. 26D is a left side view of the embodiment, FIG. 26E is a right side view of the embodiment, FIG. 26F is a top view of the embodiment, and FIG. 26G is a bottom view of the embodiment.

FIG. 27A is a front perspective view of the embodiment, FIG. 27B is a front side view of the embodiment, FIG. 27C is a rear side view of the embodiment, FIG. 27D is a left side view of the embodiment, FIG. 27E is a right side view of the embodiment, FIG. 27F is a top view of the embodiment, and FIG. 27G is a bottom view of the embodiment.

FIG. 28A is a front perspective view of the embodiment, FIG. 28B is a front side view of the embodiment, FIG. 28C is a rear side view of the embodiment, FIG. 28D is a left side view of the embodiment, FIG. 28E is a right side view of the embodiment, FIG. 28F is a top view of the embodiment, and FIG. 28G is a bottom view of the embodiment.

FIG. 29A is a front perspective view of the embodiment, FIG. 29B is a front side view of the embodiment, FIG. 29C is a rear side view of the embodiment, FIG. 29D is a left side view of the embodiment, FIG. 29E is a right side view of the embodiment, FIG. 29F is a top view of the embodiment, and FIG. 29G is a bottom view of the embodiment.

FIG. 30A is a front perspective view of the embodiment, FIG. 30B is a front side view of the embodiment, FIG. 30C is a rear side view of the embodiment, FIG. 30D is a left side view of the embodiment, FIG. 30E is a right side view of the embodiment, FIG. 30F is a top view of the embodiment, and FIG. 30G is a bottom view of the embodiment.

FIG. 31A is a front perspective view of the embodiment, FIG. 31B is a front side view of the embodiment, FIG. 31C is a rear side view of the embodiment, FIG. 31D is a left side view of the embodiment, FIG. 31E is a right side view of the embodiment, FIG. 31F is a top view of the embodiment, and FIG. 31G is a bottom view of the embodiment.

FIG. 32A is a front perspective view of the embodiment, FIG. 32B is a front side view of the embodiment, FIG. 32C is a rear side view of the embodiment, FIG. 32D is a left side view of the embodiment, FIG. 32E is a right side view of the embodiment, FIG. 32F is a top view of the embodiment, and FIG. 32G is a bottom view of the embodiment.

FIG. 33A is a front perspective view of the embodiment, FIG. 33B is a front side view of the embodiment, FIG. 33C is a rear side view of the embodiment, FIG. 33D is a left side view of the embodiment, FIG. 33E is a right side view of the embodiment, FIG. 33F is a top view of the embodiment, and FIG. 33G is a bottom view of the embodiment.

FIG. 34A is a front perspective view of the embodiment, FIG. 34B is a front side view of the embodiment, FIG. 34C is a rear side view of the embodiment, FIG. 34D is a left side view of the embodiment, FIG. 34E is a right side view of the embodiment, FIG. 34F is a top view of the embodiment, and FIG. 34G is a bottom view of the embodiment.

FIG. 35A is a front perspective view of the embodiment, FIG. 35B is a front side view of the embodiment, FIG. 35C is a rear side view of the embodiment, FIG. 35D is a left side view of the embodiment, FIG. 35E is a right side view of the embodiment, FIG. 35F is a top view of the embodiment, and FIG. 35G is a bottom view of the embodiment.

DETAILED DESCRIPTION

Figure 1:
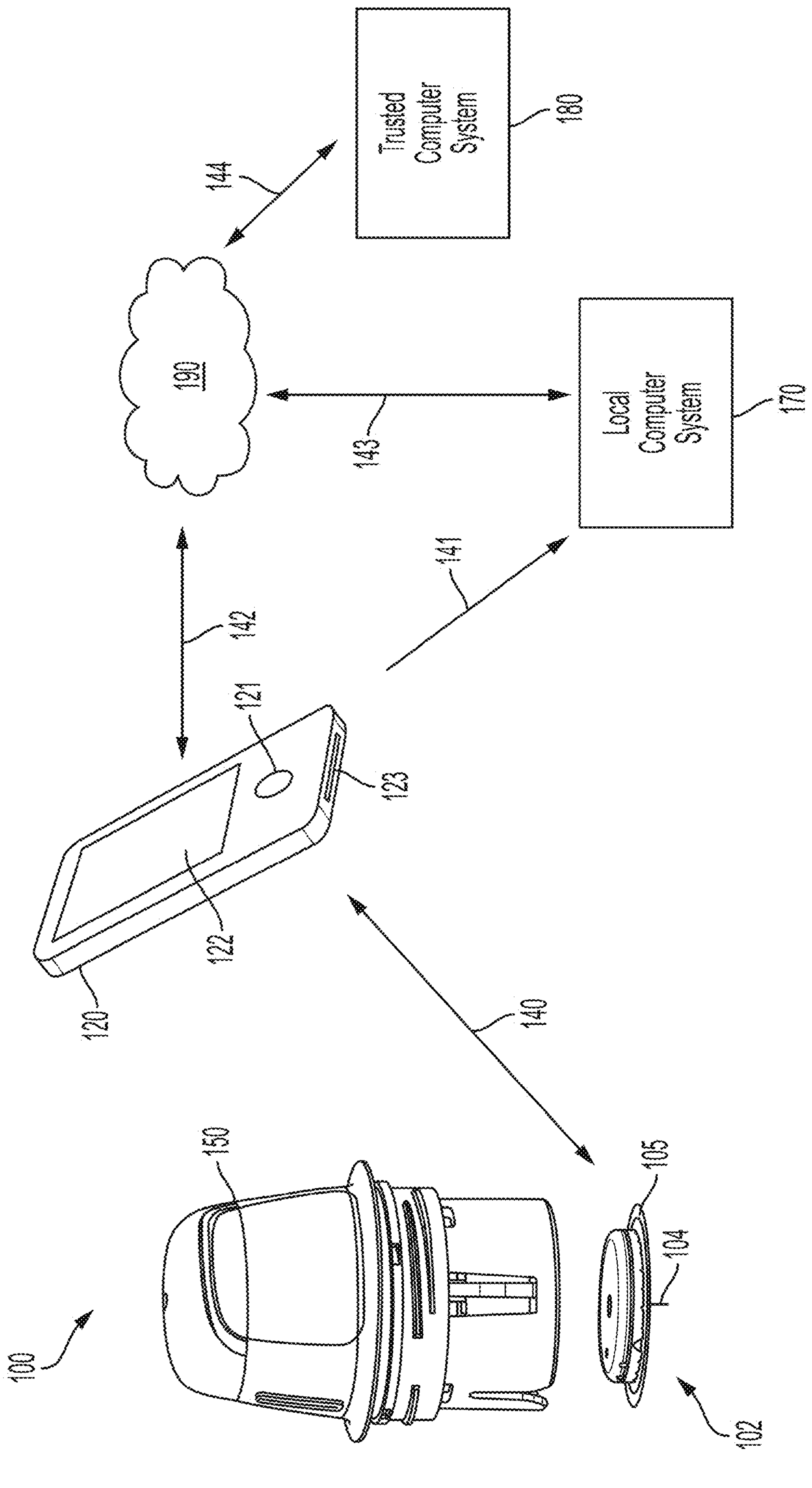
FIG. 1 is a system overview of a sensor applicator, reader device, monitoring system, network, and remote system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices, and methods for the use of analyte sensor insertion applicators for use with in vivo analyte monitoring systems. Accordingly, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

As mentioned, a number of embodiments of systems, devices, and methods are described herein that provide for the improved assembly and use of analyte sensor insertion devices for use with in vivo analyte monitoring systems. In particular, several embodiments of the present disclosure are designed to improve the method of sensor insertion with respect to in vivo analyte monitoring systems and, in particular, to minimize trauma to an insertion site during a sensor insertion process. Some embodiments, for example, include a powered sensor insertion mechanism configured to operate at a higher, controlled speed relative to a manual insertion mechanism, in order to reduce trauma to an insertion site. In other embodiments, an applicator having a compressible distal end can stretch and flatten the skin surface at the insertion site, and consequently, can reduce the likelihood of a failed insertion as a result of skin tenting. In still other embodiments, a sharp with an offset tip, or a sharp manufactured utilizing a plastic material or a coined manufacturing process can also reduce trauma to an insertion site. In sum, these embodiments can improve the likelihood of a successful sensor insertion and reduce the amount of trauma at the insertion site, to name a few advantages.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Example Embodiment of In Vivo Analyte Monitoring System

FIG. 1 is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121, and the device battery can be recharged using power port 123. While only one reader device 120 is shown, sensor control device 102 can communicate with multiple reader devices 120. Each of the reader devices 120 can communicate and share data with one another. More details about reader device 120 is set forth with respect to FIG. 2A below. Reader device 120 can communicate with local computer system 170 via a communication path 141 using a wired or wireless communication protocol. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by a wired or wireless communication protocol as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique.

Example Embodiment of Reader Device

Figure 2A:
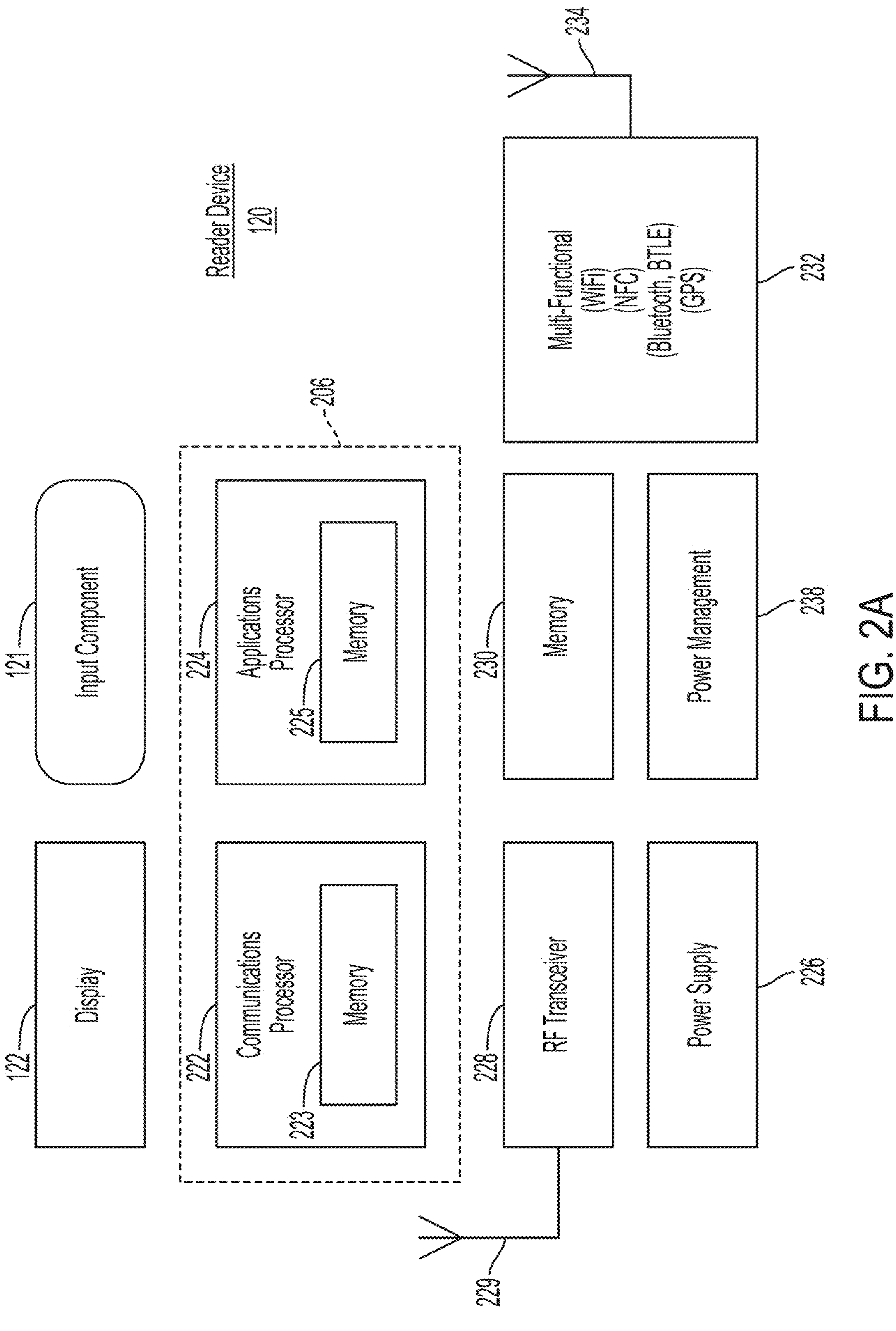
FIG. 2A is a block diagram depicting an example embodiment of a reader device.

FIG. 2A is a block diagram depicting an example embodiment of a reader device 120 configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further, reader device 120 can also include a multi-functional transceiver 232 which can communicate over Wi-Fi, NFC, Bluetooth, BTLE, and GPS with an antenna 234. As understood by one of skill in the art, these components are electrically and communicatively coupled in a manner to make a functional device.

Example Embodiments of Sensor Control Devices

Figure 2B:
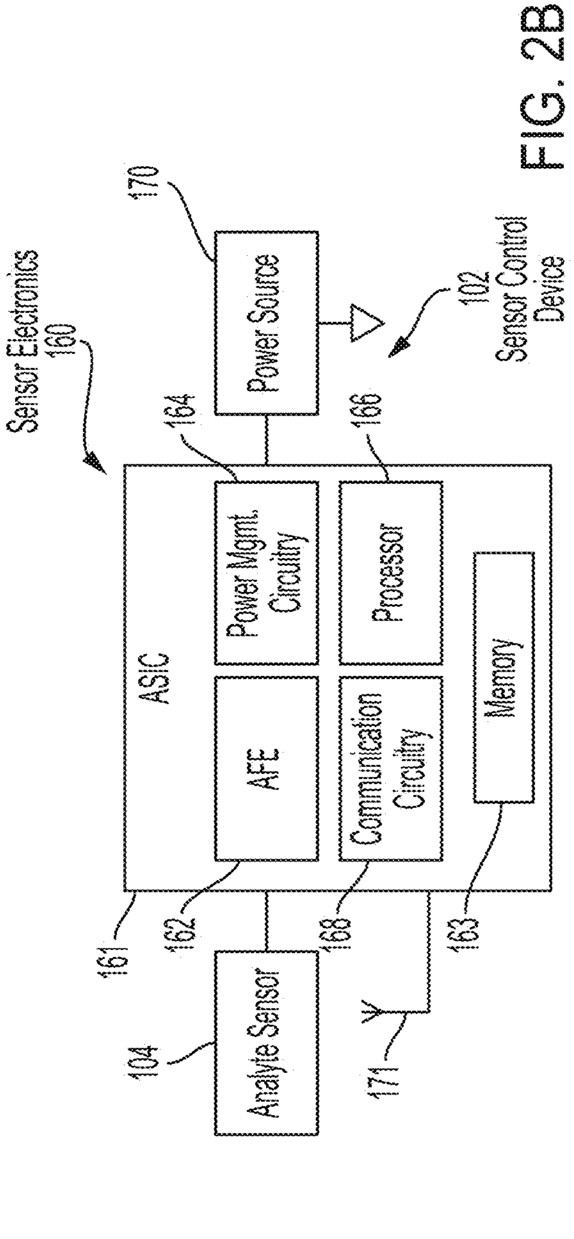
FIGS. 2B and 2C are block diagrams depicting example embodiments of sensor control devices.
Figure 2C:
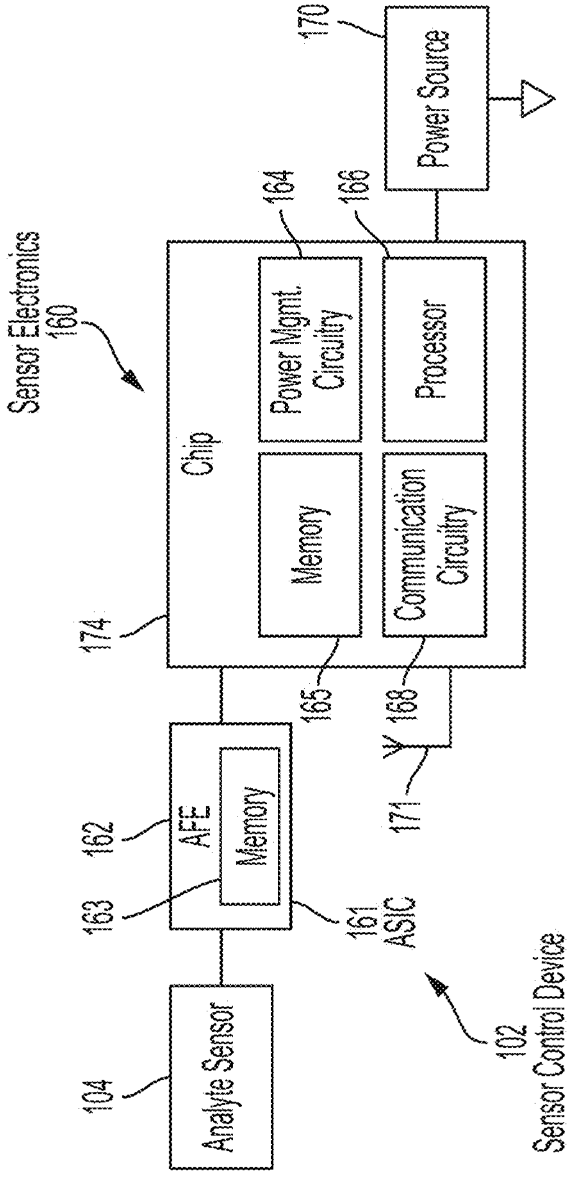

FIGS. 2B and 2C are block diagrams depicting example embodiments of sensor control devices 102 having analyte sensors 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Example Embodiments of Assembly Processes for Sensor Control Device

According to some embodiments, the components of sensor control device 102 can be acquired by a user in multiple packages requiring final assembly by the user before delivery to an appropriate user location. FIGS. 3A-3E depict an example embodiment of an assembly process for sensor control device 102 by a user, including preparation of separate components before coupling the components in order to ready the sensor for delivery. In other embodiments, such as those described with respect to FIGS. 17B to 17F, components of the sensor control device 102 and applicator 150 can be acquired by a user in a single package. FIGS. 3F-3G depict an example embodiment of delivery of sensor control device 102 to an appropriate user location by selecting the appropriate delivery location and applying device 102 to the location.

Figure 3A:
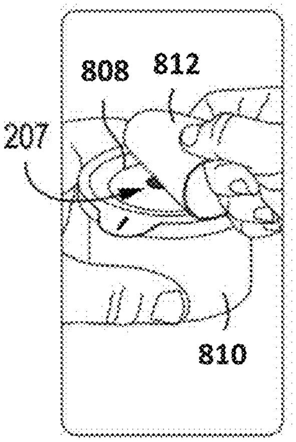
FIGS. 3A to 3G are progressive views of an example embodiment of the assembly and application of the system of FIG. 1 incorporating a two-piece architecture.

FIG. 3A depicts a sensor container or tray 810 that has a removable lid 812. The user prepares the sensor tray 810 by removing the lid 812, which acts as a sterile barrier to protect the internal contents of the sensor tray 810 and otherwise maintain a sterile internal environment. Removing the lid 812 exposes a platform 808 positioned within the sensor tray 810, and a plug assembly 207 (partially visible) is arranged within and otherwise strategically embedded within the platform 808. The plug assembly 207 includes a sensor module (not shown) and a sharp module (not shown). The sensor module carries the sensor 104 (FIG. 1), and the sharp module carries an associated sharp used to help deliver the sensor 104 transcutaneously under the user's skin during application of the sensor control device 102 (FIG. 1).

Figure 3B:
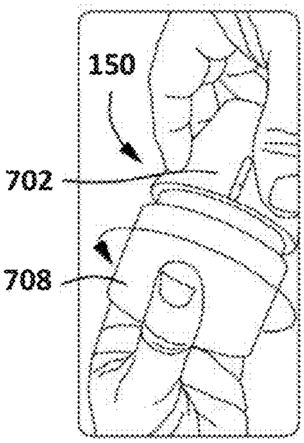

FIG. 3B depicts the sensor applicator 150 and the user preparing the sensor applicator 150 for final assembly. The sensor applicator 150 includes a housing 702 sealed at one end with an applicator cap 708. In some embodiments, for example, an O-ring or another type of sealing gasket may seal an interface between the housing 702 and the applicator cap 708. In at least one embodiment, the O-ring or sealing gasket may be molded onto one of the housing 702 and the applicator cap 708. The applicator cap 708 provides a barrier that protects the internal contents of the sensor applicator 150. In particular, the sensor applicator 150 contains an electronics housing (not shown) that retains the electrical components for the sensor control device 102 (FIG. 1), and the applicator cap 708 may or may not maintain a sterile environment for the electrical components. Preparation of the sensor applicator 150 includes uncoupling the housing 702 from the applicator cap 708, which can be accomplished by unscrewing the applicator cap 708 from the housing 702. The applicator cap 708 can then be discarded or otherwise placed aside.

Figure 3C:
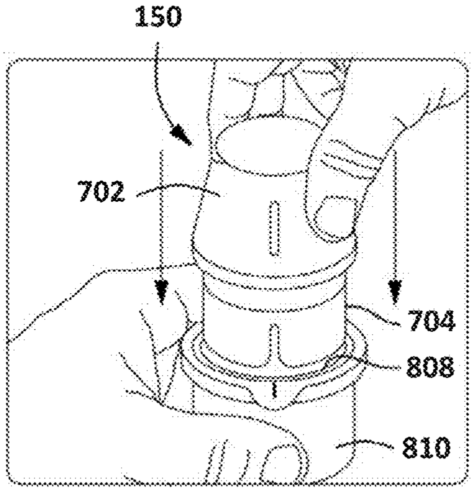

FIG. 3C depicts the user inserting the sensor applicator 150 into the sensor tray 810. The sensor applicator 150 includes a sheath 704 configured to be received by the platform 808 to temporarily unlock the sheath 704 relative to the housing 702, and also temporarily unlock the platform 808 relative to the sensor tray 810. Advancing the housing 702 into the sensor tray 810 results in the plug assembly 207 (FIG. 3A) arranged within the sensor tray 810, including the sensor and sharp modules, being coupled to the electronics housing arranged within the sensor applicator 150.

Figure 3D:
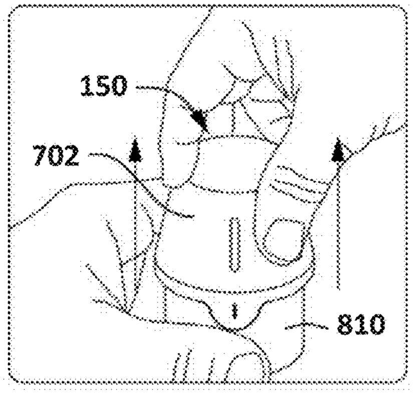

In FIG. 3D, the user removes the sensor applicator 150 from the sensor tray 810 by proximally retracting the housing 702 with respect to the sensor tray 810.

Figure 3E:
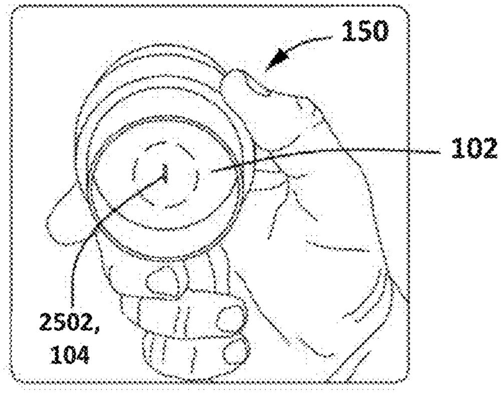
Figure 3F:
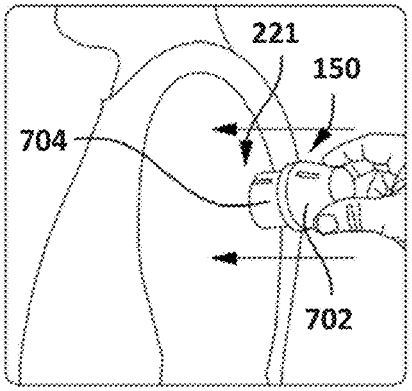
Figure 3G:
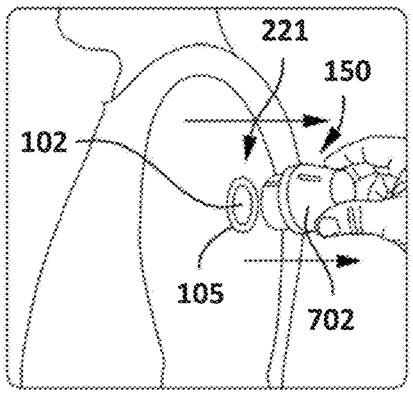

FIG. 3E depicts the bottom or interior of the sensor applicator 150 following removal from the sensor tray 810 (FIGS. 3A and 3C). The sensor applicator 150 is removed from the sensor tray 810 with the sensor control device 102 fully assembled therein and positioned for delivery to the target monitoring location. As illustrated, a sharp 2502 extends from the bottom of the sensor control device 102 and carries a portion of the sensor 104 within a hollow or recessed portion thereof. The sharp 2502 is configured to penetrate the skin of a user and thereby place the sensor 104 into contact with bodily fluid.

FIGS. 3F and 3G depict example delivery of the sensor control device 102 to a target monitoring location 221, such as the back of an arm of the user. FIG. 3F shows the user advancing the sensor applicator 150 toward the target monitoring location 221. Upon engaging the skin at the target monitoring location 221, the sheath 704 collapses into the housing 702, which allows the sensor control device 102 (FIGS. 3E and 3G) to advance into engagement with the skin. With the help of the sharp 2502 (FIG. 3E), the sensor 104 (FIG. 3E) is advanced transcutaneously into the patient's skin at the target monitoring location 221.

FIG. 3G shows the user retracting the sensor applicator 150 from the target monitoring location 221, with the sensor control device 102 successfully attached to the user's skin. The adhesive patch 105 (FIG. 1) applied to the bottom of sensor control device 102 adheres to the skin to secure the sensor control device 102 in place. The sharp 2502 (FIG. 3E) is automatically retracted when the housing 702 is fully advanced at the target monitoring location 221, while the sensor 104 (FIG. 3E) is left in position to measure analyte levels.

According to some embodiments, system 100, as described with respect to FIGS. 3A-3G and elsewhere herein, can provide a reduced or eliminated chance of accidental breakage, permanent deformation, or incorrect assembly of applicator components compared to prior art systems. Since applicator housing 702 directly engages platform 808 while sheath 704 unlocks, rather than indirect engagement via sheath 704, relative angularity between sheath 704 and housing 702 will not result in breakage or permanent deformation of the arms or other components. The potential for relatively high forces (such as in conventional devices) during assembly will be reduced, which in turn reduces the chance of unsuccessful user assembly. Further details regarding embodiments of applicators, their components, and variants thereof, are described in U.S. Patent Publication Nos. 2013/0150691, 2016/0331283, and 2018/0235520, all of which are incorporated by reference herein in their entireties and for all purposes.

Example Embodiment of Sensor Applicator Device

Figure 4C:
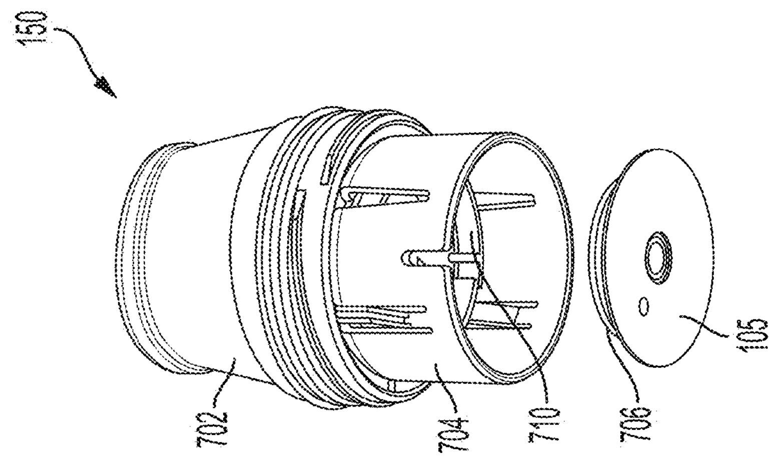
FIG. 4C is a perspective view depicting an example embodiment of a distal end of an applicator device and electronics housing.
Figure 4B:
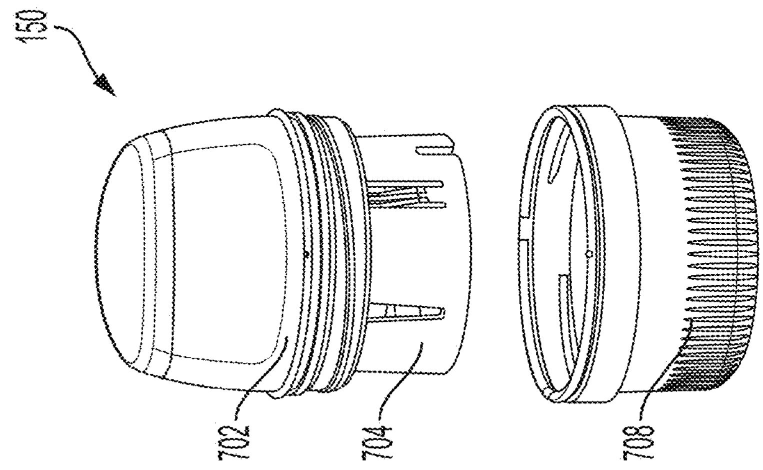
FIG. 4B is a side perspective view depicting an example embodiment of an applicator device and cap decoupled.
Figure 4A:
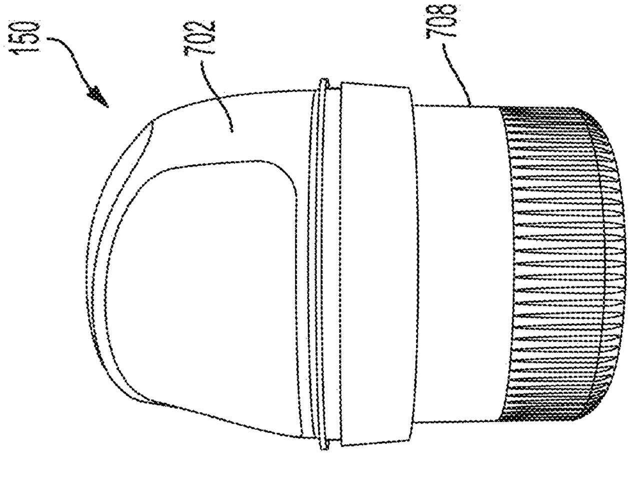
FIG. 4A is a side view depicting an example embodiment of an applicator device coupled with a cap.

FIG. 4A is a side view depicting an example embodiment of an applicator device 150 coupled with screw cap 708. This is one example of how applicator 150 is shipped to and received by a user, prior to assembly by the user with a sensor. In other embodiments, applicator 150 can be shipped to the user with the sensor and sharp contained therein. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within sensor electronics carrier 710 of sheath 704, when cap 708 is in place.

Example Embodiment of Tray and Sensor Module Assembly

Figure 5:
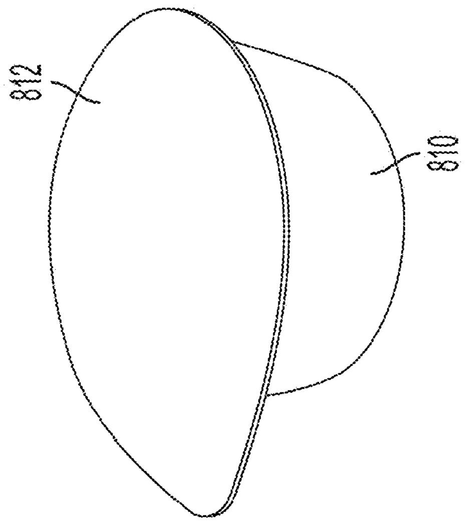
FIG. 5 is a proximal perspective view depicting an example embodiment of a tray with sterilization lid coupled.

FIG. 5 is a proximal perspective view depicting an example embodiment of a tray 810 with sterilization lid 812 removably coupled thereto, which, in some embodiments, may be representative of how the package is shipped to and received by a user prior to assembly.

Figure 6A:
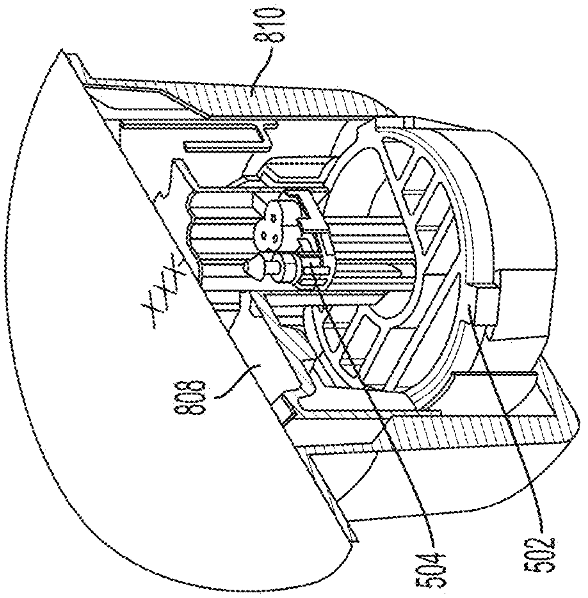
FIG. 6A is a proximal perspective cutaway view depicting an example embodiment of a tray with sensor delivery components.

FIG. 6A is a proximal perspective, cutaway view depicting sensor delivery components within tray 810, according to some embodiments. Platform 808 is slidably coupled within tray 810. Desiccant 502 is stationary with respect to tray 810. Sensor module 504 is mounted within tray 810.

Figure 6B:
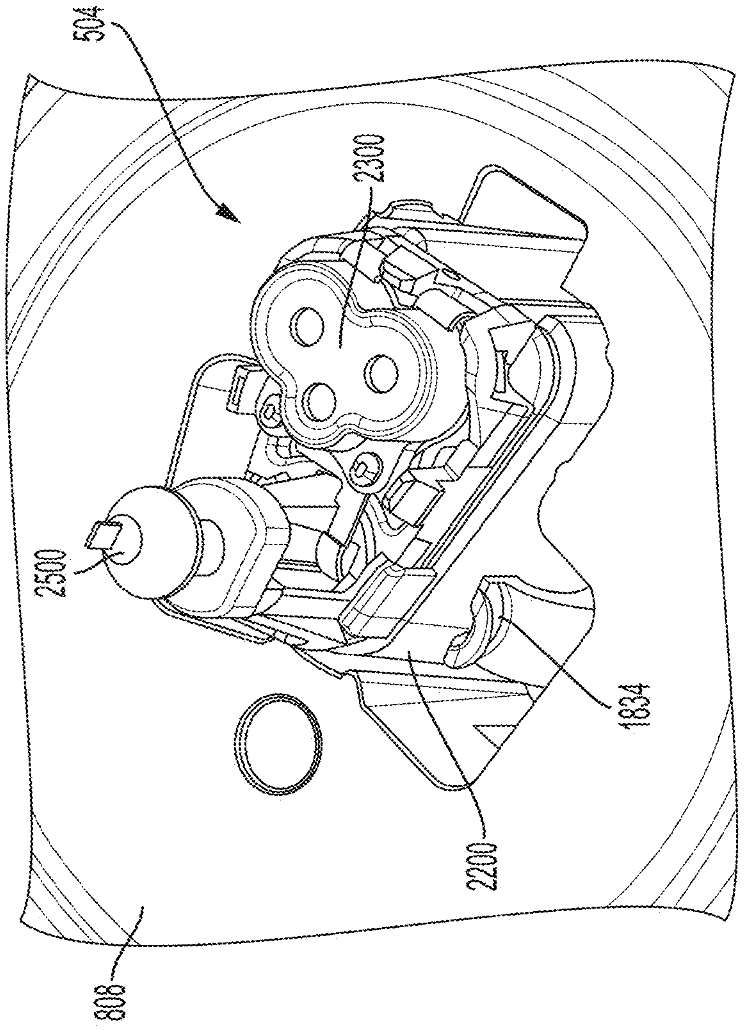
FIG. 6B is a proximal perspective view depicting sensor delivery components.

FIG. 6B is a proximal perspective view depicting an example embodiment of a sensor module 504 in greater detail. Here, retention arm extensions 1834 of platform 808 releasably secure sensor module 504 in position. Module 2200 is coupled with connector 2300, sharp module 2500 and sensor (not shown) such that during assembly they can be removed together as sensor module 504.

Example Embodiment of Applicator Housing

Figure 7A:
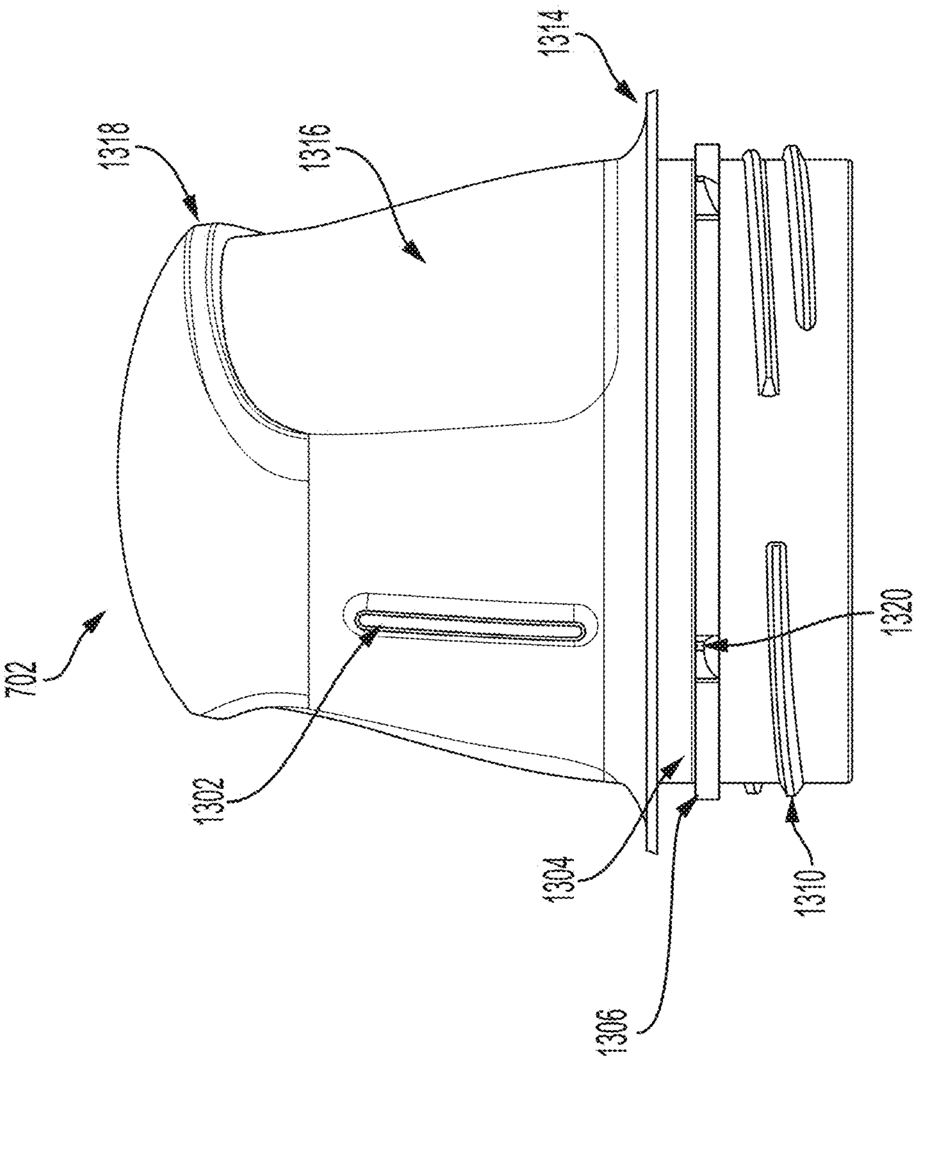
FIG. 7A is side view depicting an example embodiment of a housing.

FIG. 7A is side view depicting an example embodiment of the applicator housing 702 that can include an internal cavity with support structures for applicator function. A user can push housing 702 in a distal direction to activate the applicator assembly process and then also to cause delivery of sensor control device 102, after which the cavity of housing 702 can act as a receptacle for a sharp. In the example embodiment, various features are shown including housing orienting feature 1302 for orienting the device during assembly and use. Tamper ring groove 1304 can be a recess located around an outer circumference of housing 702, distal to a tamper ring protector 1314 and proximal to a tamper ring retainer 1306. Tamper ring groove 1304 can retain a tamper ring so users can identify whether the device has been tampered with or otherwise used. Housing threads 1310 can secure housing 702 to complimentary threads on cap 708 (FIGS. 4A and 4B) by aligning with complimentary cap threads and rotating in a clockwise or counterclockwise direction. A side grip zone 1316 of housing 702 can provide an exterior surface location where a user can grip housing 702 in order to use it. Grip overhang 1318 is a slightly raised ridge with respect to side grip zone 1316 which can aid in ease of removal of housing 702 from cap 708. A shark tooth 1320 can be a raised section with a flat side located on a clockwise edge to shear off a tamper ring (not shown), and hold tamper ring in place after a user has unscrewed cap 708 and housing 702. In the example embodiment four shark teeth 1320 are used, although more or less can be used as desired.

Figure 7B:
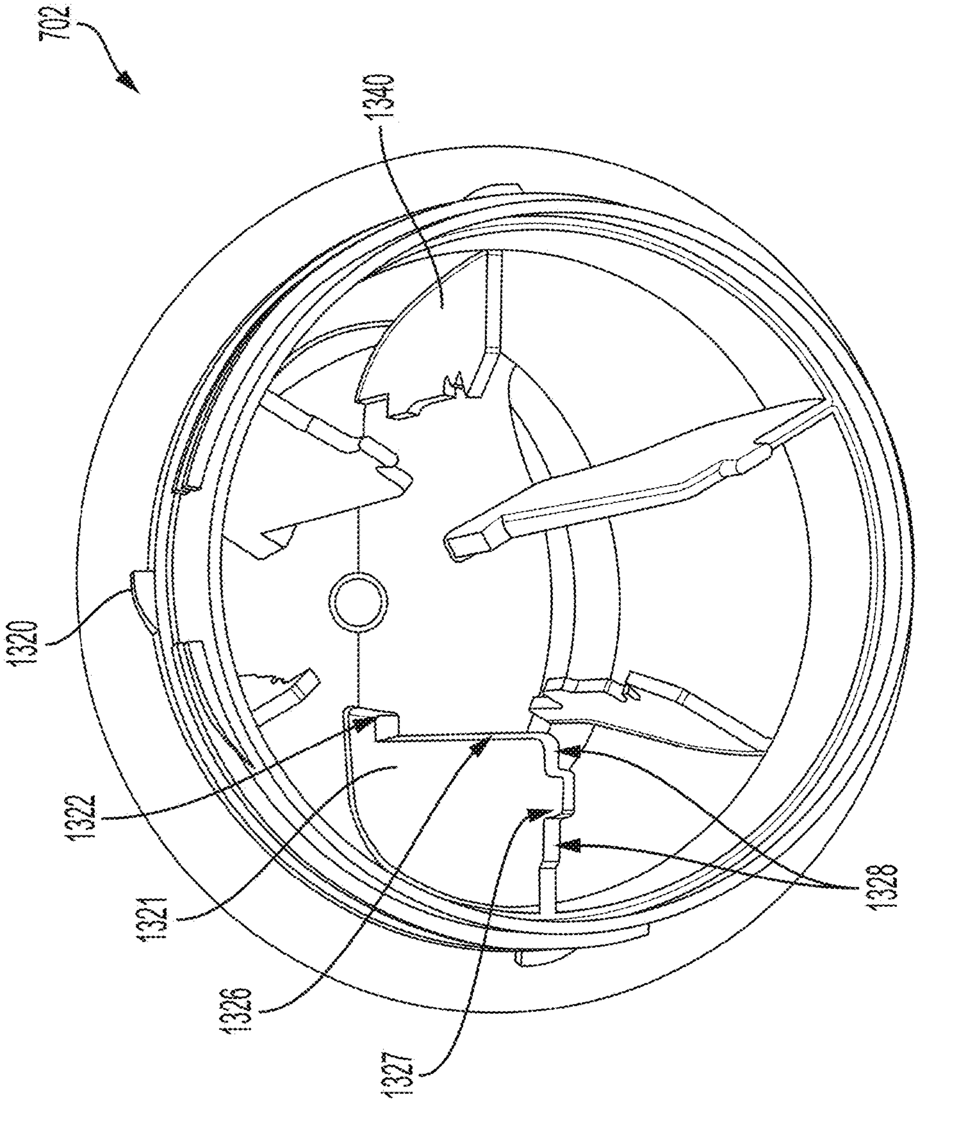
FIG. 7B is a perspective view depicting an example embodiment of a distal end of a housing.

FIG. 7B is a perspective view depicting a distal end of housing 702. Here, three housing guide structures (or "guide ribs") 1321 are located at 120 degree angles with respect to each other, and at 60 degree angles with respect to locking structures (or "locking ribs") 1340, of which there are also three at 120 degree angles with respect to each other. Other angular orientations, either symmetric or asymmetric, can be used, as well as any number of one or more structures 1321 and 1340. Here, each structure 1321 and 1340 is configured as a planar rib, although other shapes can be used. Each guide rib 1321 includes a guide edge (also called a "sheath guide rail") 1326 that can pass along a surface of sheath 704 (e.g., guide rail 1418 described with respect to FIG. 8A). An insertion hard stop 1322 can be a flat, distally facing surface of housing guide rib 1321 located near a proximal end of housing guide rib 1321. Insertion hard stop 1322 provides a surface for a sensor electronics carrier travel limiter face 1420 of a sheath 704 (FIG. 8B) to abut during use, preventing sensor electronics carrier travel limiter face 1420 from moving any further in a proximal direction. A carrier interface post 1327 passes through an aperture 1510 (FIG. 9A) of sensor electronics carrier 710 during an assembly. A sensor electronics carrier interface 1328 can be a rounded, distally facing surface of housing guide ribs 1321 which interfaces with sensor electronics carrier 710.

Figure 7C:
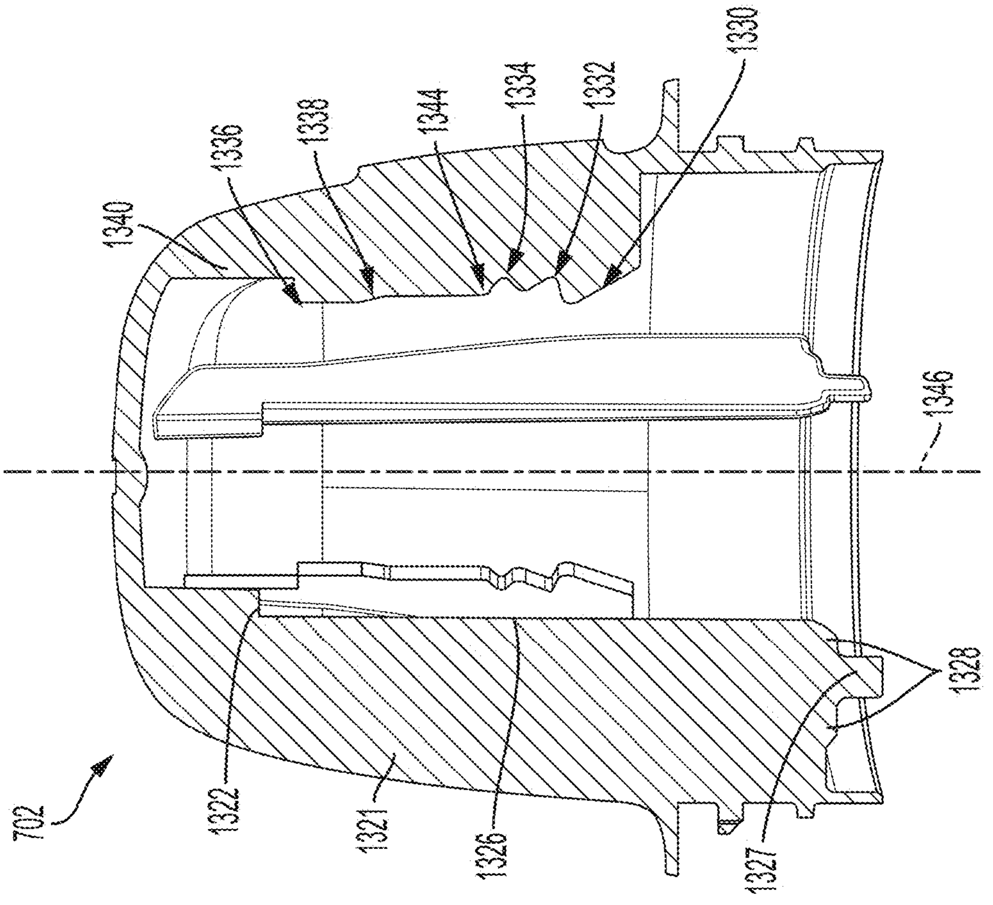
FIG. 7C is a side cross-sectional view depicting an example embodiment of a housing.

FIG. 7C is a side cross-section depicting an example embodiment of a housing. In the example embodiment, side cross-sectional profiles of housing guide rib 1321 and locking rib 1340 are shown. Locking rib 1340 includes sheath snap lead-in feature 1330 near a distal end of locking rib 1340 which flares outward from central axis 1346 of housing 702 distally. Each sheath snap lead-in feature 1330 causes detent snap round 1404 of detent snap 1402 of sheath 704 as shown in FIG. 8C to bend inward toward central axis 1346 as sheath 704 moves towards the proximal end of housing 702. Once past a distal point of sheath snap lead-in feature 1330, detent snap 1402 of sheath 704 is locked into place in locked groove 1332. As such, detent snap 1402 cannot be easily moved in a distal direction due to a surface with a near perpendicular plane to central axis 1346, shown as detent snap flat 1406 in FIG. 8C.

As housing 702 moves further in a proximal direction toward the skin surface, and as sheath 704 advances toward the distal end of housing 702, detent snaps 1402 shift into the unlocked grooves 1334, and applicator 150 is in an “armed” position, ready for use. When the user further applies force to the proximal end of housing 702, while sheath 704 is pressed against the skin, detent snap 1402 passes over firing detent 1344. This begins a firing sequence due to release of stored energy in the deflected detent snaps 1402, which travel in a proximal direction relative to the skin surface, toward sheath stopping ramp 1338 which is slightly flared outward with respect to central axis 1346 and slows sheath 704 movement during the firing sequence. The next groove encountered by detent snap 1402 after unlocked groove 1334 is final lockout groove 1336 which detent snap 1402 enters at the end of the stroke or pushing sequence performed by the user. Final lockout recess 1336 can be a proximally-facing surface that is perpendicular to central axis 1346 which, after detent snap 1402 passes, engages a detent snap flat 1406 and prevents reuse of the device by securely holding sheath 704 in place with respect to housing 702. Insertion hard stop 1322 of housing guide rib 1321 prevents sheath 704 from advancing proximally with respect to housing 702 by engaging sensor electronics carrier travel limiter face 1420.

Example Embodiment of Applicator Sheath

Figure 8A:
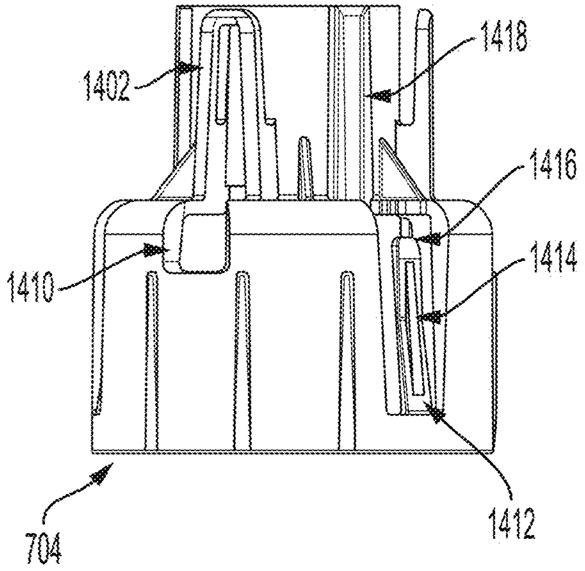
FIG. 8A is a side view depicting an example embodiment of a sheath.
Figure 8B:
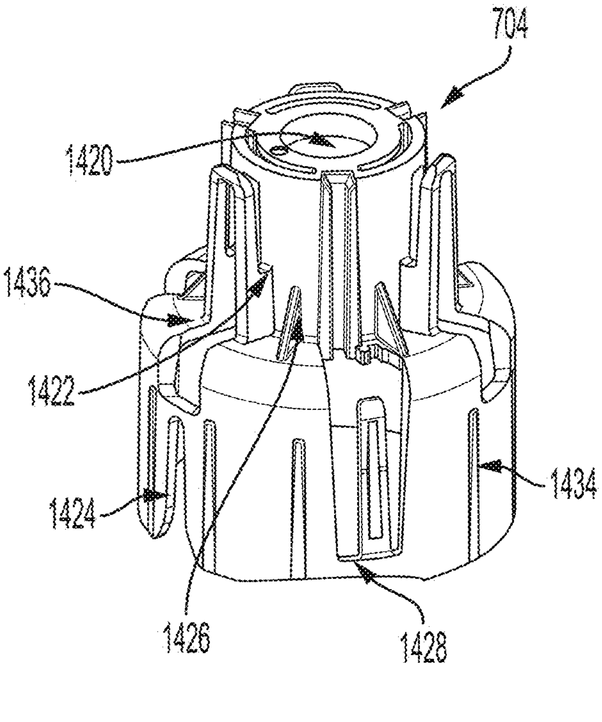
FIG. 8B is a perspective view depicting an example embodiment of a proximal end of a sheath.

FIGS. 8A and 8B are a side view and perspective view, respectively, depicting an example embodiment of sheath 704. In this example embodiment, sheath 704 can stage sensor control device 102 above a user’s skin surface prior to application. Sheath 704 can also contain features that help retain a sharp in a position for proper application of a sensor, determine the force required for sensor application, and guide sheath 704 relative to housing 702 during application. Detent snaps 1402 are near a proximal end of sheath 704, described further with respect to FIG. 8C below. Sheath 704 can have a generally cylindrical cross section with a first radius in a proximal section (closer to top of figure) that is shorter than a second radius in a distal section (closer to bottom of figure). Also shown are a plurality of detent clearances 1410, three in the example embodiment. Sheath 704 can include one or more detent clearances 1410, each of which can be a cutout with room for sheath snap lead-in feature 1330 to pass distally into until a distal surface of locking rib 1340 contacts a proximal surface of detent clearance 1410.

Guide rails 1418 are disposed between sensor electronics carrier traveler limiter face 1420 at a proximal end of sheath 704 and a cutout around lock arms 1412. Each guide rail 1418 can be a channel between two ridges where the guide edge 1326 of housing guide rib 1321 can slide distally with respect to sheath 704.

Lock arms 1412 are disposed near a distal end of sheath 704 and can include an attached distal end and a free proximal end, which can include lock arm interface 1416. Lock arms 1412 can lock sensor electronics carrier 710 to sheath 704 when lock arm interface 1416 of lock arms 1412 engage lock interface 1502 of sensor electronics carrier 710. Lock arm strengthening ribs 1414 can be disposed near a central location of each lock arm 1412 and can act as a strengthening point for an otherwise weak point of each lock arm 1412 to prevent lock arm 1412 from bending excessively or breaking.

Detent snap stiffening features 1422 can be located along the distal section of detent snaps 1402 and can provide reinforcement to detent snaps 1402. Alignment notch 1424 can be a cutout near the distal end of sheath 704, which provides an opening for user alignment with sheath orientation feature of platform 808. Stiffening ribs 1426 can include buttresses, that are triangularly shaped here, which provide support for detent base 1436. Housing guide rail clearance 1428 can be a cutout for a distal surface of housing guide rib 1321 to slide during use.

FIG. 8C is a close-up perspective view depicting an example embodiment of detent snap 1402 of sheath 704. Detent snap 1402 can include a detent snap bridge 1408 located near or at its proximal end. Detent snap 1402 can also include a detent snap flat 1406 on a distal side of detent snap bridge 1408. An outer surface of detent snap bridge 1408 can include detent snap rounds 1404 which are rounded surfaces that allow for easier movement of detent snap bridge 1408 across interior surfaces of housing 702 such as, for example, locking rib 1340.

Figure 8D:
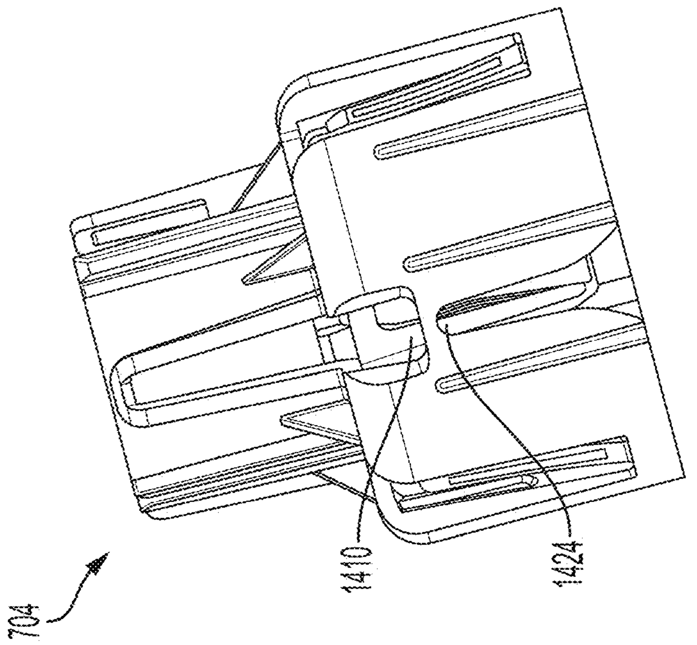
FIG. 8D is a side view depicting an example embodiment of features of a sheath.
Figure 8C:
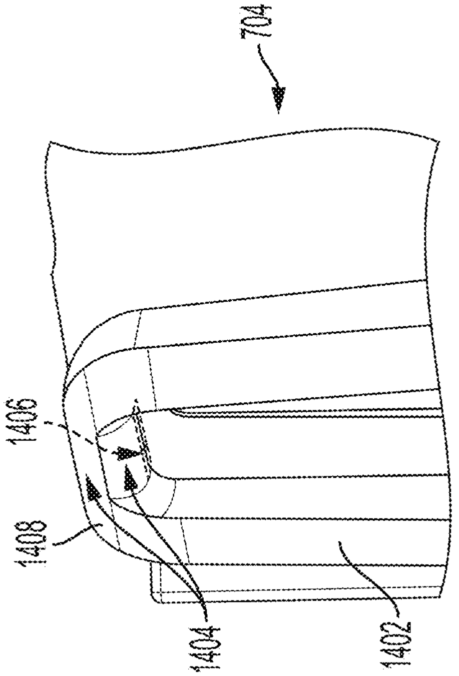
FIG. 8C is a close-up perspective view depicting an example embodiment of a distal side of a detent snap of a sheath.

FIG. 8D is a side view depicting an example embodiment of sheath 704. Here, alignment notch 1424 can be relatively close to detent clearance 1410. Detent clearance 1410 is in a relatively proximal location on distal portion of sheath 704.

Figure 8E:
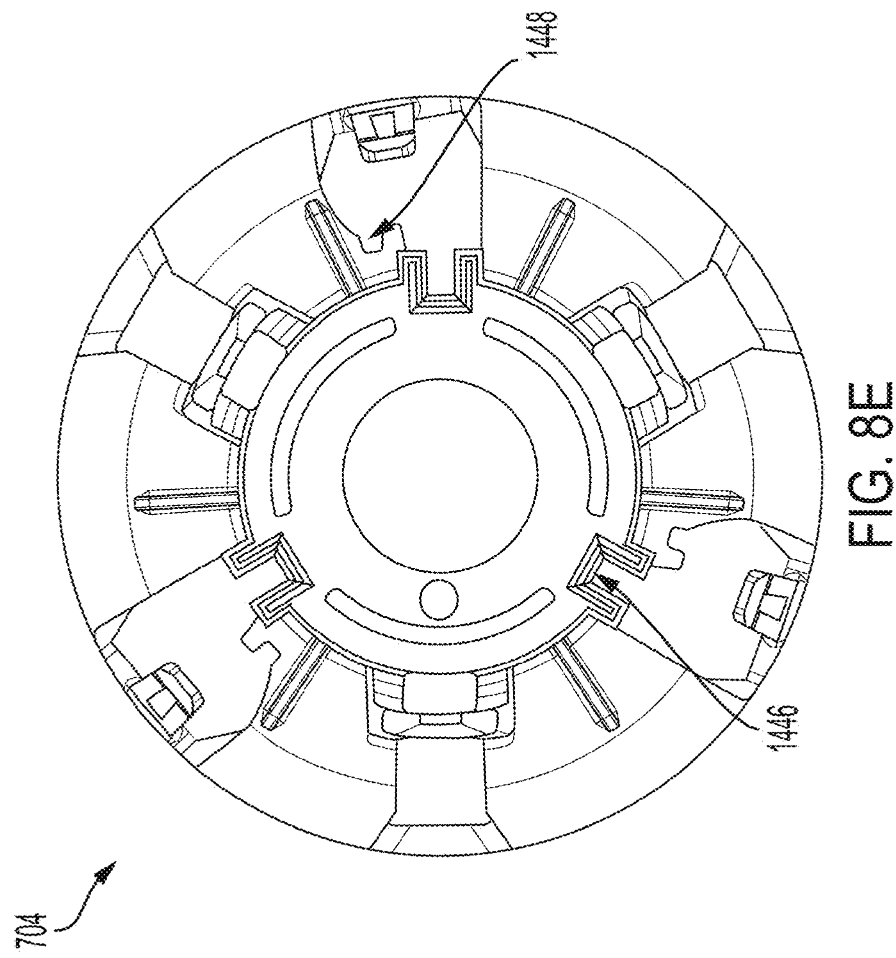
FIG. 8E is an end view of an example embodiment of a proximal end of a sheath.

FIG. 8E is an end view depicting an example embodiment of a proximal end of sheath 704. Here, a back wall for guide rails 1446 can provide a channel to slidably couple with housing guide rib 1321 of housing 702. Sheath rotation limiter 1448 can be notches which reduce or prevent rotation of the sheath 704.

Figure 8F:
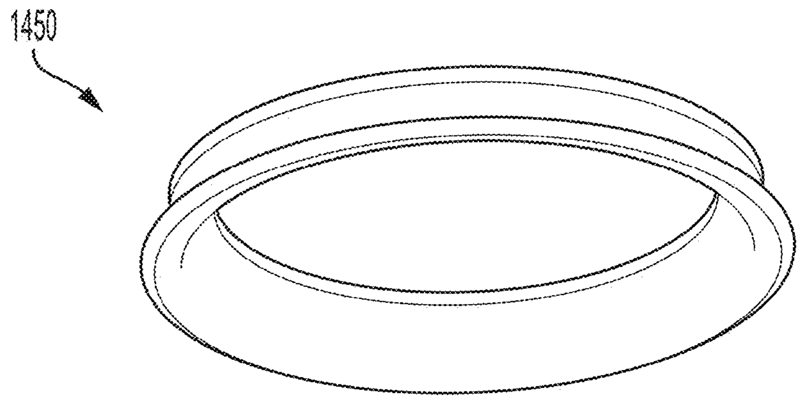
FIG. 8F is a perspective view depicting an example embodiment of a compressible distal end of an applicator.

FIG. 8F is a perspective view depicting an example embodiment of a compressible distal end 1450, which can be attached and/or detached from a sheath 704 of an applicator 150. In a general sense, the embodiments described herein operate by flattening and stretching a skin surface at a predetermined site for sensor insertion. Moreover, the embodiments described herein may also be utilized for other medical applications, such as, e.g., transdermal drug delivery, needle injection, wound closure stitches, device implantation, the application of an adhesive surface to the skin, and other like applications.

By way of background, those of skill the art will appreciate that skin is a highly anisotropic tissue from a biomechanical standpoint and varies largely between individuals. This can affect the degree to which communication between the underlying tissue and the surrounding environment can be performed, e.g., with respect to drug diffusion rates, the ability to penetrate skin with a sharp, or sensor insertion into the body at a sharp-guided insertion site.

In particular, the embodiments described herein are directed to reducing the anisotropic nature of the skin in a predetermined area by flattening and stretching the skin, and thereby improving upon the aforementioned applications. Smoothing the skin (e.g., flattening to remove wrinkles) before mating with a similarly shaped (e.g., a flat, round adhesive pad of a sensor control unit) can produce a more consistent surface area contact interface. As the surface profile of the skin approaches the profile specifications of the designed surface of the device (or, e.g., the designed area of contact for drug delivery), the more consistent contact (or drug dosing) can be achieved. This can also be advantageous with respect to wearable adhesives by creating a continuum of adhesive-to-skin contact in a predetermined area without wrinkles. Other advantages can include (1) an increased wear duration for devices that rely on skin adhesion for functionality, and (2) a more predictable skin contact area, which would improve dosing in transcutaneous drug/pharmaceutical delivery.

In addition, skin flattening (e.g., as a result of tissue compression) combined with stretching can reduce the skin's viscoelastic nature and increase its rigidity which, in turn, can increase the success rate of sharp-dependent sensor placement and functionality.

With respect to sensor insertion, puncture wounds can contribute to early signal aberration (ESA) in sensors and may be mitigated when the skin has been flattened and stretched rigid. Some known methods to minimize a puncture wound include: (1) reducing the introducers' size, or (2) limiting the length of the needle inserted into the body. However, these known methods may reduce the insertion success rate due to the compliance of the skin. For example, when a sharp tip touches the skin, before the tip penetrates the skin, the skin deforms inward into the body, a phenomenon also referred to as "skin tenting." If the sharp is not stiff enough due to a smaller cross-sectional area and/or not long enough, the sharp may fail to create an insertion point large enough, or in the desired location due to deflection, for the sensor to pass through the skin and be positioned properly. The degree of skin tenting can vary between and within subjects, meaning the distance between a sharp and a skin surface can vary between insertion instances. Reducing this variation by stretching and flattening the skin can allow for a more accurately functioning and consistent sensor insertion mechanism.

Referring to FIG. 8F, a perspective view depicts an example embodiment of a compressible distal end 1450 of an applicator 150. According to some embodiments, compressible distal end 1450 can be manufactured from an elastomeric material. In other embodiments, compressible distal end 1450 can be made of metal, plastic, composite legs or springs, or a combination thereof.

Figure 8G:
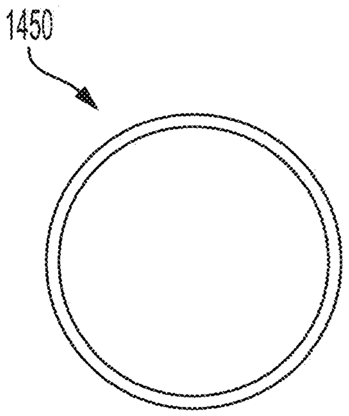
FIGS. 8G to 8K are cross-sectional views depicting example geometries for embodiments of compressible distal ends of an applicator.
Figure 8H:
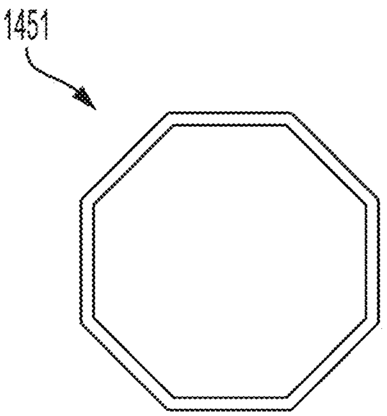
Figure 8I:
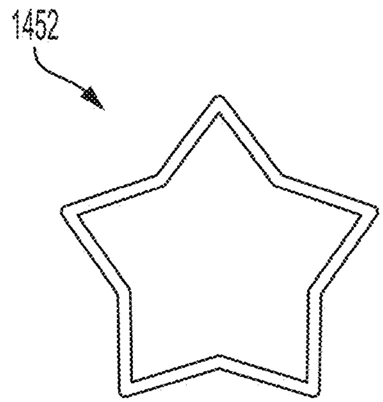
Figure 8J:
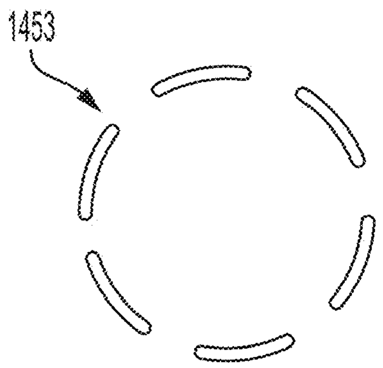
Figure 8K:
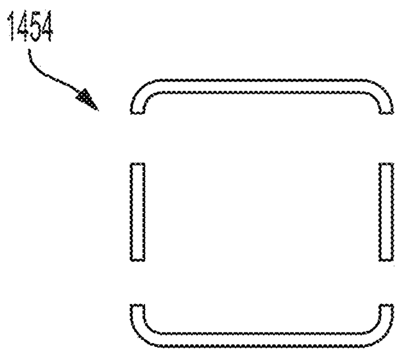

In some embodiments, compressible distal end 1450 can be detachable from an applicator 150 and used with various other similar or dissimilar applicators or medical devices. In other embodiments, compressible distal end 1450 can be manufactured as part of the sheath 704. In still other embodiments, the compressible distal end 1450 can be attached to other portions of applicator 150 (e.g., sensor electronics carrier), or, alternatively, can be used as a separate standalone device. Furthermore, although compressible distal end 1450 is shown in FIGS. 8F and 8G as having a continuous ring geometry, other configurations can be utilized. For example, FIGS. 8H to 8K are cross-sectional views depicting various example compressible distal ends, having an octagonal geometry 1451 (FIG. 8H), star-shaped geometry 1452 (FIG. 8I), a non-continuous ring geometry 1453 (FIG. 8J), and a non-continuous rectangular geometry (FIG. 8K). With respect to FIGS. 8J and 8K, a compressible distal end with a non-continuous geometry would have a plurality of points or spans to contact the predetermined area of skin. Those of skill in the art will recognize that other geometries are possible and fully within the scope of the present disclosure.

Figure 8M:
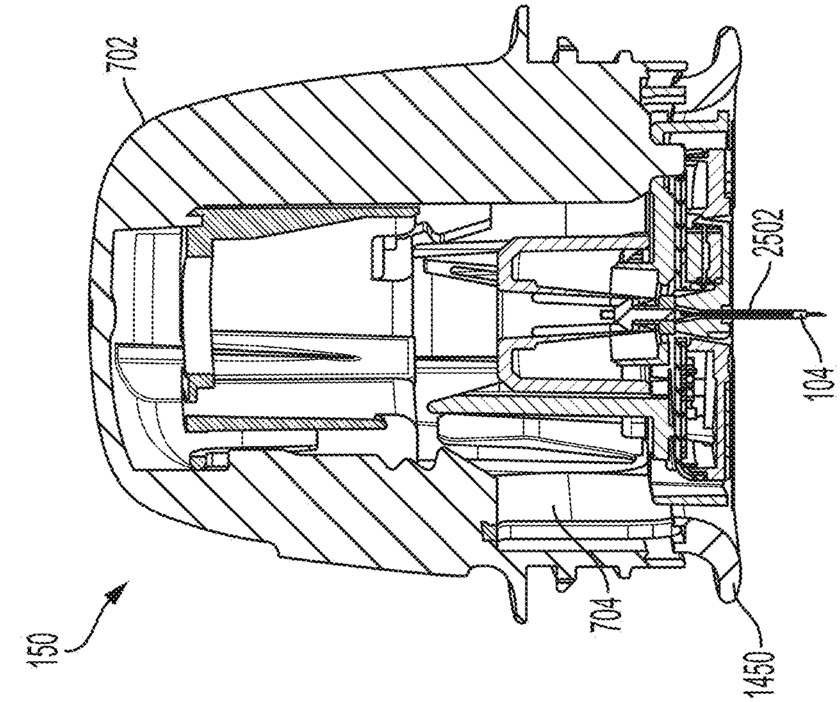
FIG. 8M is a cross-sectional view depicting an example embodiment of an applicator having a compressible distal end.
Figure 8L:
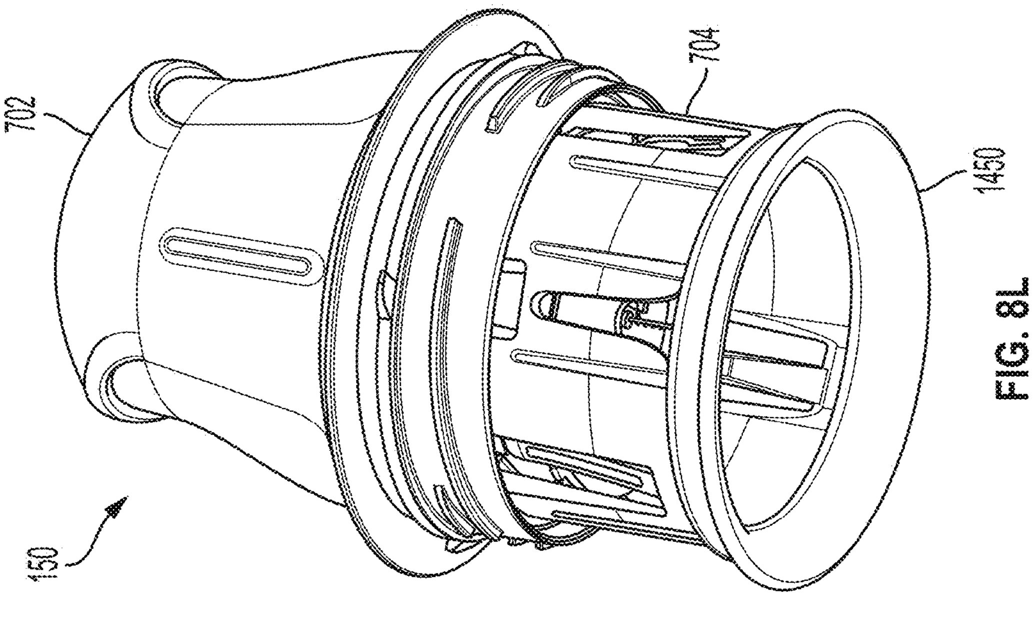
FIG. 8L is a perspective view of an example embodiment of an applicator having a compressible distal end.

FIGS. 8L and 8M are a perspective view and a cross-sectional view, respectively, depicting an applicator 150 having a compressible distal end 1450. As shown in FIGS. 8L and 8M, applicator 150 can also include applicator housing 702, sheath 704 to which compressible distal end 1450 is attached, sharp 2502, and sensor 104.

According to some embodiments, in operation, the compressible distal end 1450 of applicator is first positioned on a skin surface of the subject. The subject then applies a force on the applicator, e.g., in a distal direction, which causes compressible distal end 1450 to stretch and flatten the portion of the skin surface beneath. In some embodiments, for example, compressible distal end 1450 can be comprised of an elastomeric material and biased in a radially inward direction. In other embodiments, compressible distal end 1450 can be biased in a radially outward direction. The force on the applicator can cause an edge portion of the compressible distal end 1450 in contact with the skin surface to be displaced in a radially outward direction, creating radially outward forces on the portion of the skin surface beneath the applicator, and causing the skin surface to be stretched and flattened.

Furthermore, according to some embodiments, applying the force on the applicator also causes a medical device, such as a sensor control unit, to advance from a first position within the applicator to a second position adjacent to the skin surface. According to one aspect of some embodiments, the compressible distal end 1450 can be in an unloaded state in the first position (e.g., before the force is applied on the applicator), and a loaded state in the second position (e.g., after the force is applied on the applicator). Subsequently, the medical device is applied to the stretched and flattened portion of the skin surface beneath the compressible distal end 1450. According to some embodiments, the application of the medical device can include placing an adhesive surface 105 of a sensor control unit 102 on the skin surface and/or positioning at least a portion of an analyte sensor under the skin surface. The analyte sensor can be an in vivo analyte sensor configured to measure an analyte level in a bodily fluid of the subject. In still other embodiments, the application of the medical device can include placing a drug-loaded patch on the skin surface. Those of skill in the art will appreciate that a compressible distal end can be utilized with any of the aforementioned medical applications and is not meant to be limited to use in an applicator for analyte sensor insertion.

Example Embodiments of Sensor Electronics Carriers

Figure 9A:
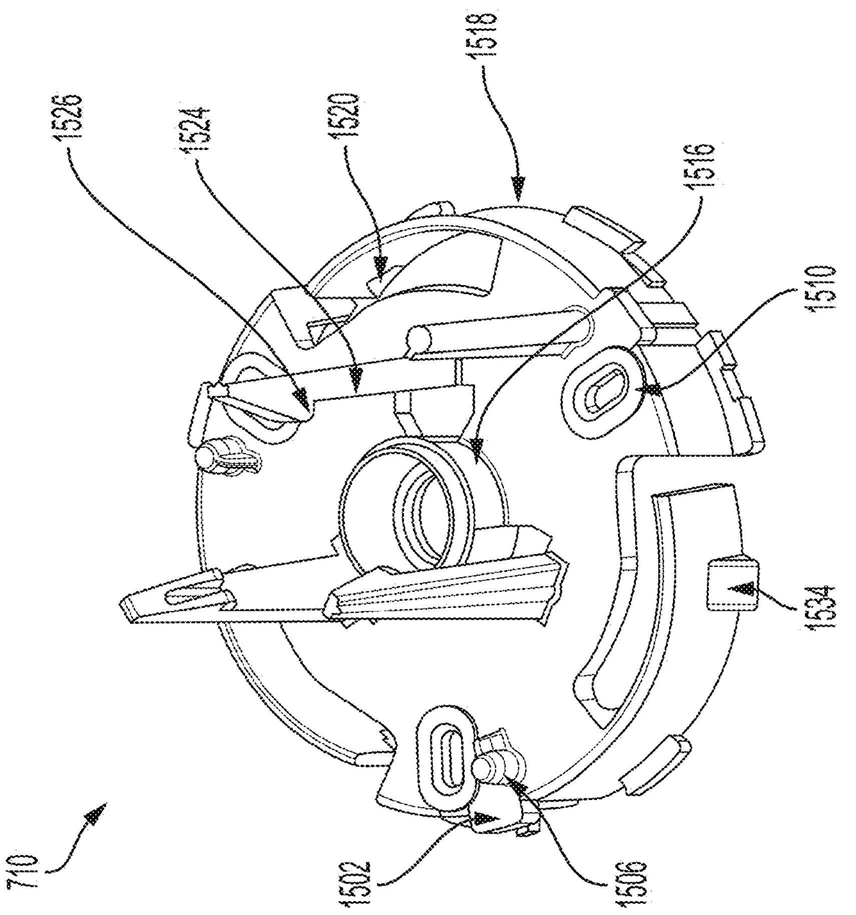
FIG. 9A is a proximal perspective view depicting an example embodiment of a sensor electronics carrier.

FIG. 9A is a proximal perspective view depicting an example embodiment of sensor electronics carrier 710 that can retain sensor electronics within applicator 150. It can also retain sharp carrier 1102 with sharp module 2500. In this example embodiment, sensor electronics carrier 710 generally has a hollow round flat cylindrical shape, and can include one or more deflectable sharp carrier lock arms 1524

(e.g., three) extending proximally from a proximal surface surrounding a centrally located spring alignment ridge 1516 for maintaining alignment of spring 1104. Each lock arm 1524 has a detent or retention feature 1526 located at or near its proximal end. Shock lock 1534 can be a tab located on an outer circumference of sensor electronics carrier 710 extending outward and can lock sensor electronics carrier 710 for added safety prior to firing. Rotation limiter 1506 can be a proximally extending relatively short protrusion on a proximal surface of sensor electronics carrier 710 which limits rotation of carrier 710. Sharp carrier lock arms 1524 can interface with sharp carrier 1102 as described with reference to FIGS. 10 and 11 below.

Figure 9B:
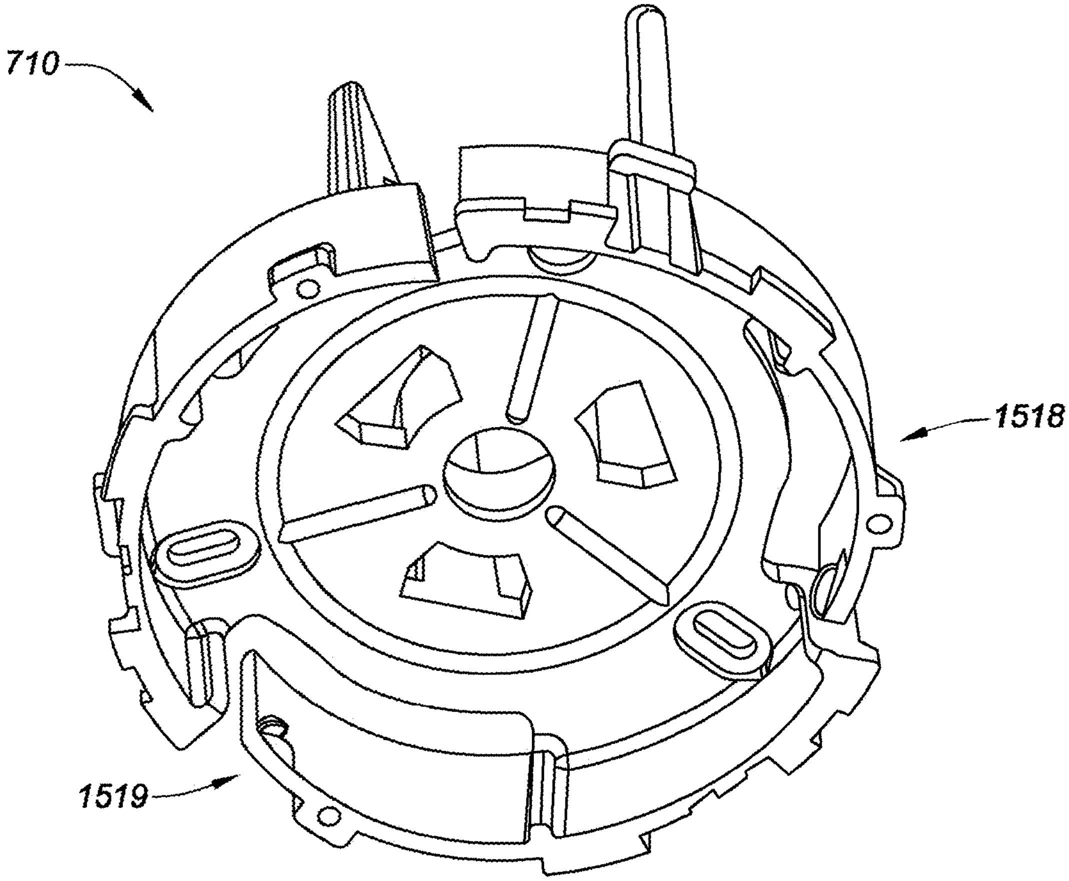
FIG. 9B is a distal perspective view depicting an example embodiment of a sensor electronics carrier.

FIG. 9B is a distal perspective view of sensor electronics carrier 710. Here, one or more sensor electronics retention spring arms 1518 (e.g., three) are normally biased towards the position shown and include a detent 1519 that can pass over the distal surface of electronics housing 706 of device 102 when housed within recess or cavity 1521. In certain embodiments, after sensor control device 102 has been adhered to the skin with applicator 150, the user pulls applicator 150 in a proximal direction, i.e., away from the skin. The adhesive force retains sensor control device 102 on the skin and overcomes the lateral force applied by spring arms 1518. As a result, spring arms 1518 deflect radially outwardly and disengage detents 1519 from sensor control device 102 thereby releasing sensor control device 102 from applicator 150.

Example Embodiments of Sharp Carriers

Figure 11:
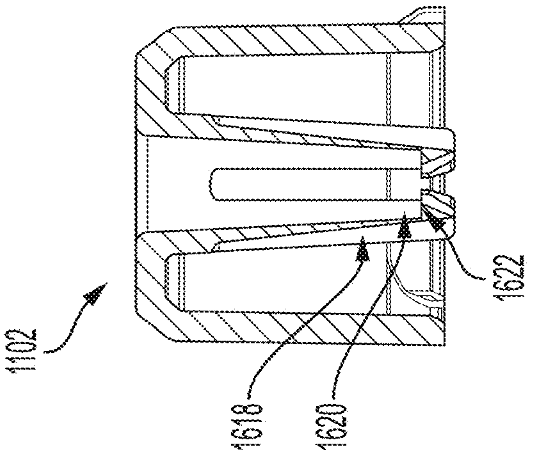
FIG. 11 is a side cross-section depicting an example embodiment of a sharp carrier.
Figure 10:
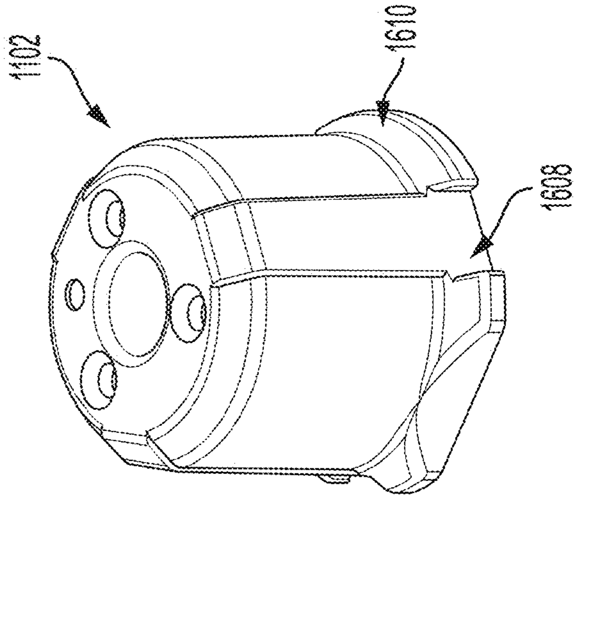
FIG. 10 is a proximal perspective view of an example embodiment of a sharp carrier.

FIGS. 10 and 11 are a proximal perspective view and a side cross-sectional view, respectively, depicting an example embodiment of sharp carrier 1102. Sharp carrier 1102 can grasp and retain sharp module 2500 within applicator 150. Near a distal end of sharp carrier 1102 can be anti-rotation slots 1608 which prevent sharp carrier 1102 from rotating when located within a central area of sharp carrier lock arms 1524 (as shown in FIG. 9A). Anti-rotation slots 1608 can be located between sections of sharp carrier base chamfer 1610, which can ensure full retraction of sharp carrier 1102 through sheath 704 upon retraction of sharp carrier 1102 at the end of the deployment procedure.

Figure 17A:
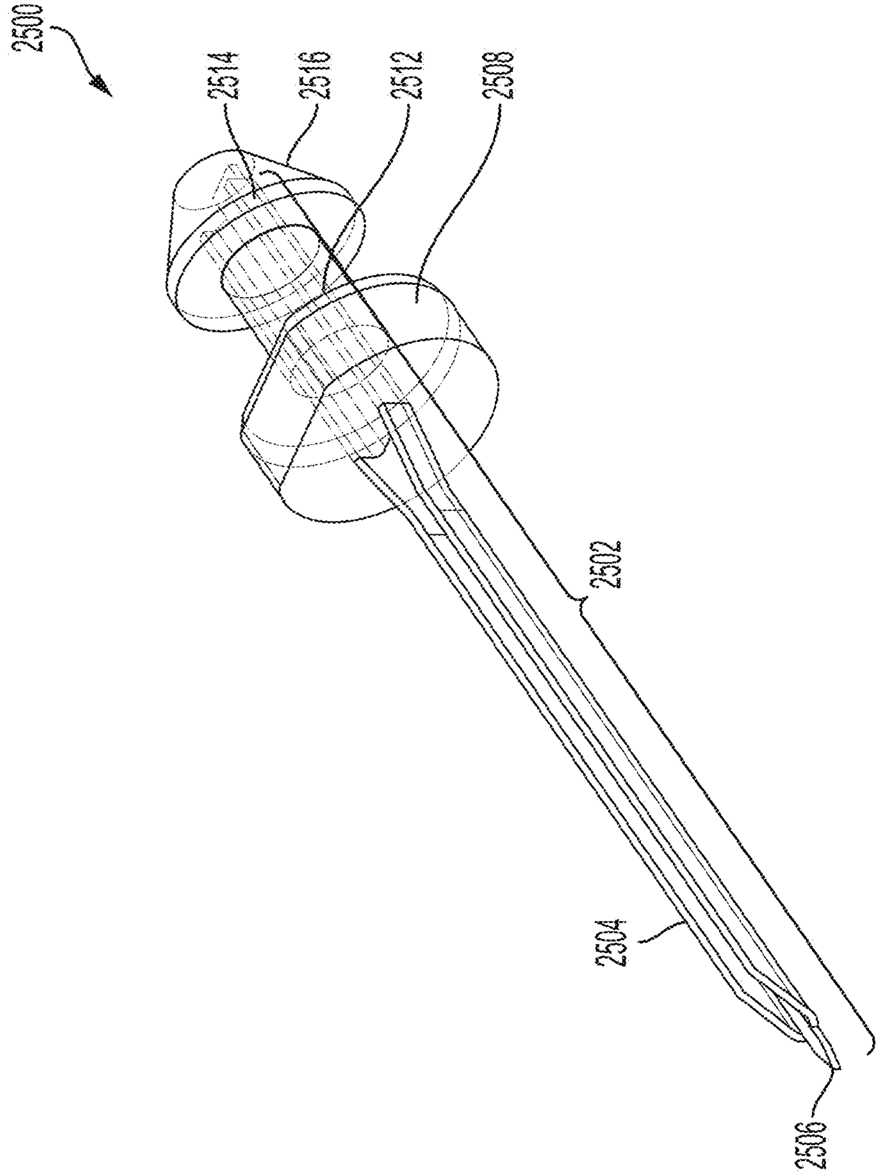
FIG. 17A is a perspective view depicting an example embodiment of a sharp module.

As shown in FIG. 11, sharp retention arms 1618 can be located in an interior of sharp carrier 1102 about a central axis and can include a sharp retention clip 1620 at a distal end of each arm 1618. Sharp retention clip 1620 can have a proximal surface which can be nearly perpendicular to the central axis and can abut a distally facing surface of sharp hub 2516 (FIG. 17A).

Example Embodiments of Sensor Modules

Figure 12A:
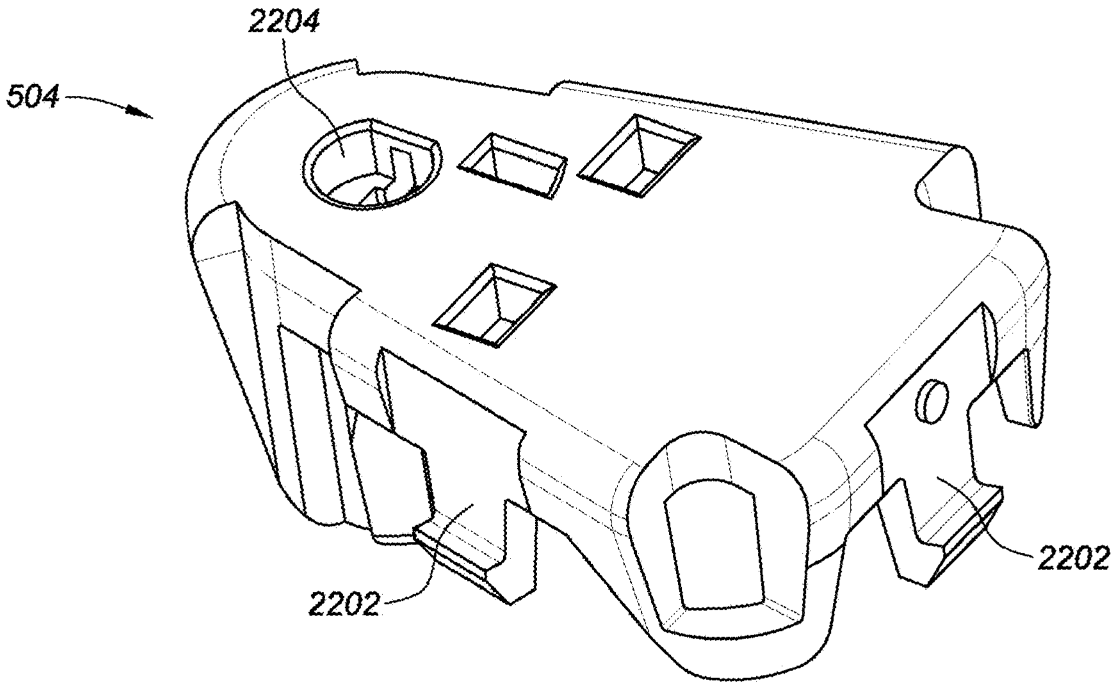
FIGS. 12A to 12B are top and bottom perspective views, respectively, depicting an example embodiment of a sensor module.
Figure 12B:
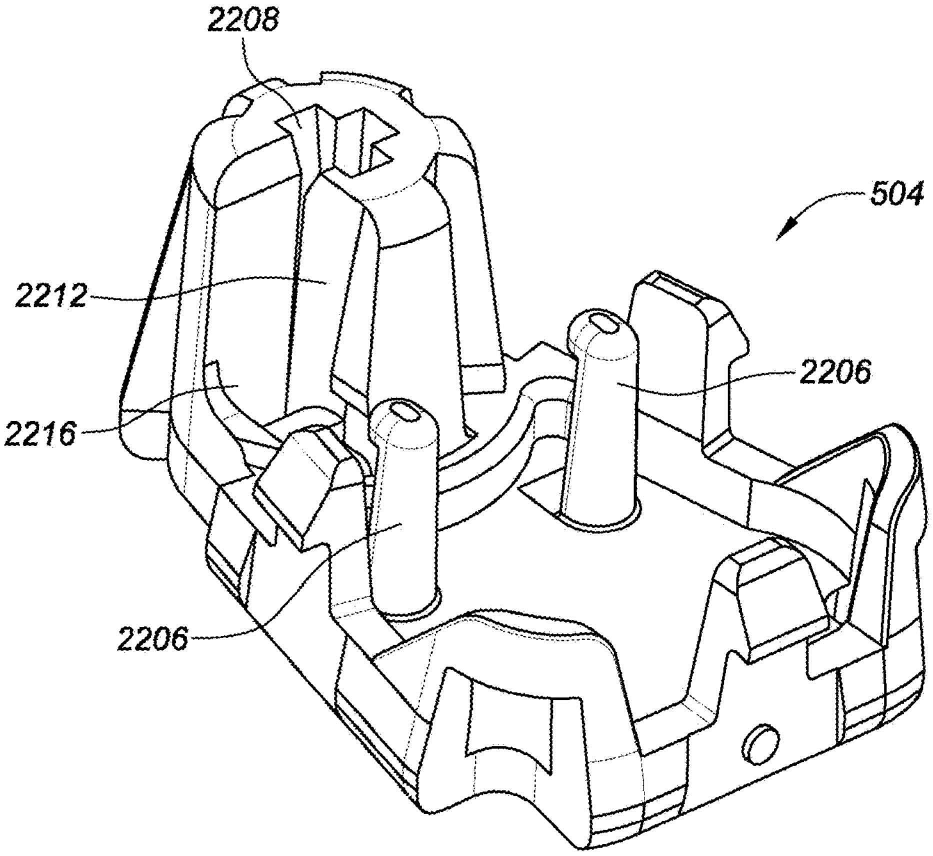

FIGS. 12A and 12B are a top perspective view and a bottom perspective view, respectively, depicting an example embodiment of sensor module 504. Module 504 can hold a connector 2300 (FIGS. 13A and 13B) and a sensor 104 (FIG. 14). Module 504 is capable of being securely coupled with electronics housing 706. One or more deflectable arms or module snaps 2202 can snap into the corresponding features 2010 of housing 706. A sharp slot 2208 can provide a location for sharp tip 2502 to pass through and sharp shaft 2504 to temporarily reside. A sensor ledge 2212 can define a sensor position in a horizontal plane, prevent a sensor from lifting connector 2300 off of posts and maintain sensor 104 parallel to a plane of connector seals. It can also define sensor bend geometry and minimum bend radius. It can limit sensor travel in a vertical direction and prevent a tower from protruding above an electronics housing surface and define a sensor tail length below a patch surface. A sensor wall 2216 can constrain a sensor and define a sensor bend geometry and minimum bend radius.

Figure 13A:
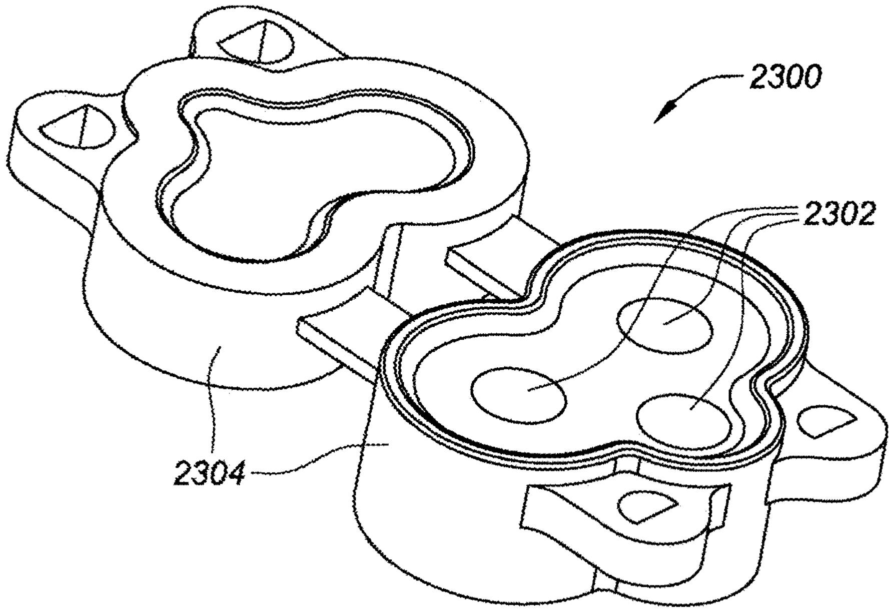
FIGS. 13A and 13B are perspective and compressed views, respectively, depicting an example embodiment of a sensor connector.
Figure 13B:
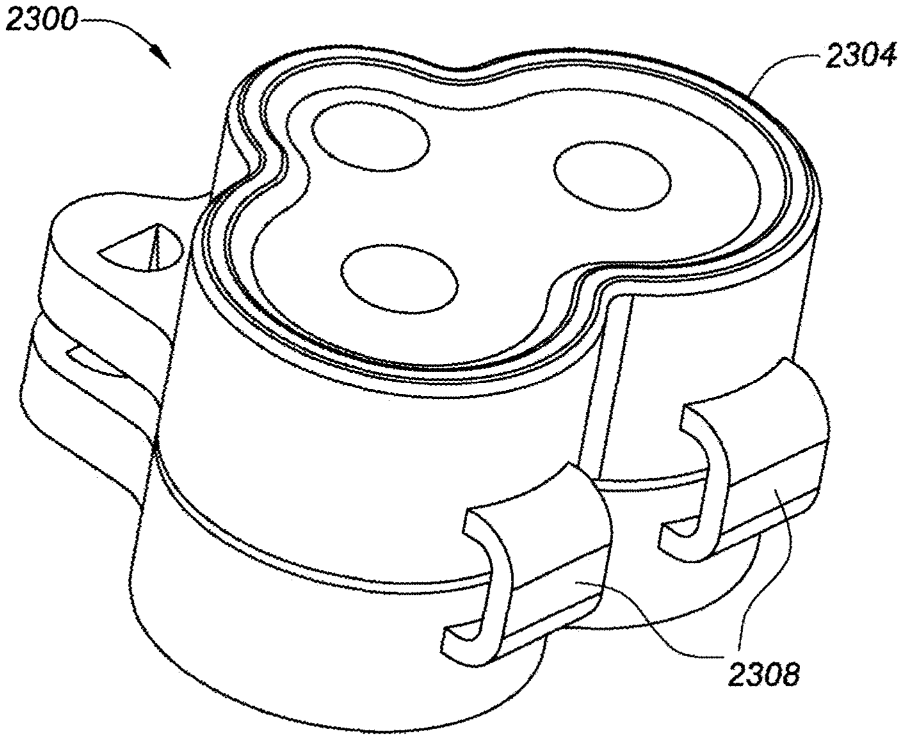
Figure 14:
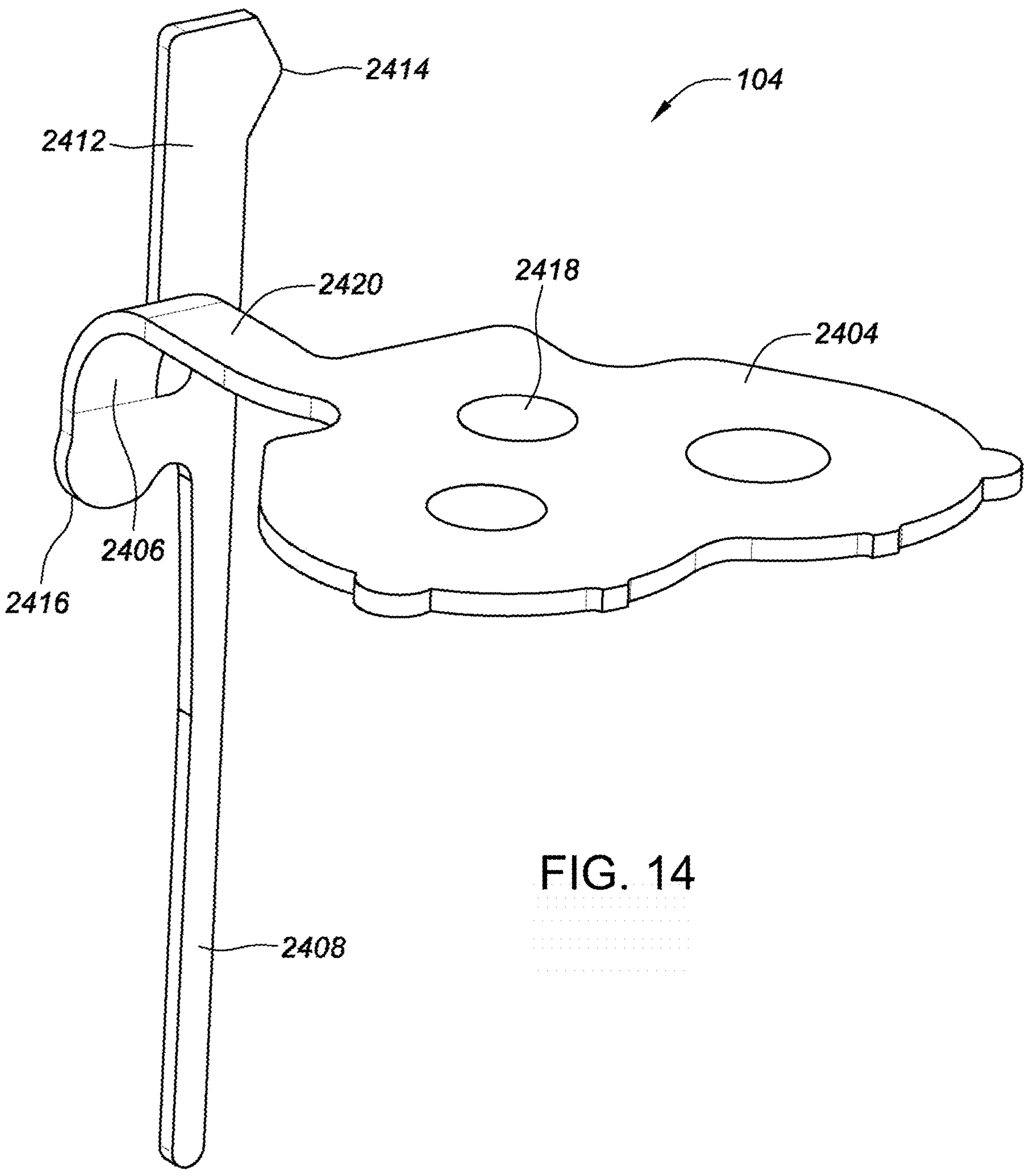
FIG. 14 is a perspective view depicting an example embodiment of a sensor.

FIGS. 13A and 13B are perspective views depicting an example embodiment of connector 2300 in an open state and a closed state, respectively. Connector 2300 can be made of silicone rubber that encapsulates compliant carbon impregnated polymer modules that serve as electrical conductive contacts 2302 between sensor 104 and electrical circuitry contacts for the electronics within housing 706. The connector can also serve as a moisture barrier for sensor 104 when assembled in a compressed state after transfer from a container to an applicator and after application to a user's skin. A plurality of seal surfaces 2304 can provide a watertight seal for electrical contacts and sensor contacts. One or more hinges 2208 can connect two distal and proximal portions of connector 2300.

FIG. 14 is a perspective view depicting an example embodiment of sensor 104. A neck 2406 can be a zone which allows folding of the sensor, for example ninety degrees. A membrane on tail 2408 can cover an active analyte sensing element of the sensor 104. Tail 2408 can be the portion of sensor 104 that resides under a user's skin after insertion. A flag 2404 can contain contacts and a sealing surface. A biasing tower 2412 can be a tab that biases the tail 2408 into sharp slot 2208. A bias fulcrum 2414 can be an offshoot of biasing tower 2412 that contacts an inner surface of a needle to bias a tail into a slot. A bias adjuster 2416 can reduce a localized bending of a tail connection and prevent sensor trace damage. Contacts 2418 can electrically couple the active portion of the sensor to connector 2300. A service loop 2420 can translate an electrical path from a vertical direction ninety degrees and engage with sensor ledge 2212 (FIG. 12B).

Figure 15B:
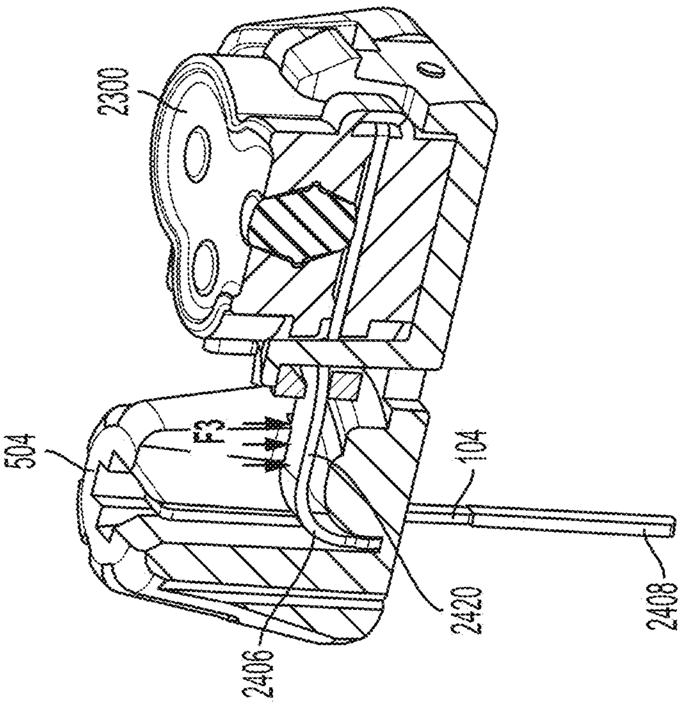
FIGS. 15A and 15B are bottom and top perspective views, respectively, of an example embodiment of a sensor module assembly.
Figure 15A:
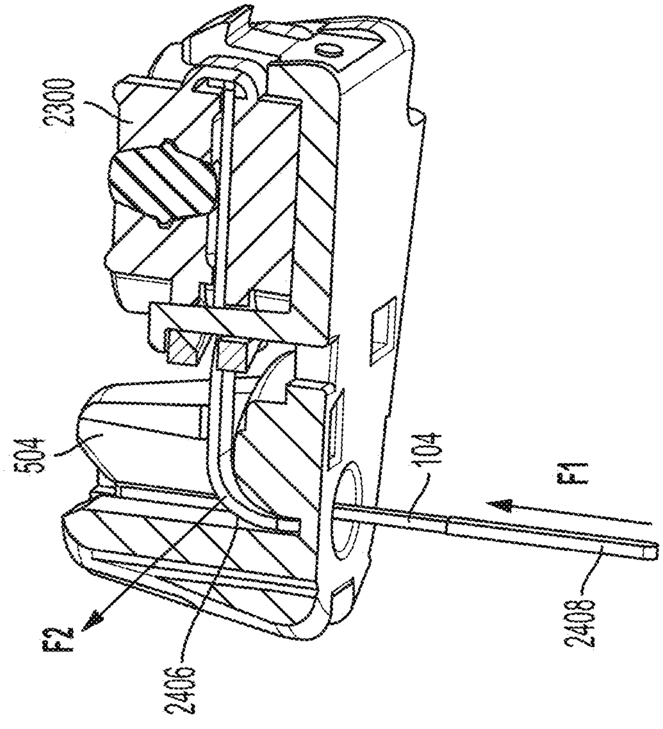

FIGS. 15A and 15B are bottom and top perspective views, respectively, depicting an example embodiment of a sensor module assembly comprising sensor module 504, connector 2300, and sensor 104. According to one aspect of the aforementioned embodiments, during or after insertion, sensor 104 can be subject to axial forces pushing up in a proximal direction against sensor 104 and into the sensor module 105, as shown by force, F1, of FIG. 15A. According to some embodiments, this can result in an adverse force, F2, being applied to neck 2406 of sensor 104 and, consequently, result in adverse forces, F3, being translated to service loop 2420 of sensor 104. In some embodiments, for example, axial forces, F1, can occur as a result of a sensor insertion mechanism in which the sensor is designed to push itself through the tissue, a sharp retraction mechanism during insertion, or due to a physiological reaction created by tissue surrounding sensor 104 (e.g., after insertion).

Figure 16B:
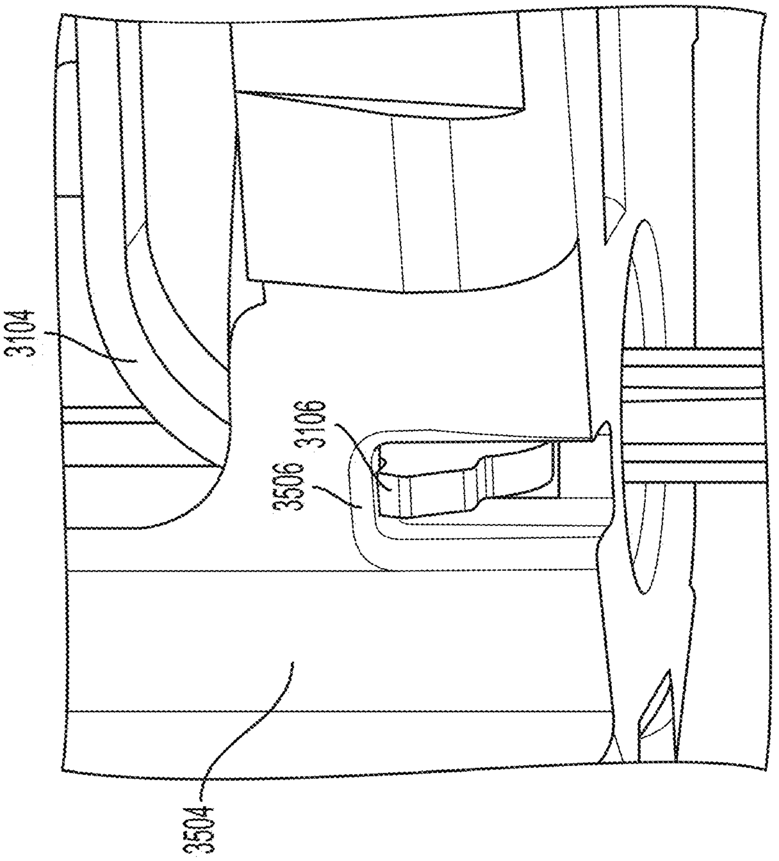
FIGS. 16A and 16B are close-up partial views of an example embodiment of a sensor module assembly.
Figure 16A:
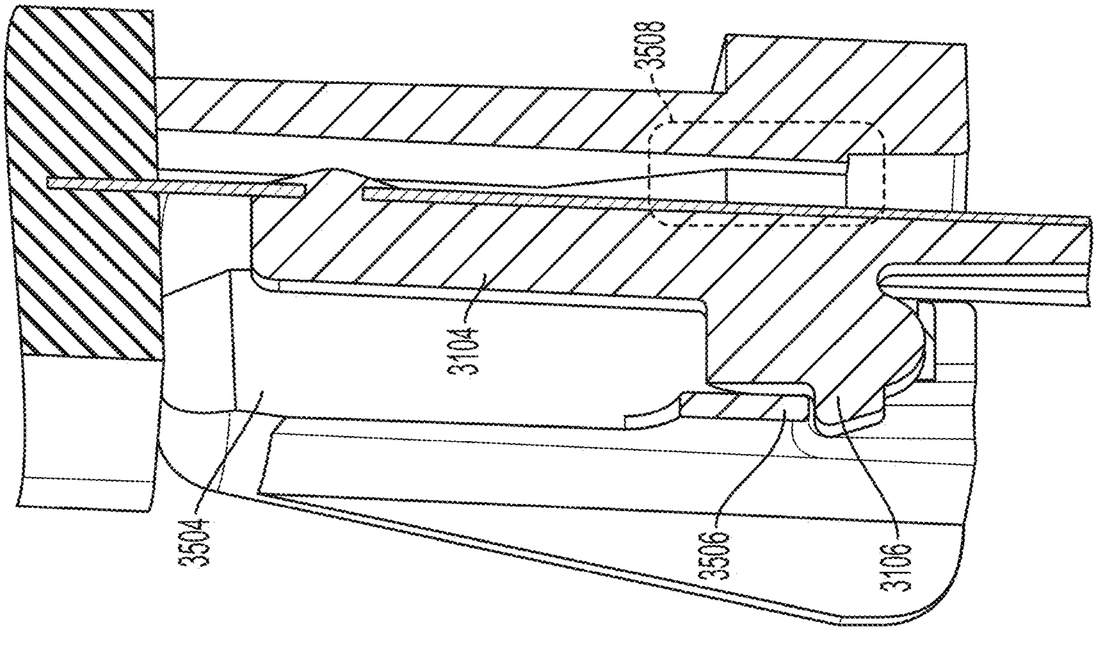

FIGS. 16A and 16B are close-up partial views of an example embodiment of a sensor module assembly having certain axial stiffening features. In a general sense, the embodiments described herein are directed to mitigating the effects of axial forces on the sensor as a result of insertion and/or retraction mechanisms, or from a physiological reaction to the sensor in the body. As can be seen in FIGS. 16A and 16B, according to one aspect of the embodiments, sensor 3104 comprises a proximal portion having a hook feature 3106 configured to engage a catch feature 3506 of the sensor module 3504. In some embodiments, sensor module 3504 can also include a clearance area 3508 to allow a distal portion of sensor 3104 to swing backwards during assembly to allow for the assembly of the hook feature 3106 of sensor 3104 over and into the catch feature 3506 of sensor module 3504.

According to another aspect of the embodiments, the hook and catch features 3106, 3506 operate in the following manner. Sensor 3104 includes a proximal sensor portion, coupled to sensor module 3504, as described above, and a distal sensor portion that is positioned beneath a skin surface in contact with a bodily fluid. As seen in FIGS. 16A and 16B, the proximal sensor portion includes a hook feature 3106 adjacent to the catch feature 3506 of sensor module 3504. During or after sensor insertion, one or more forces are exerted in a proximal direction along a longitudinal axis of sensor 3104. In response to the one or more forces, hook feature 3106 engages catch feature 3506 to prevent displacement of sensor 3104 in a proximal direction along the longitudinal axis.

According to another aspect of the embodiments, sensor 3104 can be assembled with sensor module 3504 in the following manner. Sensor 3104 is loaded into sensor module 3504 by displacing the proximal sensor portion in a lateral direction to bring the hook feature 3106 in proximity to the catch feature 3506 of sensor module 3504. More specifically, displacing the proximal sensor portion in a lateral direction causes the proximal sensor portion to move into clearance area 3508 of sensor module 3504.

Although FIGS. 16A and 16B depict hook feature 3106 as a part of sensor 3104, and catch feature 3506 as a part of sensor module 3504, those of skill in the art will appreciate that hook feature 3106 can instead be a part of sensor module 3504, and, likewise, catch feature 3506 can instead be a part of sensor 3106. Similarly, those of skill in the art will also recognize that other mechanisms (e.g., detent, latch, fastener, screw, etc.) implemented on sensor 3104 and sensor module 3504 to prevent axial displacement of sensor 3104 are possible and within the scope of the present disclosure.

Example Embodiments of Sharp Modules

FIG. 17A is a perspective view depicting an example embodiment of sharp module 2500 prior to assembly within sensor module 504 (FIG. 6B). Sharp 2502 can include a distal tip 2506 which can penetrate the skin while carrying sensor tail in a hollow or recess of sharp shaft 2504 to put the active surface of the sensor tail into contact with bodily fluid. A hub push cylinder 2508 can provide a surface for a sharp carrier to push during insertion. A hub small cylinder 2512 can provide a space for the extension of sharp hub contact faces 1622 (FIG. 11). A hub snap pawl locating cylinder 2514 can provide a distal-facing surface of hub snap pawl 2516 for sharp hub contact faces 1622 to abut. A hub snap pawl 2516 can include a conical surface that opens clip 1620 during installation of sharp module 2500. Further details regarding embodiments of sharp modules, sharps, their components, and variants thereof, are described in U.S. Patent Publication No. 2014/0171771, which is incorporated by reference herein in its entirety and for all purposes.

Figure 17B:
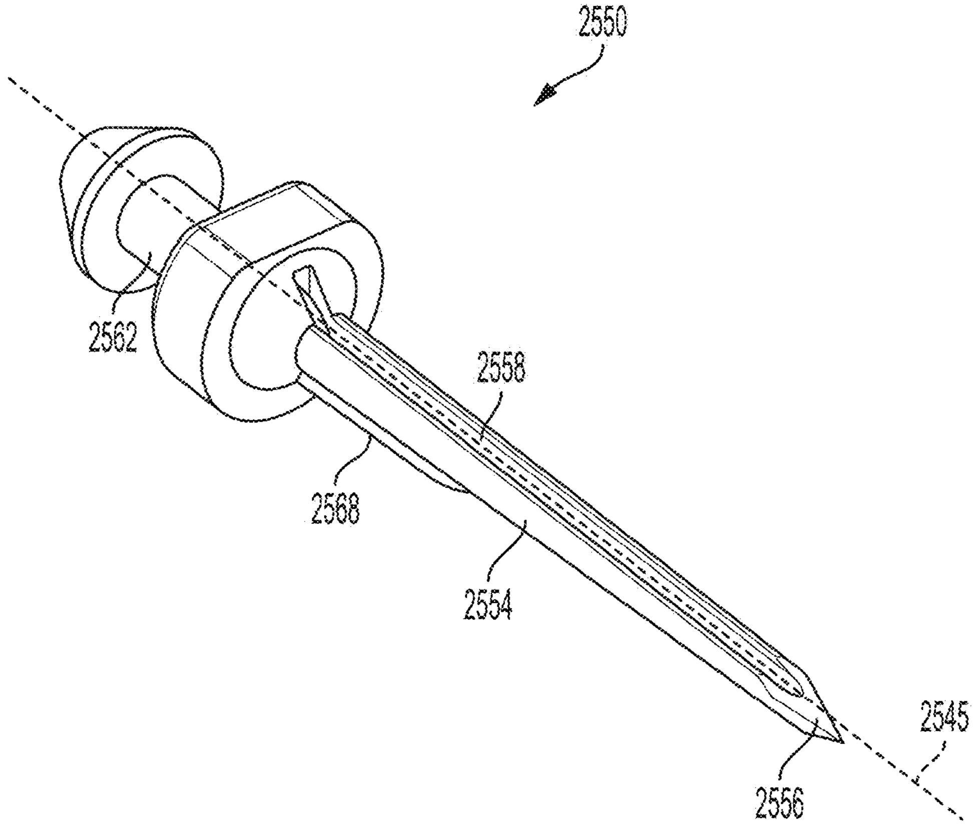
FIG. 17B is a perspective view depicting another example embodiment of a sharp module.
Figure 17D:
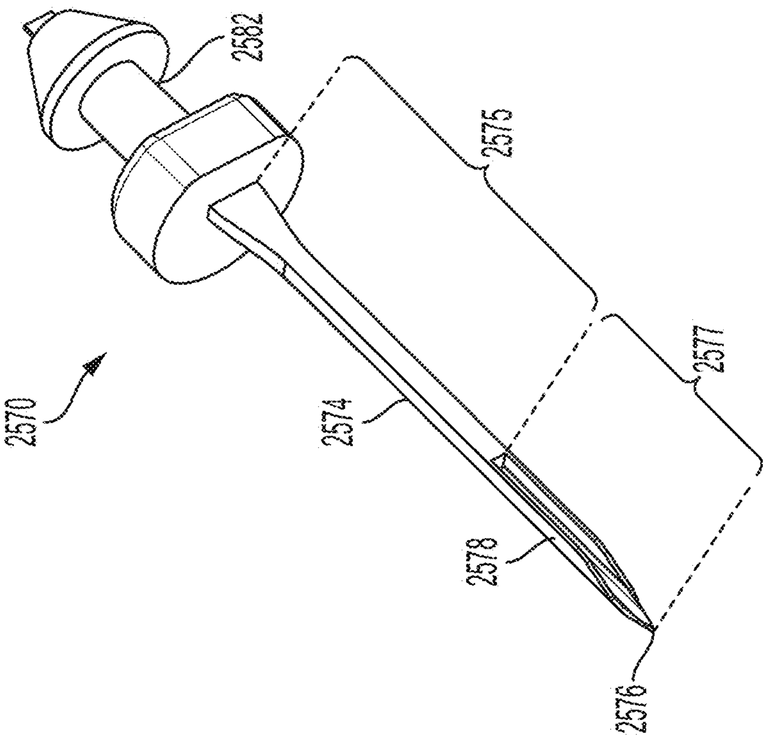
FIGS. 17C and 17D are a side view and a perspective view depicting another example embodiment of a sharp module.
Figure 17C:
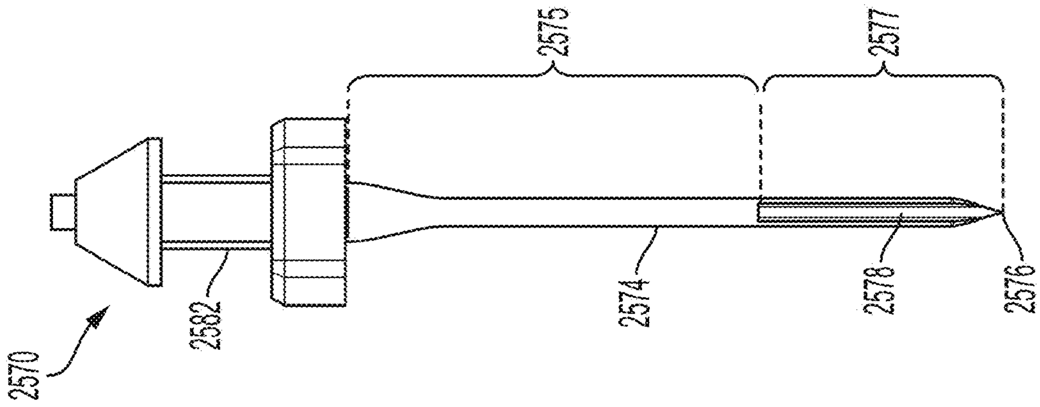

FIGS. 17B, 17C, and 17D depict example embodiments of plastic sharp modules. By way of background, according to one aspect of the embodiments, a plastic sharp can be advantageous in at least two respects.

First, relative to a metallic sharp, a plastic sharp can cause reduced trauma to tissue during the insertion process into the skin. Due to their manufacturing process, e.g., chemical etching and mechanical forming, metallic sharps are typically characterized by sharp edges and burrs that can cause trauma to tissue at the insertion site. By contrast, a plastic sharp can be designed to have rounded edges and a smooth finish to reduce trauma as the sharp is positioned through tissue. Moreover, those of skill in the art will understand that reducing trauma during the insertion process can lead to reduced ESA and improve accuracy in analyte level readings soon after insertion.

Second, a plastic sharp can simplify the applicator manufacturing and assembly process. As with earlier described embodiments, certain applicators are provided to the user in two pieces: (1) an applicator containing the sharp and sensor electronics in a sensor control unit, and (2) a sensor container. This requires the user to assemble the sensor into the sensor control unit. One reason for a two-piece assembly is to allow for electron beam sterilization of the sensor to occur separately from the applicator containing the metallic sharp and the sensor electronics. Metallic sharps, e.g., sharps made of stainless steel, have a higher density relative to sharps made of polymeric or plastic materials. As a result, electron beam scatter from an electron beam striking a metallic sharp can damage the sensor electronics of the sensor control unit. By utilizing a plastic sharp, e.g., a sharp made of polymeric materials, and additional shielding features to keep the electron beam path away from the sensor electronics, the applicator and sensor can be sterilized and packaged in a single package, thereby reducing the cost to manufacture and simplifying the assembly process for the user.

Referring to FIG. 17B, a perspective view of an example embodiment of plastic sharp module 2550 is shown, and can include a hub 2562 coupled to a proximal end of the sharp, sharp shaft 2554, a sharp distal tip 2556 configured to penetrate a skin surface, and a sensor channel 2558 configured to receive at least a portion of an analyte sensor 104. Any or all of the components of sharp module 2550 can be comprised of a plastic material such as, for example, a thermoplastic material, a liquid crystal polymer (LCP), or a similar polymeric material. According to some embodiments, for example, the sharp module can comprise a polyether ether ketone material. In other embodiments, silicone or other lubricants can be applied to an external surface of the sharp module and/or incorporated into the polymer material of the sharp module, to reduce trauma caused during the insertion process. Furthermore, to reduce trauma during insertion, one or more of sharp shaft 2554, sharp distal tip 2556, or alignment feature 2568 (described below) can include filleted and/or smoothed edges.

According to some embodiments, when assembled, the distal end of the analyte sensor can be in a proximal position relative to the sharp distal tip 2556. In other embodiments, the distal end of the analyte sensor and the sharp distal tip 2556 are co-localized.

According to another aspect of some embodiments, plastic sharp module 2550 can also include an alignment feature 2568 configured to prevent rotational movement along a vertical axis 2545 of sharp module 2550 during the insertion process, wherein the alignment feature 2568 can be positioned along a proximal portion of sharp shaft 2554.

FIGS. 17C and 17D are a side view and a perspective view, respectively, depicting another example embodiment of a plastic sharp module 2570. Like the embodiment described with respect to FIG. 17B, plastic sharp module 2570 can include a hub 2582 coupled to a proximal end of the sharp, a sharp shaft 2574, a sharp distal tip 2576 configured to penetrate a skin surface, and a sensor channel 2578 configured to receive at least a portion of an analyte sensor 104. Any or all of the components of sharp module 2570 can be comprised of a plastic material such as, for example, a thermoplastic material, LCP, or a similar polymeric material. In some embodiments, silicone or other lubricants can be applied to an external surface of sharp module 2570 and/or incorporated into the polymer material of sharp module 2570, to reduce trauma caused during the insertion process.

According to some embodiments, sharp shaft 2574 can include a distal portion 2577 that terminates at distal tip 2576, in which at least a portion of sensor channel 2578 is disposed. Sharp shaft 2574 can also have a proximal portion 2575 that is adjacent to distal portion 2577, wherein the proximal portion 2575 is solid, partially solid, or hollow, and is coupled to hub 2582. Although FIGS. 17C and 17D depict sensor channel 2578 as being located only within distal portion 2577, those of skill in the art will understand that sensor channel 2578 can also extend through a majority of, or along the entire length of, sharp shaft 2574 (e.g., as shown in FIG. 17B), including through at least a portion of proximal portion 2575. In addition, according to another aspect of some embodiments, at least a portion of proximal portion 2575 can have a wall thickness that is greater than the wall thickness of distal portion 2577, to reduce the possibility of stress buckling of the sharp during the insertion process. According to another aspect of some embodiments, plastic sharp module 2570 can include one or more ribs (not shown) adjacent to sharp hub portion 2582 to reduce the compressive load around hub 2582, and to mitigate stress buckling of the sharp during the insertion process.

Figure 17E:
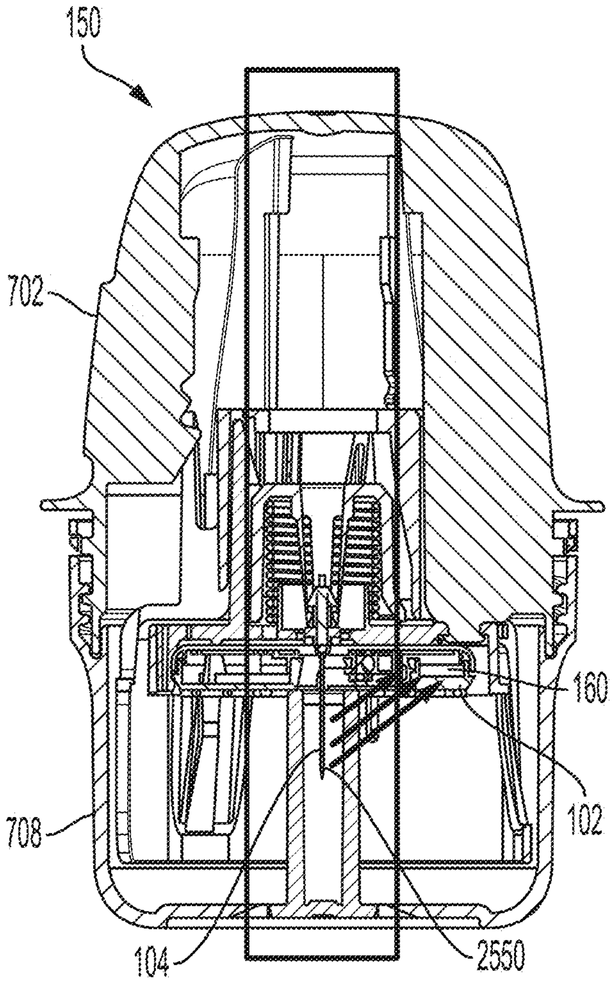
FIG. 17E is a cross-sectional view depicting an example embodiment of an applicator.

FIG. 17E is a cross-sectional view depicting an example embodiment of an applicator 150 with a plastic sharp module during an electron beam sterilization process. As indicated by the rectangular area, A, an electron beam is focused on sensor 104 and plastic sharp 2550 of applicator 150 during a sterilization process. According to some embodiments, a cap 708 has been secured to applicator housing 702 to seal sensor control device 102 within applicator 150. During the sterilization process, electron beam scatter, as indicated by the diagonal arrows originating from plastic sharp 2550, in the direction and path of sensor electronics 160 has been reduced because a plastic sharp 2550 has been utilized instead of a metallic sharp. Although FIG. 17E depicts a focused electron beam sterilization process, those of skill in the art will recognize that an applicator with a plastic sharp module embodiment can also be utilized during a non-focused electron beam sterilization process.

Figure 17F:
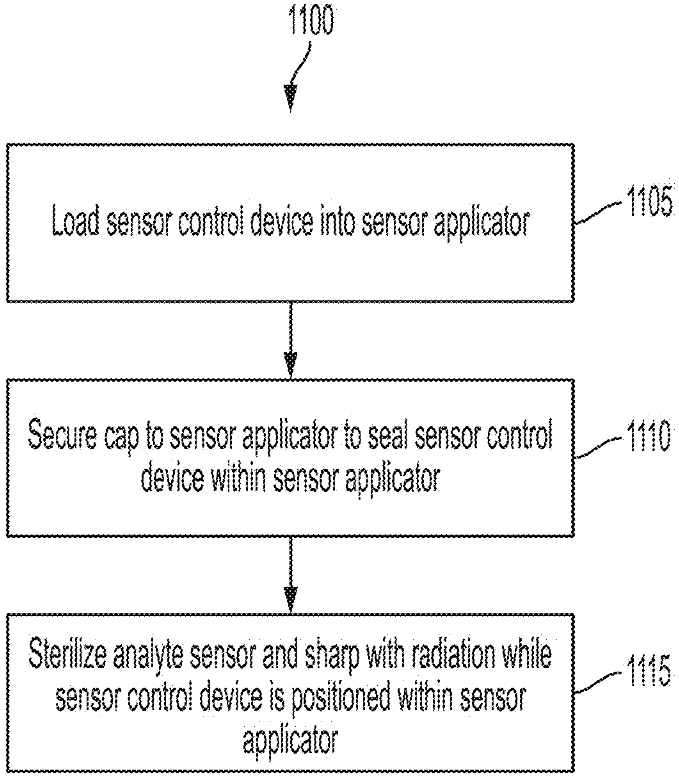
FIG. 17F is a flow diagram depicting an example embodiment method for sterilizing an applicator assembly.

FIG. 17F is a flow diagram depicting an example embodiment method 1100 for sterilizing an applicator assembly, according to the embodiments described above. At Step 1105, a sensor control device 102 is loaded into the applicator 150. Sensor control device 102 can include various components, including an electronics housing, a printed circuit board positioned within the electronics housing and containing processing circuitry, an analyte sensor extending from a bottom of the electronics housing, and a plastic sharp module having a plastic sharp that extends through the electronics housing. According to some embodiments, the plastic sharp can also receive the portion of the analyte sensor extending from the bottom of the electronics housing. As previously described, at Step 1110, a cap 708 is secured to the applicator housing 702 of applicator 150, thereby sealing the sensor control device 102 within applicator 150. At Step 1115, the analyte sensor 104 and plastic sharp 2550 are sterilized with radiation while sensor control device 102 is positioned within applicator 150.

According to some embodiments, sensor control device 102 can also include at least one shield positioned within the electronics housing, wherein the one or more shields are configured to shield the processing circuitry from radiation during the sterilization process. In some embodiments, the shield can comprise a magnet that generates a static magnetic field to divert radiation away from the processing circuitry. In this manner, the combination of the plastic sharp module and the magnetic shields/deflectors can operate in concert to protect the sensor electronics from radiation during the sterilization process.

Figure 17G:
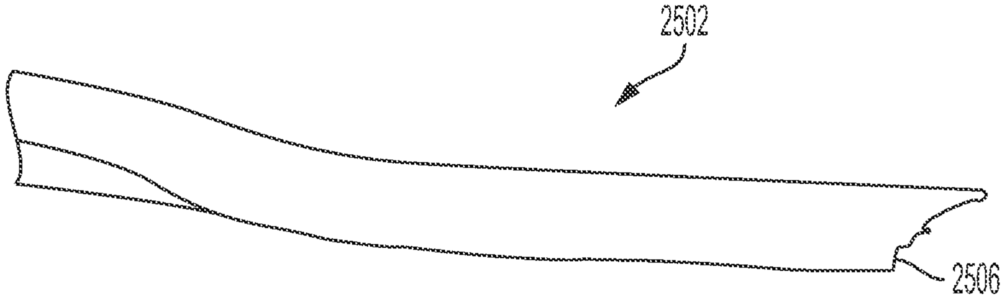
FIGS. 17G and 17H are photographs depicting example embodiments of sharp tips.
Figure 17H:
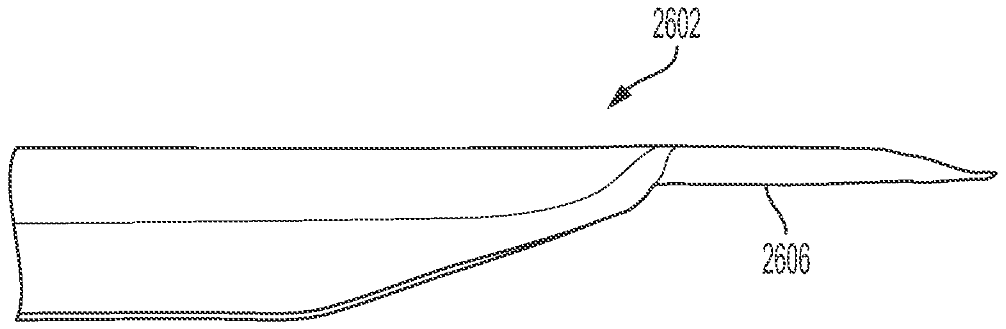

Another example embodiment of a sharp designed to reduce trauma during a sensor insertion and retraction process will now be described. More specifically, certain embodiments described herein are directed to sharps comprising a metallic material (e.g., stainless steel) and manufactured through a coining process. According to one aspect of the embodiments, a coined sharp can be characterized as having a sharp tip with all other edges comprising rounded edges. As previously described, metallic sharps manufactured through a chemical etching and mechanical forming process can result in sharp edges and unintended hook features. For example, FIG. 17G is a photograph depicting a metallic sharp 2502 manufactured by a chemical etching and mechanical forming process. As can be seen in FIG. 17G, metallic sharp 2502 includes a sharp distal tip 2506 with a hook feature. These and other unintended transition features can result in increased trauma to tissue during a sensor insertion and retraction process. By contrast, FIG. 17H is a photograph depicting a coined sharp 2602, that is, a metallic sharp manufactured through a coining process. As can be seen in FIG. 17H, coined sharp 2602 also includes a sharp distal tip 2606. Coined sharp 2602, however, includes only smooth, rounded edges without any unintended sharp edges or transitions.

As with previously described sharp embodiments, the coined sharp 2602 embodiments described herein can also be assembled into a sharp module having a sharp portion and a hub portion. Likewise, the sharp portion comprises a sharp shaft, a sharp proximal end coupled to a distal end of the hub portion, and a sharp distal tip configured to penetrate a skin surface. According to one aspect of the embodiments, one or all of the sharp portion, the sharp shaft, and/or the sharp distal tip of a coined sharp 2602 can comprise one or more rounded edges.

Furthermore, it will be understood by those of skill in the art that the coined sharp 2602 embodiments described herein can similarly be used with any of the sensors described herein, including in vivo analyte sensors that are configured to measure an analyte level in a bodily fluid of a subject. For example, in some embodiments, coined sharp 2602 can include a sensor channel (not shown) configured to receive at least a portion of an analyte sensor. Likewise, in some embodiments of the sharp module assembly utilizing a coined sharp 2602, the distal end of the analyte sensor can be in a proximal position relative to the sharp distal tip 2606. In other embodiments, the distal end of the analyte sensor and the sharp distal tip 2606 are co-localized.

Other example embodiments of sharps designed to reduce trauma during a sensor insertion process will now be described. Referring back to FIG. 17A, an example embodiment of sharp module 2500 (shown without analyte sensor) is depicted, and includes a sharp 2502 comprising a sensor channel having a U-shaped geometry configured to receive at least a portion of an analyte sensor, and a distal tip 2506 configured to penetrate a skin surface during the sensor insertion process.

Figure 17I:
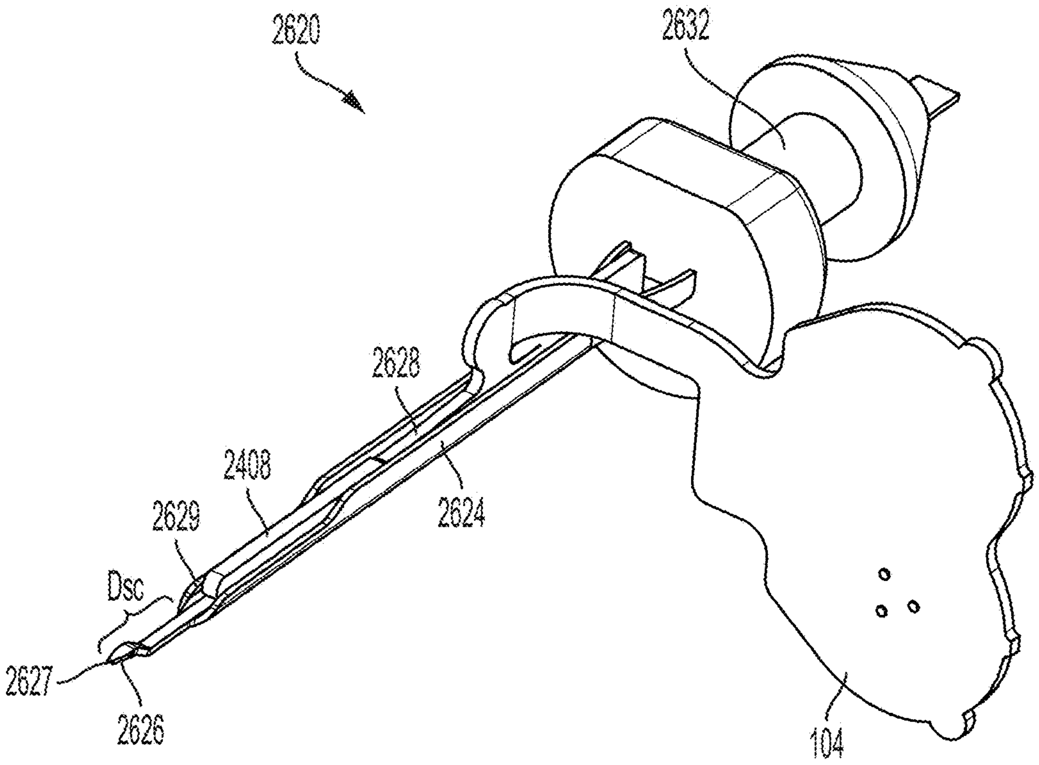
FIGS. 17I and 17J are perspective views depicting example embodiments of sharp modules.

In certain embodiments, sharp module can include a sharp having a distal tip with an offset geometry configured to create a smaller opening in the skin relative to other sharps (e.g., sharp 2502 depicted in FIG. 17A). Turning to FIG. 17I, a perspective view of an example embodiment of a sharp module 2620 (with analyte sensor 104) having an offset tip portion is shown. Similar to the previously described sharp modules, sharp module 2620 can include a sharp shaft 2624 coupled to hub 2632 at a proximal end, sensor channel 2628 configured to receive at least a portion of analyte sensor 104, and a distal tip 2626 configured to penetrate a skin surface during the sensor insertion process.

According to one aspect of the embodiment, one or more sidewalls 2629 that form sensor channel 2628 are disposed along sharp shaft 2624 at a predetermined distance, Dsc, from distal tip 2626. In certain embodiments, predetermined distance, Dsc, can be between 1 mm and 8 mm. In other embodiments, predetermined distance, Dsc, can be between 2 mm and 5 mm. Those of skill in the art will recognize that other predetermined distances, Dsc, can be utilized and are fully within the scope of the present disclosure. In other words, according to some embodiments, sensor channel 2628 is in a spaced relation to distal tip 2626. In this regard, distal tip 2626 has a reduced cross-sectional footprint relative to, for example, distal tip 2506 of sharp module 2500, whose sensor channel is adjacent to distal tip 2506. According to another aspect of the embodiment, at the terminus of distal tip 2626 is an offset tip portion 2627 configured to prevent sensor tip 2408 from being damaged during insertion and to create a small opening in the skin. In some embodiments, offset tip portion 2627 can be a separate element coupled to a distal end of sharp shaft 2624. In other embodiments, offset tip portion 2627 can be formed from a portion of distal tip 2506 or sharp shaft 2624. During insertion, as the sharp moves into the skin surface, offset tip portion 2627 can cause the skin surrounding the skin opening to stretch and widen in a lateral direction without further cutting of skin tissue. In this regard, less trauma results during the sensor insertion process.

Figure 17J:
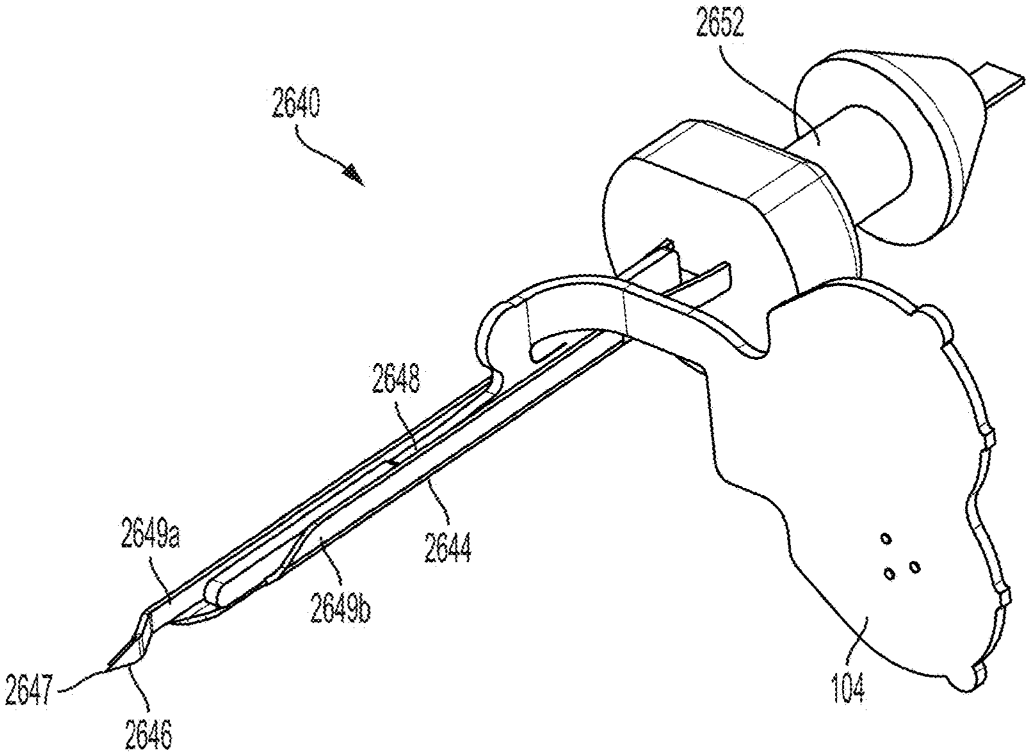

Referring next to FIG. 17J, a perspective view of another example embodiment of a sharp module 2640 (with analyte sensor 104) having an offset tip portion is shown. Like the previous embodiments, sharp module 2640 can include a sharp shaft 2644 coupled to hub 2652 at a proximal end, sensor channel 2648 configured to receive at least a portion of analyte sensor 104, and a distal tip 2646 configured to penetrate a skin surface during the sensor insertion process. According to one aspect of the embodiment, sensor channel 2648 can comprise a first sidewall **2649*a* and a second sidewall 2649*b*, wherein first sidewall 2649*a* extends to the distal tip 2646, wherein a terminus of first sidewall 2649*a* forms the offset tip portion 2647, and wherein second sidewall 2649*b* is disposed along sharp shaft 2644 at a predetermined distance from distal tip 2646, and wherein a terminus of second sidewall 2649*b* is proximal to the terminus of first sidewall 2649*a*. Those of skill in the art will appreciate that in other embodiments, second sidewall 2649*b* can extend to the distal tip 2646 to form the offset tip portion 2647, instead of first sidewall 2649*a*. In addition, offset tip portion 2647** can be formed from a third or fourth sidewall (not shown), and such geometries are fully within the scope of the present disclosure.

With respect to the sharp and sharp module embodiments described herein, those of skill in the art will recognize that any or all of the components can comprise either a metallic material, such as stainless steel, or a plastic material, such as a liquid crystal polymer. Furthermore, it will be understood by those of skill in the art that any of the sharp and/or sharp module embodiments described herein can be used or combined with any of the sensors, sensor modules, sensor electronics carriers, sheaths, applicator devices, or any of the other analyte monitoring system components described herein.

Example Embodiments of Powered Applicator

Figure 18B:
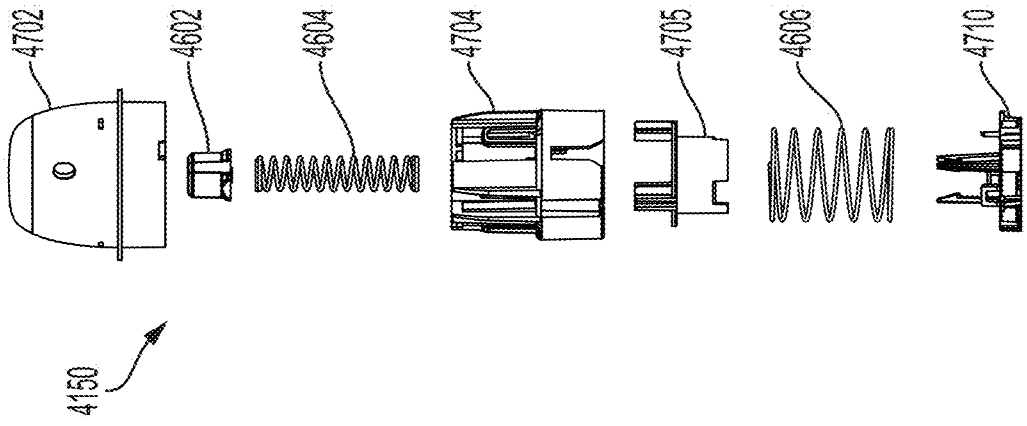
FIG. 18B is an exploded view depicting various components of an example embodiment of an applicator.
Figure 18A:
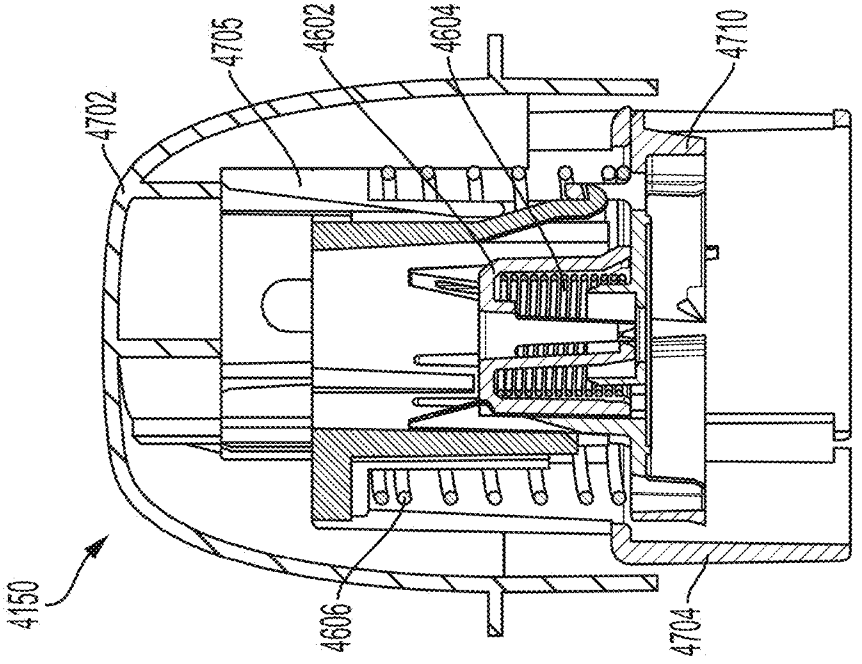
FIG. 18A is a cross-sectional view depicting an example embodiment of an applicator.

FIGS. 18A and 18B are a cross-sectional view and an exploded view, respectively, depicting an example embodiment of a powered applicator 4150 for insertion of an analyte sensor in a subject. According to one aspect of the embodiments, housing 4702 of powered applicator 4150 operates as a trigger that releases under light pressure and activates a drive spring 4606 to push sensor electronics carrier 4710 downward and insert a sharp and the analyte sensor in the subject. As the subject pulls applicator 4150 away from the skin, a retraction spring 4604 is triggered causing the sharp to withdraw from the subject. According to an aspect of the embodiments, powered applicator 4150 can provide for a higher, more controlled insertion speed, relative to an applicator that relies upon manual force for insertion. Powered applicator 4150 is further advantageous in that it can improve upon insertion success and can also reduce trauma at the insertion site, relative to an applicator that relies upon manual force for insertion.

Referring to FIGS. 18A and 18B, the various components of powered applicator 4150 will now be described. As can be seen in FIG. 18A, as a cross-sectional view of an assembled powered applicator 4150 (in an initial state), and in FIG. 18B as an exploded view, powered applicator 4150 can include the following components: housing 4702, sharp carrier 4602, retraction spring 4604, sheath 4704, firing pin 4705, drive spring 4606, sensor electronics carrier 4710. Furthermore, although not depicted, powered applicator 4150 can also include any of the embodiments of sensor control units, analyte sensors, and sharps described herein, or in other publications which have been incorporated by reference.

FIGS. 19A to 19L are various views depicting an example embodiment of a powered applicator 4150 during various stages of deployment.

Figure 19B:
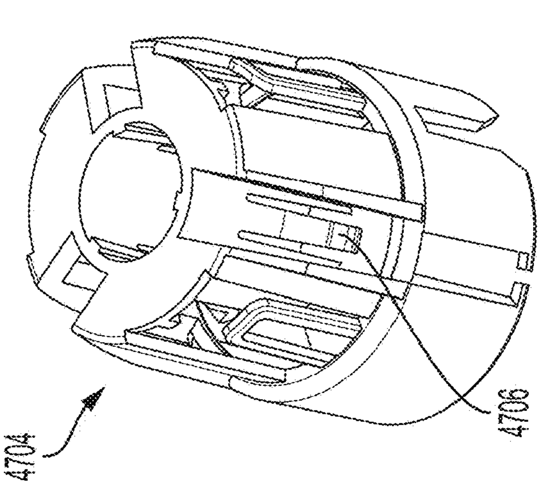
FIGS. 19B and 19C are perspective views, respectively, of an example embodiment of a sheath and a sensor electronics carrier.
Figure 19C:
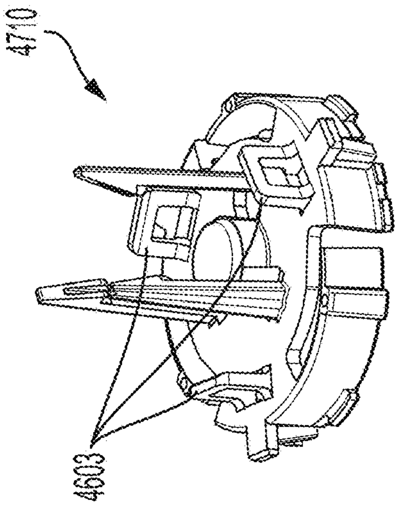
Figure 19A:
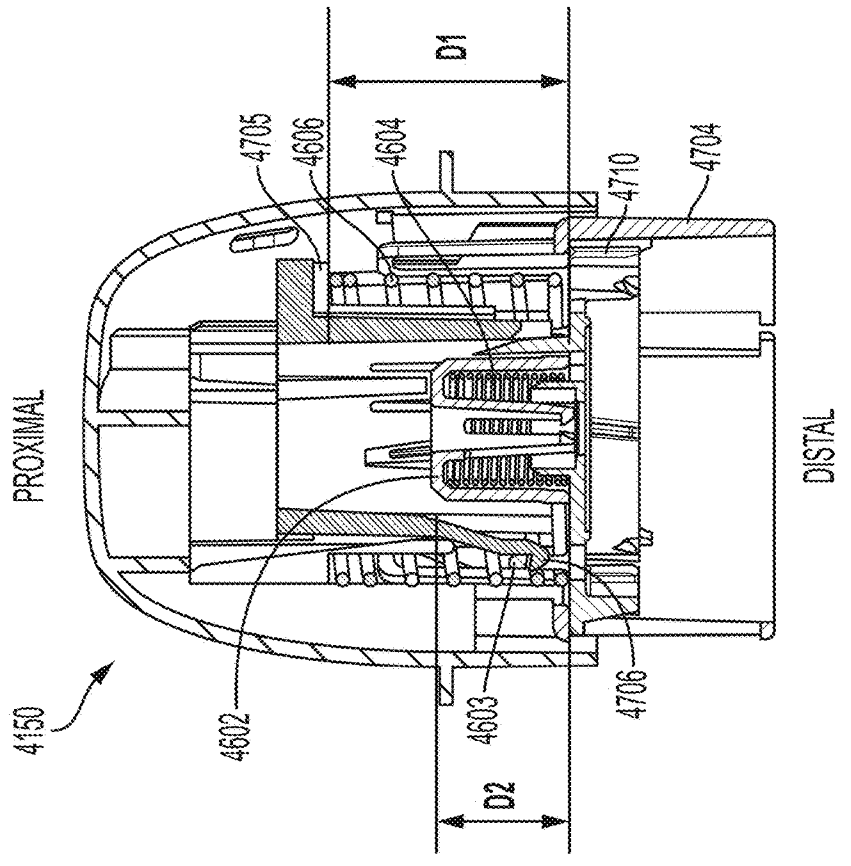
FIG. 19A is a cross-sectional view depicting an example embodiment of an applicator during a stage of deployment.

FIG. 19A is a cross-sectional view showing powered applicator 4150 in an initial state, wherein a distal end of applicator 4150 is ready to be positioned on a subject's skin surface. In the initial state, the drive spring 4606 and retraction spring 4604 are each in a preloaded state. Drive spring 4606 includes a first end coupled to firing pin 4705 and a second end coupled to sensor electronics carrier 4710. Retraction spring 4604 includes a first end coupled to sharp carrier 4602 and a second end coupled to sensor electronics carrier 4710. As best seen in FIG. 19A, in the initial state, sensor electronics carrier 4710 and sharp carrier 4602 are in a first position within applicator 4150, in a spaced relation with the skin surface.

According to an aspect of the embodiments, in the initial state, sensor electronics carrier 4710 is coupled to sheath 4704 by one or more latch-tab structures. FIG. 19B depicts a perspective view of sheath 4704 comprising one or more sheath tabs 4706. FIG. 19C depicts a perspective view of sensor electronics carrier 4710 comprising one or more corresponding sensor electronics carrier latches 4603. In the initial state, each of the one or more sensor electronics carrier latches 4603 is engaged to a corresponding sheath latch 4706, as best seen in FIG. 19A. Although FIGS. 19B and 19C depict three sheath tabs 4706 and three sensor electronics carrier latches 4603, those of skill in the art will appreciate that fewer or more latch-tab structures can be utilized, and those embodiments are fully within the scope of the present disclosure.

Figure 19E:
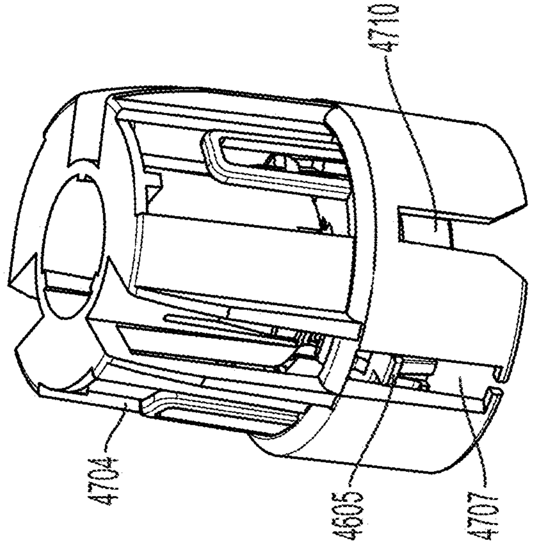
FIGS. 19E and 19F are perspective and close-up partial views, respectively, of an example embodiment of a sheath-sensor electronics carrier assembly.
Figure 19F:
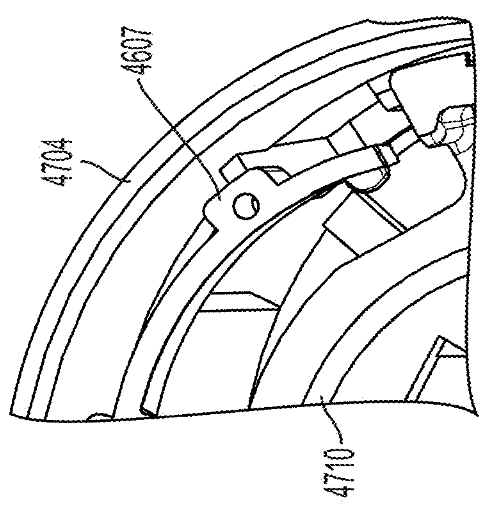
Figure 19D:
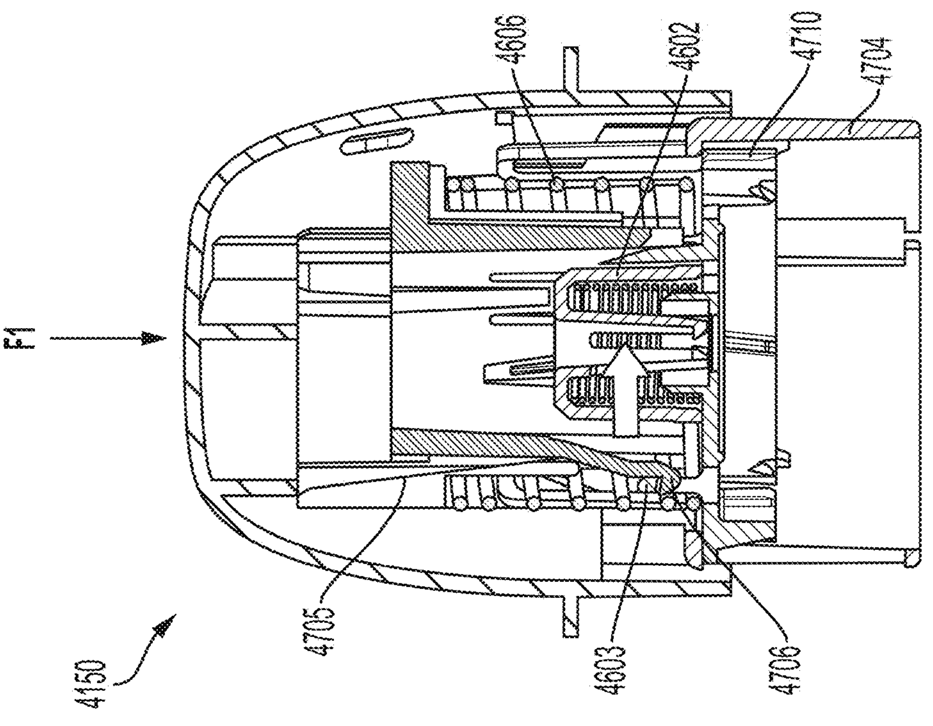
FIG. 19D is a cross-sectional view depicting an example embodiment of an applicator during a stage of deployment.

FIG. 19D is a cross-sectional view showing powered applicator 4150 in a firing state, wherein a force, F1, is applied to applicator 4150, in a distal direction (as indicated by the dark arrow). According to one aspect of the embodiments, application of force, F1, causes firing pin 4705 to move along sheath 4704 in a distal direction and, subsequently, disengages sheath tabs 4706 from sensor electronics carrier latches 4603 (as indicated by the white arrow). Disengagement of sheath tabs 4706 from sensor electronics carrier latches 4603 causes drive spring 4606 to expand in a distal direction, thereby "firing" applicator 4150. As drive spring 4606 expands in a distal direction, sensor electronics carrier 4710 and sharp carrier 4602 are displaced, also in a distal direction, to a second position adjacent to the skin surface.

According to some embodiments, prior to disengagement of sheath tabs 4706, application of force, F1, can increase the load on drive spring 4606 by further compressing it.

According to one aspect of the embodiments, the "cylinder-on-cylinder" design of sheath 4704 and firing pin 4705 can provide for a stable and simultaneous release of all three sensor electronics carrier latches 4603. Furthermore, in some embodiments, certain features can provide for enhanced stability while sensor electronics carrier 4710 and sharp carrier 4602 are being displaced from the first position to the second position. For example, as seen in FIG. 19E, sensor electronics carrier 4710 can include one or more sensor electronics carrier tabs 4605 that are configured to travel in a distal direction along one or more sheath rails 4707 of the sheath 4704. In addition, as seen in FIG. 19F, according to some embodiments, sensor electronics carrier 4710 can include one or more sensor electronics carrier bumpers 4607, each of which can be biased against an internal surface of sheath 4704 while the sensor electronics carrier 4710 and sharp carrier 4602 are displaced from the first position to the second position.

Figure 19H:
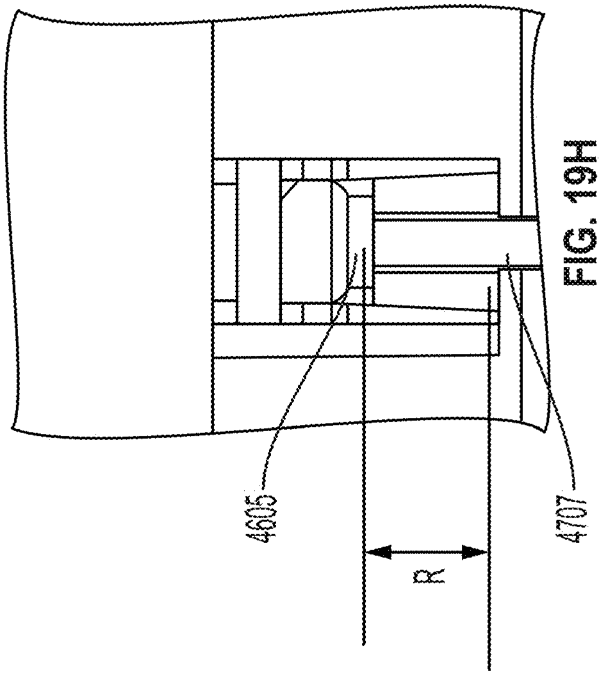
FIGS. 19H and 19I are close-up partial views of an example embodiment of a sheath-sensor electronics carrier assembly.
Figure 19I:
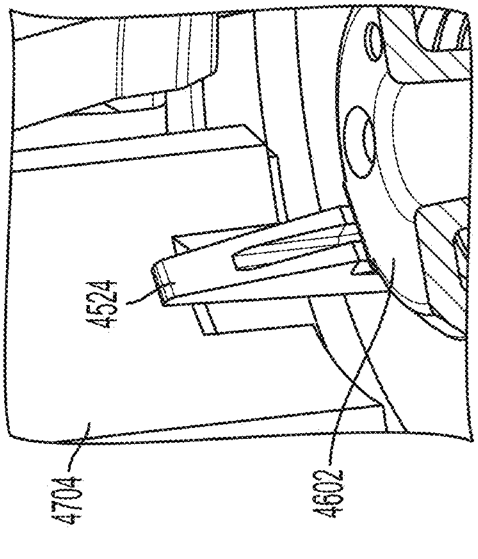
Figure 19G:
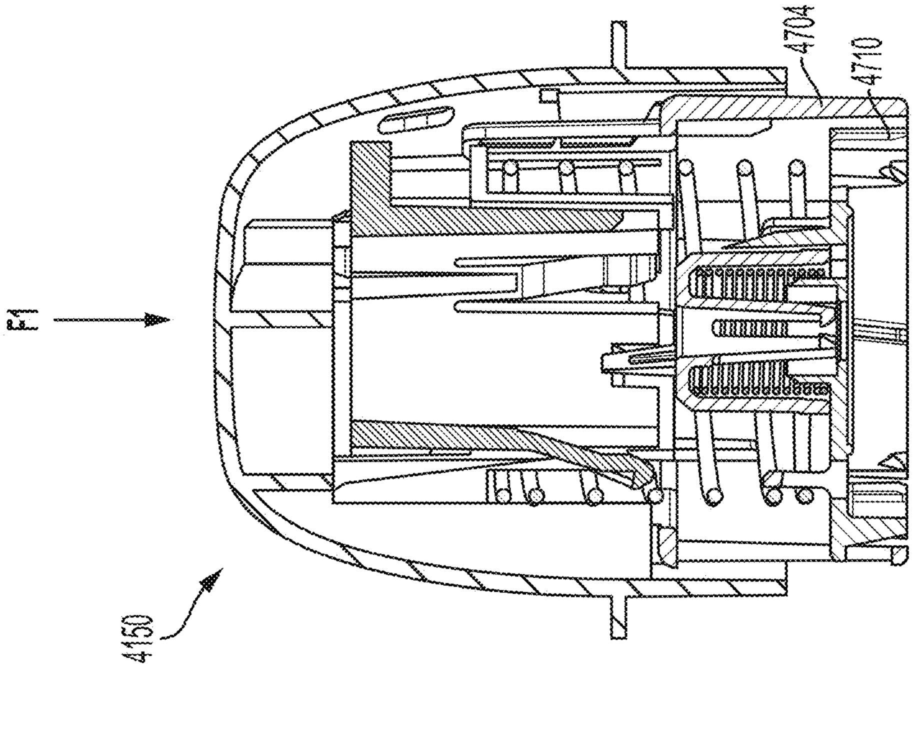
FIG. 19G is a cross-sectional view depicting an example embodiment of an applicator during a stage of deployment.

FIG. 19G is a cross-sectional view showing powered applicator 4150 in an insertion state, wherein a force, F1, is still being applied to applicator 4150, in a distal direction (as indicated by the dark arrow). Force, F1, can be the subject pushing and holding applicator 4150 against the skin during insertion. During the insertion state, the sharp and a portion of the analyte sensor (not shown) are positioned under the skin surface and in contact with a bodily fluid of the subject. Moreover, at this stage, a sharp retraction process has not yet been initiated. As best seen in FIG. 19I, sensor electronics carrier locks arms 4524 continue to be constrained by sheath 4704, thereby preventing the sharp carrier 4602 (and also the sharp) from retracting.

According to another aspect of the embodiments, during the insertion state, as sensor electronics carrier 4710 reaches the second position, the sensor electronics carrier 4710 and a distal portion of a sensor control unit (not shown) coupled with the sensor electronics carrier 4710 comes into resting contact with the skin surface. In some embodiments, the distal portion of the sensor control unit can be an adhesive surface.

Furthermore, according to some embodiments, as best seen in FIG. 19H, during the insertion state, sensor electronics carrier tabs 4605, which are positioned within sheath rails 4707, have traveled in a distal direction to the second position, but are still positioned above a bottom portion of applicator 4150, as indicated by distance, R.

Figure 19K:
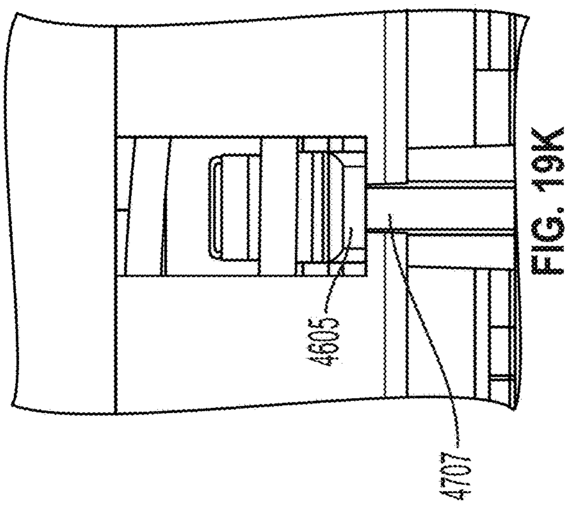
FIGS. 19K and 19L are close-up partial views of an example embodiment of a sheath-sensor electronics carrier assembly.
Figure 19L:
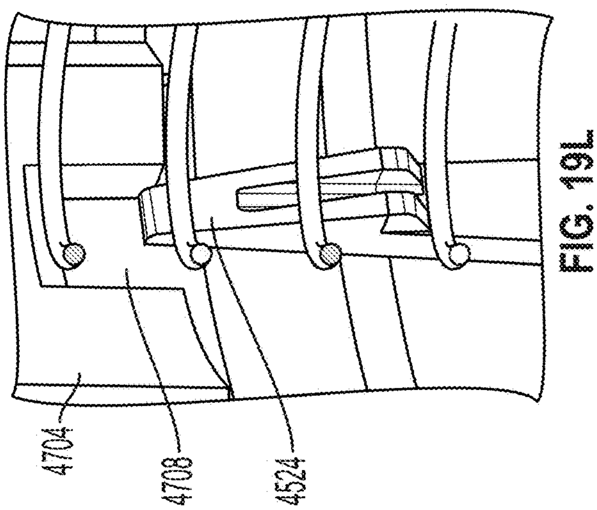
Figure 19J:
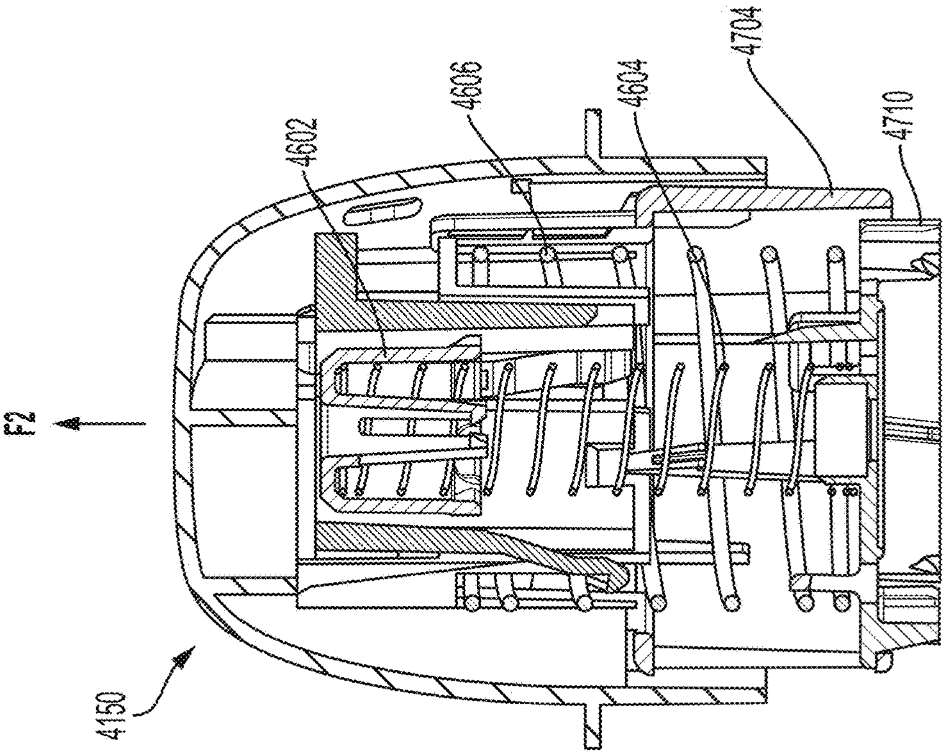
FIG. 19J is a cross-sectional view depicting an example embodiment of an applicator during a stage of deployment.
Figure 20A:
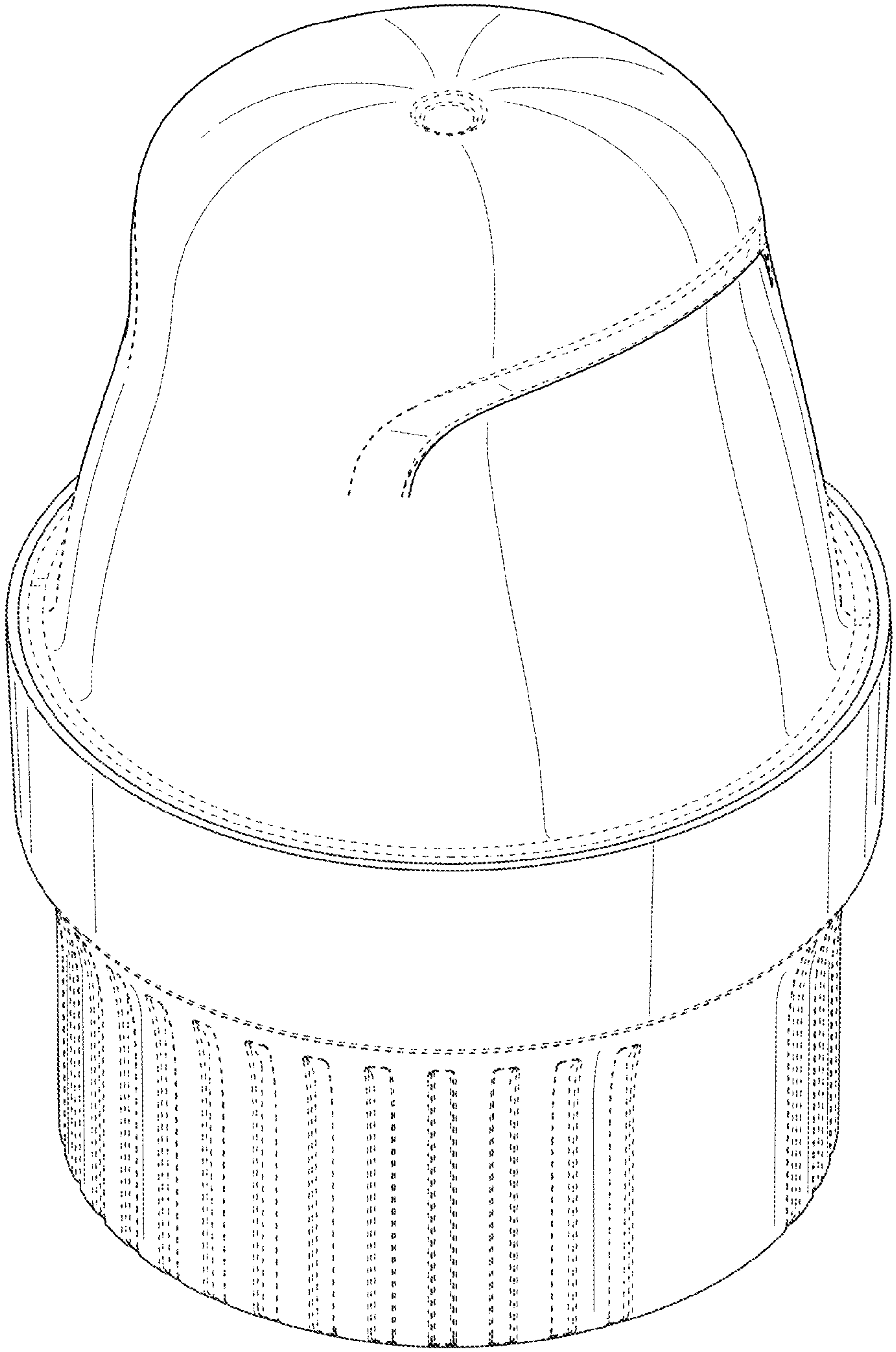
FIGS. 20A-20G depict an example embodiment of an applicator, where
Figure 20B:
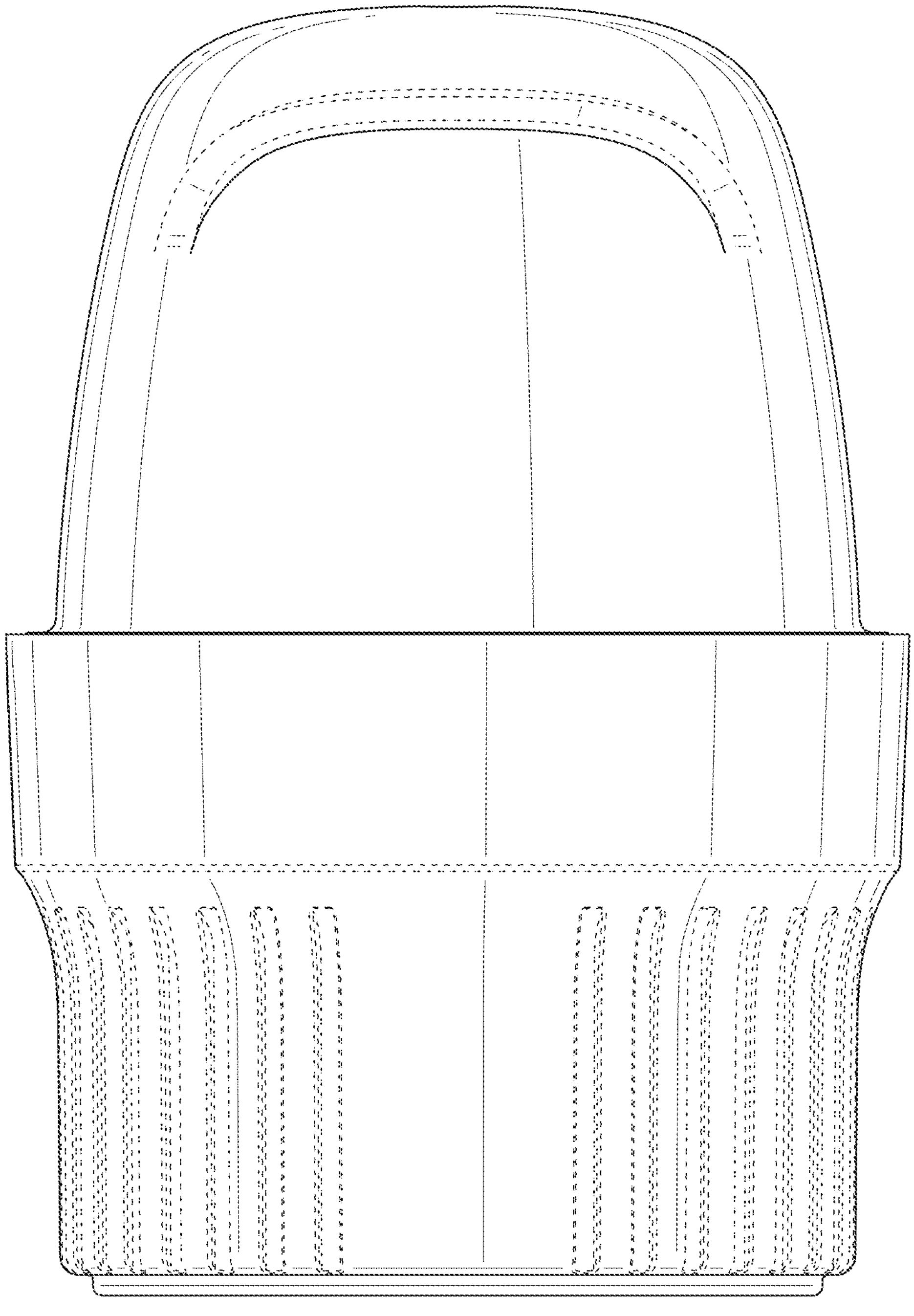
Figure 20C:
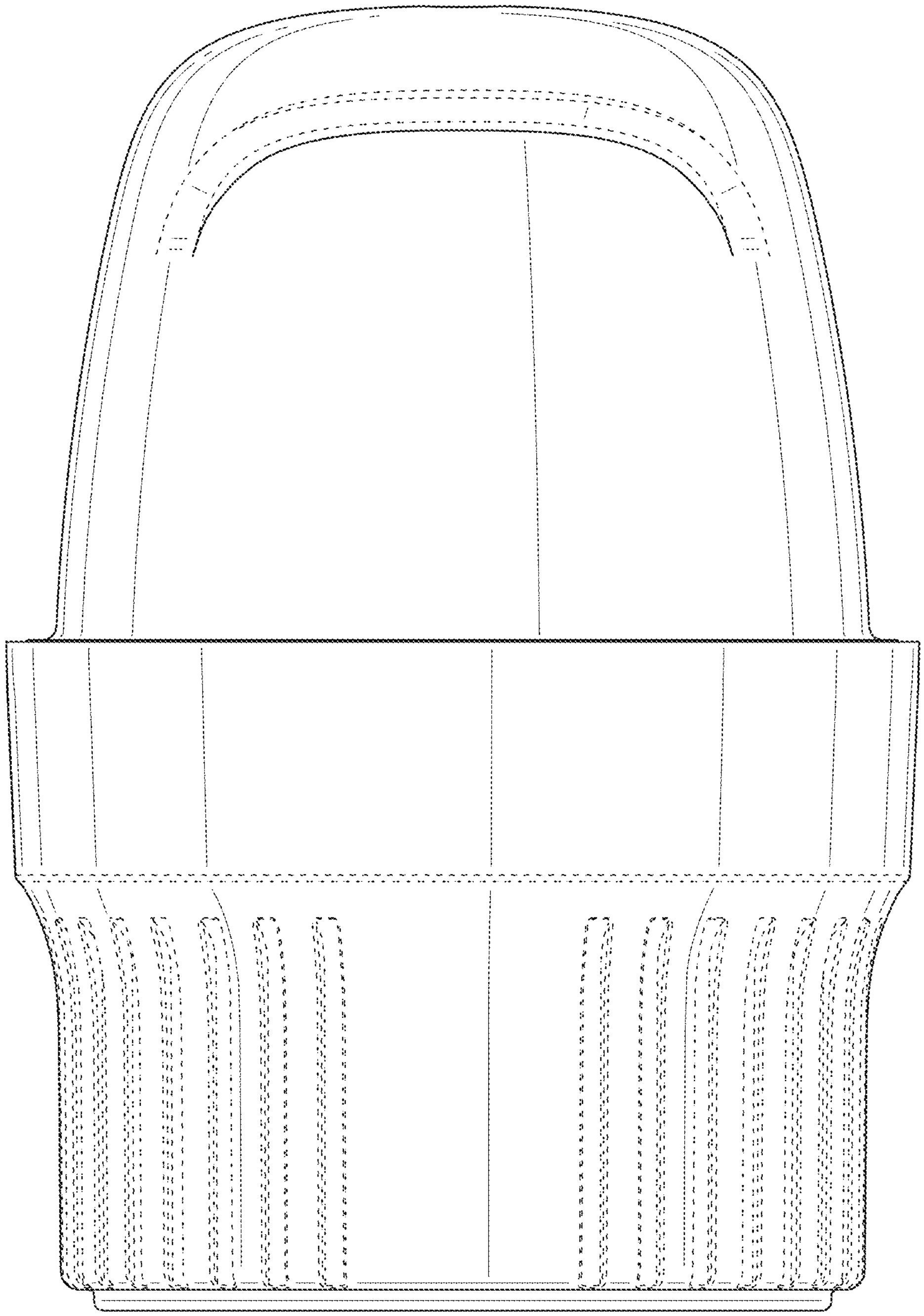
Figure 20D:
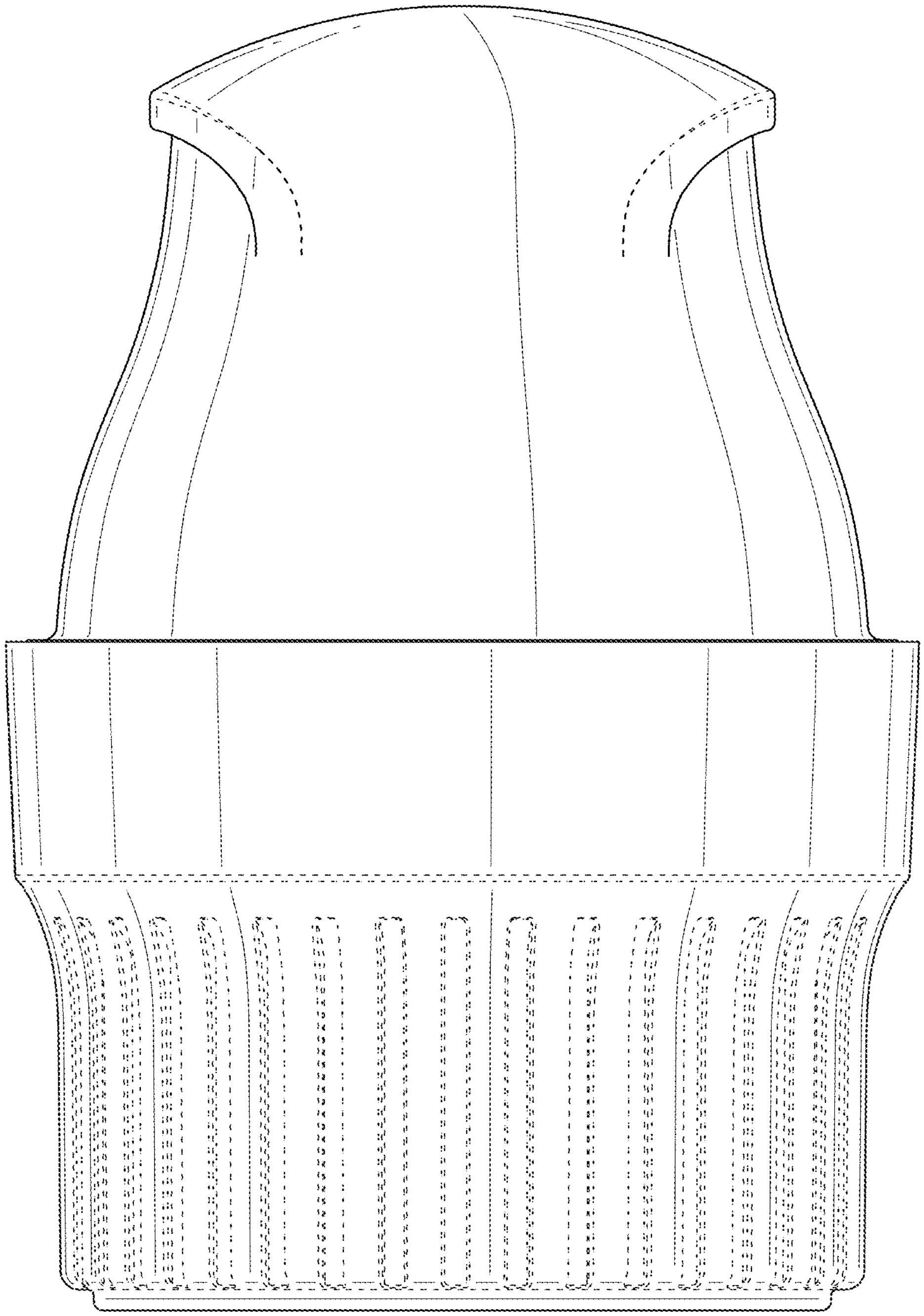
Figure 20E:
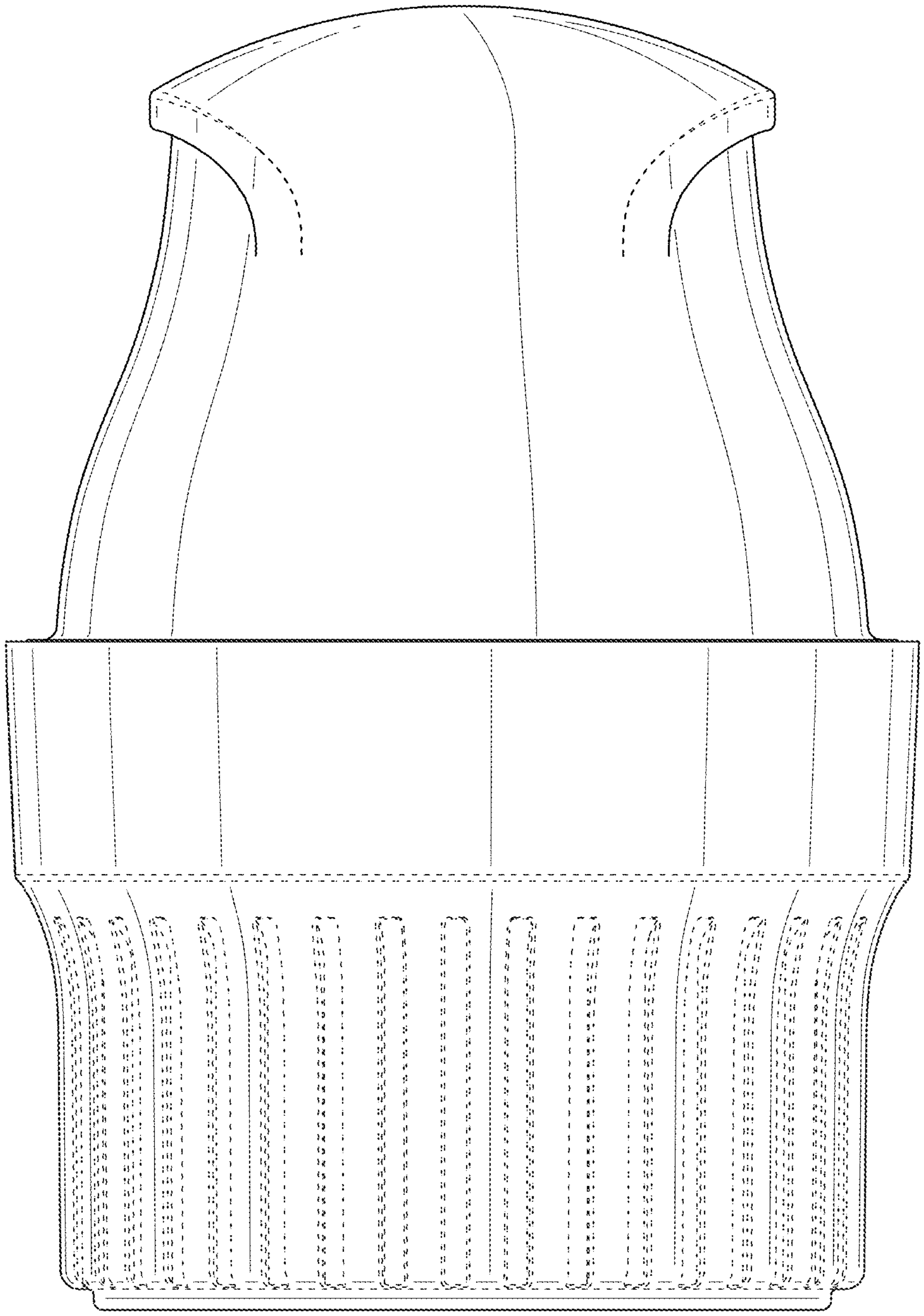
Figure 20F:
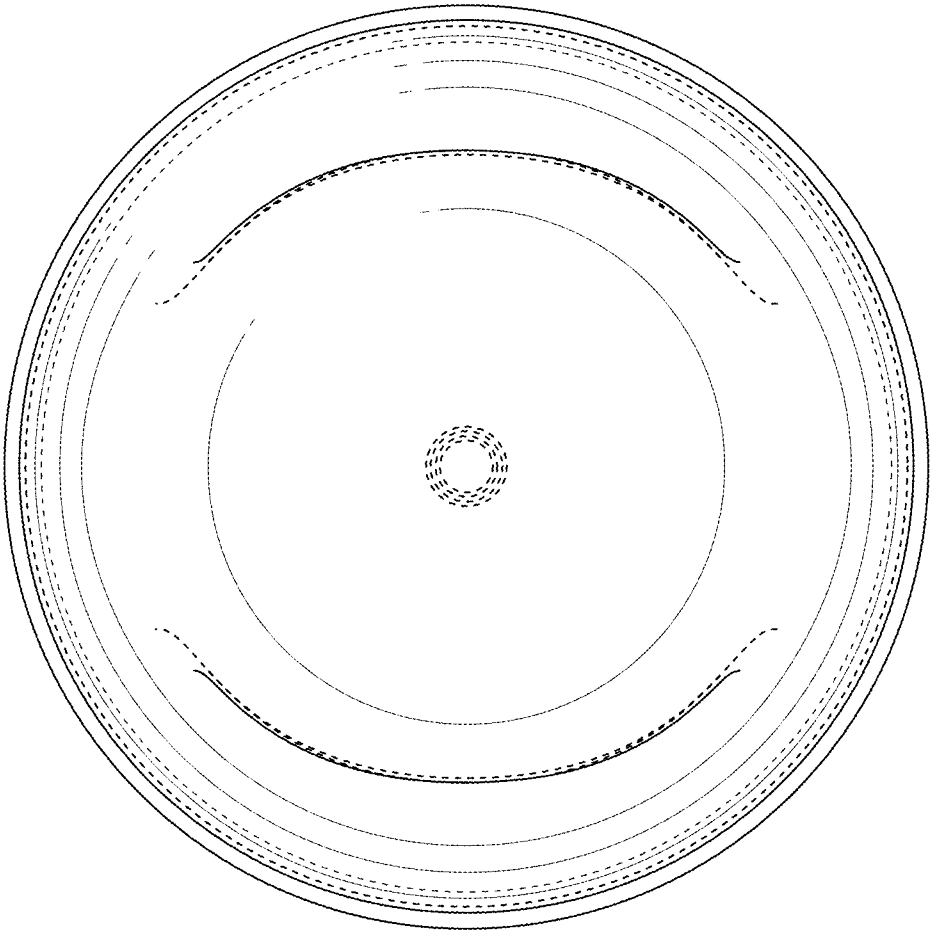
Figure 20G:
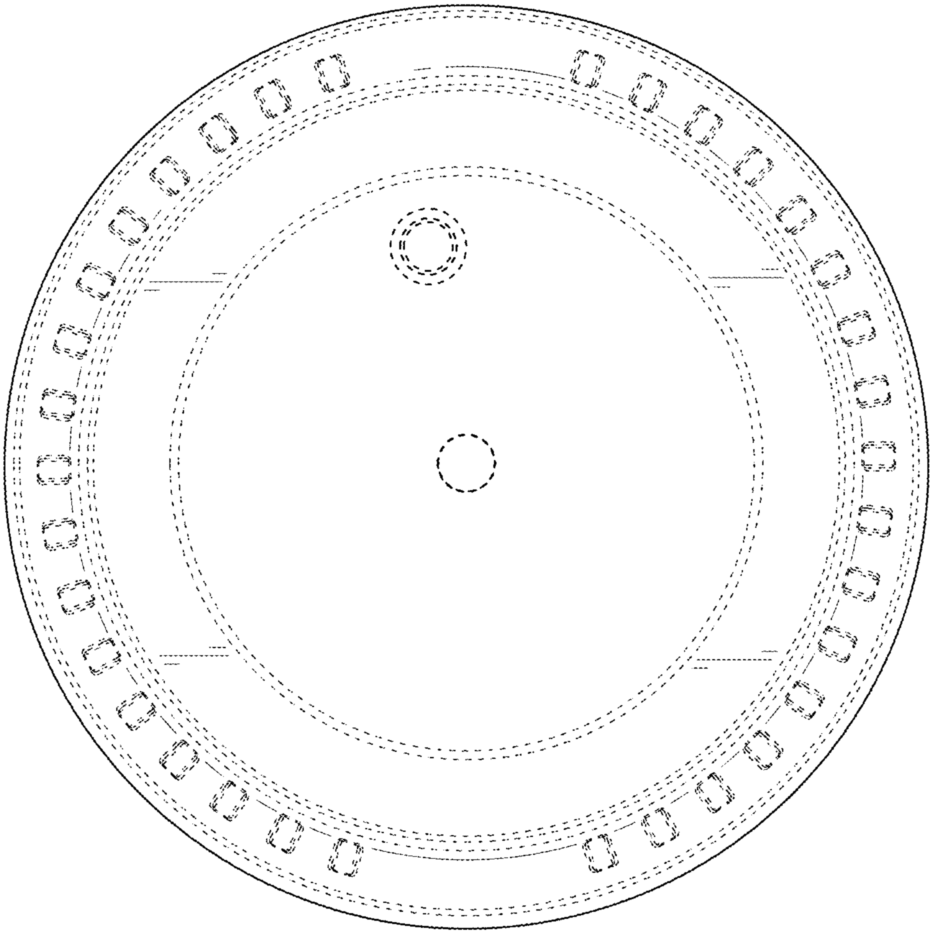
Figure 21A:
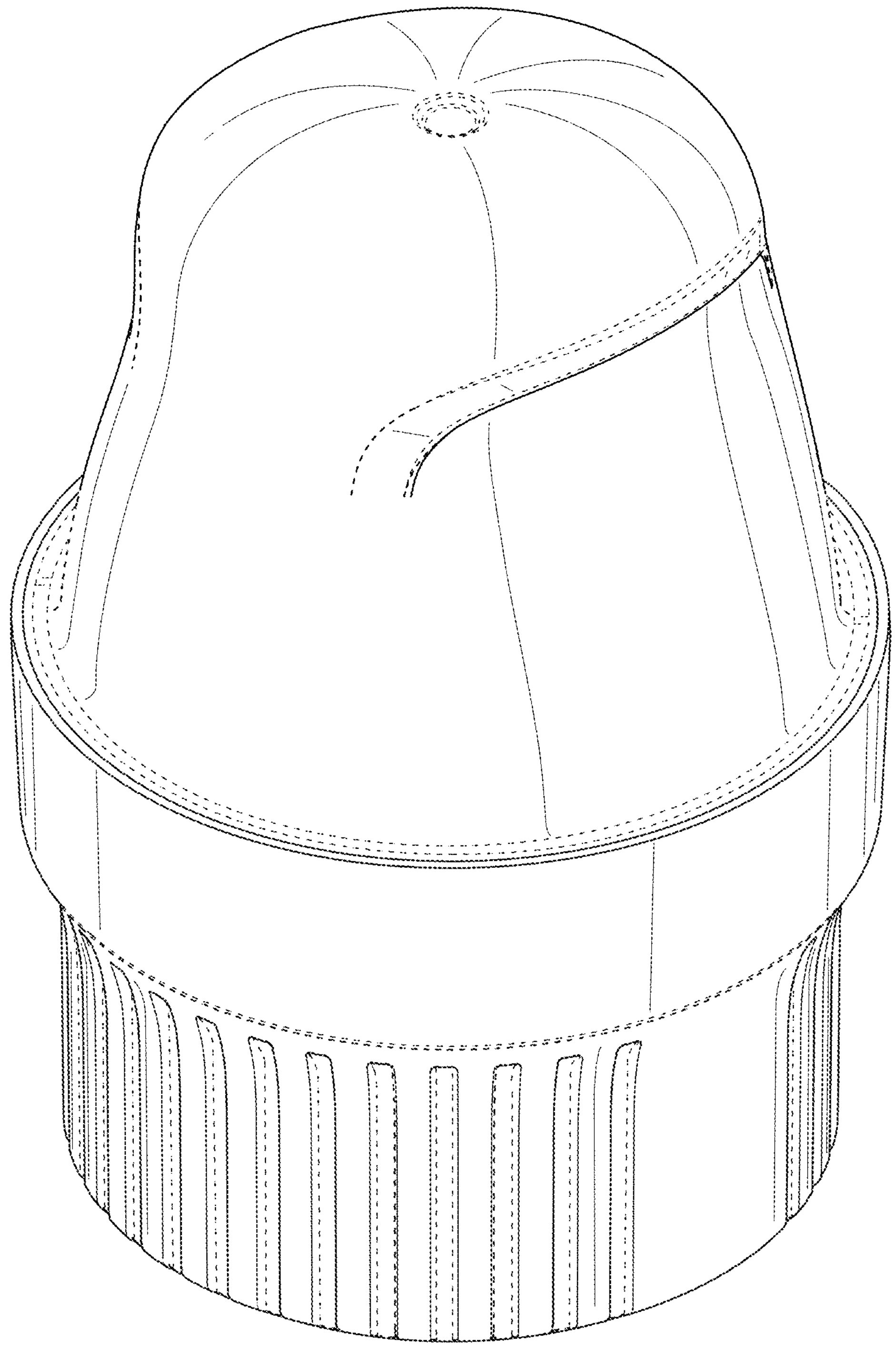
FIGS. 21A-21G depict another example embodiment of an applicator, where
Figure 21B:
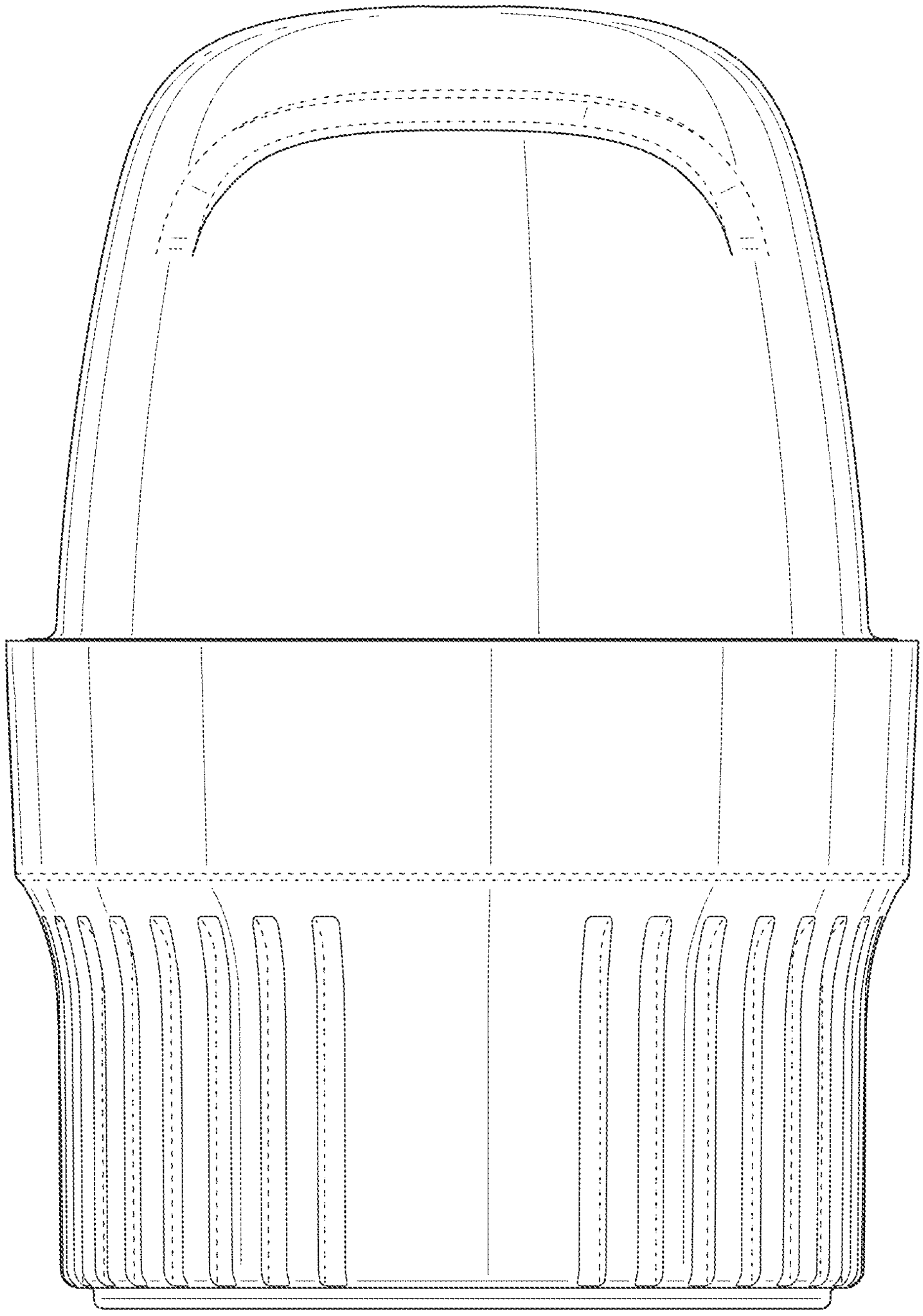
Figure 21C:
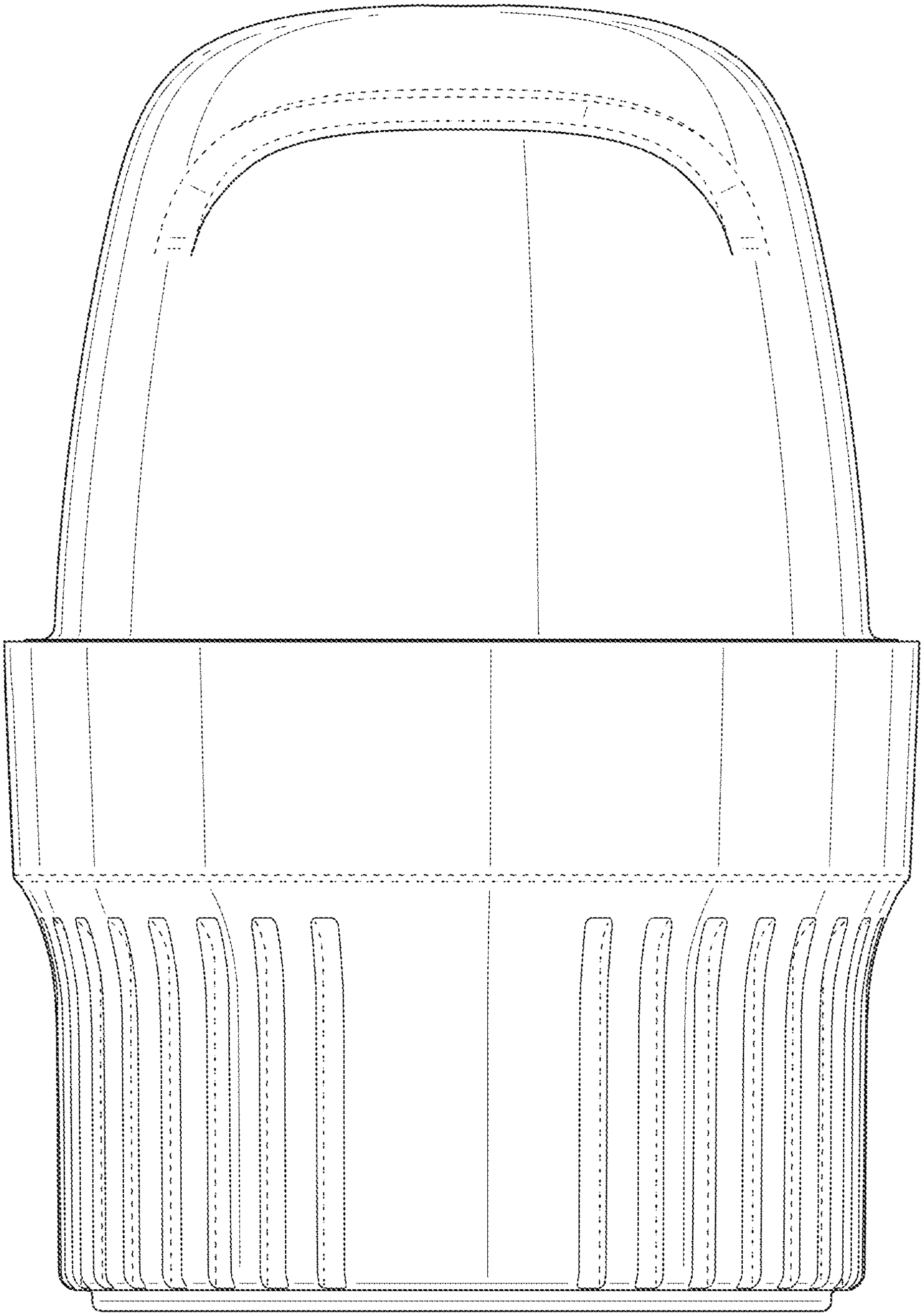
Figure 21D:
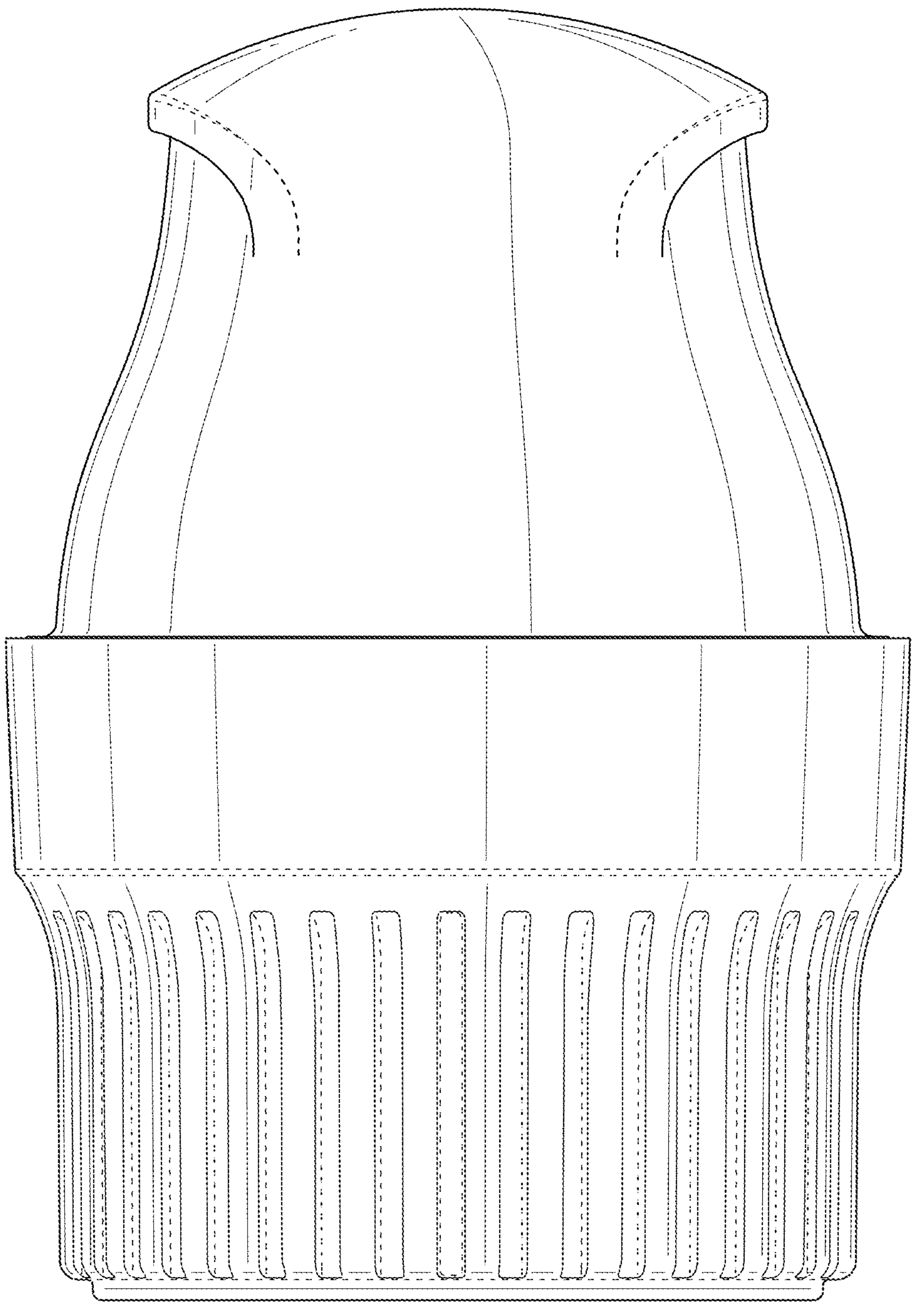
Figure 21E:
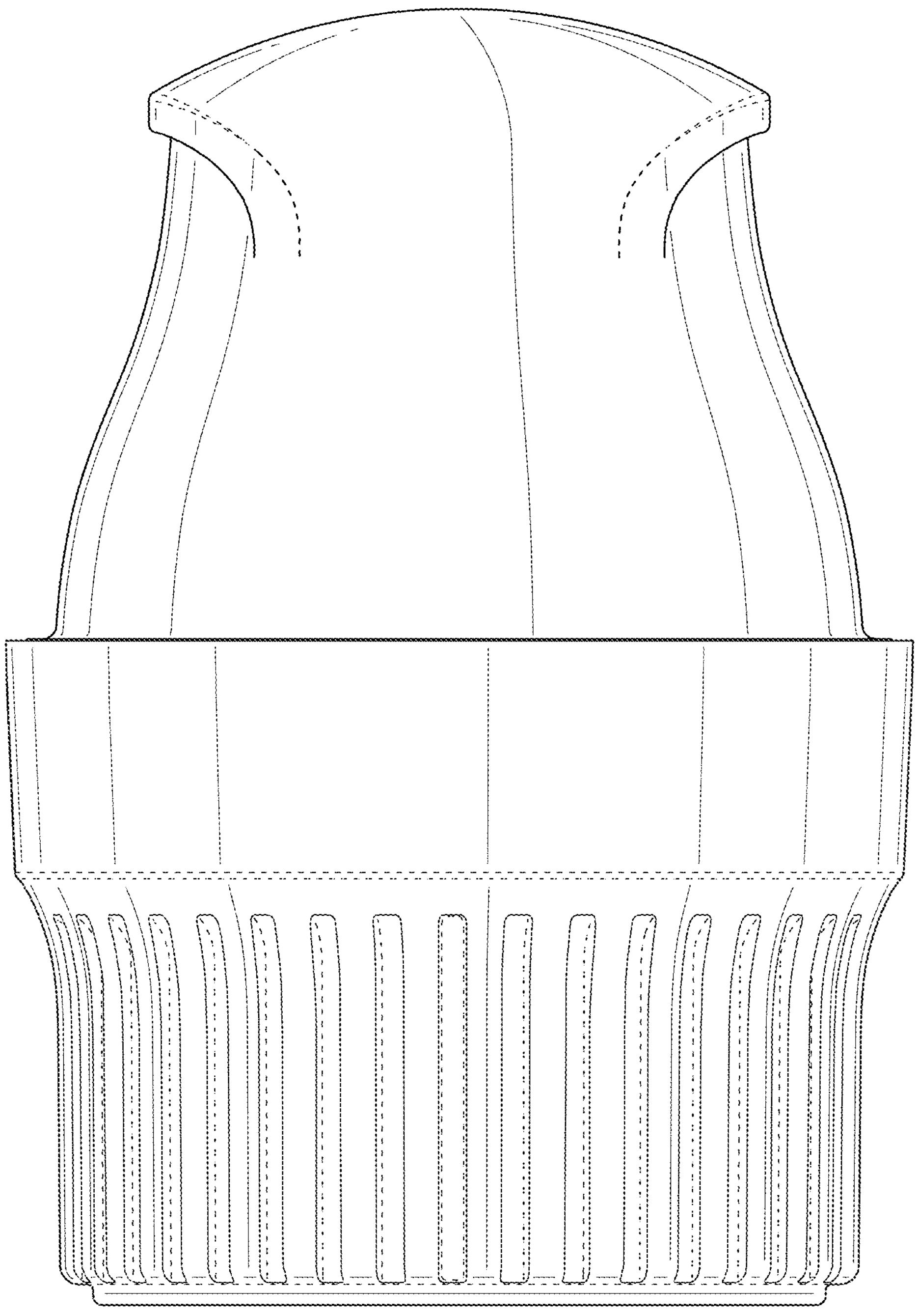
Figure 21F:
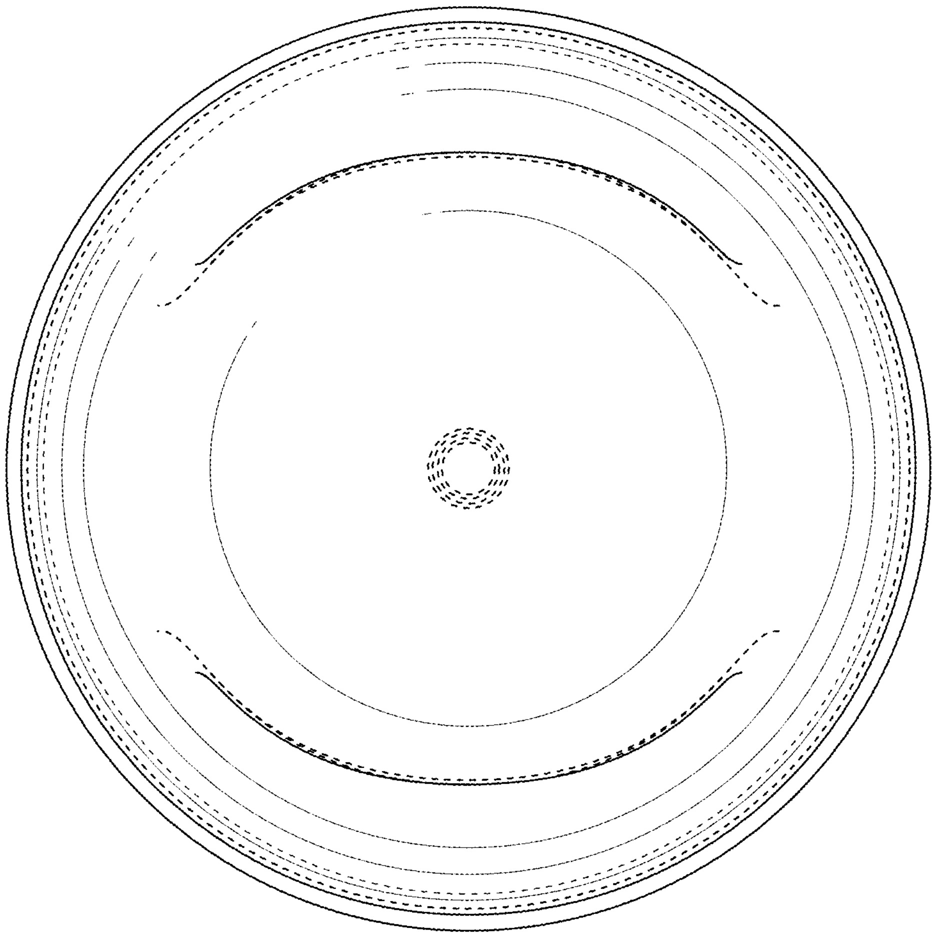
Figure 21G:
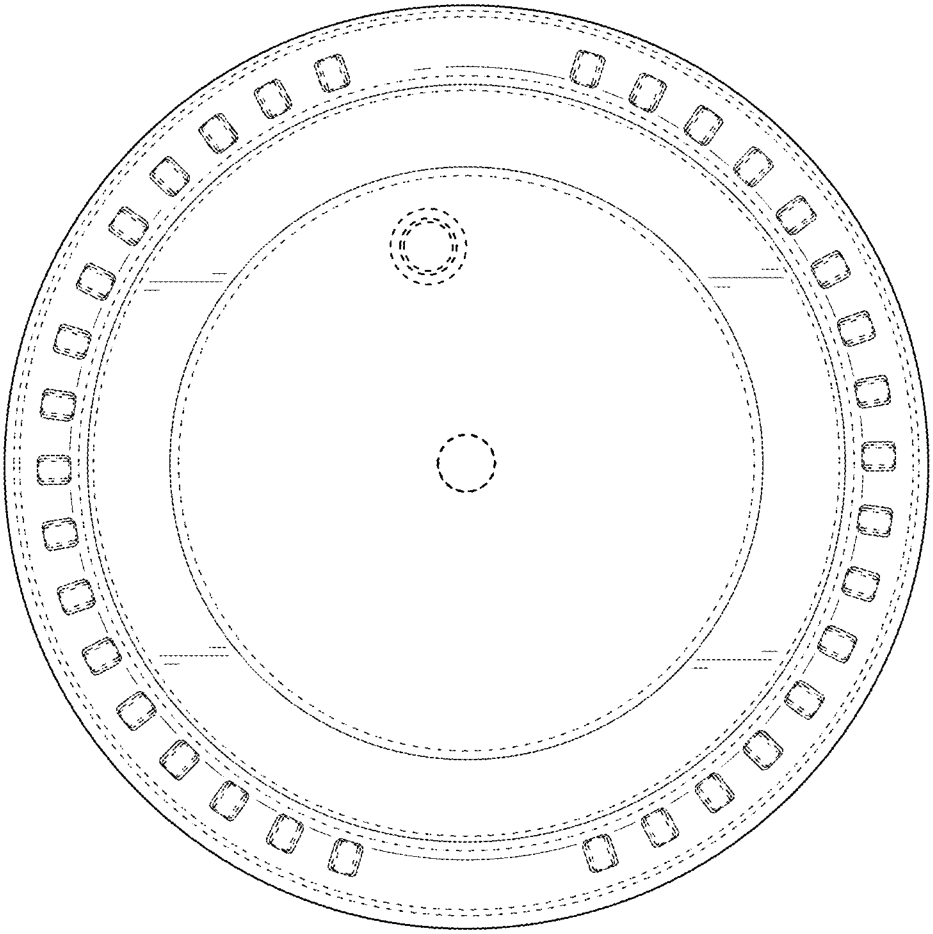
Figure 22A:
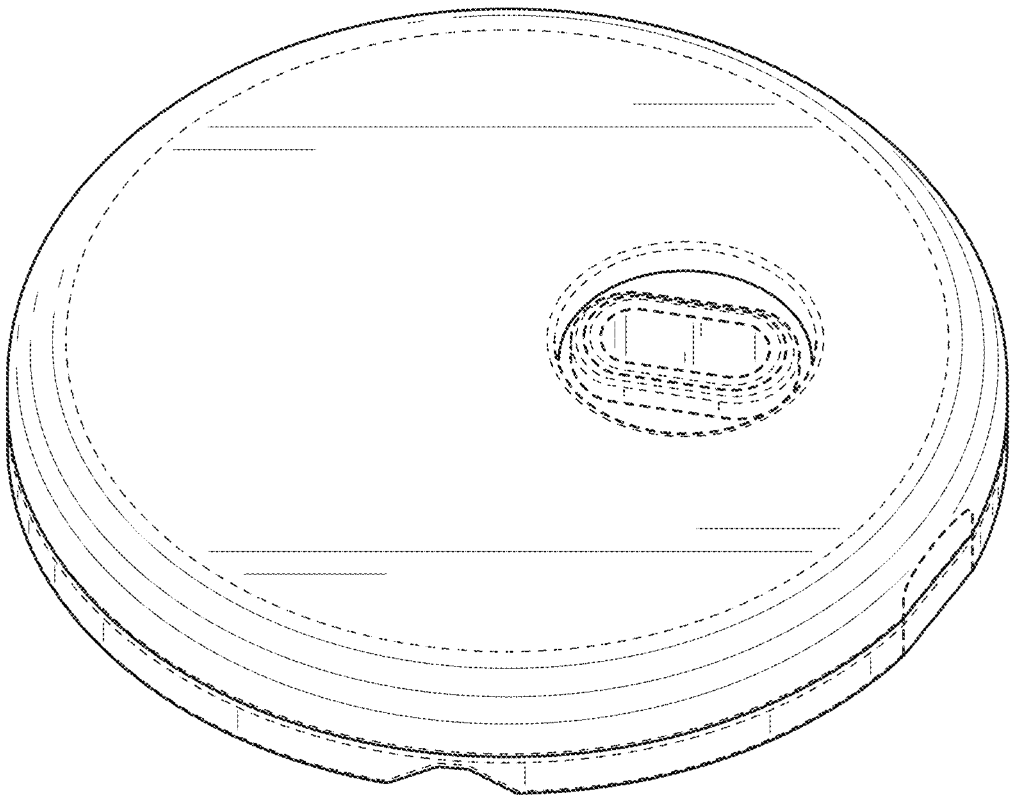
FIGS. 22A-22G depict an example embodiment of a sensor control device, where
Figure 22B:
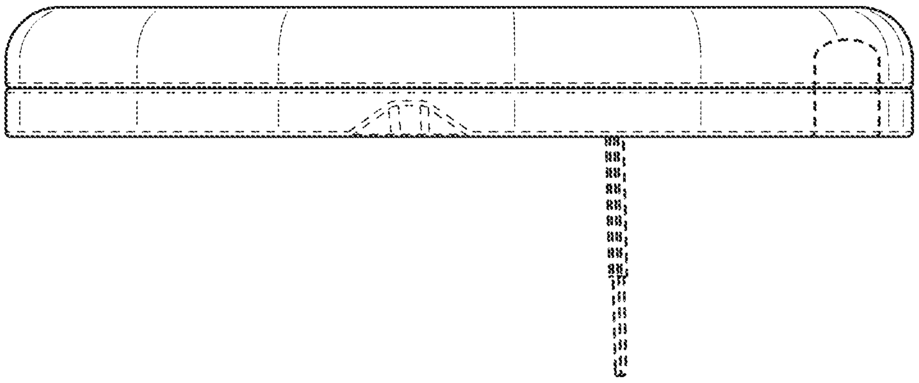
Figure 22C:
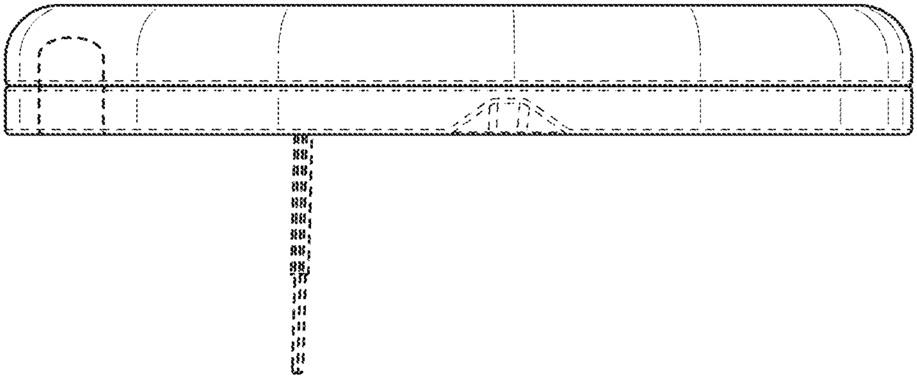
Figure 22D:
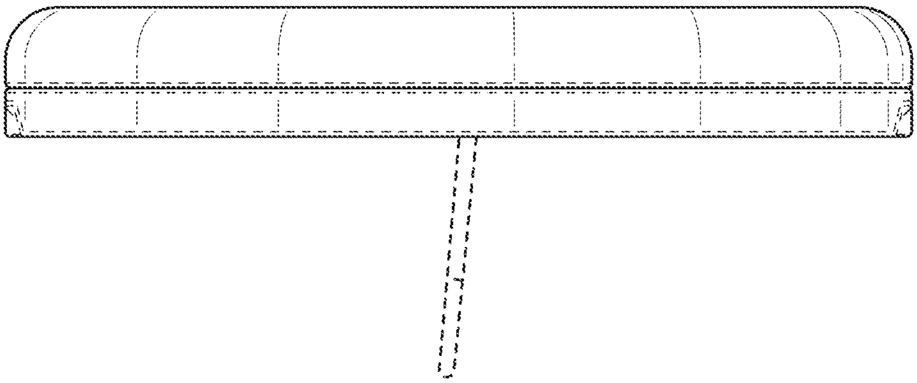
Figure 22E:
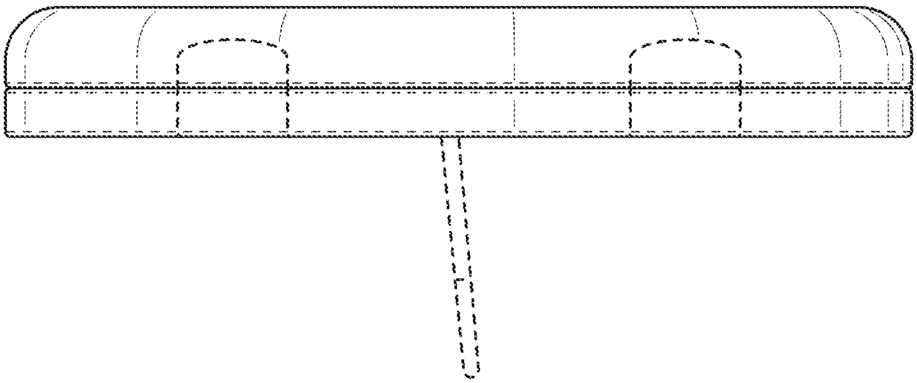
Figure 22F:
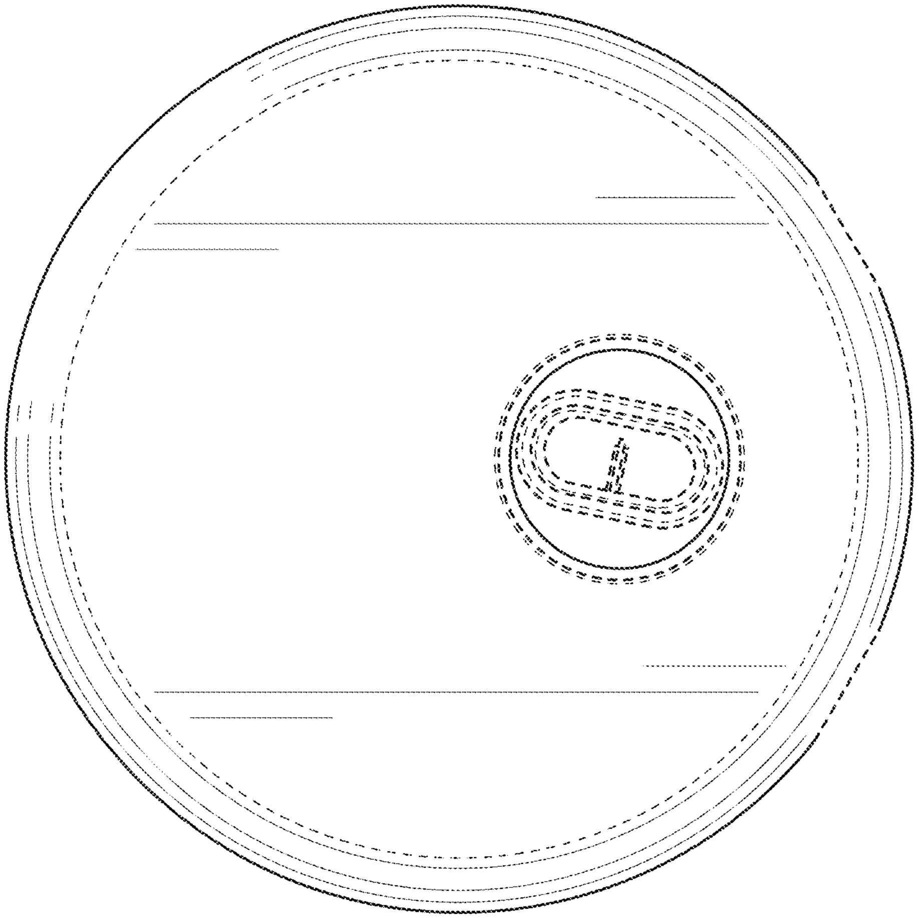
Figure 22G:
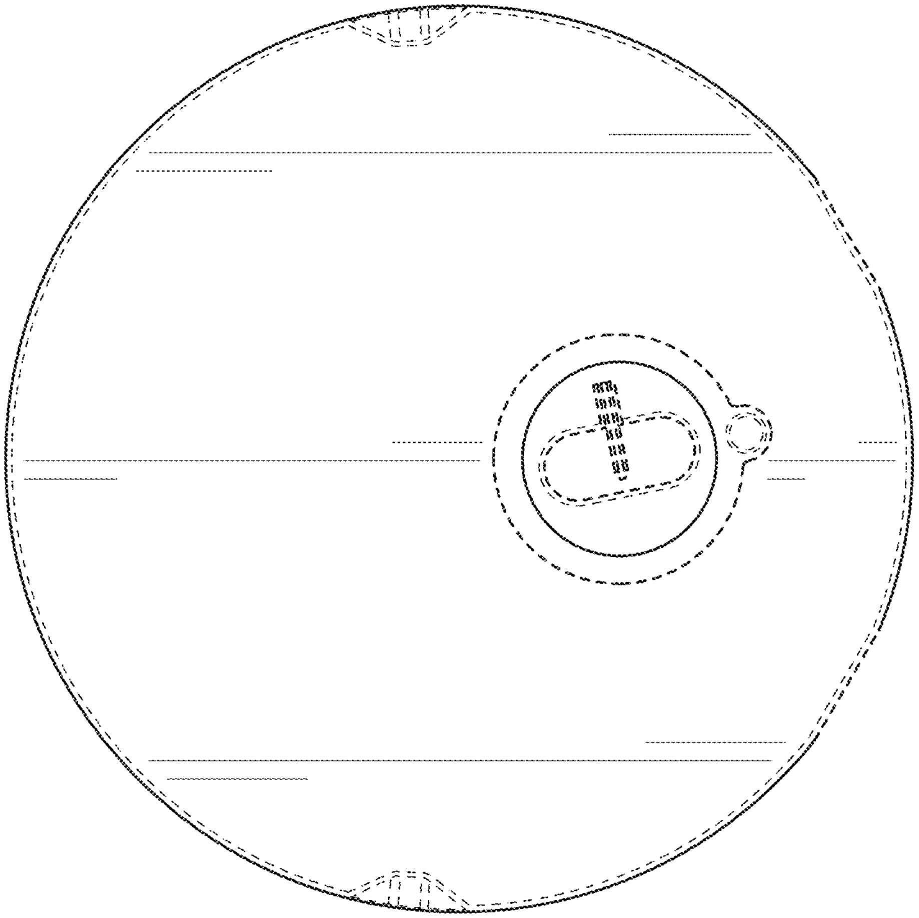
Figure 23A:
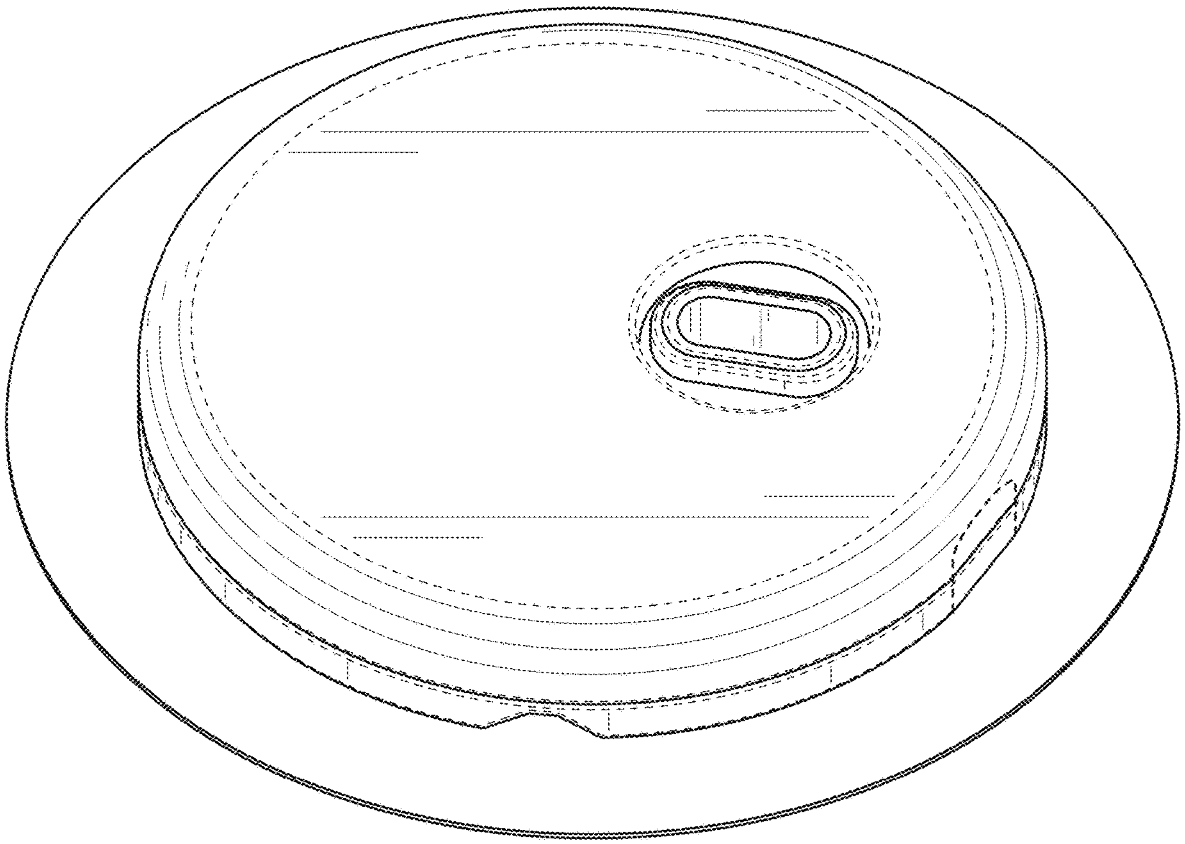
FIGS. 23A-23G depict another example embodiment of a sensor control device, where
Figure 23B:
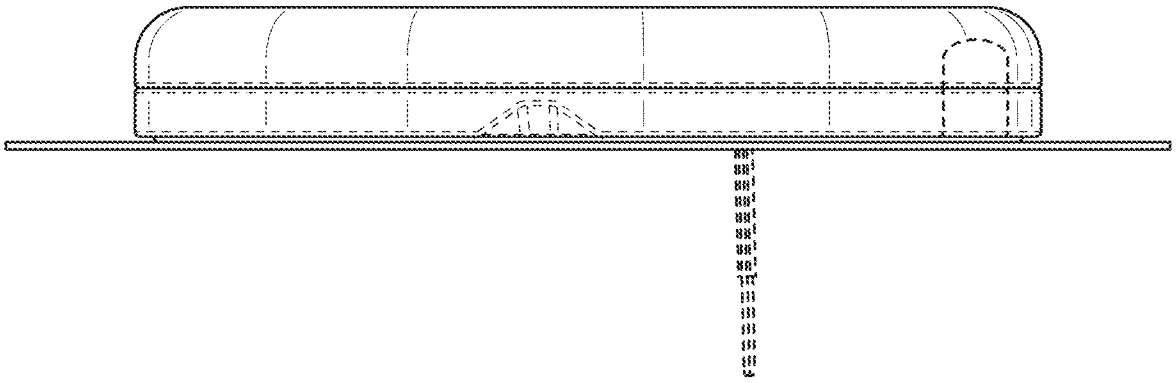
Figure 23C:
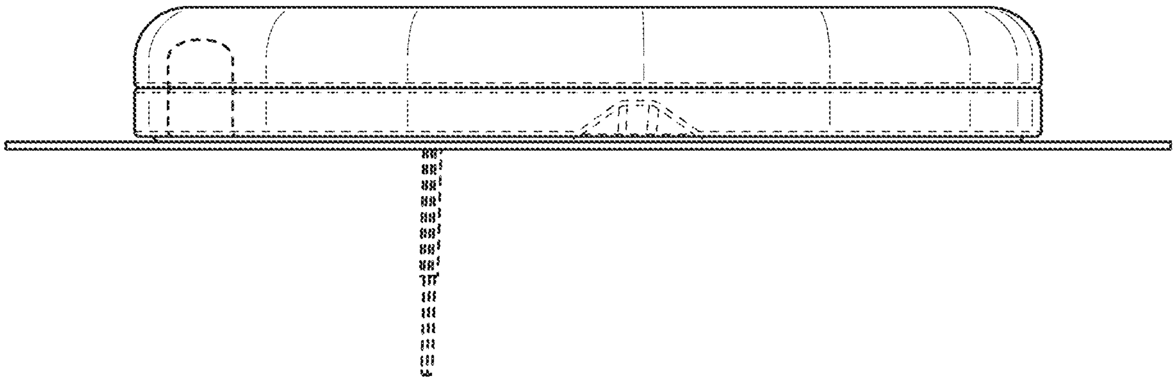
Figure 23D:
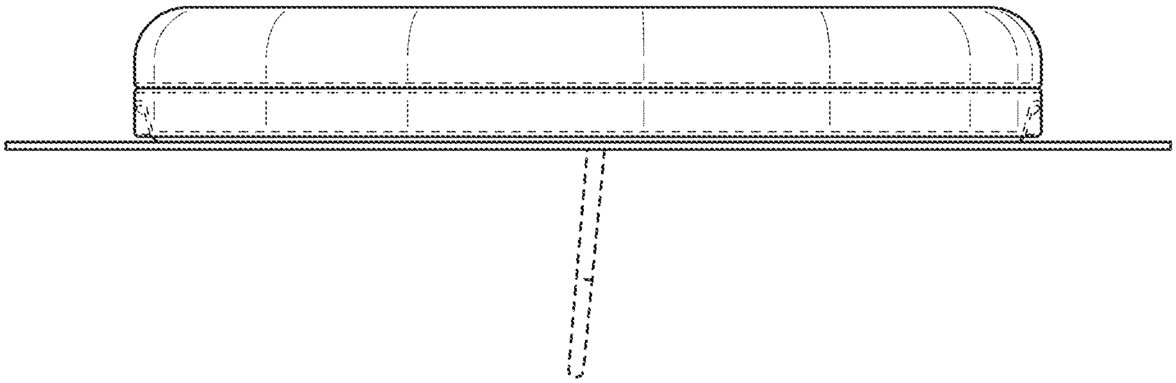
Figure 23E:
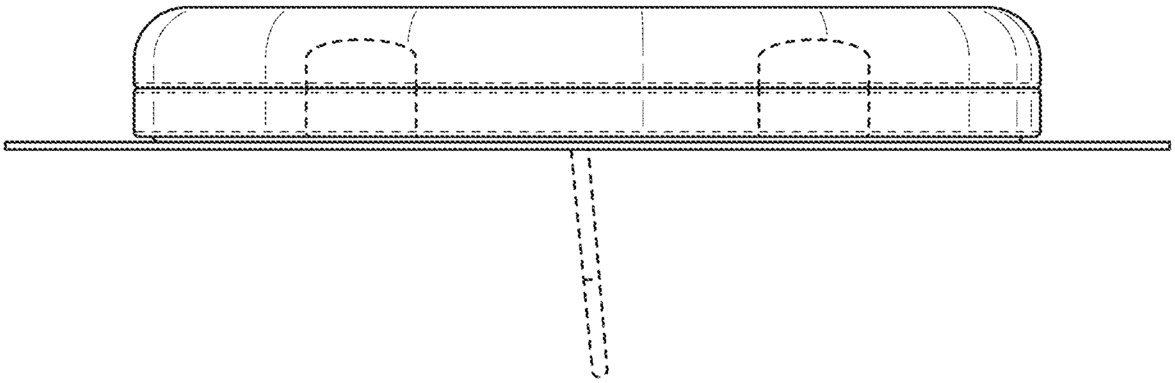
Figure 23F:
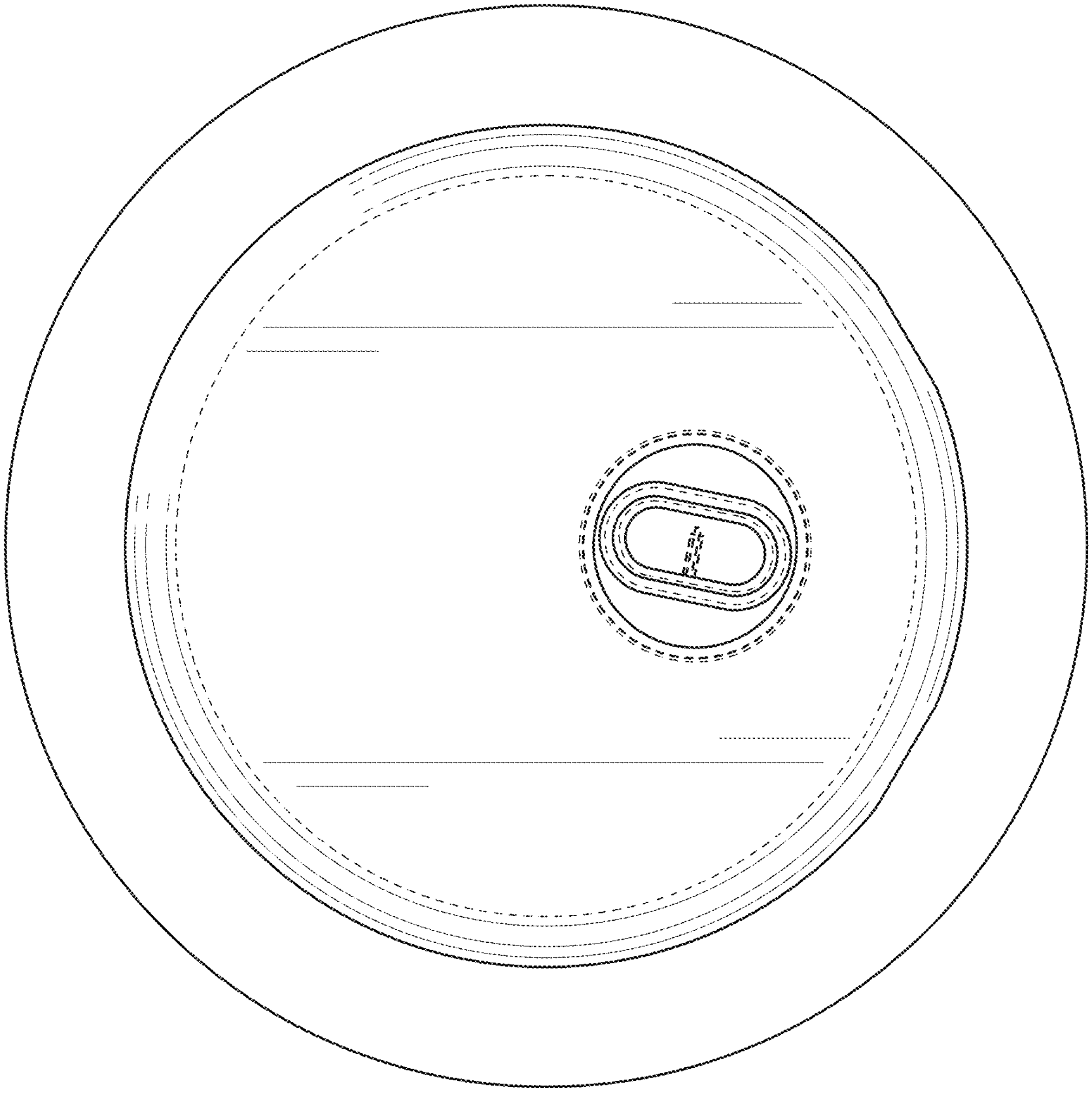
Figure 23G:
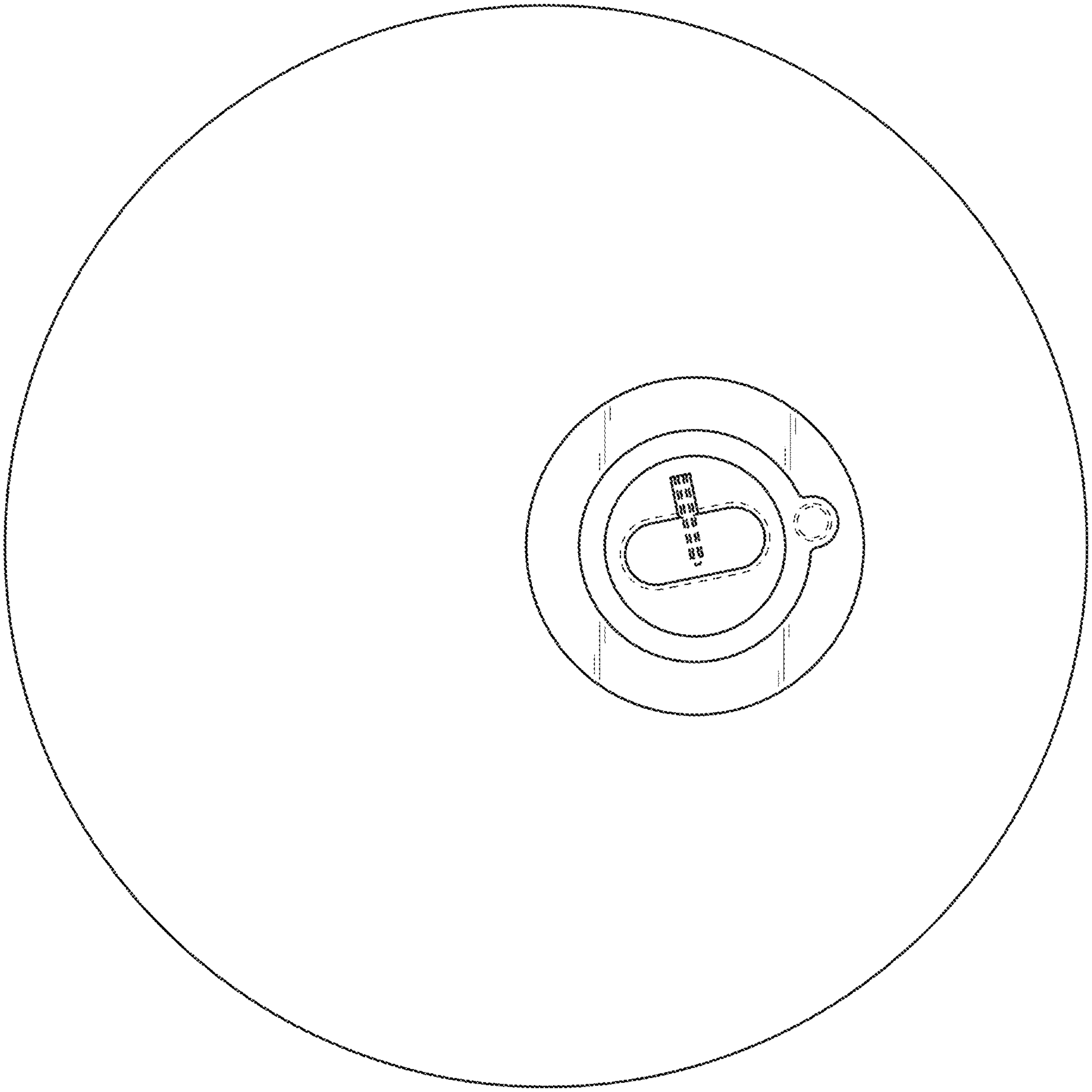
Figure 24A:
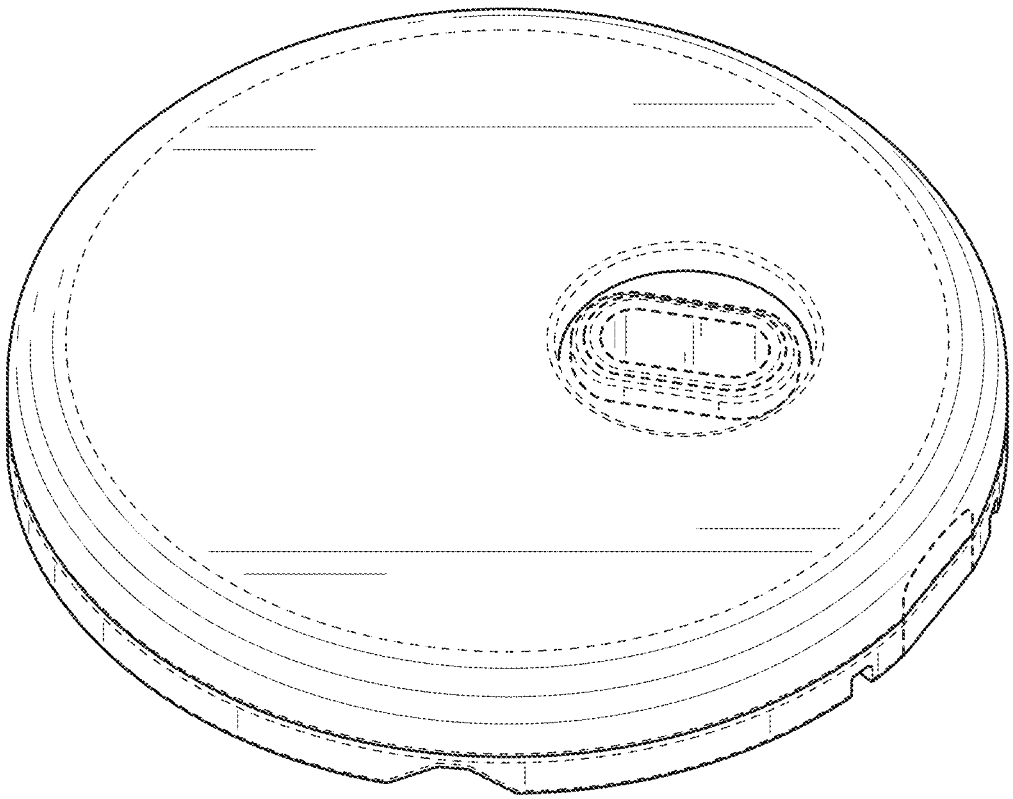
FIGS. 24A-24G depict another example embodiment of a sensor control device, where
Figure 24B:
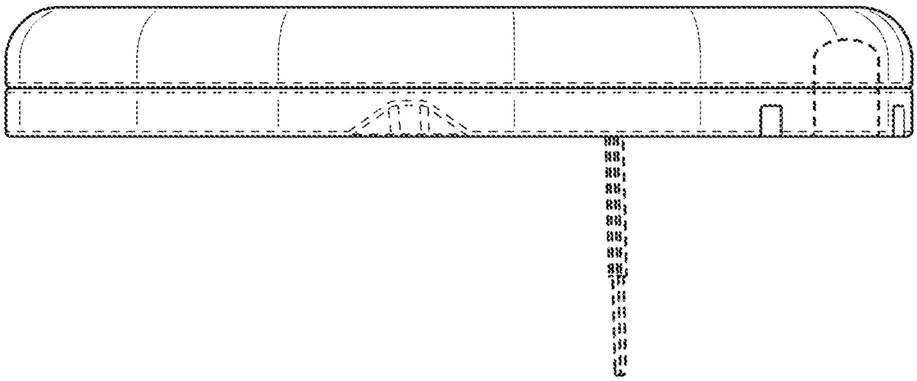
Figure 24C:
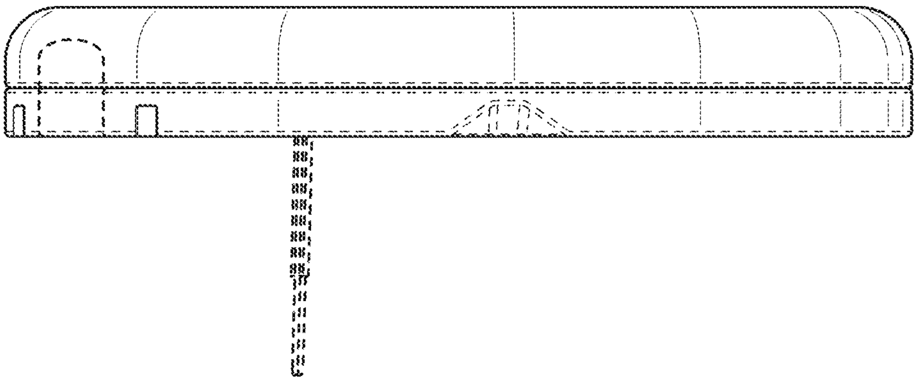
Figure 24D:
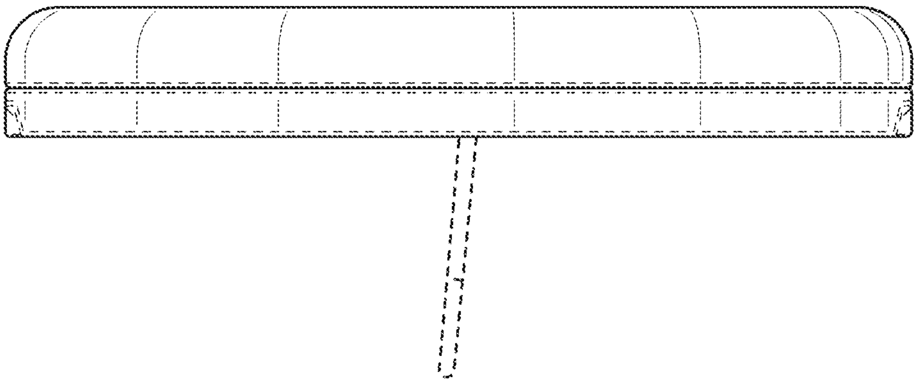
Figure 24E:
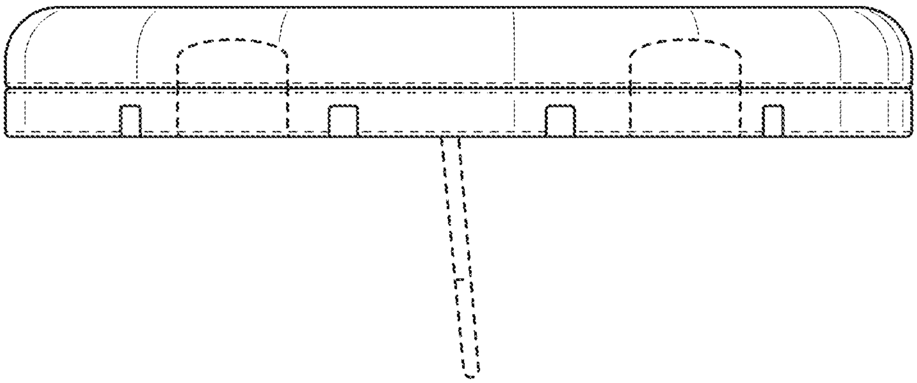
Figure 24F:
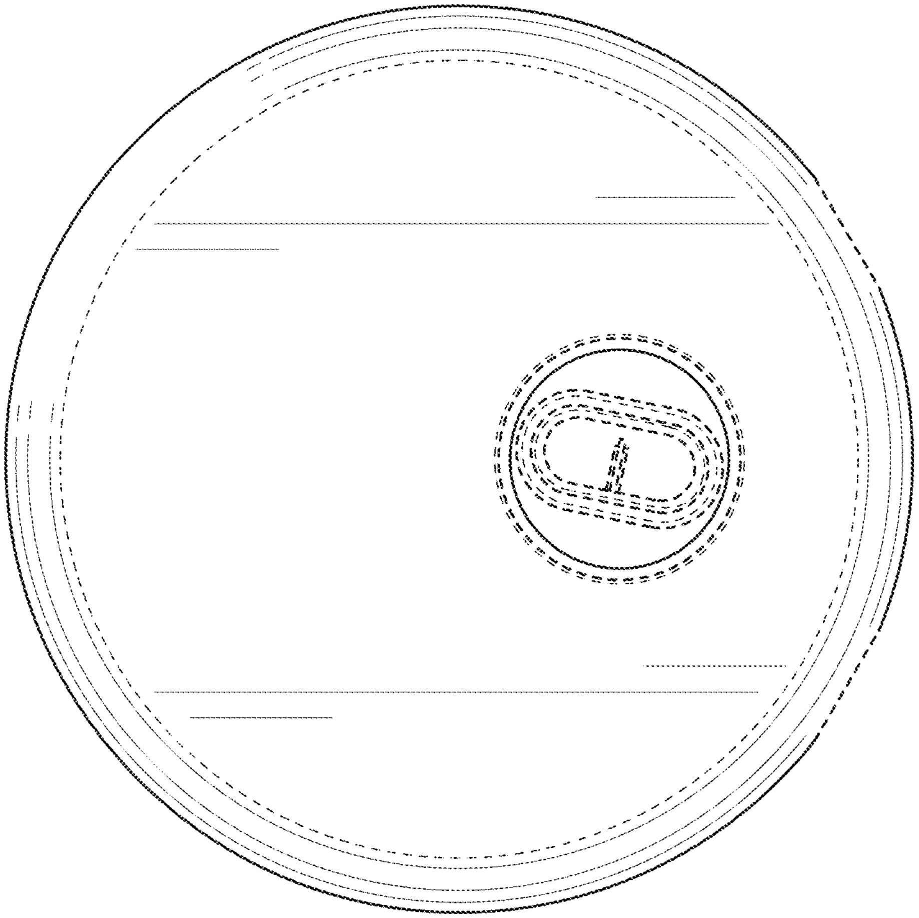
Figure 24G:
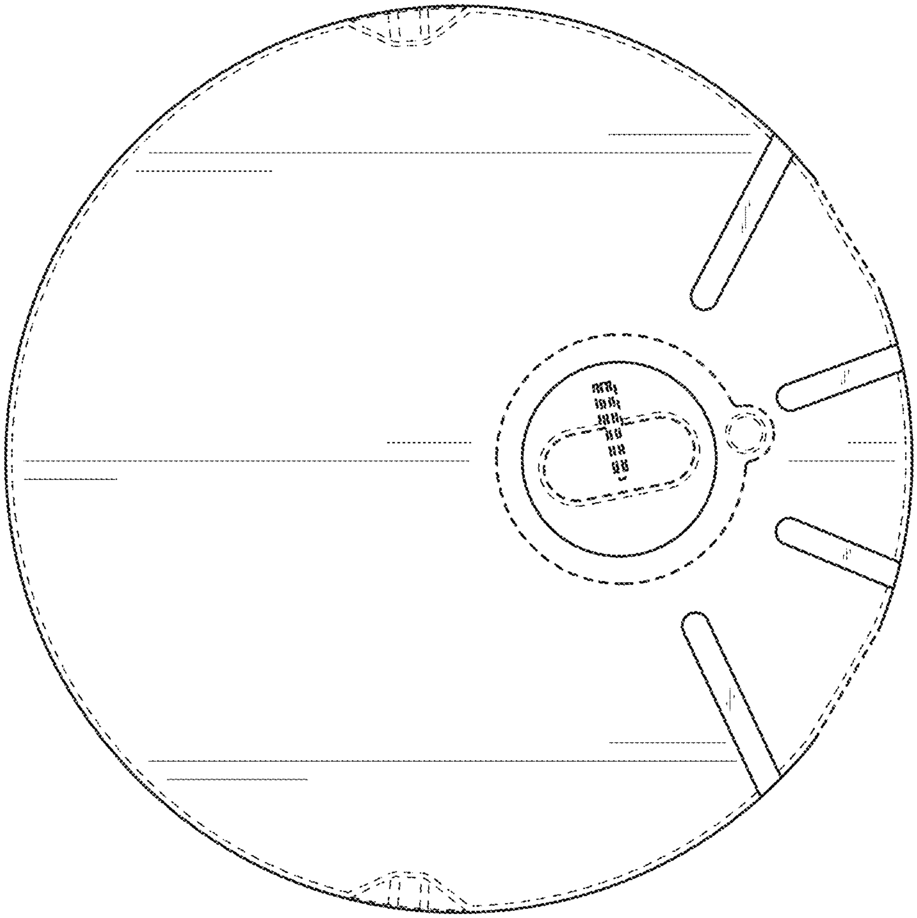
Figure 25A:
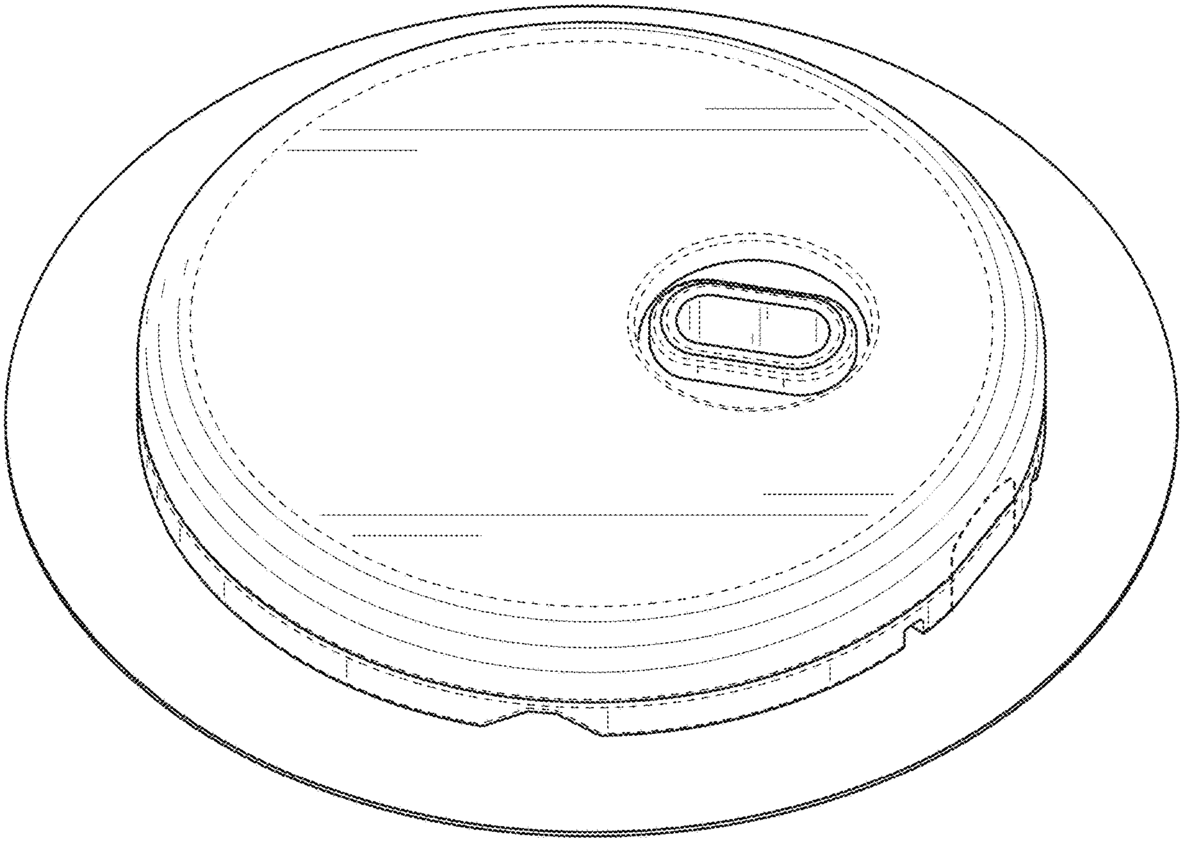
FIGS. 25A-25G depict another example embodiment of a sensor control device, where
Figure 25B:
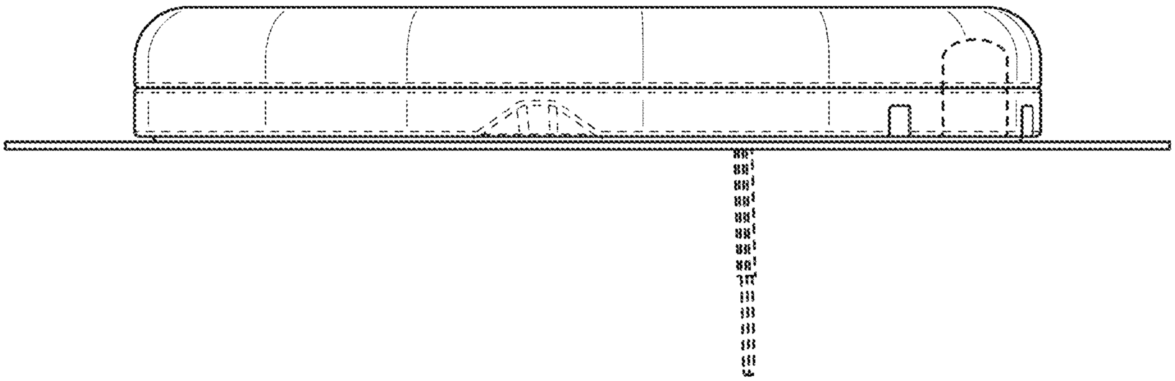
Figure 25C:
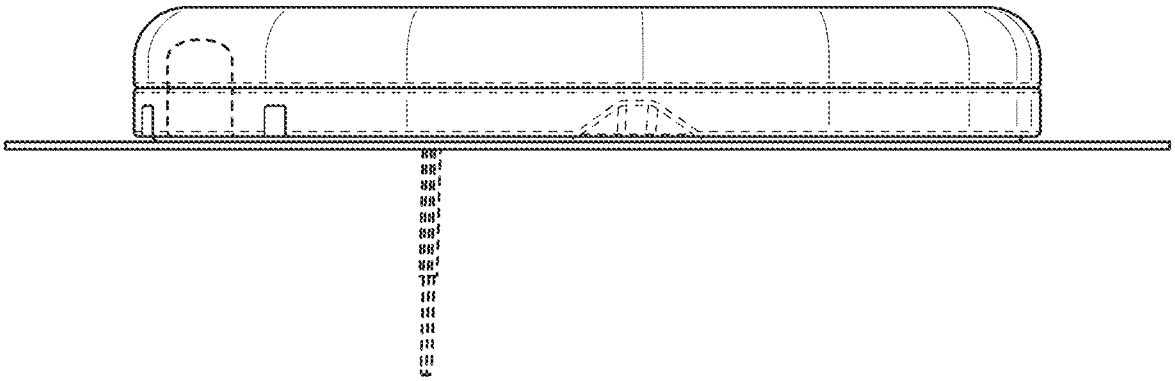
Figure 25D:
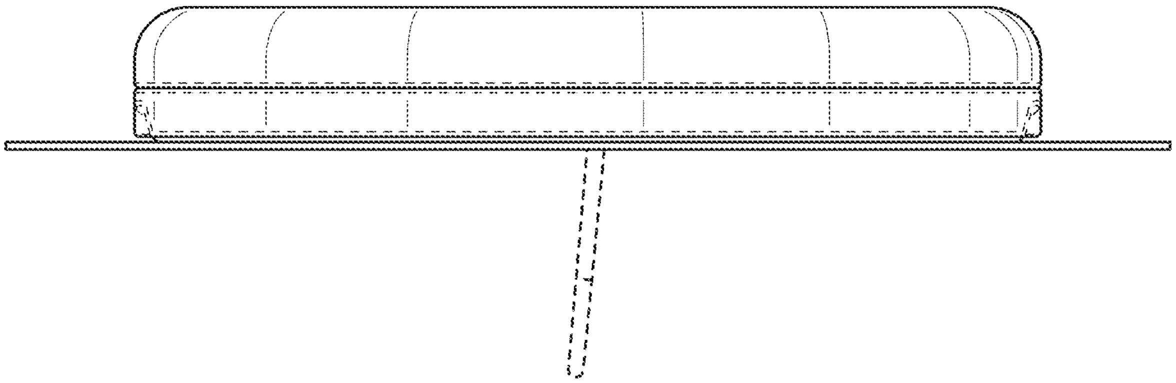
Figure 25E:
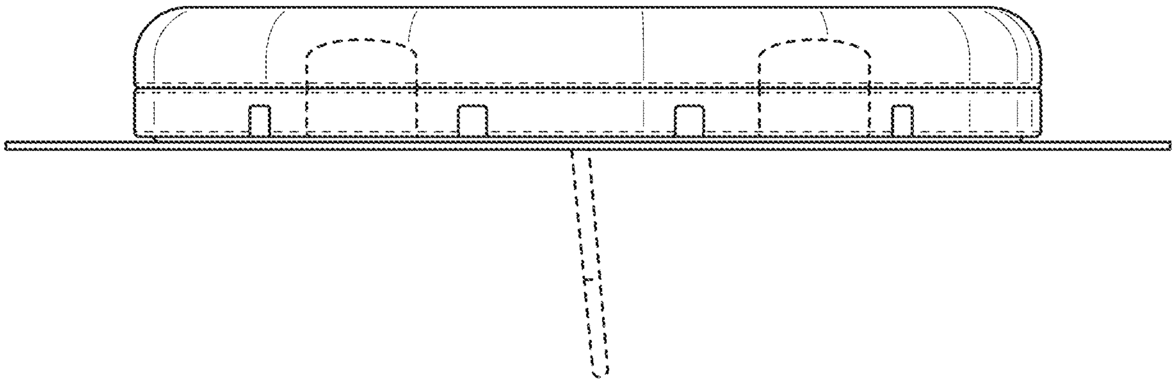
Figure 25F:
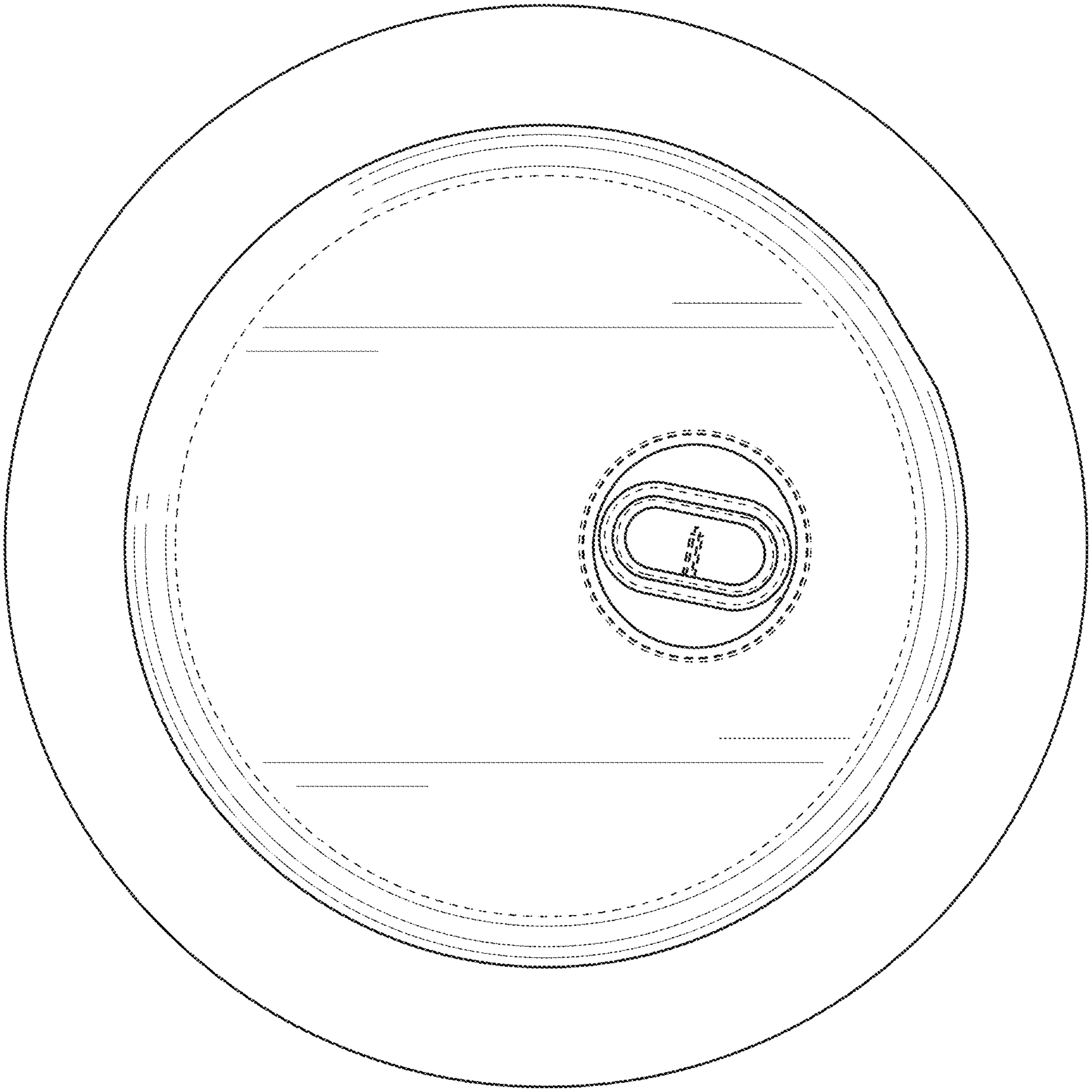
Figure 25G:
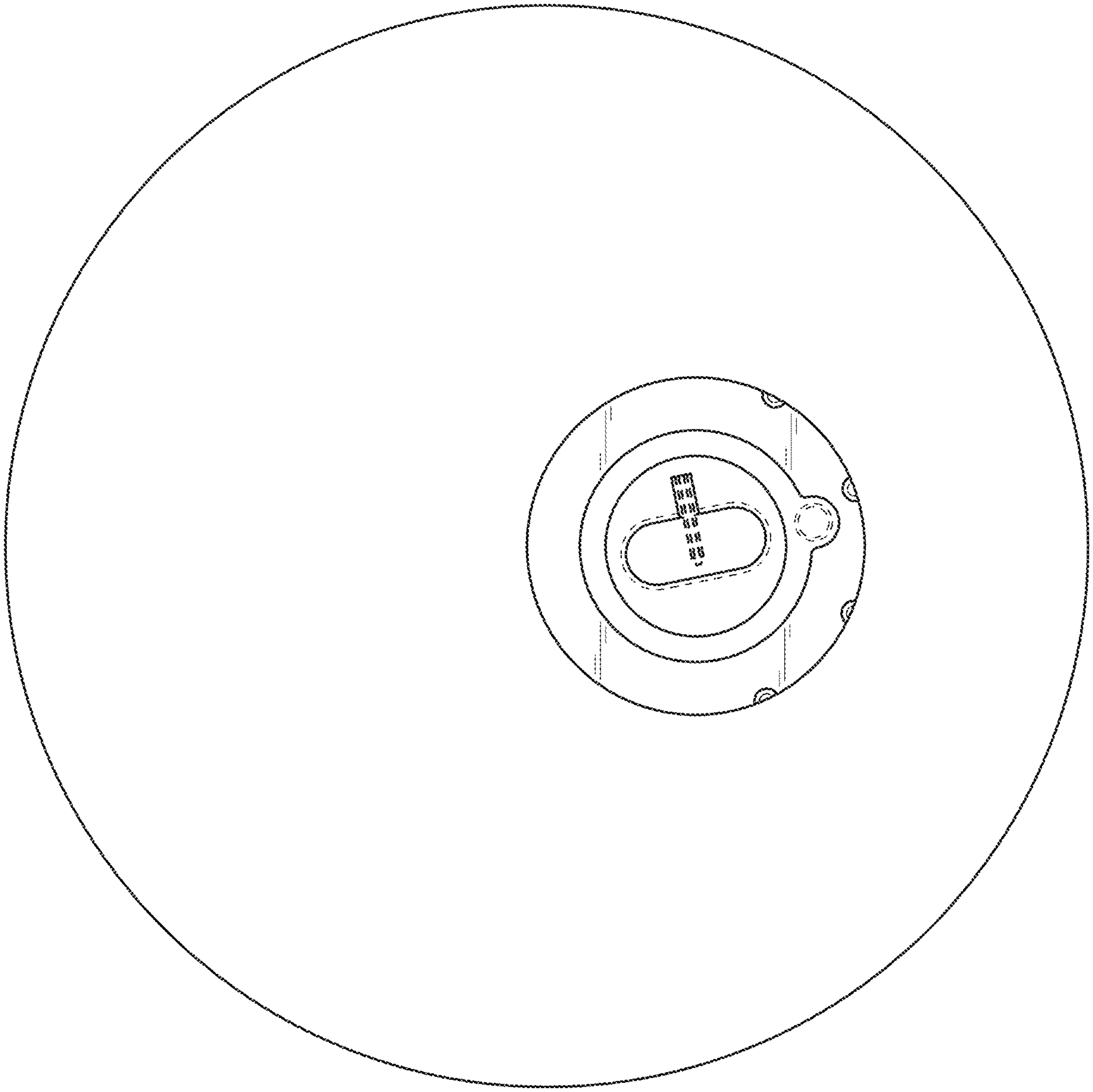
Figure 26A:
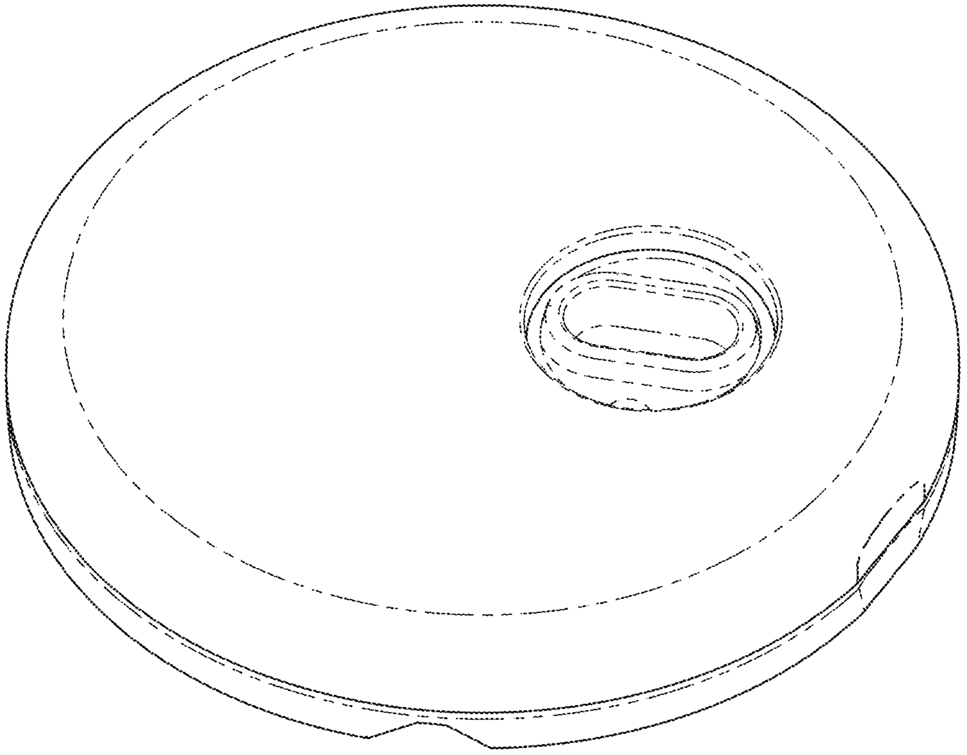
FIGS. 26A-26G depict another example embodiment of a sensor control device, where
Figure 26B:
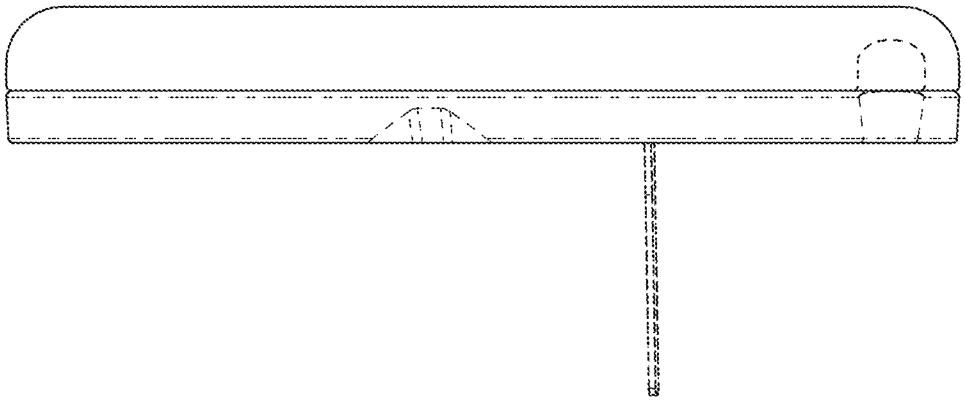
Figure 26C:
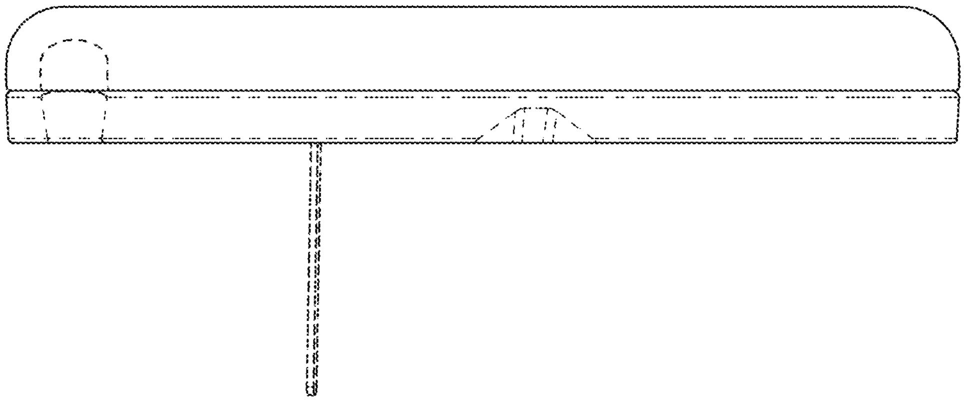
Figure 26D:
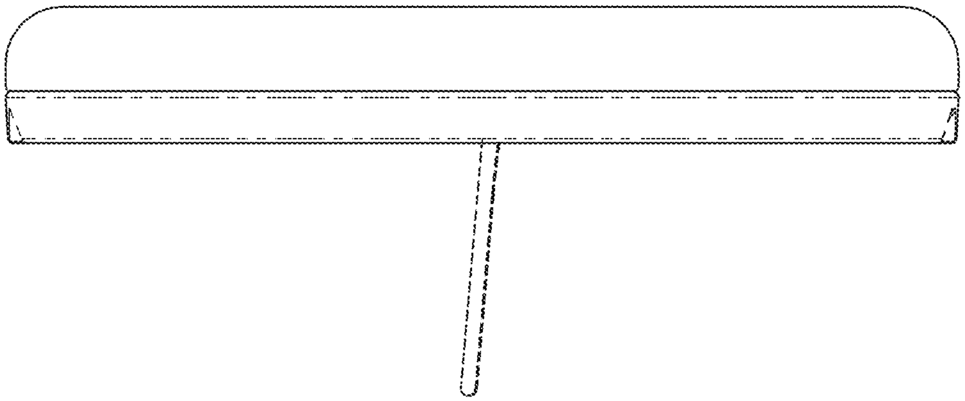
Figure 26E:
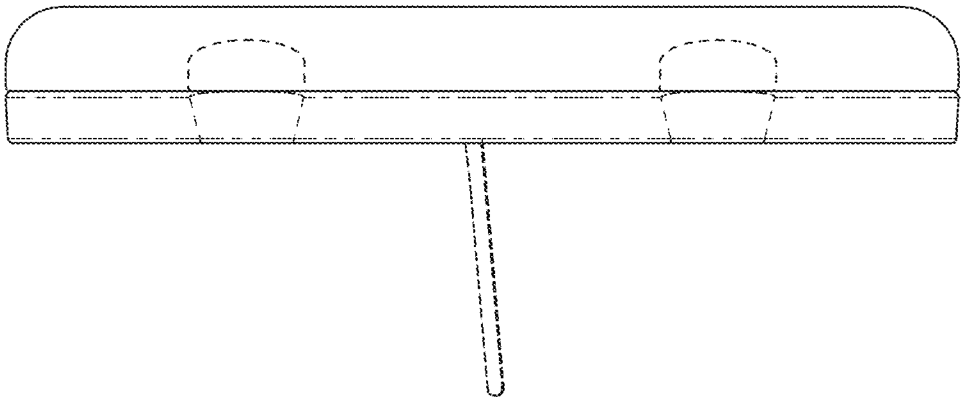
Figure 26F:
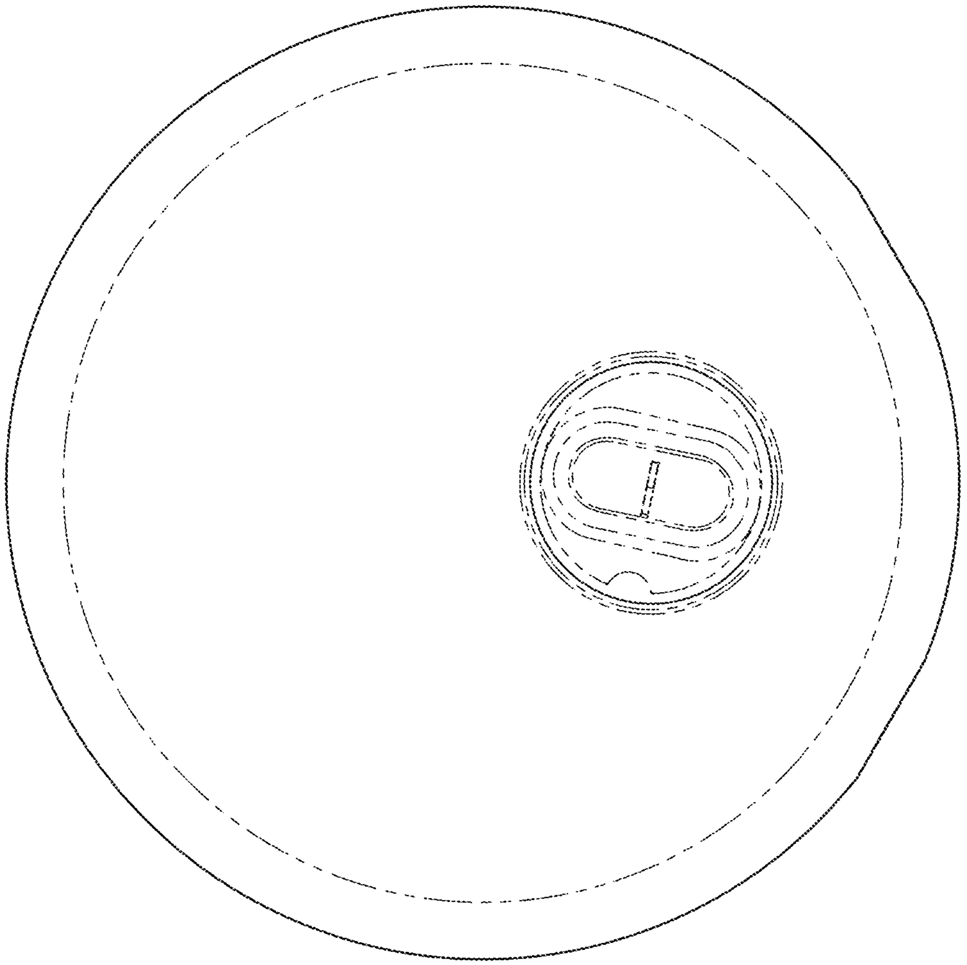
Figure 26G:
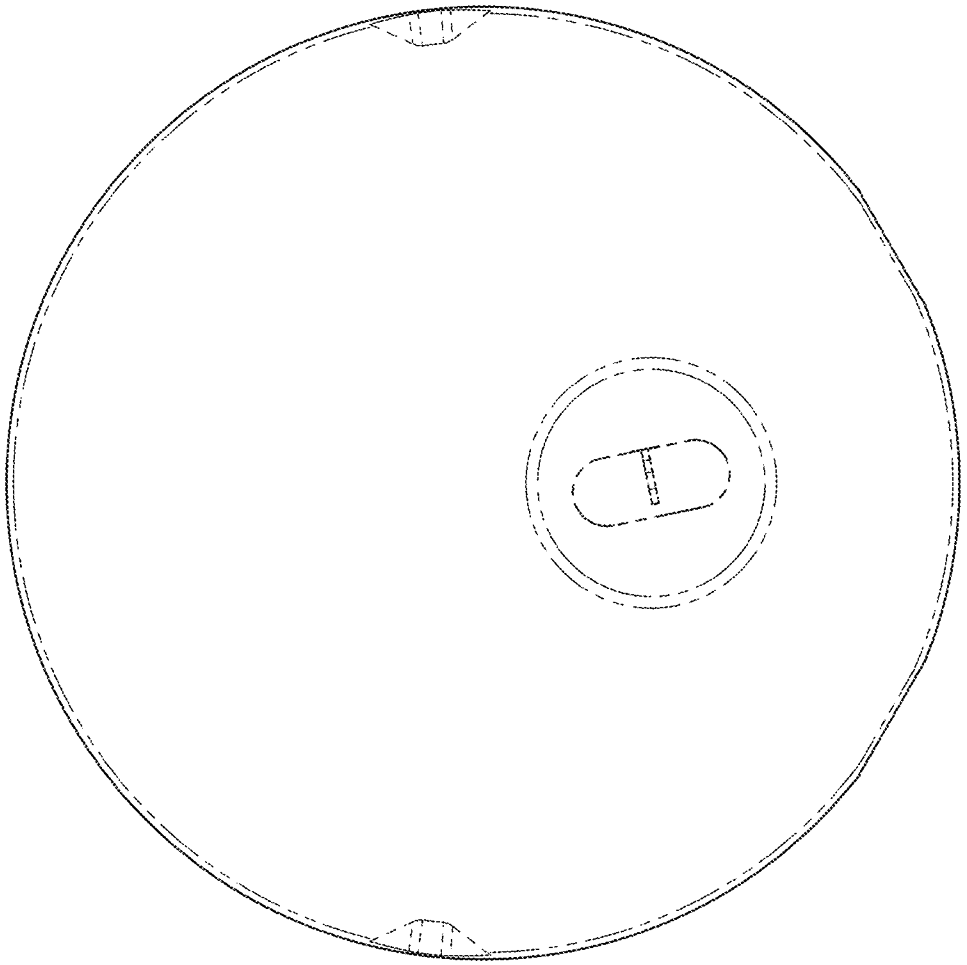
Figure 27A:
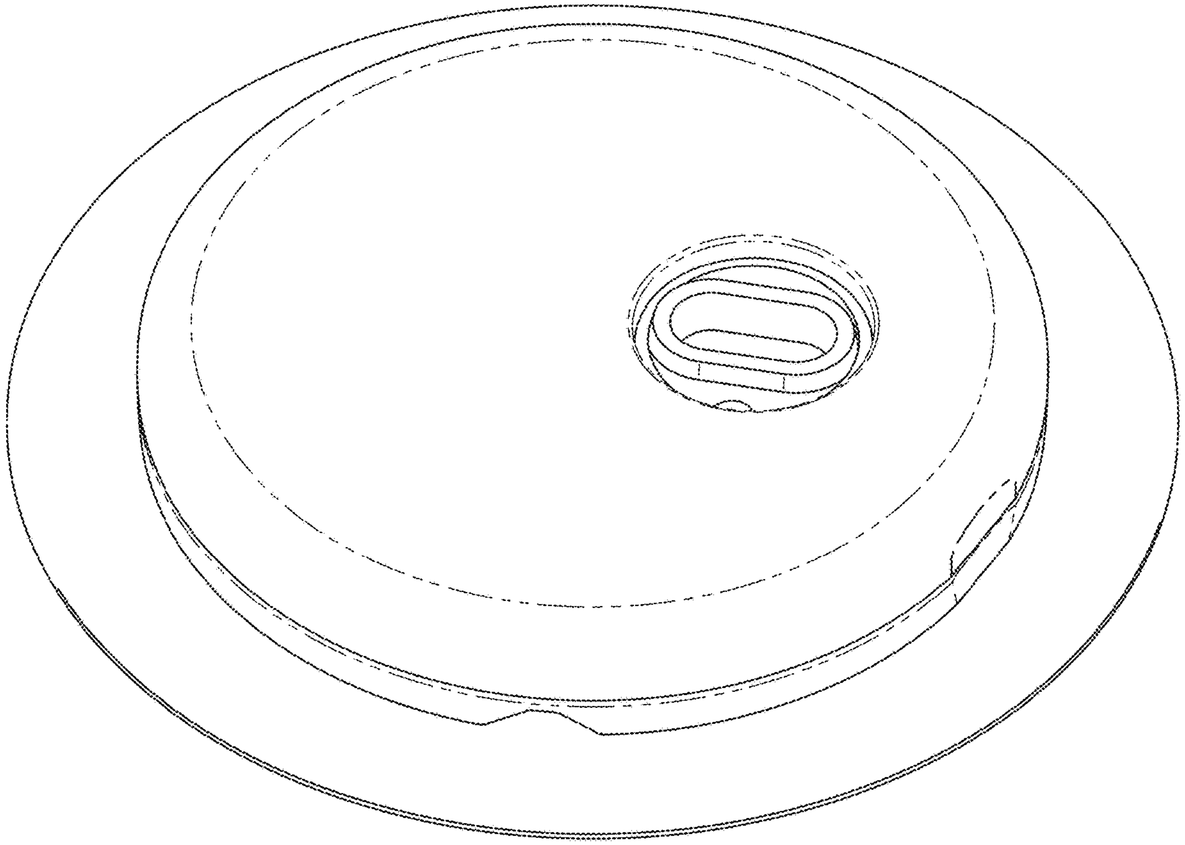
FIGS. 27A-27G depict another example embodiment of a sensor control device, where
Figure 27B:
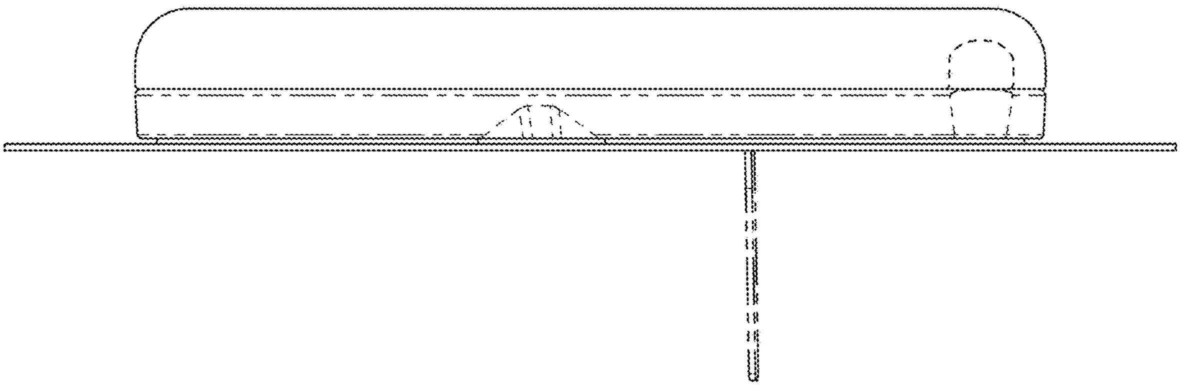
Figure 27C:
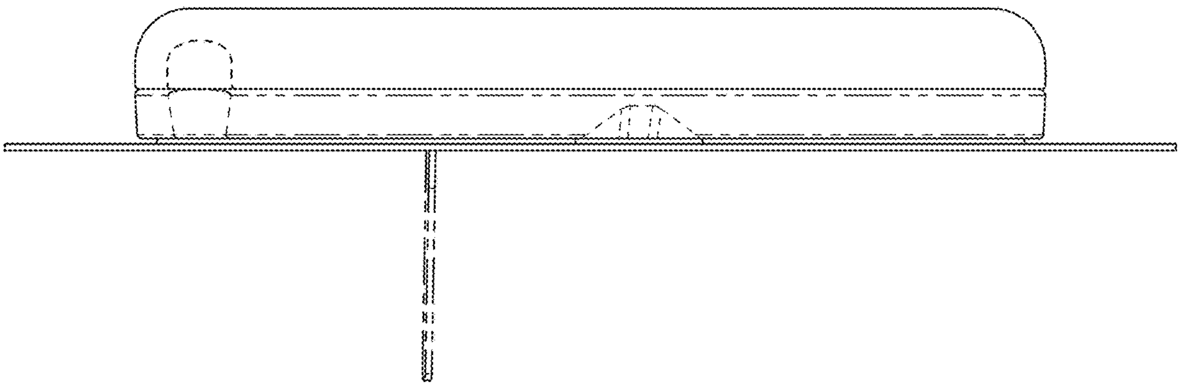
Figure 27D:
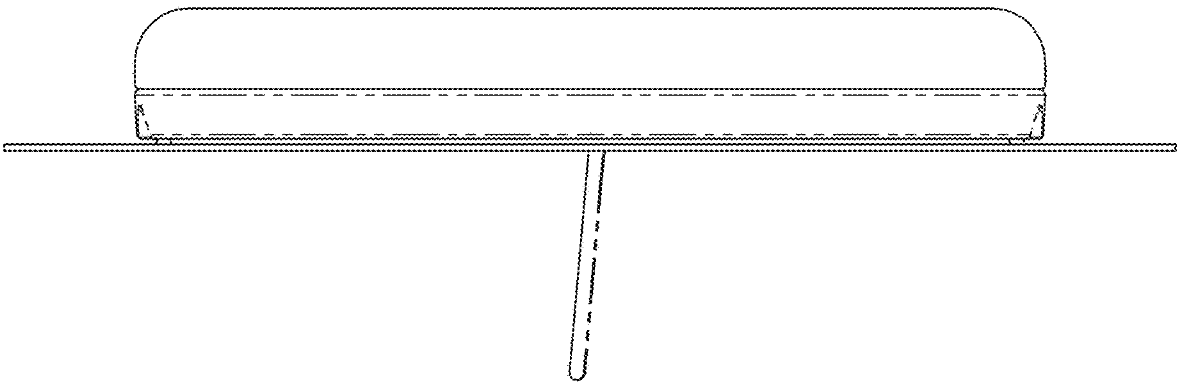
Figure 27E:
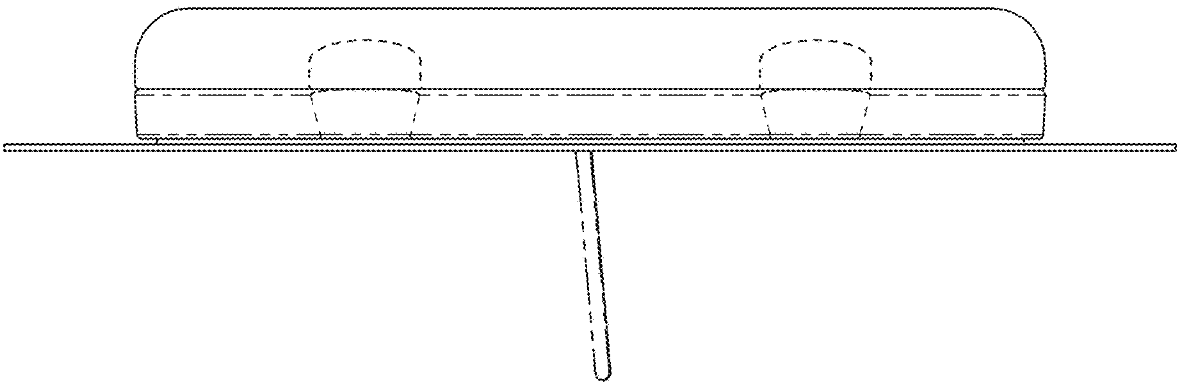
Figure 27F:
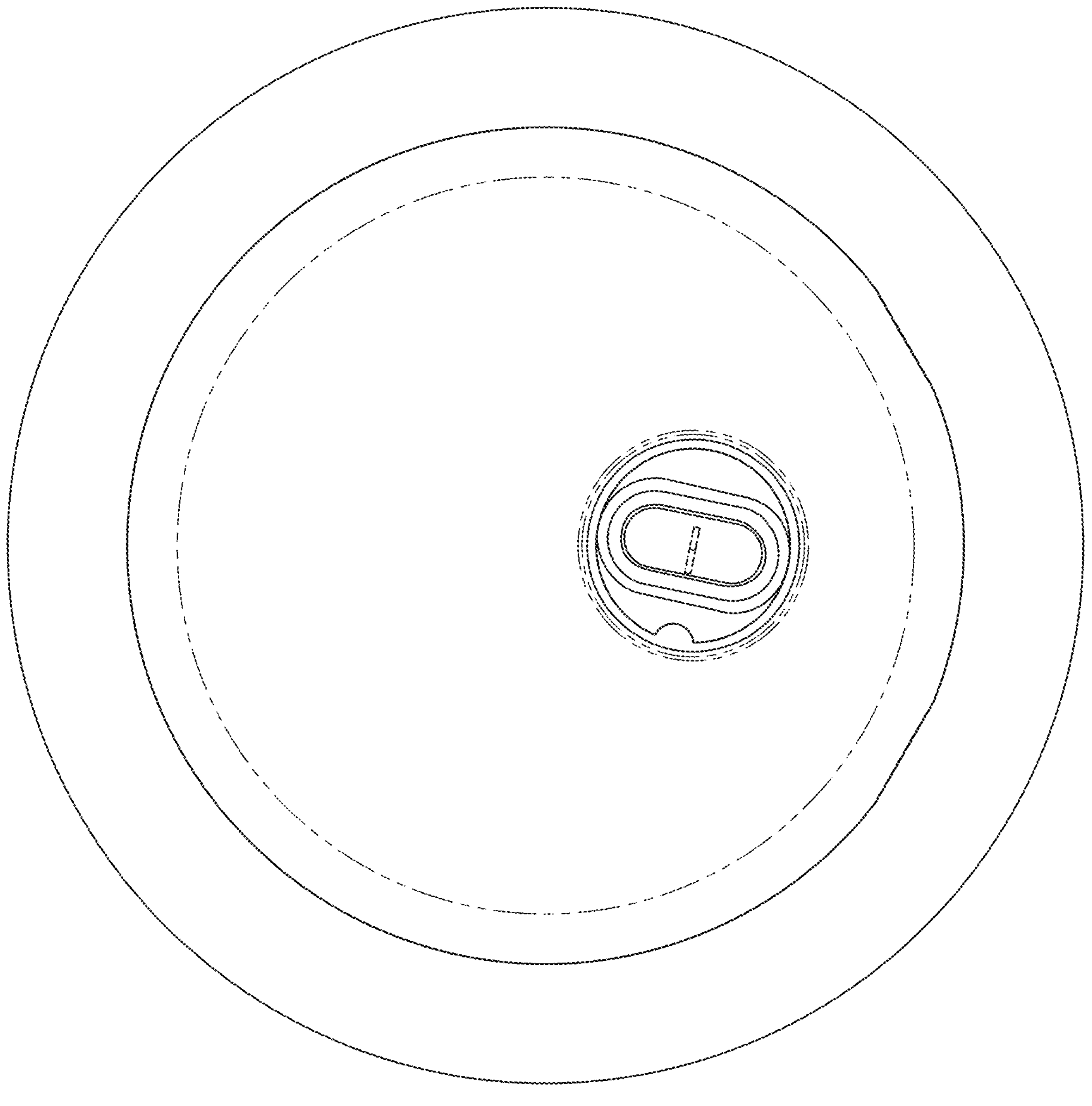
Figure 27G:
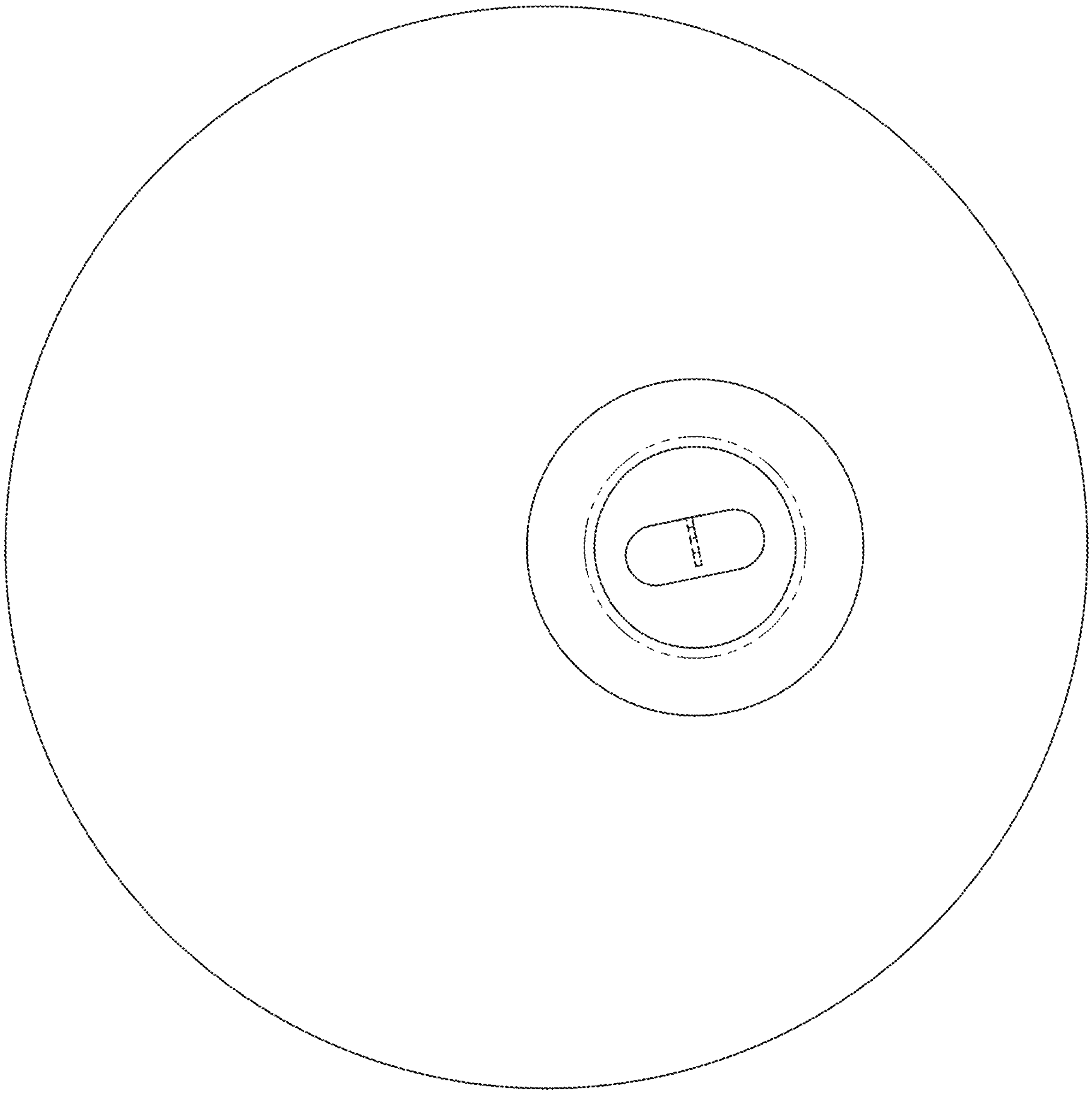
Figure 28A:
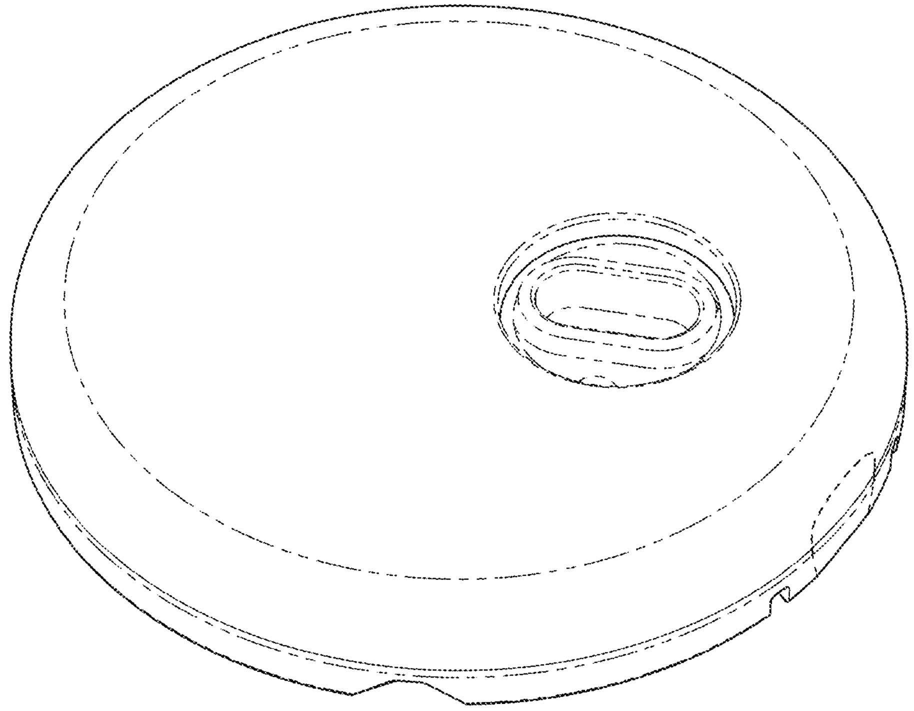
FIGS. 28A-28G depict another example embodiment of a sensor control device, where
Figure 28B:
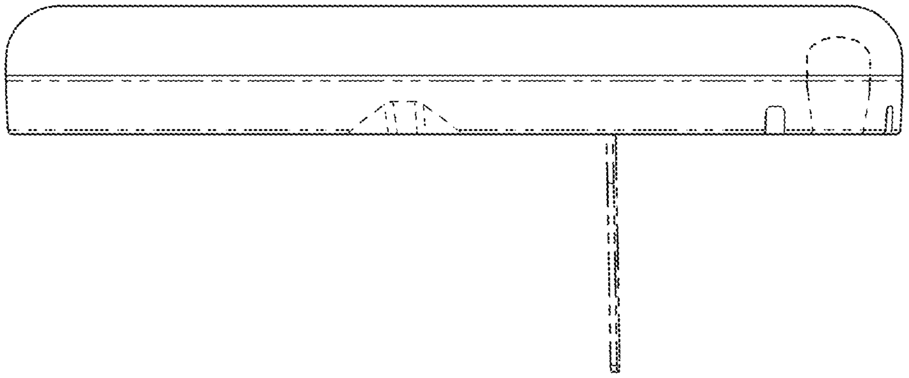
Figure 28C:
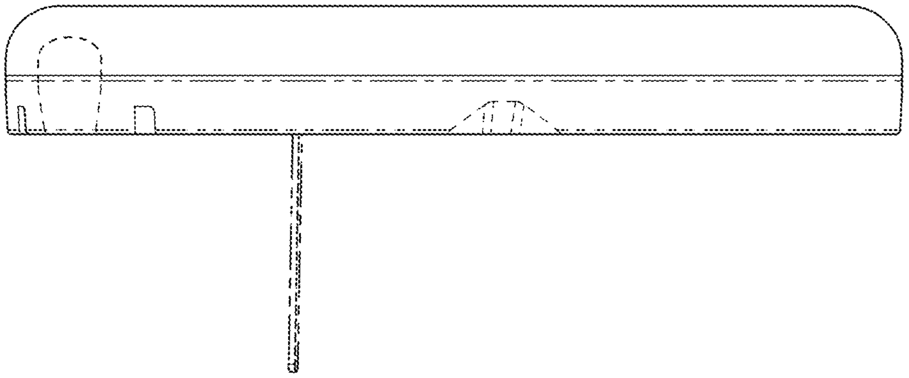
Figure 28D:
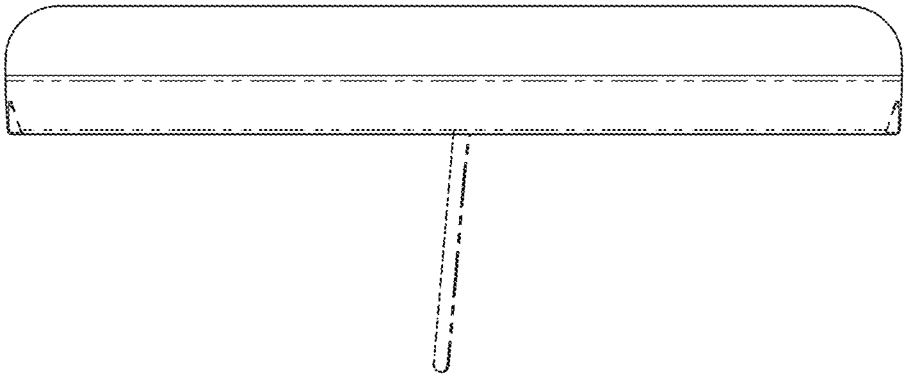
Figure 28E:
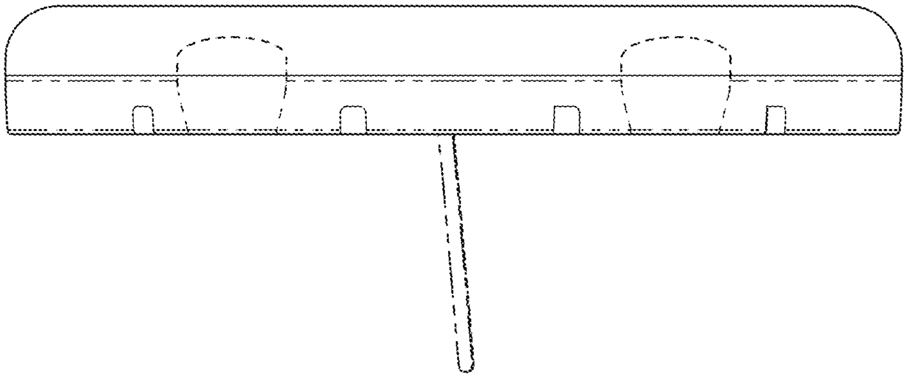
Figure 28F:
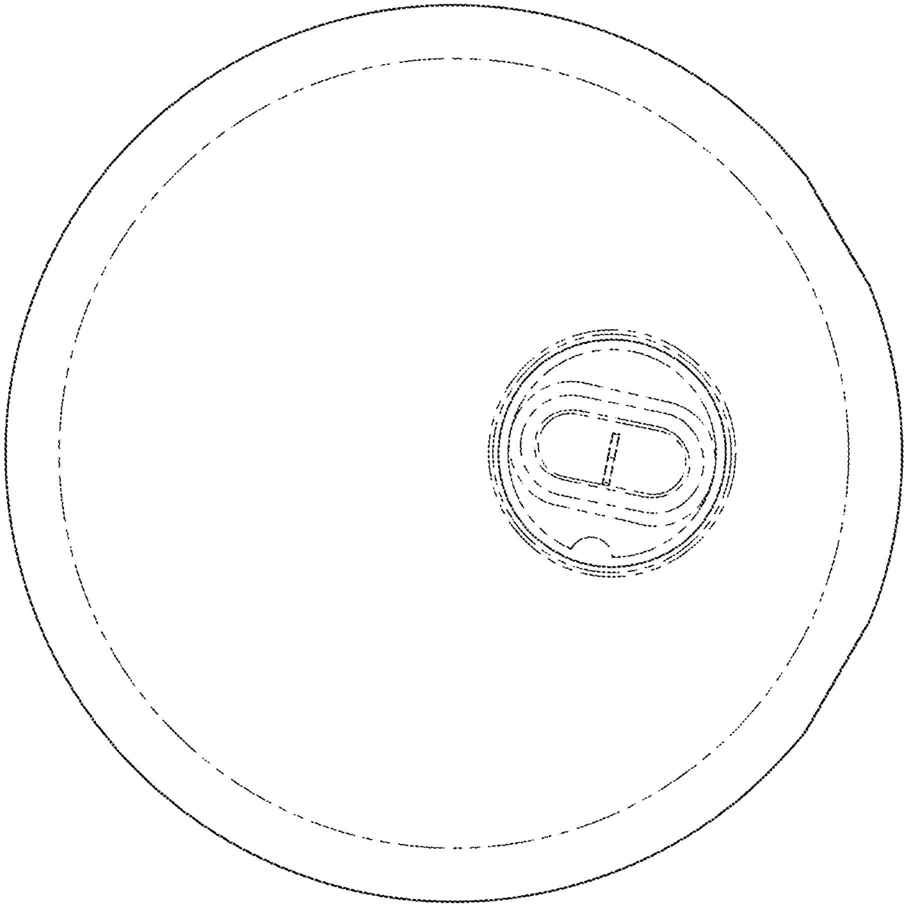
Figure 28G:
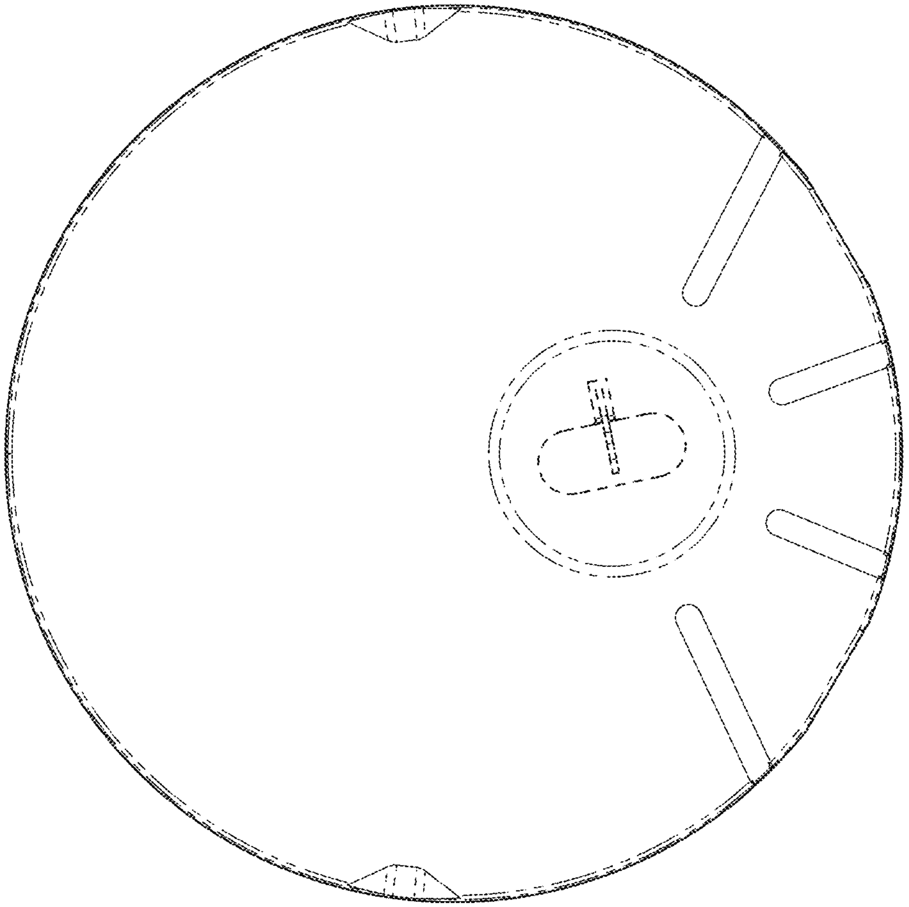
Figure 29A:
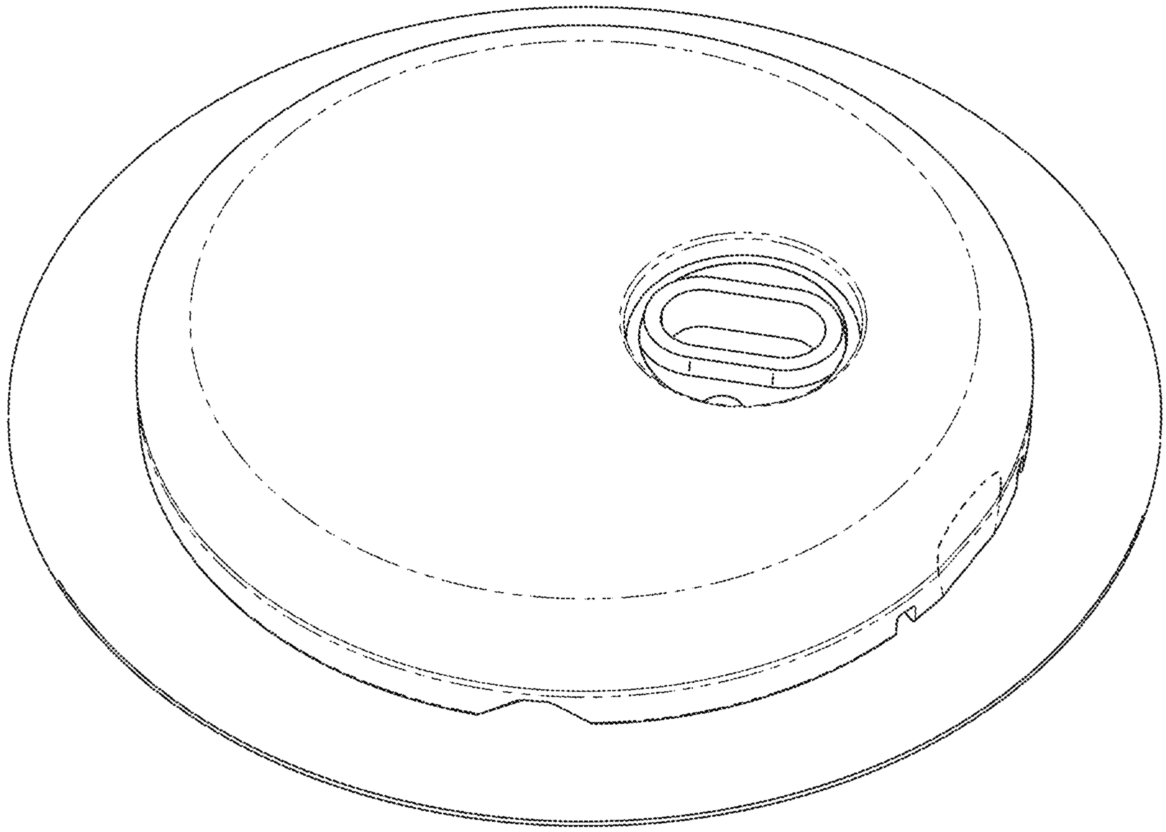
FIGS. 29A-29G depict another example embodiment of a sensor control device, where
Figure 29B:
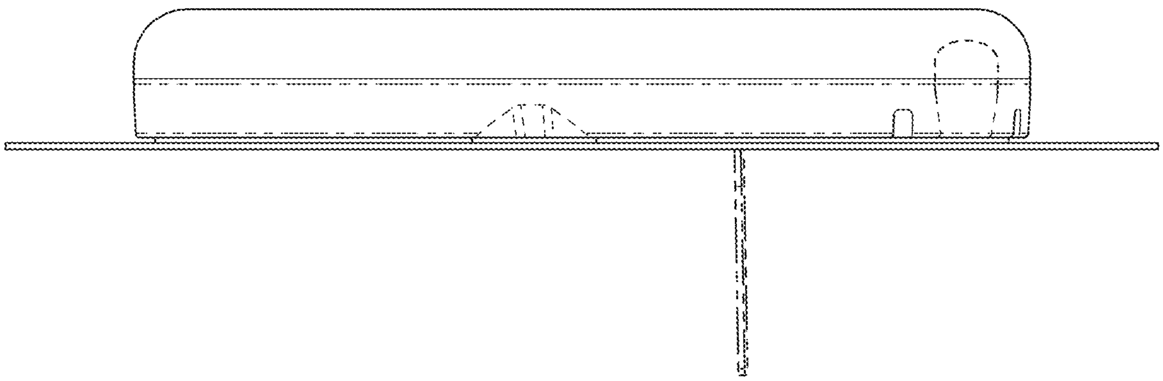
Figure 29C:
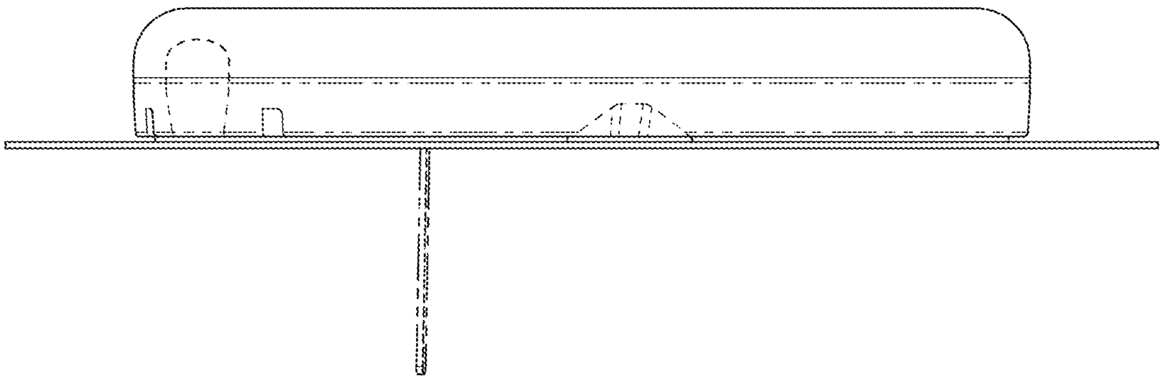
Figure 29D:
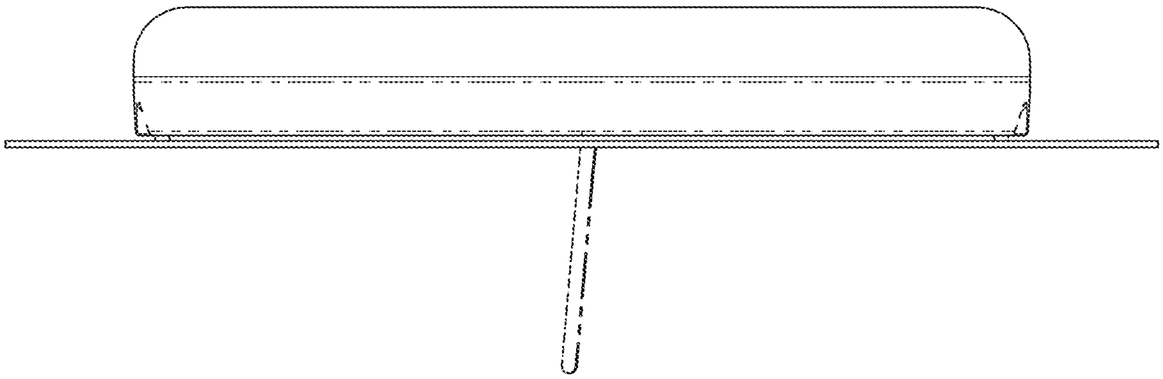
Figure 29E:
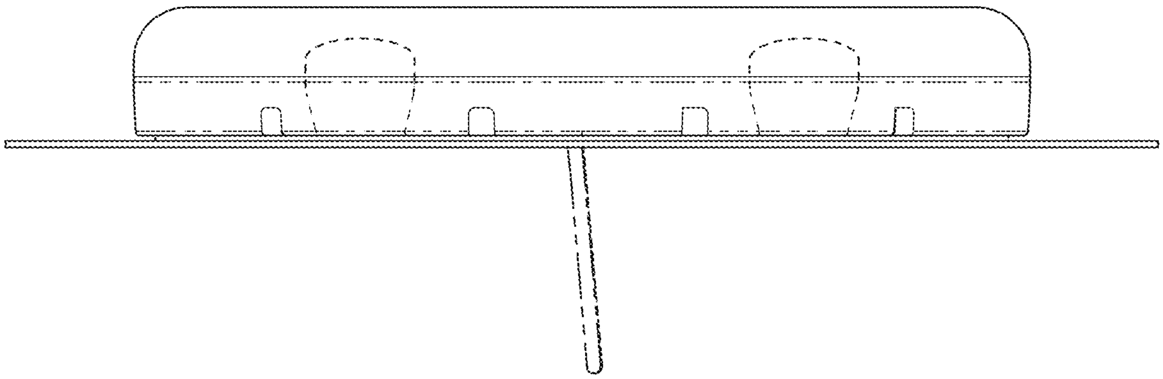
Figure 29F:
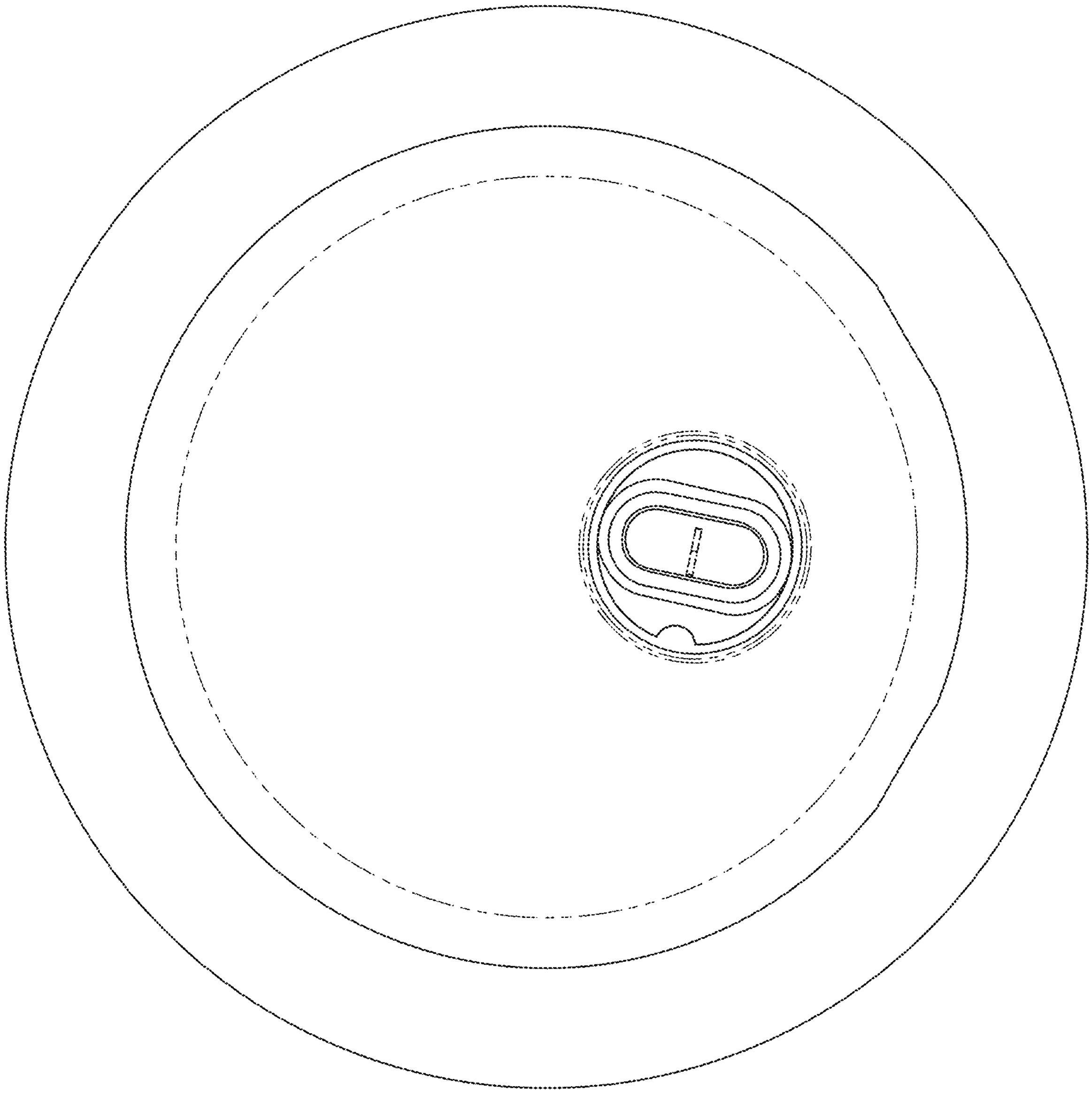
Figure 29G:
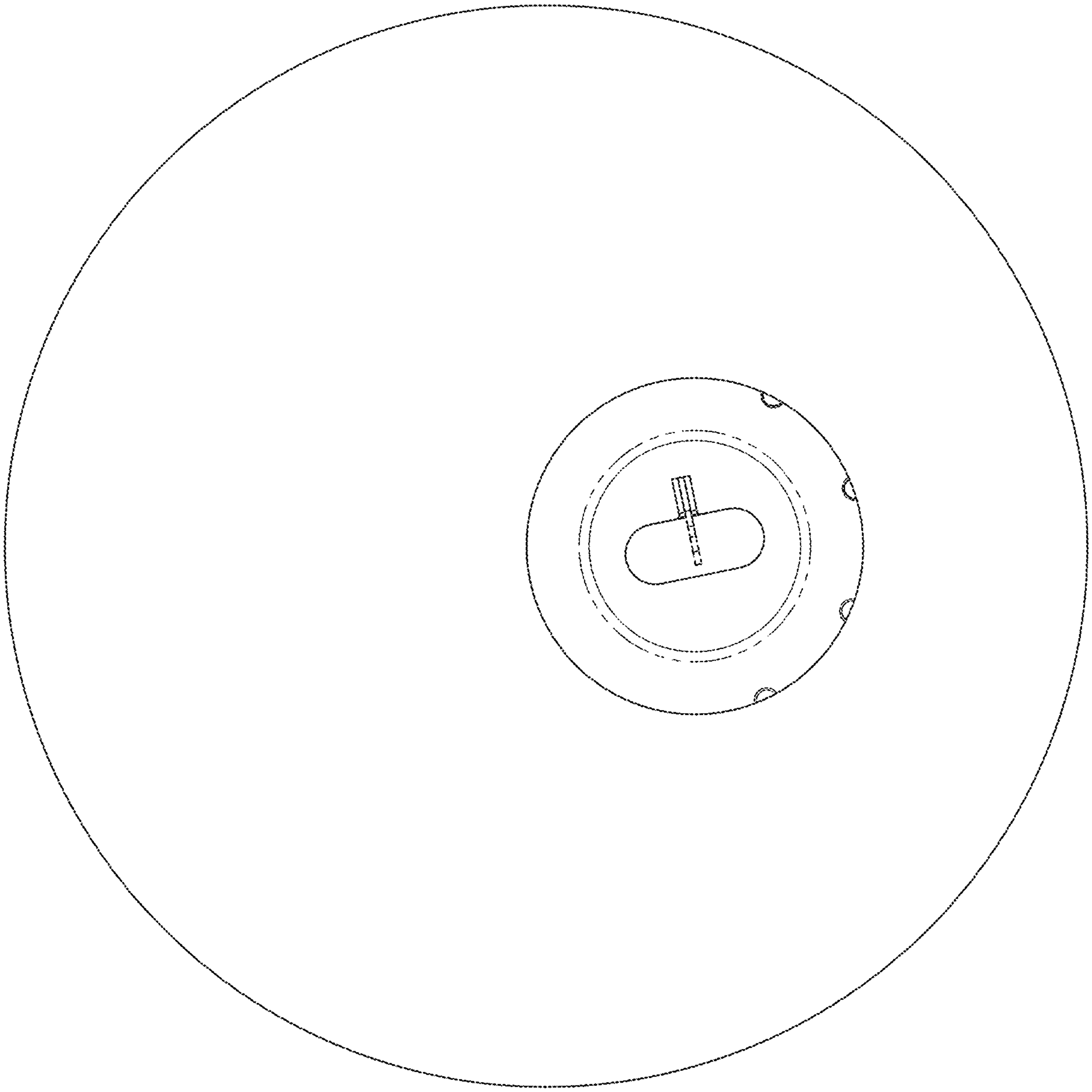
Figure 30A:
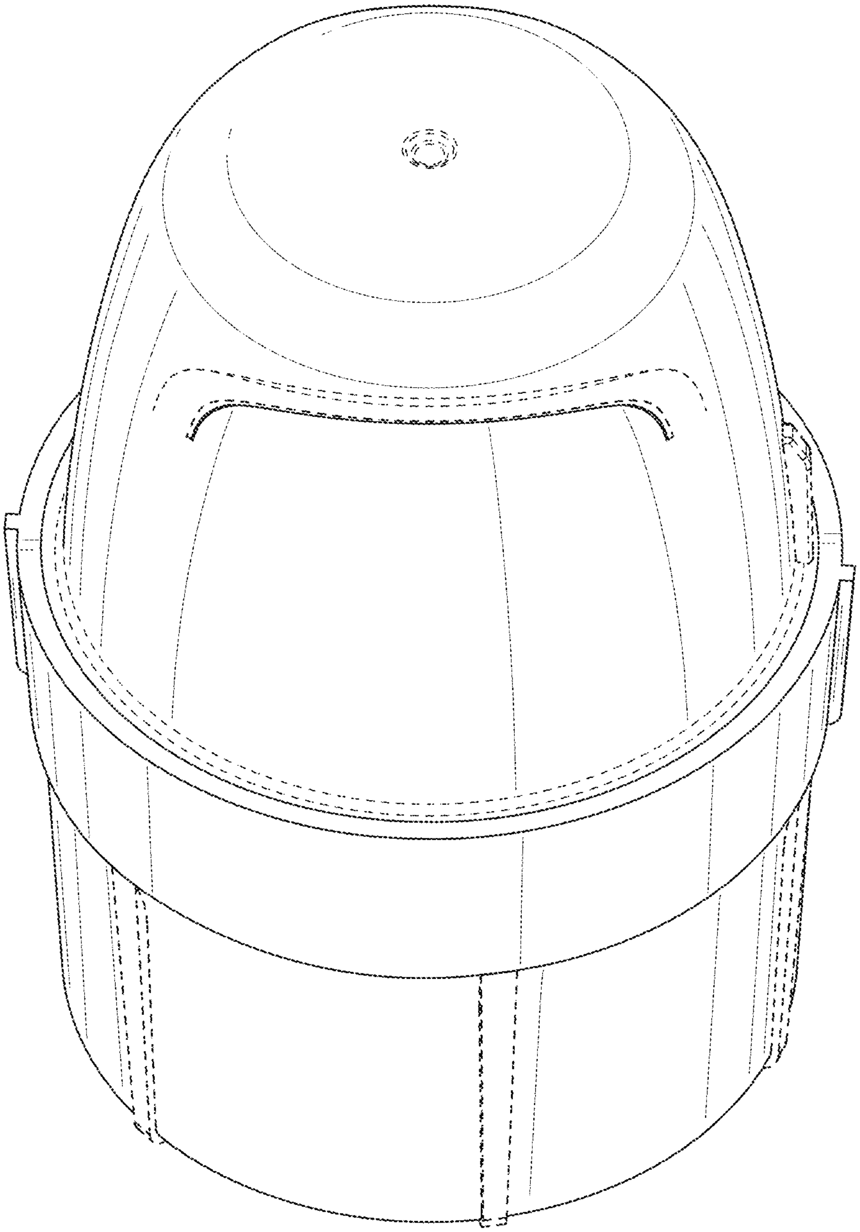
FIGS. 30A-30G depict an example embodiment of an applicator, where
Figure 30B:
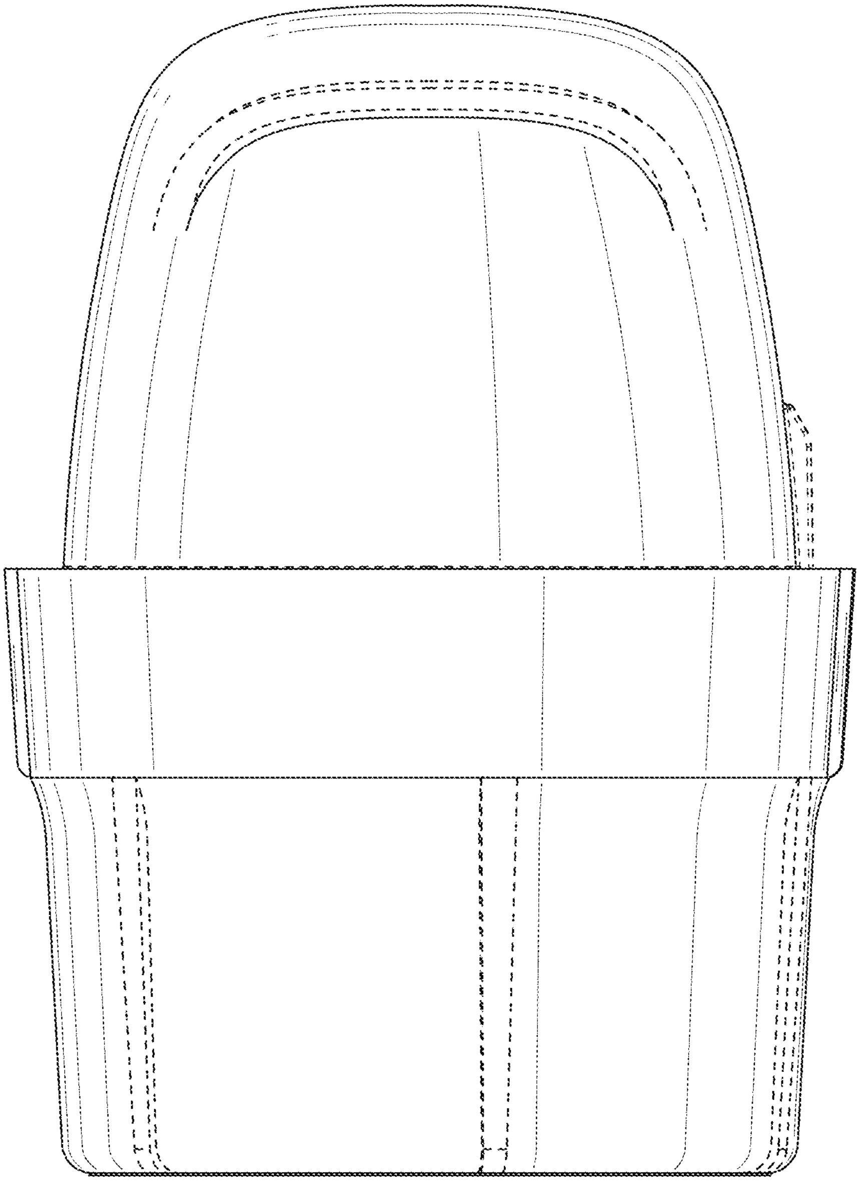
Figure 30C:
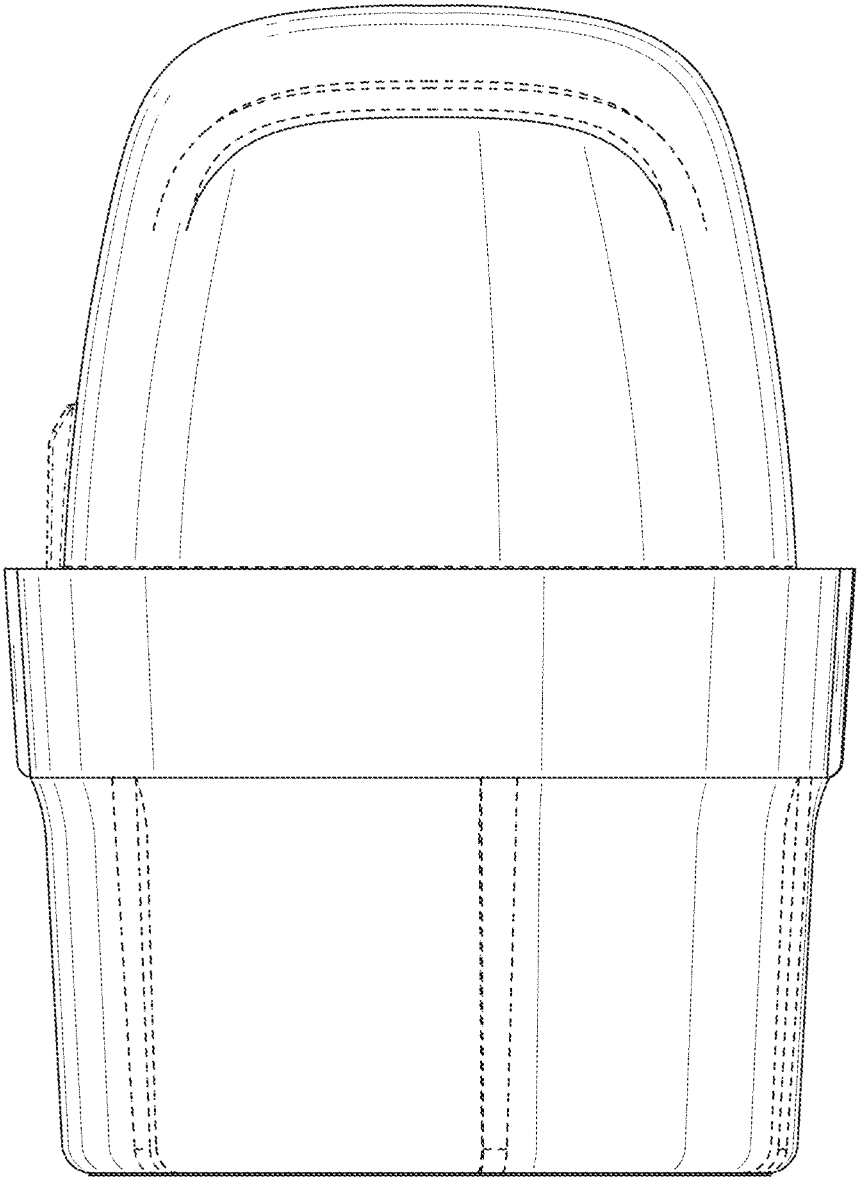
Figure 30D:
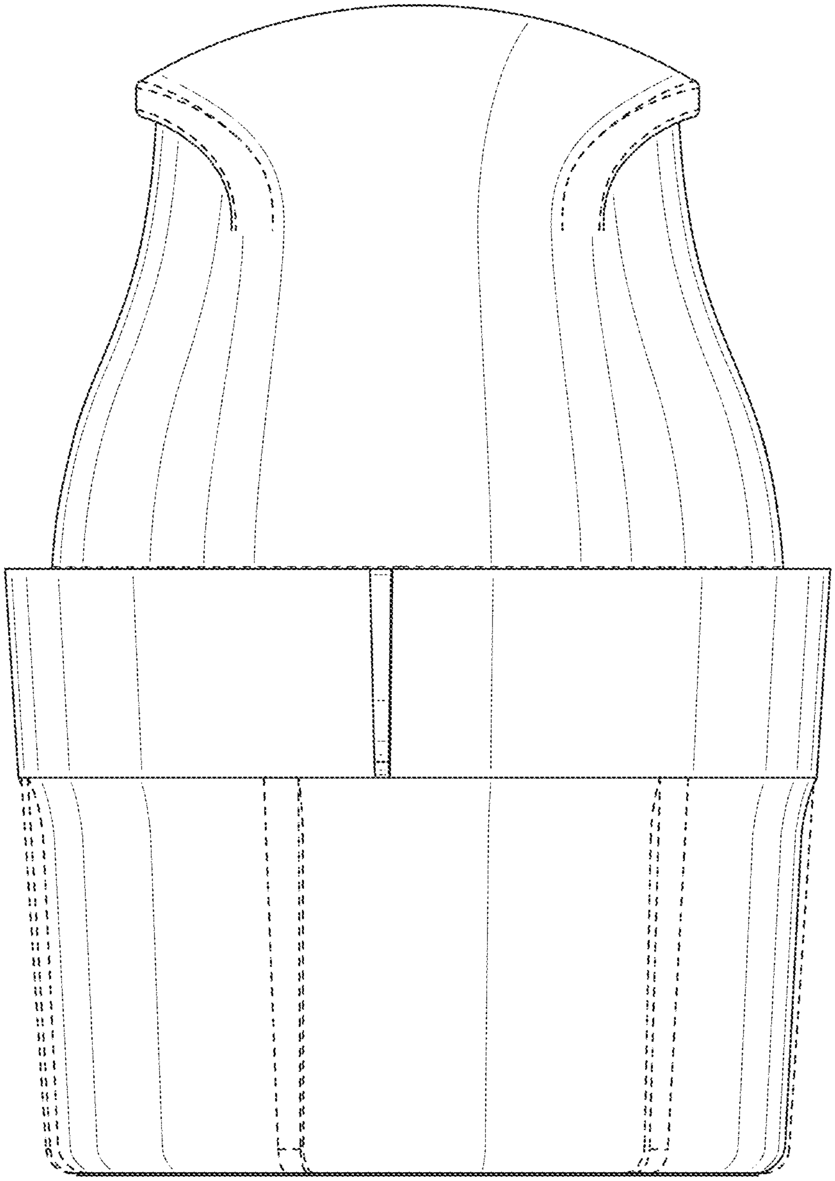
Figure 30E:
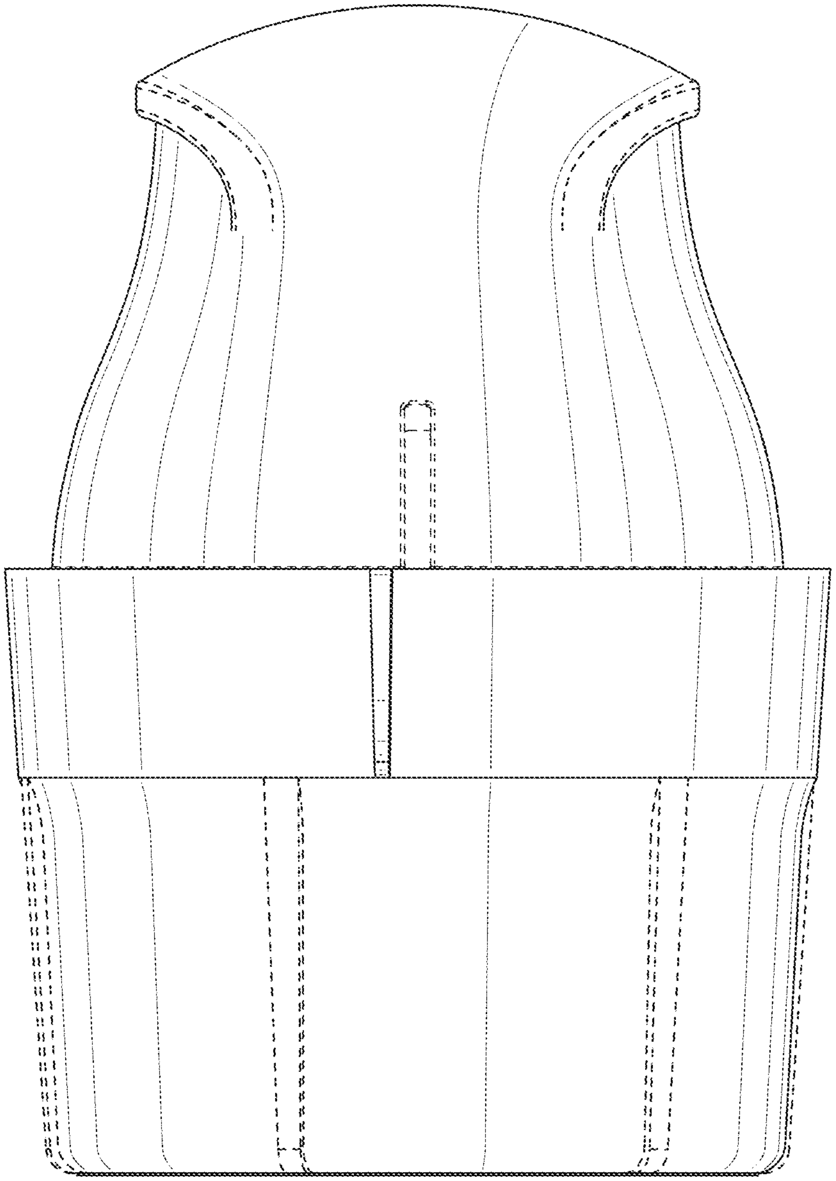
Figure 30F:
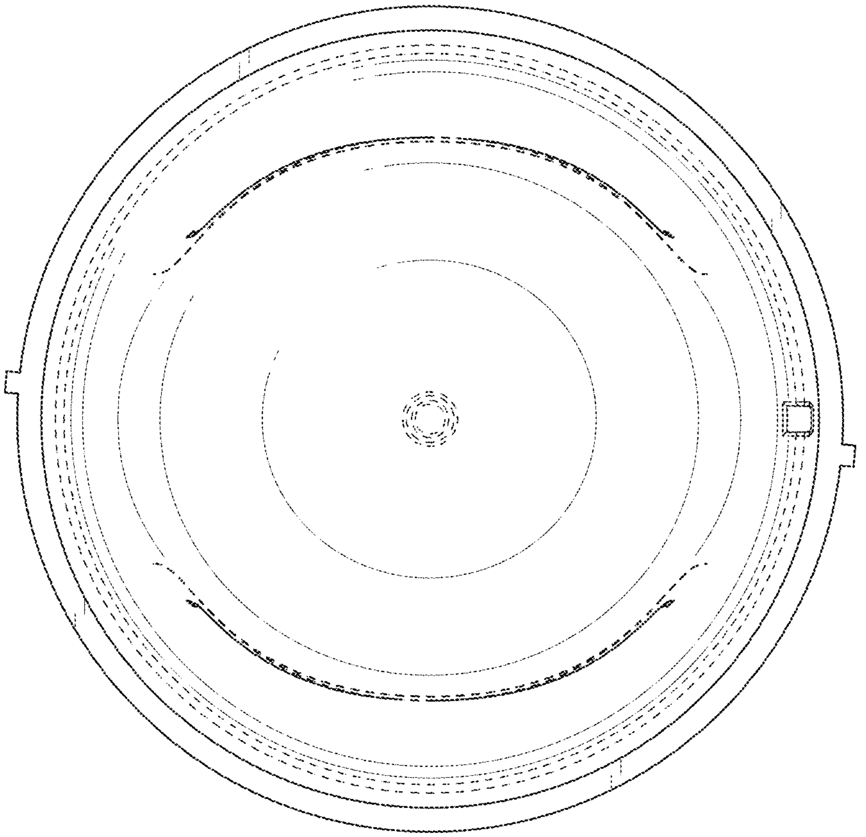
Figure 30G:
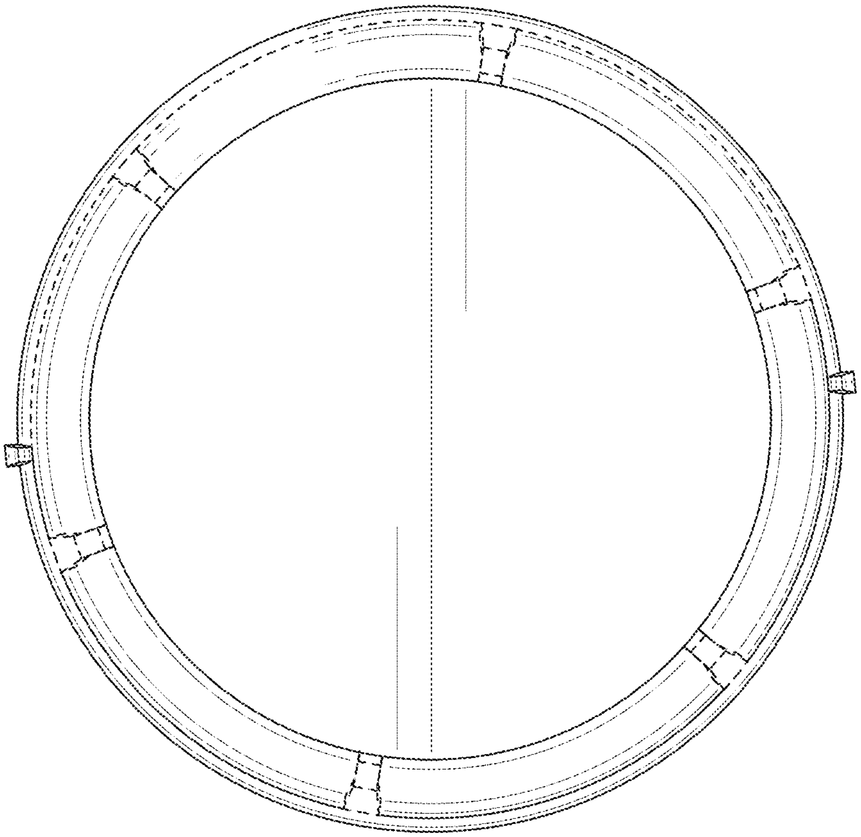
Figure 31A:
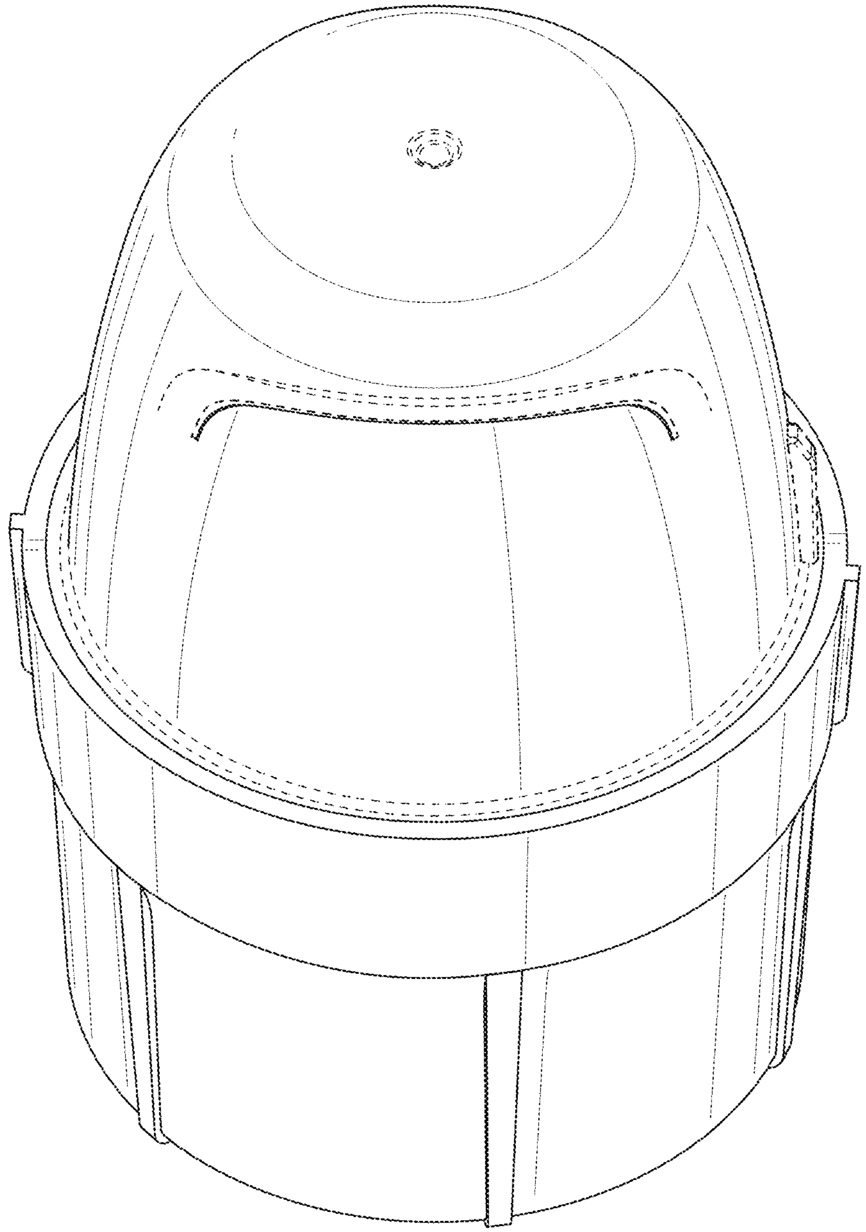
FIGS. 31A-31G depict another example embodiment of an applicator, where
Figure 31B:
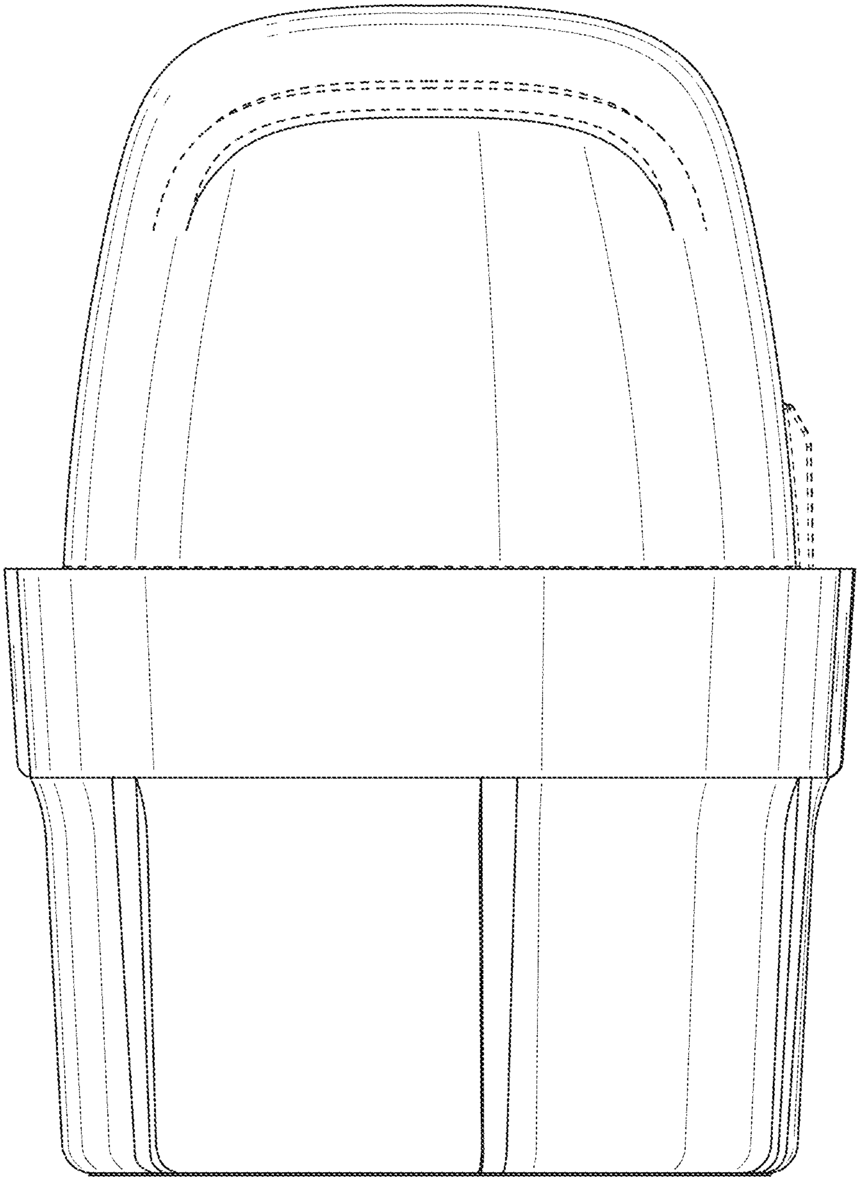
Figure 31C:
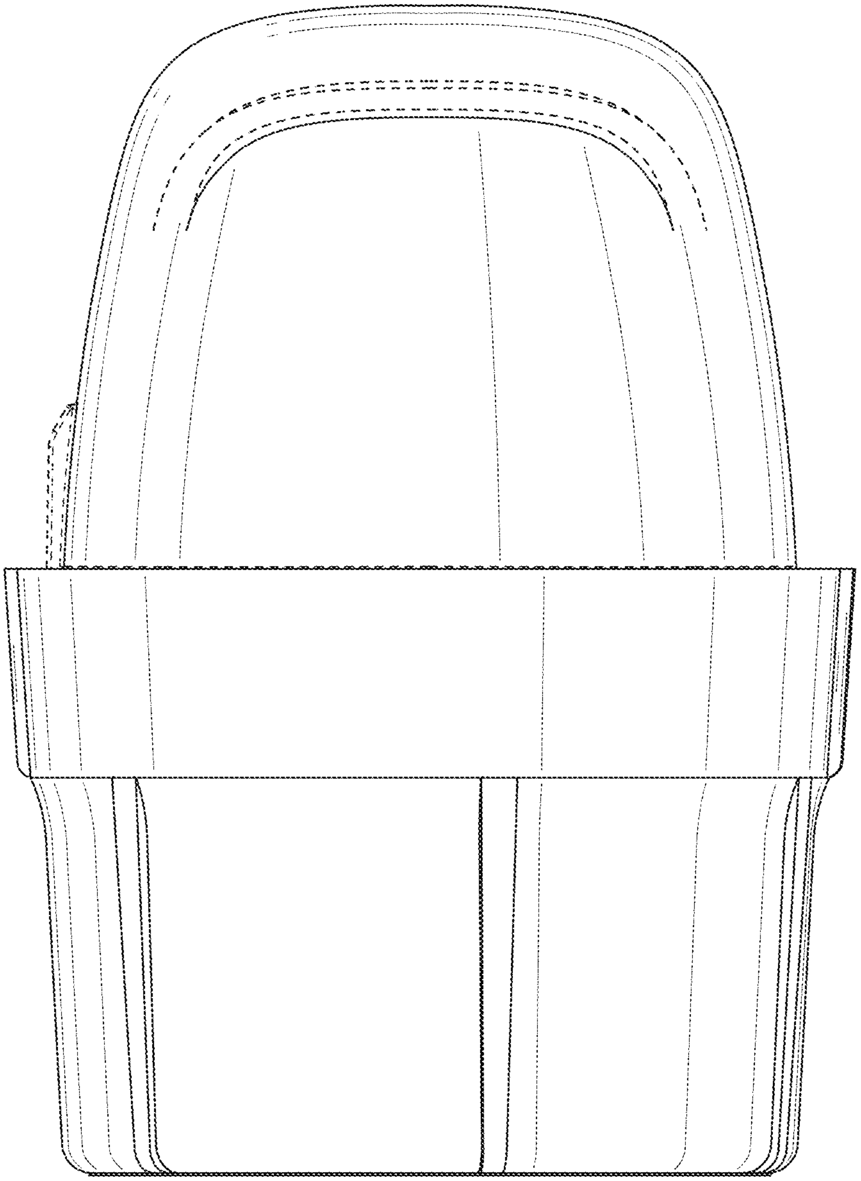
Figure 31D:
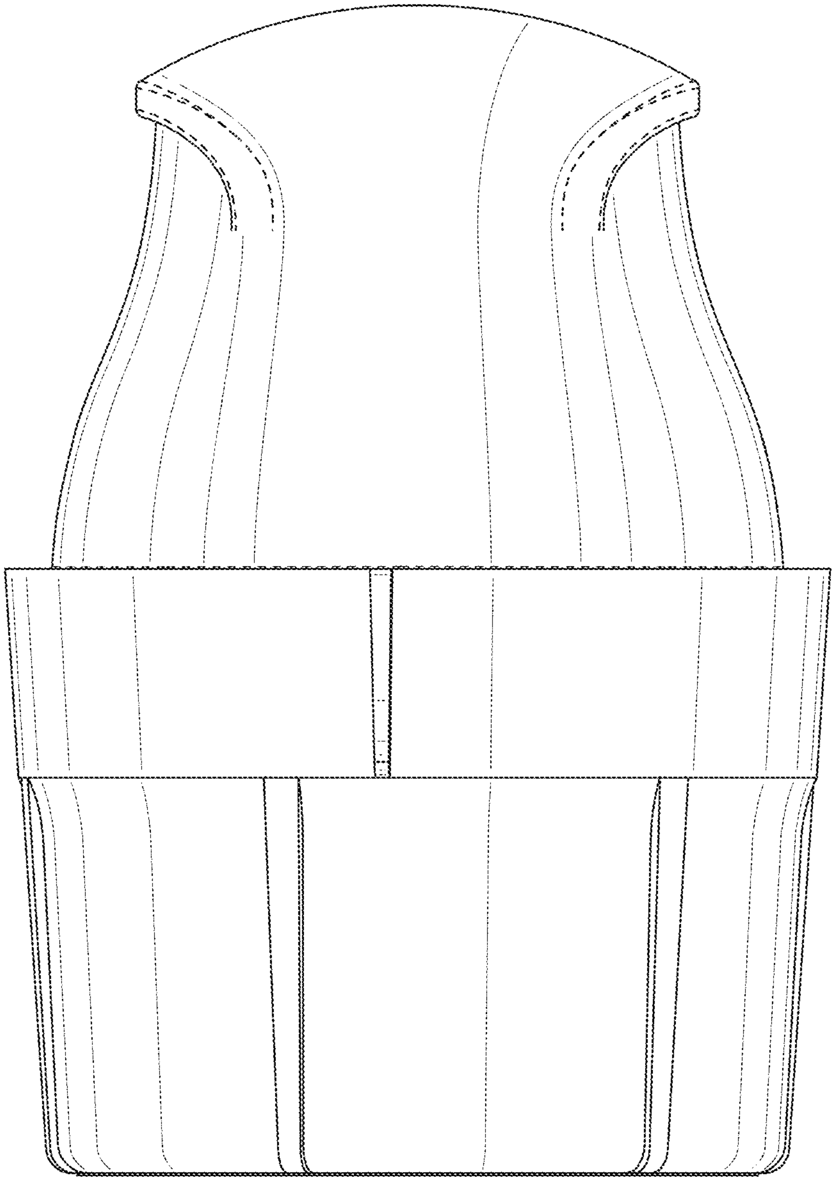
Figure 31E:
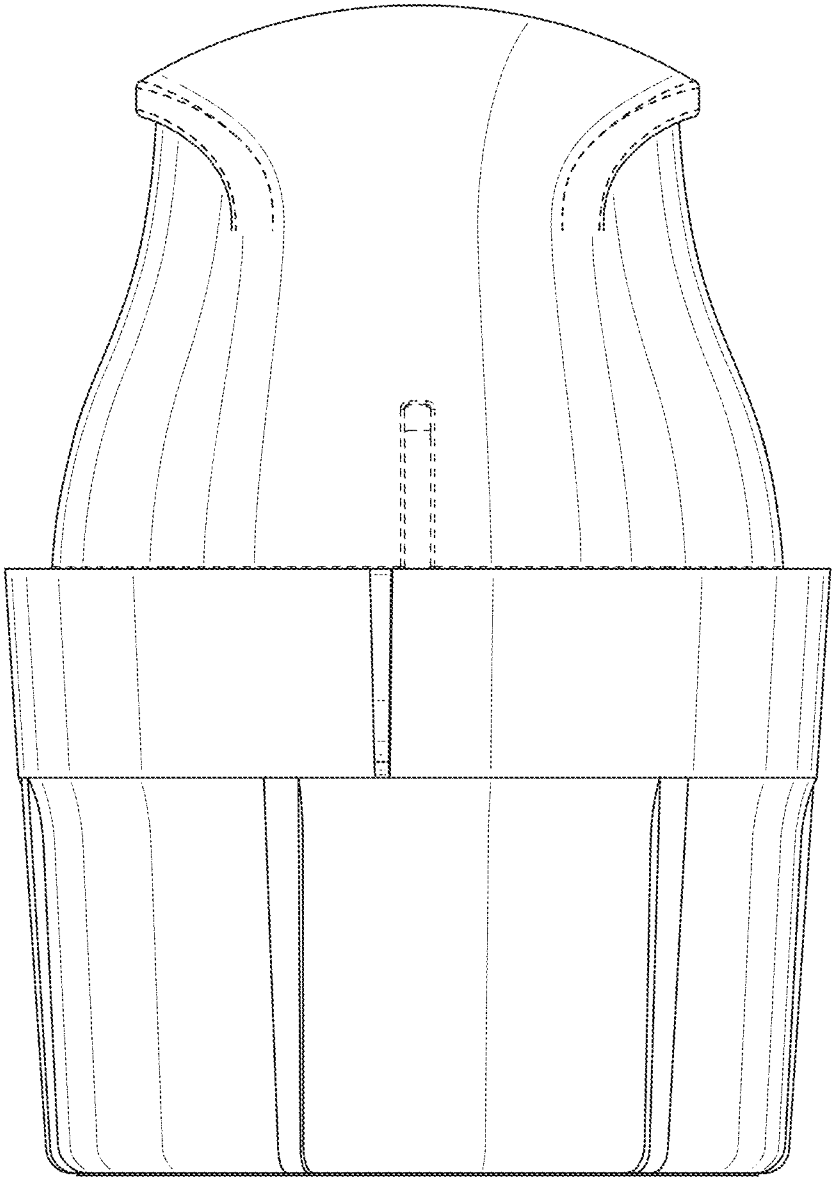
Figure 31F:
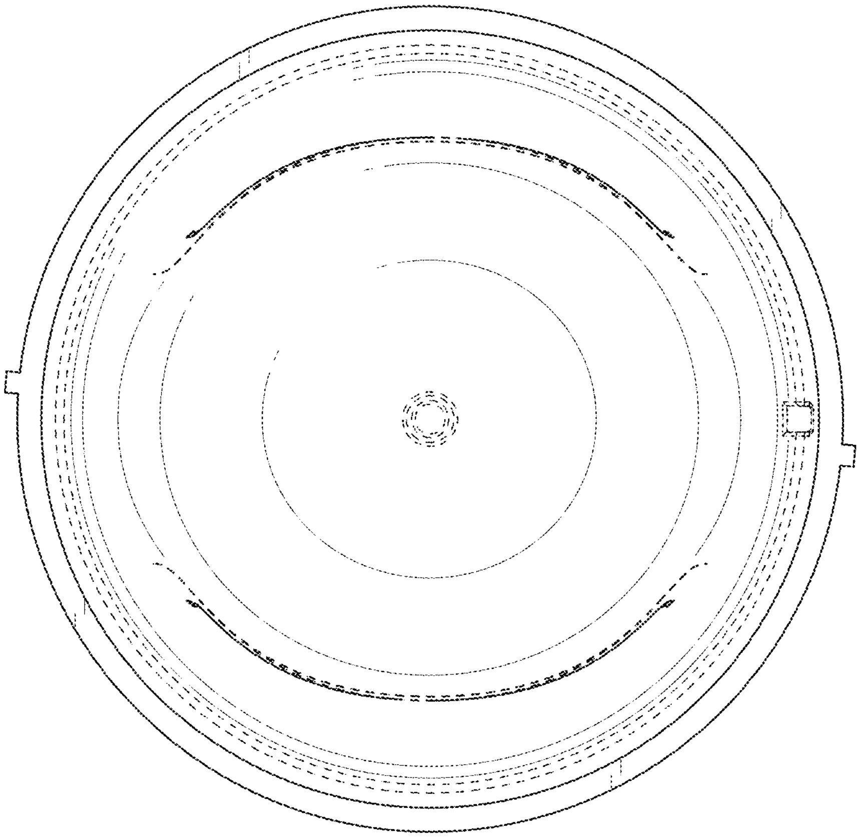
Figure 31G:
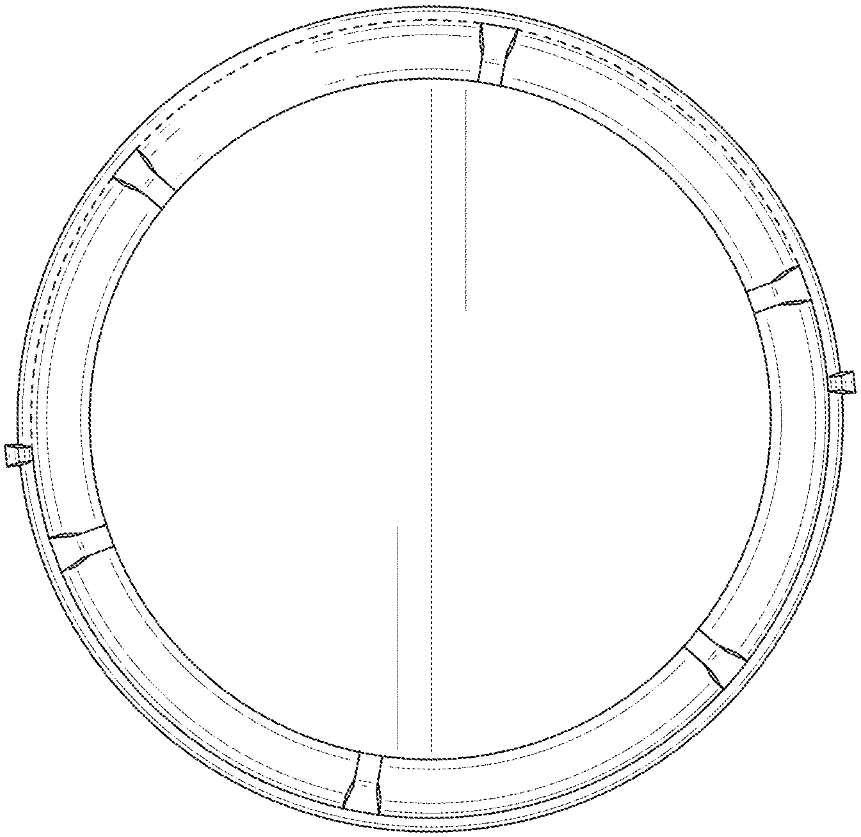
Figure 32A:
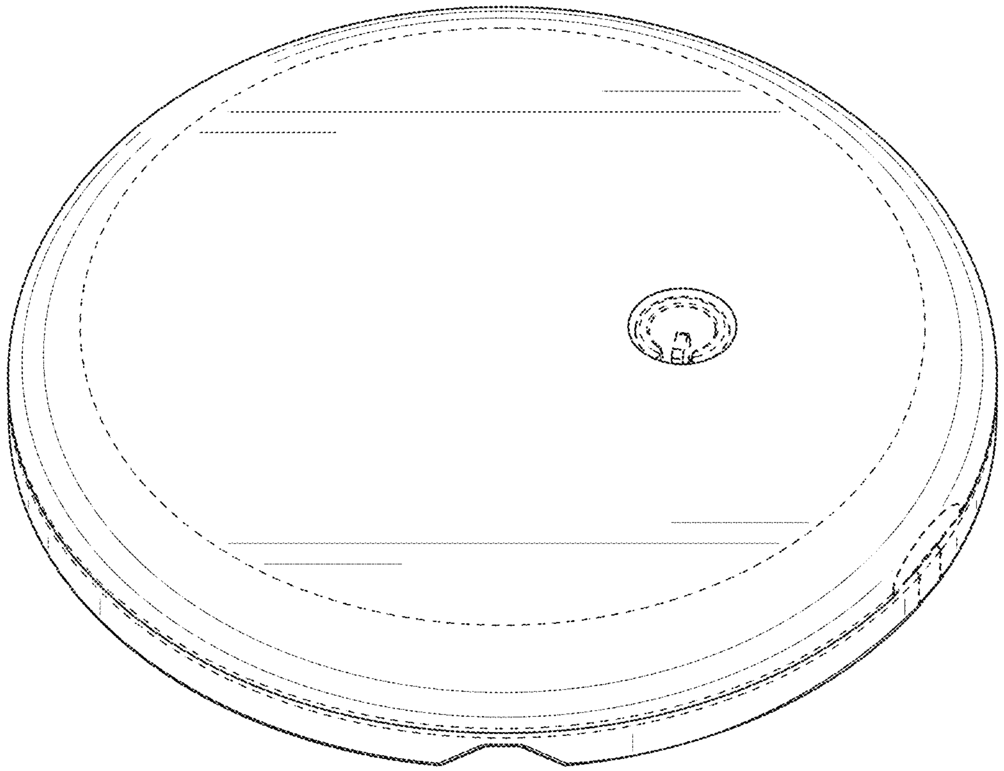
FIGS. 32A-32G depict an example embodiment of a sensor control device, where
Figure 32B:
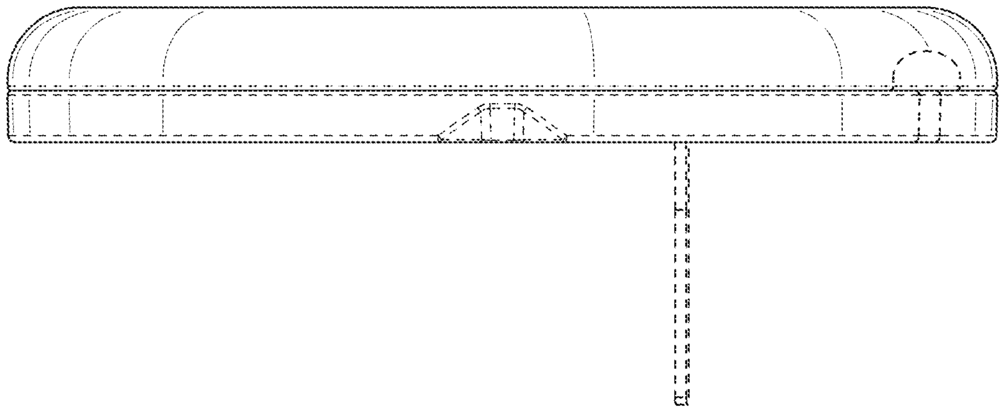
Figure 32C:
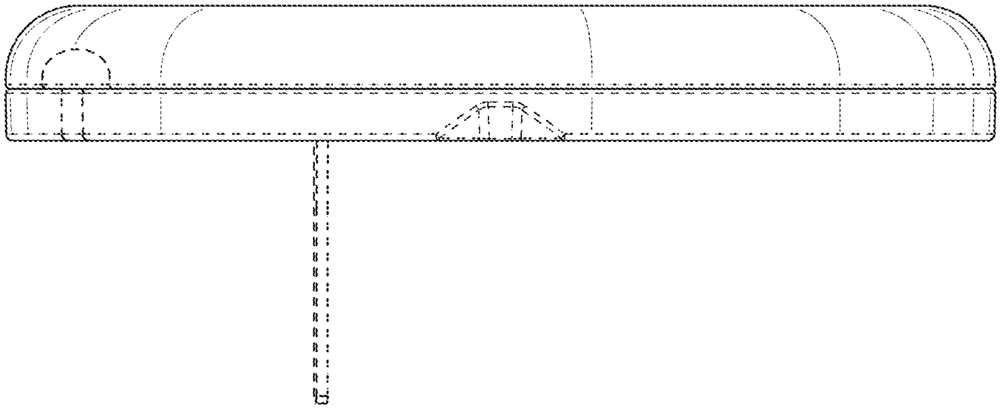
Figure 32D:
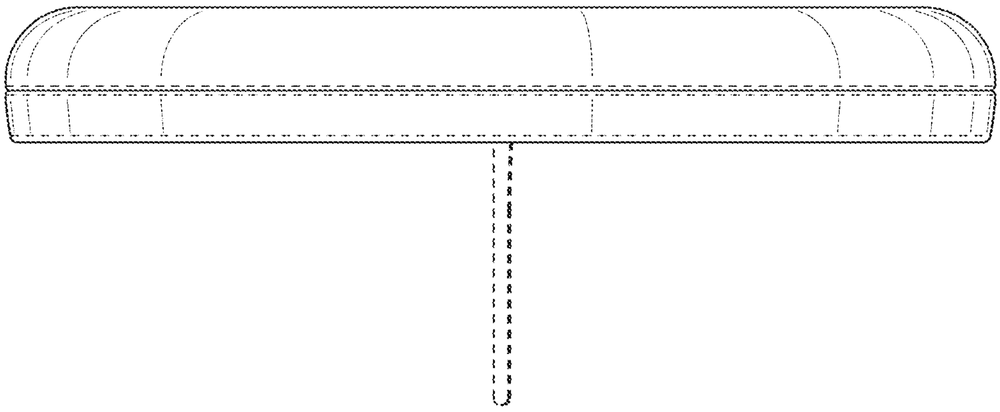
Figure 32E:
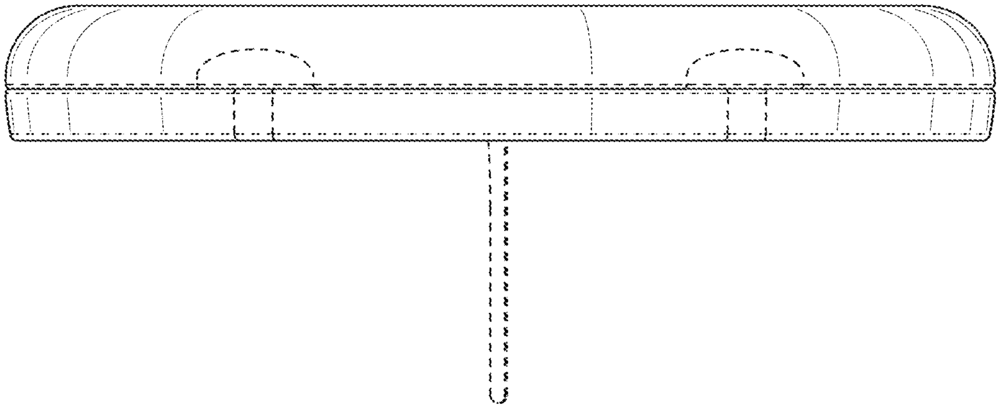
Figure 32F:
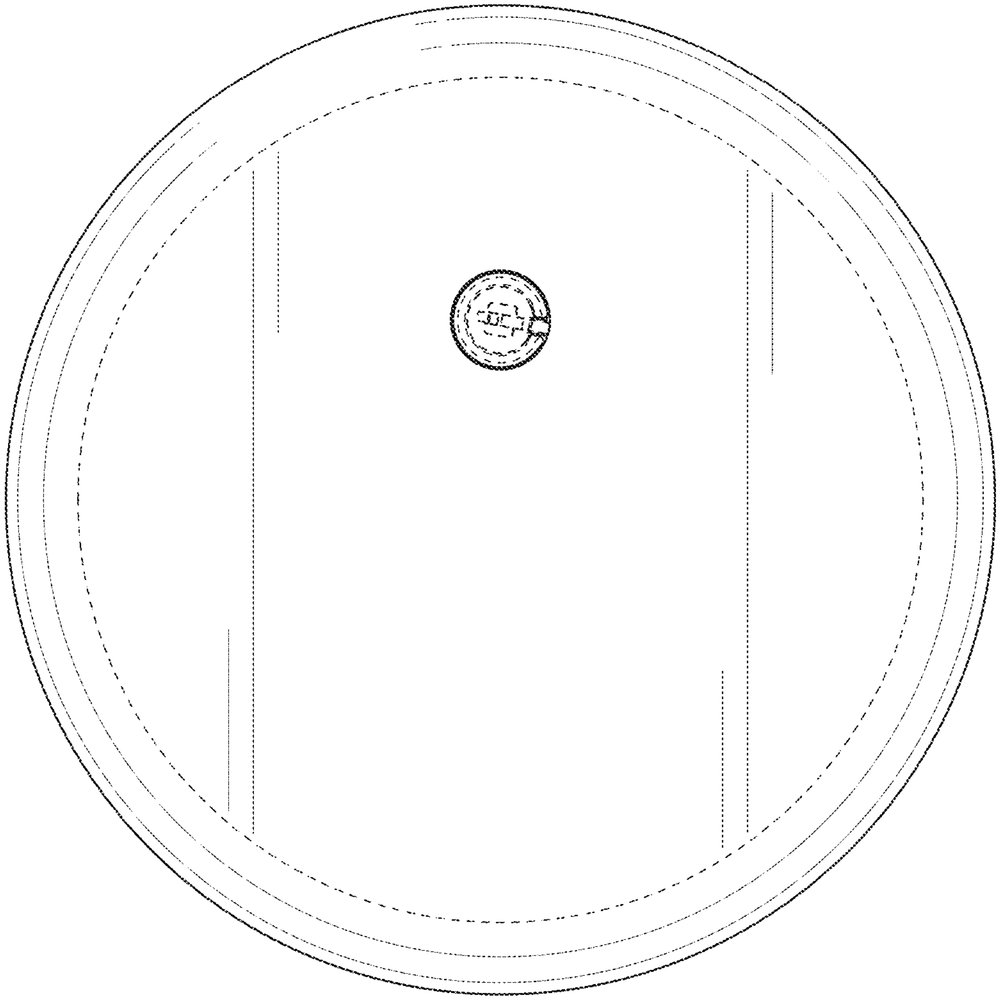
Figure 32G:
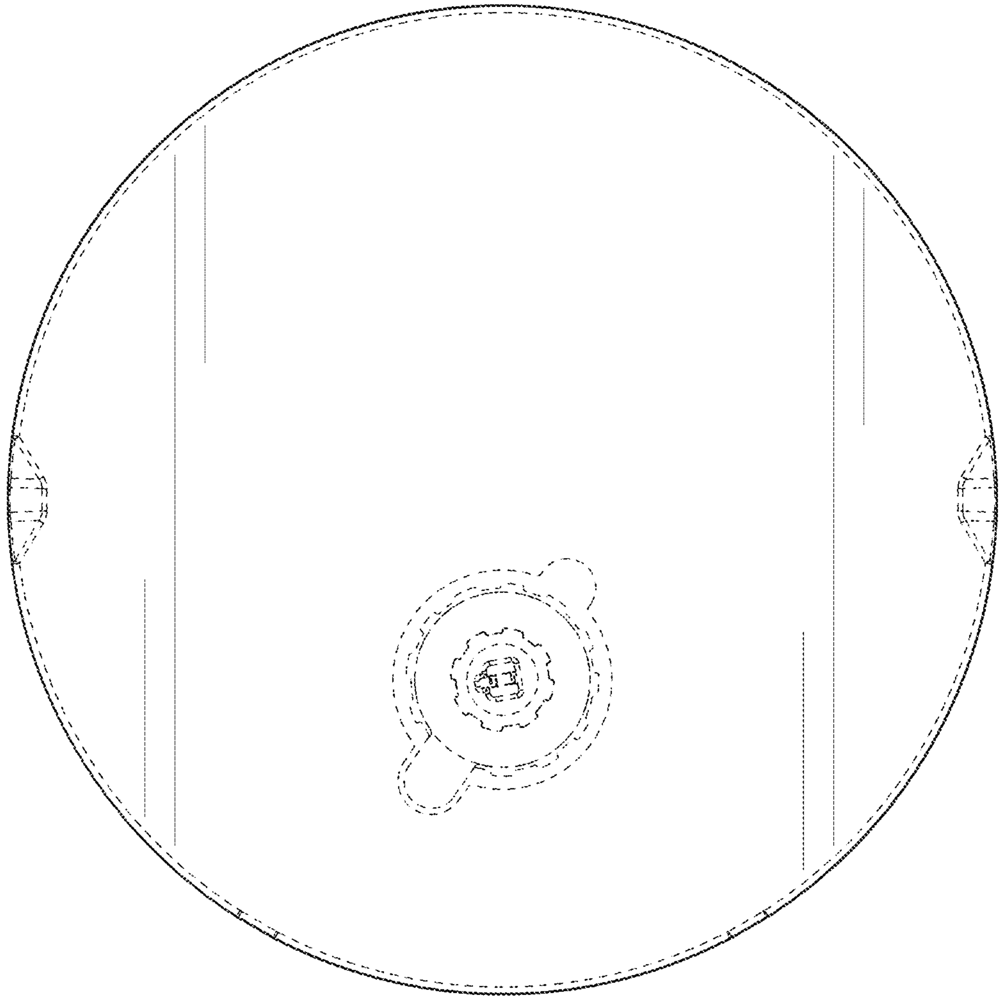
Figure 33A:
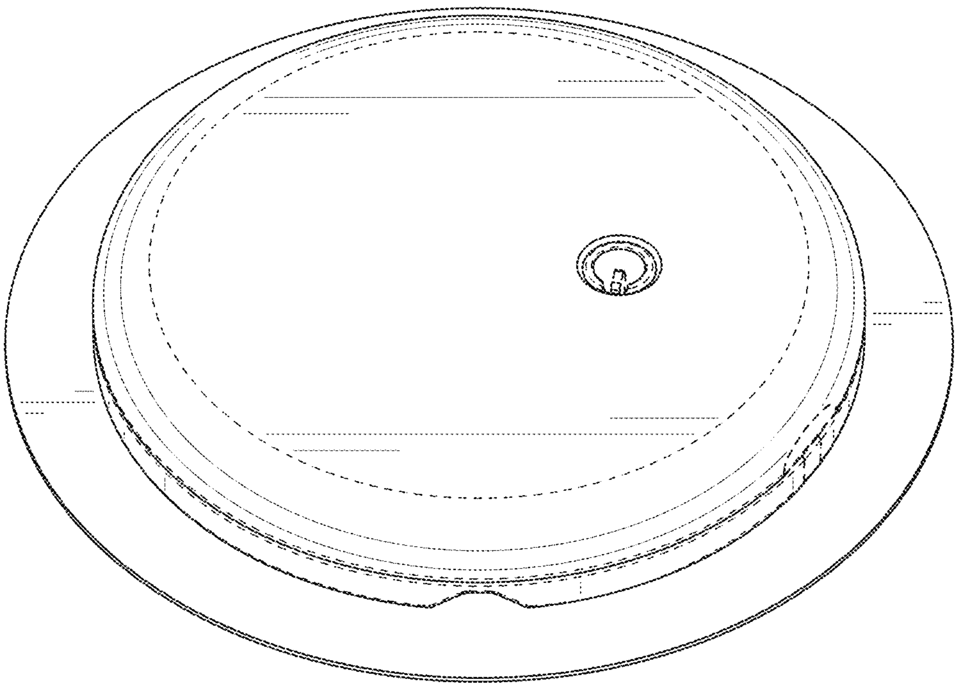
FIGS. 33A-33G depict another example embodiment of a sensor control device, where
Figure 33B:
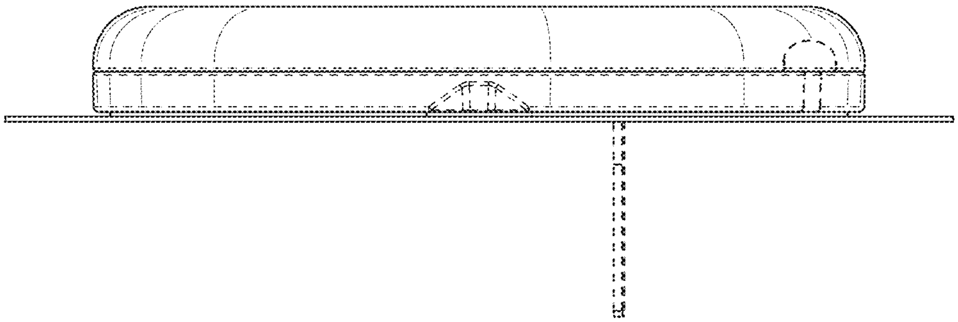
Figure 33C:
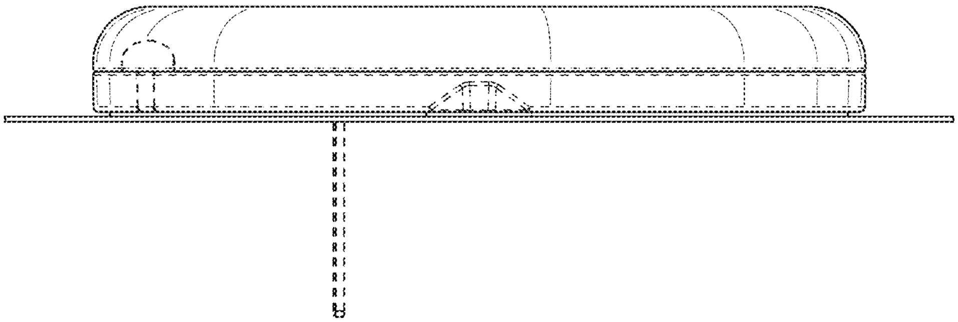
Figure 33D:
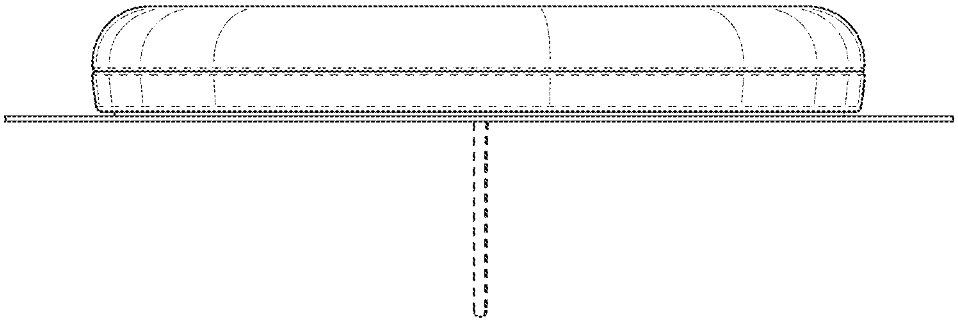
Figure 33E:
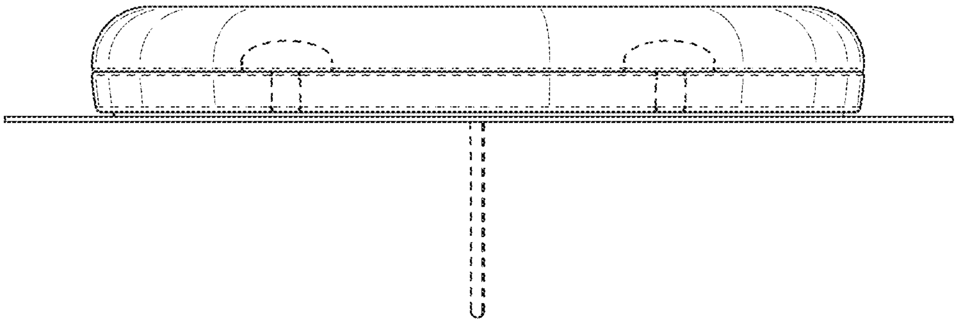
Figure 33F:
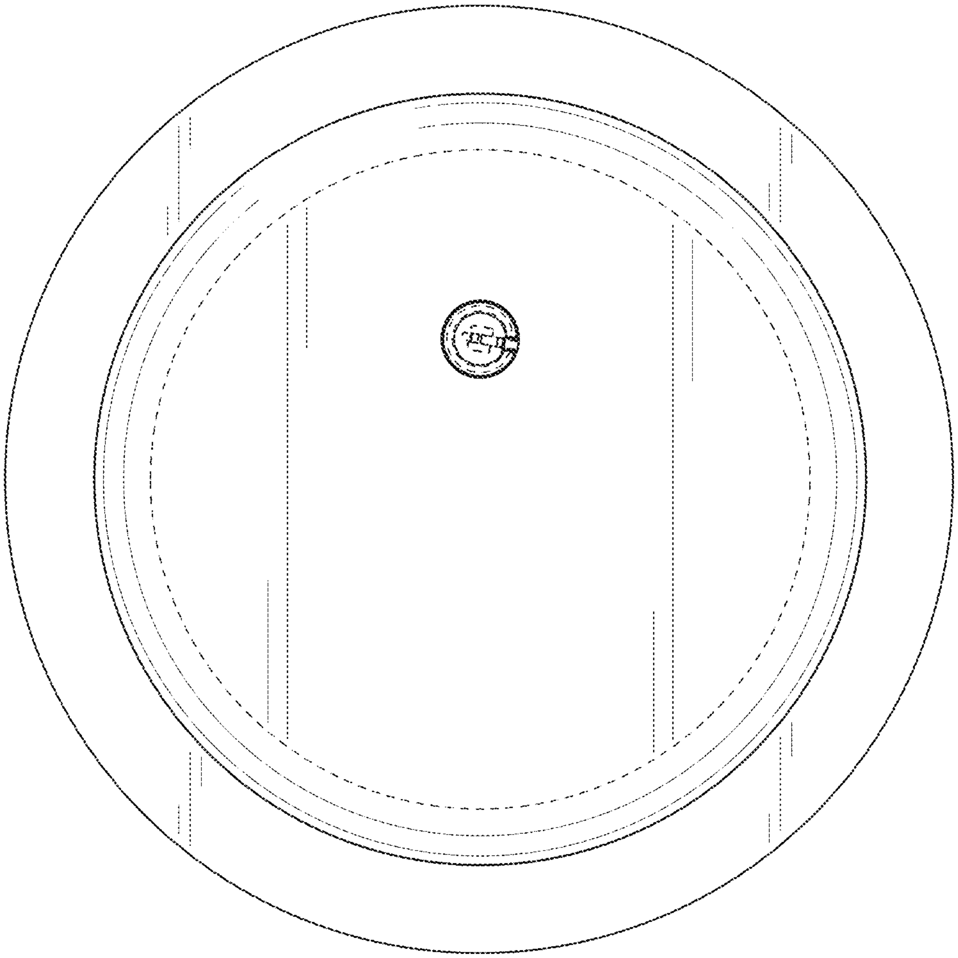
Figure 33G:
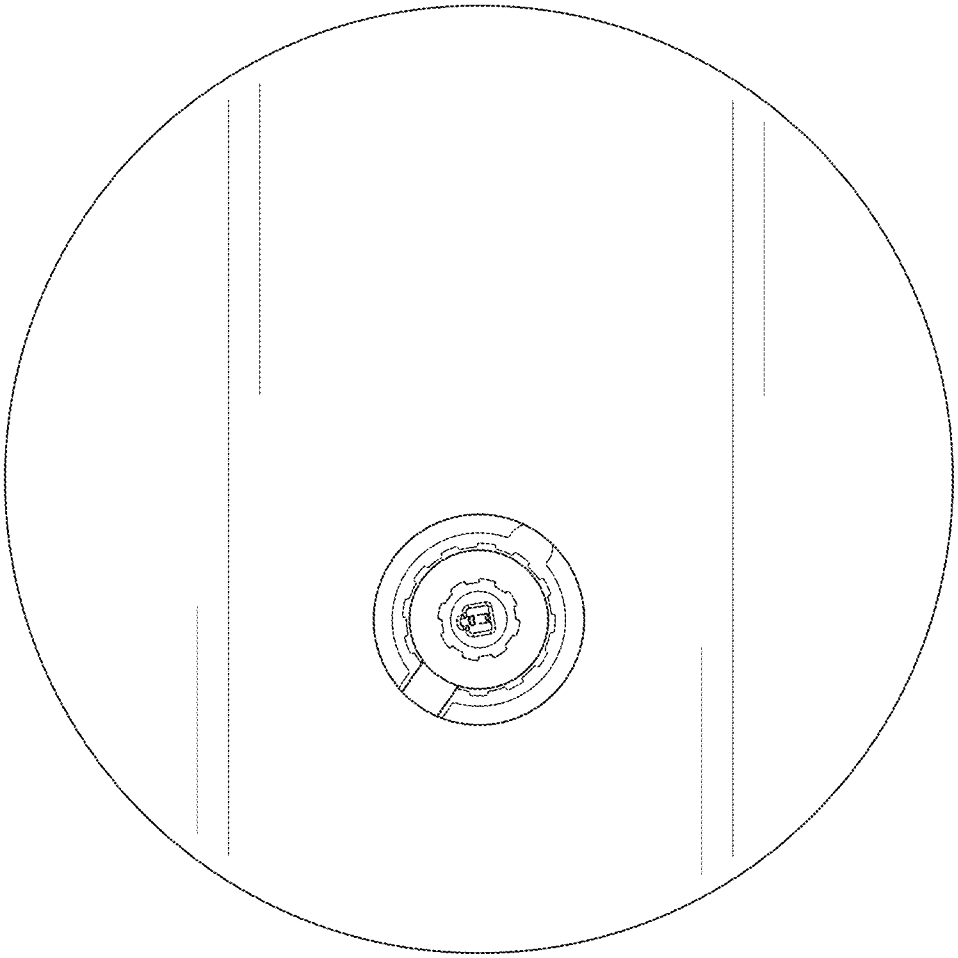
Figure 34A:
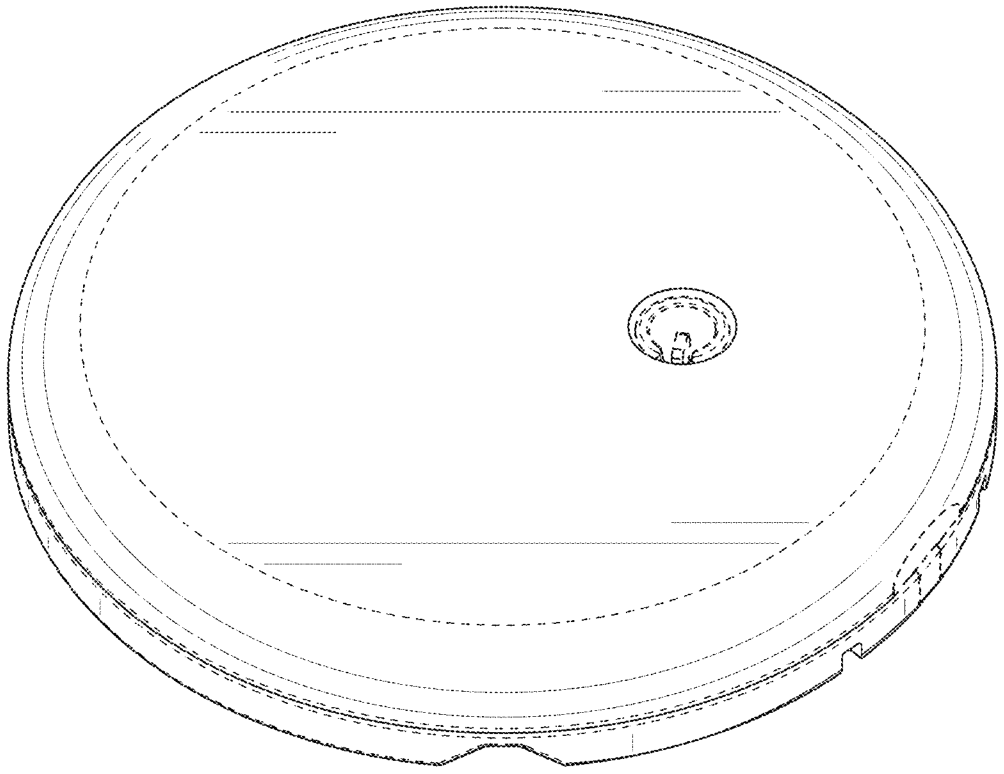
FIGS. 34A-34G depict another example embodiment of a sensor control device, where
Figure 34B:
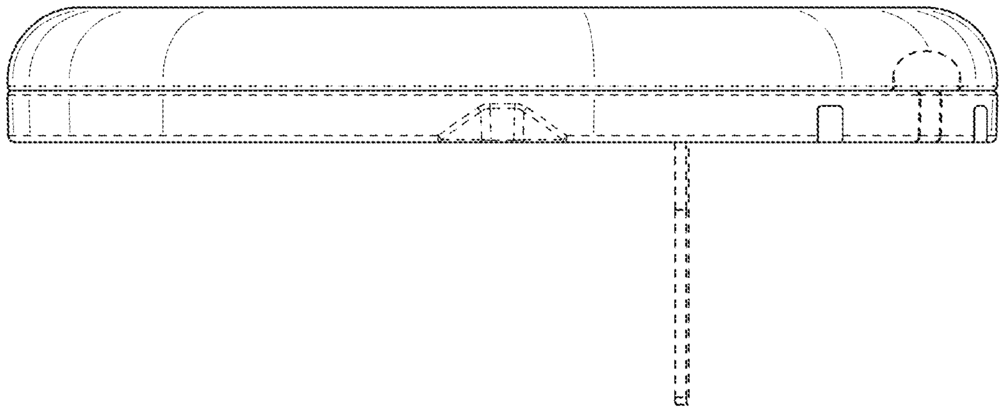
Figure 34C:
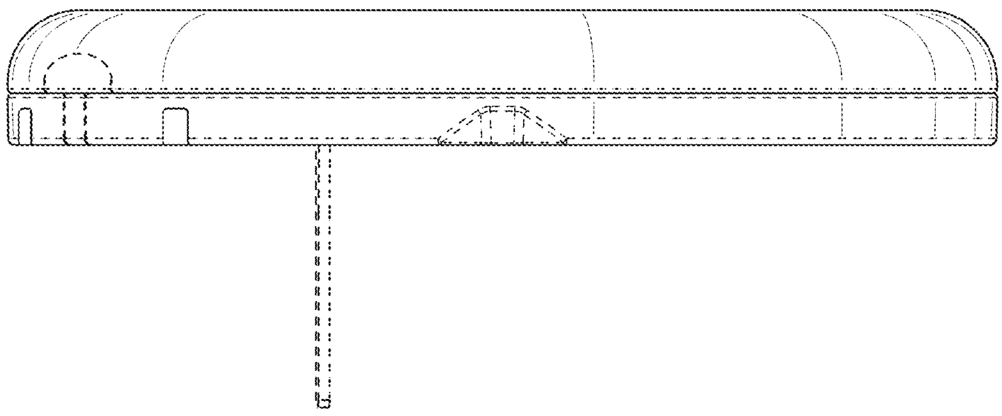
Figure 34D:
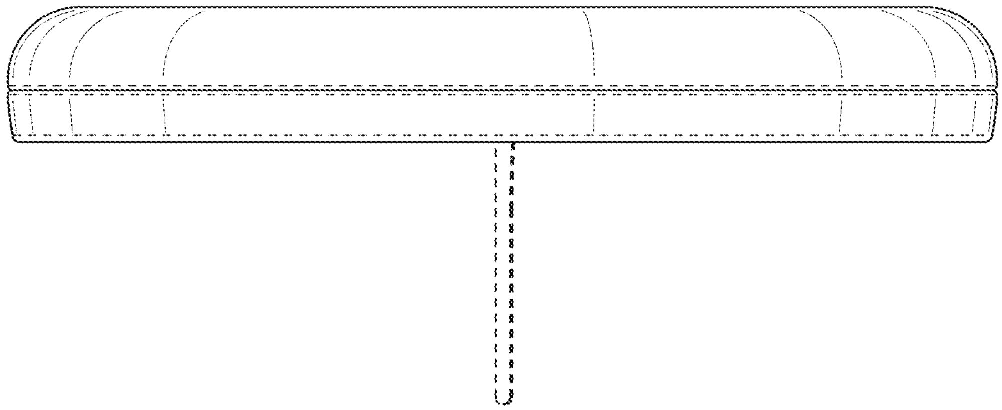
Figure 34E:
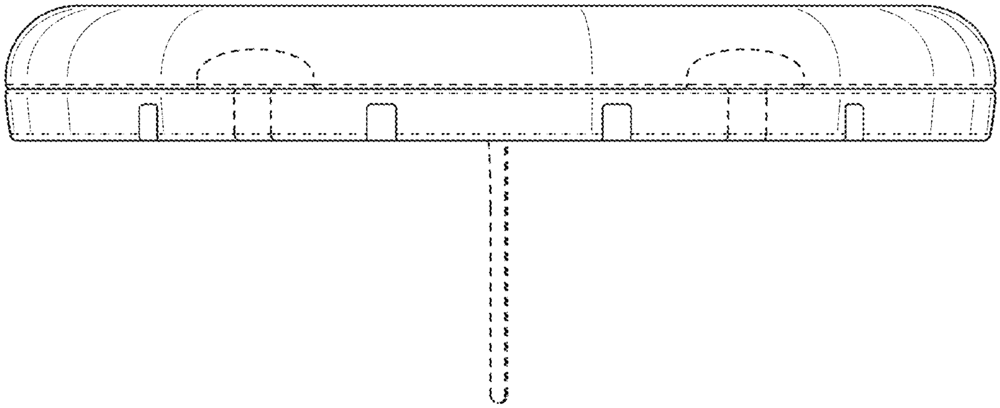
Figure 34F:
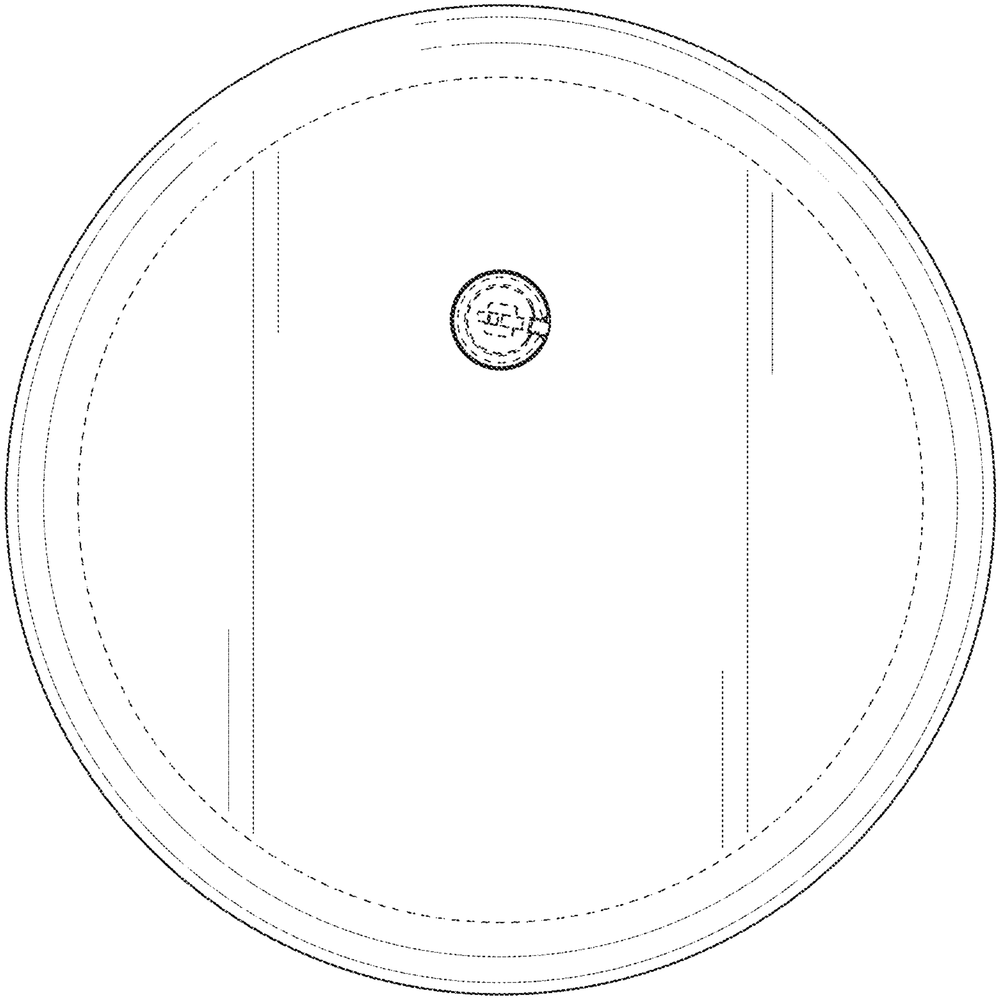
Figure 34G:
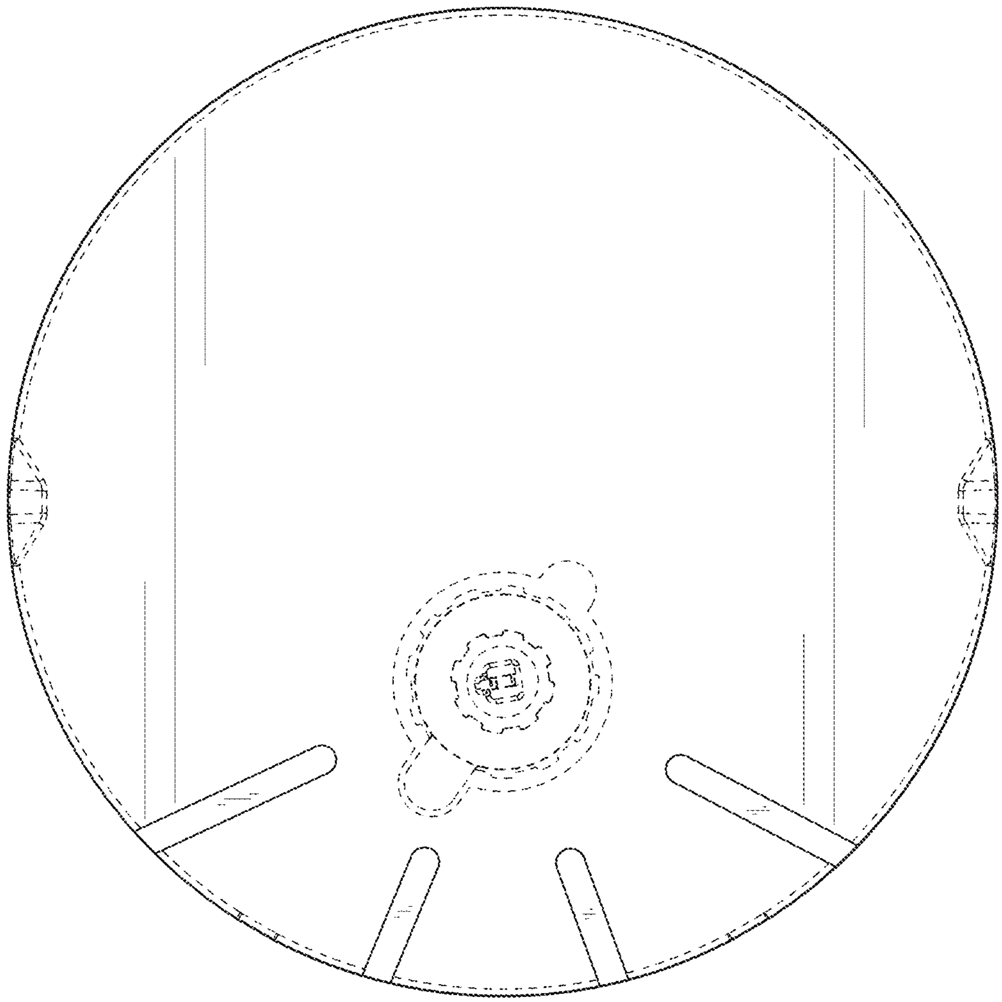
Figure 35A:
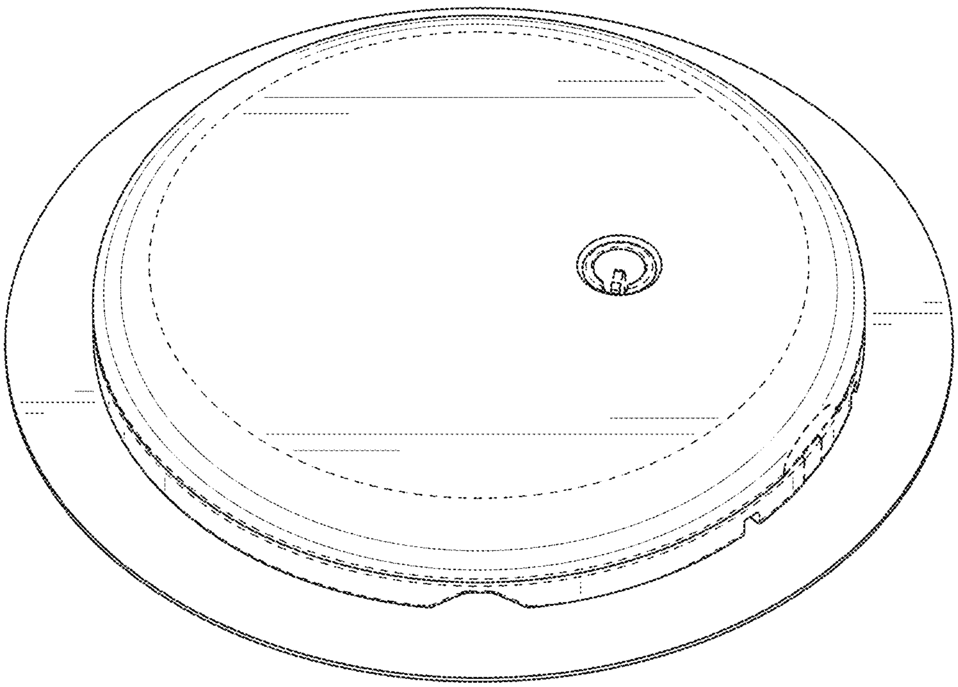
FIGS. 35A-35G depict another example embodiment of a sensor control device, where
Figure 35B:
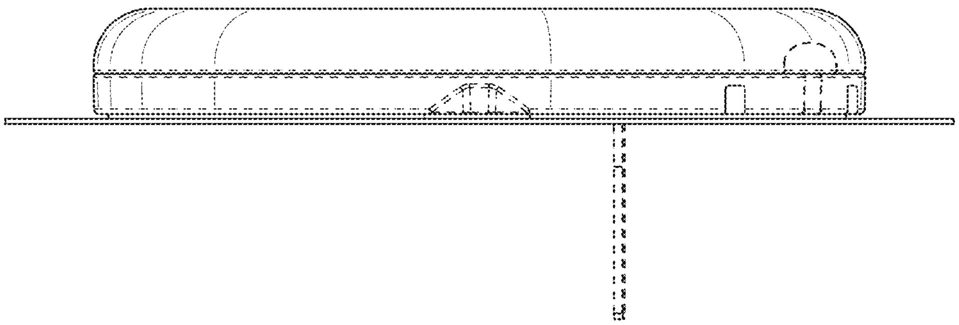
Figure 35C:
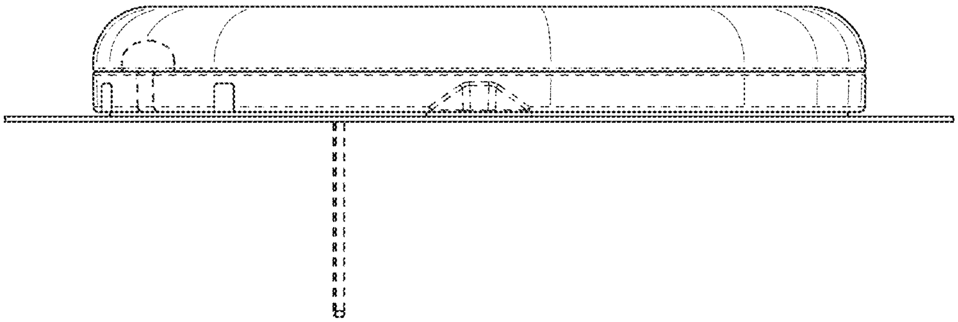
Figure 35D:
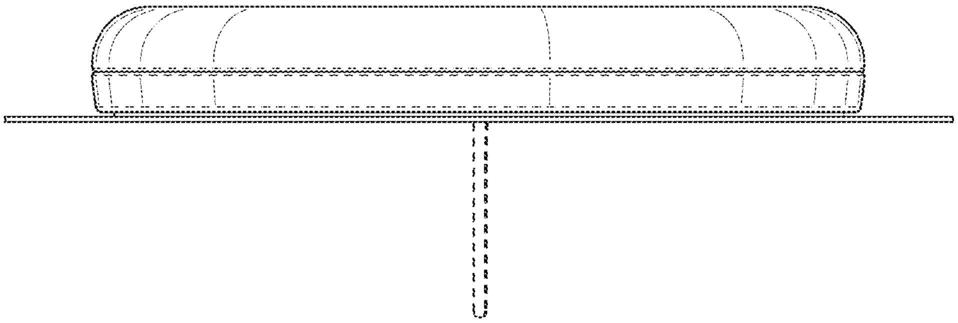
Figure 35E:
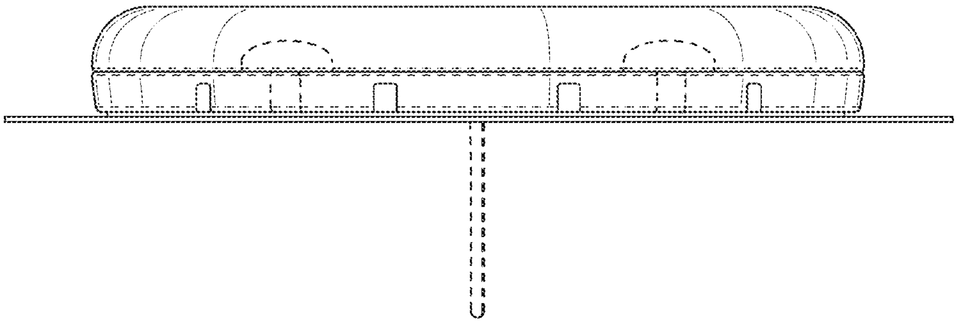
Figure 35F:
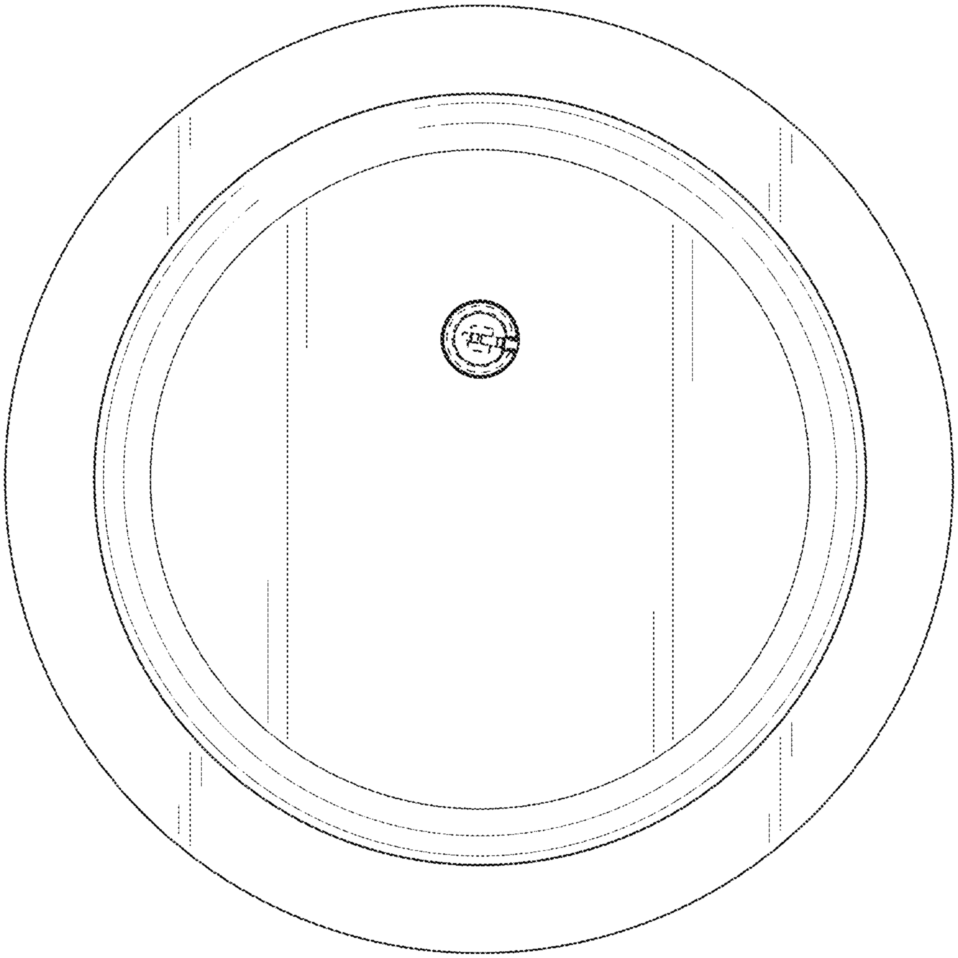
Figure 35G:
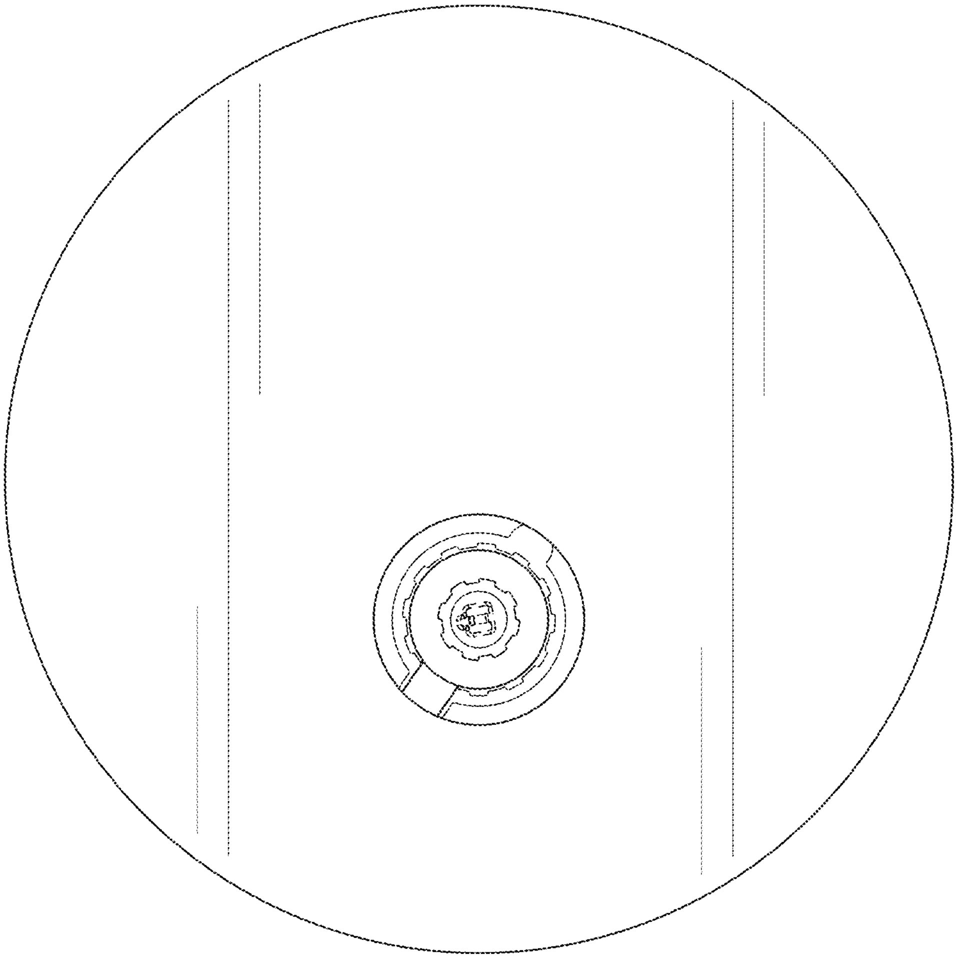

FIG. 19J is a cross-sectional view showing powered applicator 4150 in a sharp retraction state. According to one aspect of the embodiments, after the insertion state is complete, the subject applies force, F2, to applicator 4150, this time in a proximal direction. Force, F2, can be the subject pulling or removing applicator 4150 away from the skin surface. Application of force, F2, causes retraction spring 4604 to displace sharp carrier 4602 from the second position (e.g., adjacent to the skin surface) to a third position within applicator 4150, which causes the sharp to withdraw from the skin surface.

More specifically, as force, F2, is applied, drive spring 4606 displaces sensor electronics carrier 4710 to a bottom portion of applicator 4150. As can be seen in FIG. 19J, a portion of sensor electronics carrier 4710 protrudes beneath the bottom of sheath 4704. Similarly, as shown in FIG. 19K, during the sharp retraction state, the sensor electronics carrier tabs 4605 are flush with the bottom of sheath slot 4707.

According to another aspect of the embodiments, as force, F2, continues to be applied, each of the sensor electronics carrier lock arms 4524 is positioned into a sheath notch 4708, as best seen in FIG. 19L. Consequently, sensor electronics carrier lock arms 4524, which are biased in a radially outward direction, can expand in a radially outward direction through sheath notches 4708. In turn, sensor electronics carrier lock arms 4524 disengage from and release sharp carrier 4602, and retraction spring 4604 is free to expand in a proximal direction. As retraction spring 4604 expands in a proximal direction, sharp carrier 4602 is displaced to the third position within applicator 4150 (e.g., top of sheath 4704), which causes the sharp to withdraw from the skin surface.

With respect to drive spring 4606 and sharp retraction spring 4604, it should be noted that although compression springs are shown in FIGS. 18A to 18B and 19A to 19L, those of skill in the art will appreciate that other types of springs can be utilized in any of the embodiments described herein, including but not limited to torsion springs, disc springs, leaf springs and others. Furthermore, those of skill in the art will understand that the insertion and retraction speeds of the applicator embodiments described herein can be changed by changing the stiffness or length of the drive spring and the retraction spring, respectively. Similarly, those of skill in the art will understand that the timing of the sharp retraction can be modified by modifying the depth of the sheath channels (e.g., increasing depth of sheath channels can result in an earlier sharp retraction).

With respect to any of the applicator embodiments described herein, as well as any of the components thereof, including but not limited to the sharp, sharp module and sensor module embodiments, those of skill in the art will understand that said embodiments can be dimensioned and configured for use with sensors configured to sense an analyte level in a bodily fluid in the epidermis, dermis, or subcutaneous tissue of a subject. In some embodiments, for example, sharps and distal portions of analyte sensors disclosed herein can both be dimensioned and configured to be positioned at a particular end-depth (i.e., the furthest point of penetration in a tissue or layer of the subject's body, e.g., in the epidermis, dermis, or subcutaneous tissue). With respect to some applicator embodiments, those of skill in the art will appreciate that certain embodiments of sharps can be dimensioned and configured to be positioned at a different end-depth in the subject's body relative to the final end-depth of the analyte sensor. In some embodiments, for example, a sharp can be positioned at a first end-depth in the subject's epidermis prior to retraction, while a distal portion of an analyte sensor can be positioned at a second end-depth in the subject's dermis. In other embodiments, a sharp can be positioned at a first end-depth in the subject's dermis prior to retraction, while a distal portion of an analyte sensor can be positioned at a second end-depth in the subject's subcutaneous tissue. In still other embodiments, a sharp can be positioned at a first end-depth prior to retraction and the analyte sensor can be positioned at a second end-depth, wherein the first end-depth and second end-depths are both in the same layer or tissue of the subject's body.

Additionally, with respect to any of the applicator embodiments described herein, including but not limited to the powered applicator of FIGS. 18A, 18B, and 19A to 19L, those of skill in the art will understand that an analyte sensor, as well as one or more structural components coupled thereto, including but not limited to one or more spring-mechanisms, can be disposed within the applicator in an off-center position relative to one or more axes of the applicator. In some applicator embodiments, for example, an analyte sensor and a spring mechanism can be disposed in a first off-center position relative to an axis of the applicator on a first side of the applicator, and the sensor electronics can be disposed in a second off-center position relative to the axis of the applicator on a second side of the applicator. In other applicator embodiments, the analyte sensor, spring mechanism, and sensor electronics can be disposed in an off-center position relative to an axis of the applicator on the same side. Those of skill in the art will appreciate that other permutations and configurations in which any or all of the analyte sensor, spring mechanism, sensor electronics, and other components of the applicator are disposed in a centered or off-centered position relative to one or more axes of the applicator are possible and fully within the scope of the present disclosure.

A number of deflectable structures are described herein, including but not limited to deflectable detent snaps 1402, deflectable locking arms 1412, sharp carrier lock arms 1524, sharp retention arms 1618, and module snaps 2202. These deflectable structures are composed of a resilient material such as plastic or metal (or others) and operate in a manner well known to those of ordinary skill in the art. The deflectable structures each has a resting state or position that the resilient material is biased towards. If a force is applied that causes the structure to deflect or move from this resting state or position, then the bias of the resilient material will cause the structure to return to the resting state or position once the force is removed (or lessened). In many instances these structures are configured as arms with detents, or snaps, but other structures or configurations can be used that retain the same characteristics of deflectability and ability to return to a resting position, including but not limited to a leg, a clip, a catch, an abutment on a deflectable member, and the like.

Example Embodiments of Applicators and Sensor Control Devices for One Piece Architectures As previously described, certain embodiments of sensor control device 102 and applicator 150 can be provided to the user in multiple packages. For example, some embodiments, such as those described with respect to FIGS. 3A-3G, can comprise a "two-piece" architecture that requires final assembly by a user before the sensor can be properly delivered to the target monitoring location. More specifically, the sensor and the associated electrical components included in the sensor control device are provided to the user in multiple (e.g., two) packages, where each may or may not be sealed with a sterile barrier but are at least enclosed in packaging. The user must open the packaging and follow instructions to manually assemble the components and subsequently deliver the sensor to the target monitoring location with the applicator. For example, referring again to FIGS. 3A-3G, the sensor tray and applicator are provided to the user as separate packages, thus requiring the user to open each package and finally assembly the system. In some applications, the discrete, sealed packages allow the tray and the applicator to be sterilized in separate sterilization processes unique to the contents of each package and otherwise incompatible with the contents of the other.

More specifically, the tray, which includes a plug assembly, including the sensor and sharp, may be sterilized using radiation sterilizations, such as electron beam (or "e-beam") irradiation. Radiation sterilization, however, can damage the electrical components arranged within the housing of the sensor control device. Consequently, if the applicator, which contains the housing of the sensor control device, needs to be sterilized, it may be sterilized via another method, such as gaseous chemical sterilization using, for example, ethylene oxide. Gaseous chemical sterilization, however, can damage the enzymes or other chemistry and biologics included on the sensor. Because of this sterilization incompatibility, the tray and applicator may be sterilized in separate sterilization processes and subsequently packaged separately, and thereby require the user to finally assembly the components upon receipt.

According to other embodiments of the present disclosure, the sensor control device (e.g., analyte sensor device) may comprise a one-piece architecture that incorporates sterilization techniques specifically designed for a one-piece architecture. The one-piece architecture allows the sensor control device assembly to be shipped to the user in a single, sealed package that does not require any final user assembly steps. Rather, the user need only open one package and subsequently deliver the sensor control device to the target monitoring location. The one-piece system architecture described herein may prove advantageous in eliminating component parts, various fabrication process steps, and user assembly steps. As a result, packaging and waste are reduced, and the potential for user error or contamination to the system is mitigated.

According to some embodiments, a sensor sub-assembly (SSA) can be built and sterilized. The sterilization may be, for example, radiation, such as electron beam (e-beam radiation), but other methods of sterilization may alternatively be used including, but not limited to, gamma ray radiation, X-ray radiation, or any combination thereof. Embodiments of methods of manufacturing an analyte monitoring system using this SSA are now described, as are embodiments of sensor control devices having this SSA and applicators for use therewith. An SSA can be manufactured and then sterilized. During sterilization the SSA can include both an analyte sensor and an insertion sharp. The sterilized SSA can then be assembled to form (e.g., assembled into) a sensor control device, e.g., the sterilized SSA can be placed such that the sensor is in electrical contact with any electronics in a sensor electronics carrier. This sensor control device can then be assembled to form (e.g., assembled into) an applicator (e.g., as a one-piece assembly) where the applicator (also referred to as an analyte sensor inserter) is configured to apply the sensor control device to a user's body. The one-piece assembly can be packaged and/or distributed (e.g., shipped) to a user or health care professional.

FIGS. 20A-20G depict a first embodiment of an applicator for use with a sensor control device having an SSA. FIGS. 21A-21G depict a second embodiment of the applicator for use with a sensor control device having an SSA.

FIGS. 22A-22G depict a first embodiment of a sensor control device having an SSA but without an adhesive patch. FIGS. 23A-23G depict a second embodiment of the sensor control device having an SSA and an adhesive patch.

FIGS. 24A-24G depict a third embodiment of a sensor control device having an SSA and bottom surface grooves, but without an adhesive patch. FIGS. 25A-25G depict a fourth embodiment of the sensor control device having an SSA, bottom surface grooves, and an adhesive patch.

FIGS. 26A-26G depict a fifth embodiment of a sensor control device having an SSA but without an adhesive patch. FIGS. 27A-27G depict a sixth embodiment of the sensor control device having an SSA and an adhesive patch.

FIGS. 28A-28G depict a seventh embodiment of a sensor control device having an SSA and bottom surface grooves, but without an adhesive patch. FIGS. 29A-29G depict an eight embodiment of the sensor control device having an SSA, bottom surface grooves, and an adhesive patch.

According to other embodiments, the sensor control device, including a battery and sensor, can be built into the applicator as a one-piece assembly, and sterilized using a focused electron beam (FEB). Other methods of sterilization may alternatively be used including, but not limited to, gamma ray radiation, X-ray radiation, or any combination thereof. Embodiments of methods of manufacturing an analyte monitoring system and sterilizing with, for example, an FEB are now described, as are embodiments of sensor control devices and applicators for use therewith. A sensor control device including a sensor and a sharp can be manufactured or assembled, e.g., the sensor can be placed in electrical contact with any electronics in a sensor electronics carrier of the sensor control device. This sensor control device can then be assembled to form (e.g., assembled into) an applicator (e.g., as a one-piece assembly) where the applicator is configured to apply the sensor control device to a user's body. This assembled applicator, having the sensor control device therein, can then be sterilized with, for example, an FEB. The sterilized applicator can then be packaged and/or distributed (e.g., shipped) to a user or health care professional. In some embodiments a dessicant and foil seal can be added to the sterilized one-piece assembly prior to packaging.

FIGS. 30A-30G depict a first embodiment of an applicator for sterilization with, e.g., an FEB. FIGS. 31A-31G depict a second embodiment of the applicator for sterilization with, e.g., an FEB.

FIGS. 32A-32G depict a first embodiment of a sensor control device for sterilization with, e.g., an FEB, and without an adhesive patch. FIGS. 33A-33G depict a second embodiment of the sensor control device for sterilization with, e.g., an FEB, along with an adhesive patch.

FIGS. 34A-34G depict a third embodiment of a sensor control device having bottom surface grooves and for sterilization with, e.g., an FEB, but without an adhesive patch. FIGS. 35A-35G depict a fourth embodiment of the sensor control device having bottom surface grooves and for sterilization with, e.g., an FEB, along with an adhesive patch.

For all of the embodiments shown and described in FIGS. 20A-35G, solid lines can be alternatively depicted as broken lines, which form no part of the design. For all of the embodiments of sensor control devices described in FIGS. 22A-29G and 32A-35G, the adhesive patch, if shown in solid line, can alternatively be shown in broken line, and the adhesive patch, if not shown, can be shown in broken or solid line.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many example embodiments, a method for applying a medical device to a subject using an applicator is provided, the method including: positioning a distal end of the applicator on a skin surface of the subject, where at least a portion of the distal end includes a compressible material; applying a force on the applicator to cause the medical device to advance from a first position within the applicator to a second position adjacent to the skin surface, and to cause the distal end of the applicator to stretch and flatten a portion of the skin surface adjacent to the applicator; and applying the medical device to the stretched and flattened portion of the skin surface.

In these method embodiments, applying a force on the applicator can further include displacing the at least the compressible portion of the distal end of the applicator in a radially outward direction. Displacing the at least the compressible portion of the distal end of the applicator can further include creating radially outward forces on the portion of the skin surface adjacent to the applicator.

In these method embodiments, applying the medical device to the stretched and flattened portion of the skin surface can further include placing an adhesive surface on the skin surface.

In these method embodiments, applying the medical device to the stretched and flattened portion of the skin surface can further include positioning at least a portion of an analyte sensor under the skin surface. The analyte sensor can be an in vivo analyte sensor configured to measure an analyte level in a bodily fluid of the subject.

In these method embodiments, the at least the compressible portion of the distal end of the applicator can be biased in a radially inward direction. Alternatively, the at least the compressible portion of the distal end of the applicator can be biased in a radially outward direction.

In these method embodiments, the at least the compressible portion of the distal end can be in an unloaded state in the first position, and the at least the compressible portion of the distal end can be in a loaded state in the second position.

In these method embodiments, the at least the compressible portion of the distal end of the applicator can include one or more of an elastomeric material, metal, plastic, or composite legs or springs, or a combination thereof.

In these method embodiments, a cross-section of the at least the compressible portion of the distal end of the applicator can include a continuous ring or a non-continuous shape.

In these method embodiments, the distal end of the applicator can be configured to be detached from the applicator.

In many example embodiments, an apparatus is provided including: a medical device; and an applicator including a distal end configured to be positioned on a skin surface of a subject, where at least a portion of the distal end includes a compressible material, where, in response to an application of force to the applicator: the medical device can be configured to advance from a first position within the applicator to a second position adjacent to the skin, the distal end of the applicator can be configured to stretch and flatten a portion of the skin surface adjacent to the applicator, and the medical device can be further configured to be applied to the stretched and flattened portion of the skin surface.

In these apparatus embodiments, the at least the compressible portion of the distal end of the applicator can be configured to displace in a radially outward direction in response to the application of force to the applicator. The at least the compressible portion of the distal end of the applicator can be further configured to create radially outward forces on the portion of the skin surface adjacent to the applicator.

In these apparatus embodiments, the medical device can include an adhesive surface that can be configured to interface with the skin surface.

In these apparatus embodiments, the medical device can include an analyte sensor at least a portion of which can be configured to be positioned under the skin surface. The analyte sensor can be an in vivo analyte sensor configured to measure an analyte level in a bodily fluid of the subject.

In these apparatus embodiments, the at least the compressible portion of the distal end of the applicator can be biased in a radially inward direction. Alternatively, the at least the compressible portion of the distal end of the applicator can be biased in a radially outward direction.

In these apparatus embodiments, the at least the compressible portion of the distal end can be in an unloaded state in the first position, and where the at least the compressible portion of the distal end can be in a loaded state in the second position.

In these apparatus embodiments, the at least the compressible portion of the distal end of the applicator can include one or more of an elastomeric material, metal, plastic, or composite legs or springs, or a combination thereof.

In these apparatus embodiments, a cross-section of the at least the compressible portion of the distal end of the applicator can include a continuous ring or a non-continuous shape.

In these apparatus embodiments, the distal end of the applicator can be configured to be detached from the applicator.

In many embodiments, an assembly for use in an applicator is provided, the assembly including: a sharp module including a sharp portion and a hub portion, where the sharp portion can include a sharp shaft, a sharp proximal end coupled to a distal end of the hub portion, and a sharp distal tip configured to penetrate a skin surface of a subject, where the sharp module can further include a plastic material.

In these assembly embodiments, the sharp shaft can include one or more filleted edges.

In these assembly embodiments, the sharp module can further include a thermoplastic material.

In these assembly embodiments, the sharp module can further include a polyether ether ketone material.

In these assembly embodiments, the sharp shaft can include an alignment ledge configured to prevent rotational movement along a vertical axcan be of the sharp module during an insertion process. The alignment ledge can be positioned along a proximal portion of the sharp shaft.

In these assembly embodiments, the assembly can further include an analyte sensor, where the analyte sensor can be an in vivo analyte sensor configured to measure an analyte level in a bodily fluid of the subject. A distal end of the analyte sensor can be in a proximal position relative to the sharp distal tip. A distal end of the analyte sensor and the sharp distal tip can be co-localized. At least a portion of the analyte sensor can be positioned within a sensor channel of the sharp shaft.

In these assembly embodiments, the sharp module can further include a liquid crystal polymer material.

In these assembly embodiments, the assembly can further include a lubricant disposed on an external surface of the sharp module.

In these assembly embodiments, the plastic material can include a lubricant.

In these assembly embodiments, the assembly can further include a sensor channel, where at least a portion of the sensor channel can be disposed in a distal portion of the sharp shaft. The sensor channel can extend from the proximal portion of the sharp shaft to the distal portion of the sharp shaft. The sensor channel can be configured such that it does not extend beyond the distal portion of the sharp shaft. The proximal portion of the sharp shaft can be hollow. The proximal portion of the sharp shaft can be solid. A wall thickness of at least a portion of the proximal portion of the sharp shaft can be greater than a wall thickness of the distal portion of the sharp shaft.

In these assembly embodiments, the assembly can further include one or more rib structures adjacent to the hub portion, where the one or more rib structures can be configured to reduce a compressive load around the hub portion.

In many embodiments, a method of preparing an analyte monitoring system is provided, the method including: loading a sensor control device into a sensor applicator, the sensor control device including: an electronics housing; a printed circuit board positioned within the electronics housing and including a processing circuitry; an analyte sensor extending from a bottom of the electronics housing; and a sharp module including a plastic material and removably coupled to the electronics housing, where the sharp module includes a sharp, and where the sharp extends through the electronics housing and receives a portion of the analyte sensor extending from the bottom of the electronics housing; securing a cap to the sensor applicator and thereby providing a barrier that seals the sensor control device within the sensor applicator; and sterilizing the analyte sensor and the sharp with radiation while the sensor control device can be positioned within the sensor applicator.

In these method embodiments, the sensor control device can further include at least one shield positioned within the electronics housing, and where the method can further include shielding the processing circuitry with the at least one shield from the radiation during the sterilization. The at least one shield can include a magnet, and where shielding the processing circuitry with the at least one shield can include: generating a static magnetic field with the magnet; and diverting the radiation away from the processing circuitry with the static magnetic field. Sterilizing the analyte sensor and the sharp with radiation can further include using a non-focused electron beam to sterilize the analyte sensor and the sharp.

In these method embodiments, the analyte sensor can be an in vivo analyte sensor configured to measure an analyte level in a bodily fluid located in the subject.

In these method embodiments, the sharp module can further include a thermoplastic material.

In these method embodiments, the sharp module can further include a polyether ether ketone material.

In these method embodiments, sterilizing the analyte sensor and the sharp can further include focusing an electron beam on the analyte sensor and the sharp.

In many embodiments, an assembly for use in an applicator is provided, the assembly including: a sharp module including a sharp portion and a hub portion, where the sharp portion can include a sharp shaft, a sharp proximal end coupled to a distal end of the hub portion, and a sharp distal tip configured to penetrate a skin surface of a subject, where the sharp portion can further include a metal material and can be formed through a coining process.

In these assembly embodiments, the sharp portion can further include a stainless steel material.

In these assembly embodiments, the sharp portion includes no sharp edges.

In these assembly embodiments, the sharp portion can include one or more rounded edges.

In these assembly embodiments, the sharp shaft can include one or more rounded edges.

In these assembly embodiments, the sharp shaft and the sharp distal tip can include one or more rounded edges.

In these assembly embodiments, the assembly can further include an analyte sensor, where the analyte sensor can be an in vivo analyte sensor configured to measure an analyte level in a bodily fluid of the subject. A distal end of the analyte sensor can be in a proximal position relative to the sharp distal tip. A distal end of the analyte sensor and the sharp distal tip can be co-localized. At least a portion of the analyte sensor can be positioned within a sensor channel of the sharp shaft.

In many embodiments, a method of maintaining structural integrity of a sensor control unit including an analyte sensor and a sensor module is provided, the method including: positioning a distal sensor portion of the analyte sensor beneath a skin surface and in contact with a bodily fluid, where the analyte sensor can include a proximal sensor portion coupled to the sensor module, and where the proximal sensor portion includes a hook feature adjacent to a catch feature of the sensor module; receiving one or more forces in a proximal direction along a longitudinal axcan be of the analyte sensor; and causing the hook feature to engage the catch feature and prevent displacement of the analyte sensor in the proximal direction along the longitudinal axis.

In these method embodiments, the method can further include loading the analyte sensor into the sensor module by displacing the proximal sensor portion in a lateral direction to bring the hook feature in proximity to the catch feature of the sensor module. Displacing the proximal sensor portion in a lateral direction can include causing the proximal sensor portion to move into a clearance area of the sensor module.

In these method embodiments, the one or more forces can be generated by a sharp retraction process.

In these method embodiments, the one or more forces can be generated by a physiological reaction to the analyte sensor.

In these method embodiments, the analyte sensor can be an in vivo analyte sensor configured to measure an analyte level in the bodily fluid of the subject.

In many embodiments, a sensor control unit is provided, the sensor control unit including: a sensor module including a catch feature; an analyte sensor including a distal sensor portion and a proximal sensor portion, where the distal sensor portion can be configured to be positioned beneath a skin surface and in contact with a bodily fluid, and where the proximal sensor portion can be coupled to the sensor module and can include a hook feature adjacent to the catch feature, where the hook feature can be configured to engage the catch feature and prevent displacement of the analyte sensor caused by one or more forces received by the analyte sensor and in a proximal direction along a longitudinal axis of the analyte sensor.

In these sensor control unit embodiments, the sensor module can be configured to receive the analyte sensor by displacing the proximal sensor portion in a lateral direction and bringing the hook feature in proximity to the catch feature of the sensor module. The sensor module can further include a clearance area configured to receive the proximal sensor portion as the proximal sensor portion can be displaced in a lateral direction.

In these sensor control unit embodiments, the one or more forces can be generated by a sharp retraction process.

In these sensor control unit embodiments, the one or more forces can be generated by a physiological reaction to the analyte sensor.

In these sensor control unit embodiments, the analyte sensor can be an in vivo analyte sensor configured to measure an analyte level in the bodily fluid of the subject.

In many embodiments, a method of inserting an analyte sensor into a subject using an applicator is provided, the method including: positioning a distal end of the applicator on a skin surface, where the applicator can include a drive spring, a retraction spring, a sensor electronics carrier, a sharp carrier, and the analyte sensor; applying a first force to the applicator to cause the drive spring to displace the sensor electronics carrier and the sharp carrier from a first position within the applicator in spaced relation with a skin surface to a second position adjacent to the skin surface, and to position a sharp of the sharp carrier and a portion of the analyte sensor under the skin surface and in contact with a bodily fluid of the subject; and applying a second force to the applicator to cause the retraction spring to displace the sharp carrier from the second position to a third position within the applicator, and to withdraw the sharp from the skin surface.

In these method embodiments, applying the first force can include applying a force in a distal direction, and where applying the second force can include applying a force in a proximal direction.

In these method embodiments, the applicator can further include a firing pin and a sheath, and where applying the first force to the applicator further causes the firing pin to disengage one or more sheath tabs of the sheath from one or more sensor electronics carrier latches of the sensor electronics carrier and to cause the drive spring to expand. The drive spring can be in a preloaded state prior to applying the first force, and where disengaging the one or more sheath tabs causes the drive spring to expand in a distal direction. Applying the first force to the applicator increases a load on the drive spring prior to causing the firing pin to disengage the one or more sheath tabs. The drive spring can be in a preloaded state prior to applying the first force, and where the drive spring can include a first end coupled to the firing pin and a second end coupled to the sensor electronics carrier.

In these method embodiments, the applicator can further include a sensor control unit coupled with the sensor electronics carrier, and where a distal portion of the sensor control unit can be in contact with the skin surface in the second position. Displacing the sensor electronics carrier and the sharp carrier from the first position to the second position can include one or more sensor electronics carrier tabs of the sensor electronics carrier traveling in a distal direction along one or more sheath rails of the sheath. One or more sensor electronics carrier bumpers of the sensor electronics carrier can be biased against an internal surface of the sheath while the sensor electronics carrier and the sharp carrier can be displaced from the first position to the second position.

In these method embodiments, applying the second force further causes a plurality of sensor electronics carrier lock arms of the sensor electronics carrier to disengage from the sharp carrier and to cause the retraction spring to expand. Disengaging the plurality of sensor electronics carrier lock arms from the sharp carrier can include positioning the plurality of sensor electronics carrier lock arms into a plurality of sheath notches of the sheath. Each of the plurality of sensor electronics carrier locks arms can be biased in a radially outward direction, and where the sheath notches can be configured to allow the plurality of sensor electronics carrier lock arms to expand in a radially outward direction. The retraction spring can be in a preloaded state prior to applying the second force, and where disengaging the plurality of sensor electronics carrier lock arms causes the retraction spring to expand in a proximal direction.

In these method embodiments, the retraction spring can be in a preloaded state prior to applying the second force, and where the retraction spring can include a first end coupled to the sharp carrier and a second end coupled to the sensor electronics carrier.

In these method embodiments, applying the second force further causes the drive spring to displace the sensor electronics carrier to a bottom portion of the applicator.

In these method embodiments, the analyte sensor can be an in vivo analyte sensor configured to measure an analyte level in the bodily fluid of the subject.

In many embodiments, an applicator for inserting an analyte sensor into a subject is provided, the applicator including: a drive spring; a retraction spring; a sensor electronics carrier; a sharp carrier coupled to a sharp; and the analyte sensor; where the drive spring can be configured to displace the sensor electronics carrier and the sharp carrier from a first position within the applicator in spaced relation with a skin surface to a second position adjacent to the skin surface upon an application of a first force to the applicator, and where the sharp and a portion of the analyte sensor can be positioned under the skin surface and in contact with a bodily fluid of the subject at the second position, and where the retraction spring can be configured to displace the sharp carrier from the second position to a third position within the applicator and to withdraw the sharp from the skin surface upon an application of a second force to the applicator.

In these applicator embodiments, the application of the first force can include an application of a force in a distal direction, and where the application of the second force can include an application of a force in a proximal direction.

In these applicator embodiments, the applicator can further include a firing pin and a sheath, where the firing pin can be configured to, upon application of the first force, disengage one or more sheath tabs of the sheath from one or more sensor electronics carrier latches of the sensor electronics carrier and to cause the drive spring to expand. The drive spring can be in a preloaded state prior to the application of the first force, and where the drive spring can be configured to expand in a distal direction in response to the one or more sheath tabs disengaging from the one or more sensor electronics carrier latches. The drive spring can be configured to receive an increased load prior to the firing pin disengaging the one or more sheath tabs. The drive spring can be in a preloaded state prior to the application of the first force, and where the drive spring can include a first end coupled to the firing pin and a second end coupled to the sensor electronics carrier.

In these applicator embodiments, the applicator can further include a sensor control unit coupled with the sensor electronics carrier, where a distal portion of the sensor control unit can be configured to contact the skin surface in the second position.

In these applicator embodiments, the applicator can further include one or more sensor electronics carrier tabs of the sensor electronics carrier configured to travel in a distal direction along one or more sheath rails of the sheath between the first position and the second position.

In these applicator embodiments, the applicator can further include one or more sensor electronics carrier bumpers of the sensor electronics carrier configured to bias against an internal surface of the sheath between the first position and the second position.

In these applicator embodiments, the applicator can further include a plurality of sensor electronics carrier lock arms of the sensor electronics carrier, where the sensor electronics carrier lock arms can be configured to disengage from the sharp carrier and cause the retraction spring to expand in response to the application of the second force. The applicator can further include a plurality of sheath notches of the sheath, where the plurality of sheath notches can be configured to receive the plurality of sensor electronics carrier lock arms and to cause the sensor electronics carrier lock arms to disengage from the sharp carrier. Each of the plurality of sensor electronics carrier locks arms can be biased in a radially outward direction, and where the sheath notches can be configured to allow the plurality of sensor electronics carrier lock arms to expand in a radially outward direction. The retraction spring can be in a preloaded state prior to the application of the second force, and where the retraction spring can be configured to expand in a proximal direction when the plurality of sensor electronics carrier lock arms disengages from the sharp carrier.

In these applicator embodiments, the retraction spring can be in a preloaded state prior to the application of the second force, and where the retraction spring can include a first end coupled to the sharp carrier and a second end coupled to the sensor electronics carrier.

In these applicator embodiments, the drive spring can be further configured to displace the sensor electronics carrier to a bottom portion of the applicator in response to the application of the second force.

In these applicator embodiments, the analyte sensor can be an in vivo analyte sensor configured to measure an analyte level in the bodily fluid of the subject.

In many embodiments, an assembly for use in an applicator is provided, the assembly including: a sharp module including a sharp portion and a hub portion, where the sharp portion can include a sharp shaft, a sharp proximal end coupled to the hub portion, and a sharp distal tip configured to penetrate a skin surface of a subject, where the sharp shaft includes a sensor channel configured to receive at least a portion of an analyte sensor, where the sensor channel can be in a spaced relation to the sharp distal tip, and where the sharp distal tip includes an offset tip portion configured to create an opening in the skin surface.

In these assembly embodiments, the sharp module can further include a stainless steel material.

In these assembly embodiments, the sharp module can further include a plastic material.

In these assembly embodiments, where the offset tip portion can be further configured to prevent damage to a sensor tip portion of the analyte sensor during a sensor insertion process.

In these assembly embodiments, a cross-sectional area of the offset tip portion can be less than a cross-sectional area of the sharp shaft.

In these assembly embodiments, the offset tip portion can include a separate element coupled to the sharp shaft.

In these assembly embodiments, the sensor channel can include one or more sidewalls of the sharp shaft. The offset tip portion can be formed from a portion of the one or more sidewalls of the sharp shaft. The sensor channel can include a first sidewall and a second sidewall, where the offset tip portion can be formed from a terminus of the first sidewall of the sharp shaft, and where a terminus of the second sidewall can be proximal to the terminus of the first sidewall.

In many embodiments, a method of manufacturing an analyte monitoring system is provided, including: sterilizing a sensor sub-assembly including a sensor and a sharp; assembling the sterilized sensor sub-assembly into a sensor control device; assembling the sensor control device into an applicator; and packaging the applicator, having the sensor control device therein, for distribution.

In these method embodiments, the sensor control device can be as shown or substantially as shown in any of FIGS. 20A-21G.

In these method embodiments, the applicator can be as shown or substantially as shown in any of FIGS. 22A-29G.

In many embodiments, a method of manufacturing an analyte monitoring system is provided, the method including: assembling a sensor control device including a sensor and a sharp; assembling the sensor control device into an applicator; sterilizing the applicator, having the sensor control device therein, with a focused electron beam; and packaging the applicator, having the sensor control device therein, for distribution.

In these method embodiments, the sensor control device can be as shown or substantially as shown in any of FIGS. 30A-31G.

In these method embodiments, the applicator can be as shown or substantially as shown in any of FIGS. 32A-35G.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An assembly for use in an applicator, the assembly comprising:

a glucose sensor; and a sharp module comprising a sharp and a hub, wherein the sharp comprises a sharp shaft, a sharp proximal end coupled with a distal end of the hub, and a sharp distal end comprising a distal extension and an offset distal tip portion configured to penetrate a skin surface of a subject, wherein the sharp shaft comprises one or more sidewalls defining a U-shaped sensor channel with an open side, wherein an edge of a first sidewall of the one or more sidewalls defines an edge of the open side, wherein the distal extension portion is located between a terminus of the sensor channel and the offset distal tip portion, wherein the distal extension portion extends from the first sidewall, and wherein the offset distal tip portion comprises an angled portion and a sharp tip portion, wherein at least a portion of the glucose sensor is positioned within the sensor channel, wherein a distal region of the glucose sensor is positioned near the terminus of the sensor channel, wherein the offset distal tip portion is configured to prevent the glucose sensor from contacting the skin surface during insertion of the offset distal tip portion, and wherein the sharp further comprises a metal material and is formed through a coining process.

2. The assembly of claim 1, wherein the sharp further comprises a stainless steel material.

3. The assembly of claim 1, wherein the sharp includes the sharp tip portion and all other edges comprise smooth or rounded edges.

4. The assembly of claim 1, wherein the sharp comprises one or more rounded edges.

5. The assembly of claim 1, wherein the sharp shaft comprises one or more rounded edges.

6. The assembly of claim 1, wherein the sharp shaft and the sharp distal end comprise one or more rounded edges.

7. The assembly of claim 1, wherein the glucose sensor is an in vivo glucose sensor configured to measure a glucose level in a bodily fluid of the subject.

8. The assembly of claim 1, wherein the distal region of the glucose sensor is in a proximal position relative to the offset distal tip portion.

9. The assembly of claim 1, wherein the distal region of the glucose sensor and the sharp distal end are co-localized.

10. The assembly of claim 1, wherein a terminus of the sensor channel is a first predetermined distance from the sharp offset distal tip portion, wherein the first predetermined distance is between 1 mm and 8 mm.

11. The assembly of claim 1, wherein the sensor channel is a first predetermined distance from the offset distal tip portion, wherein the sensor channel is in a spaced relation with the offset distal tip portion.

12. The assembly of claim 1, wherein the offset distal tip portion is coupled with a distal end of the sharp shaft through the distal extension.

13. The assembly of claim 1, wherein the offset distal tip portion is formed from a portion of the sharp shaft.

14. The assembly of claim 1, wherein the one or more sidewalls further includes a second sidewall, wherein the first sidewall extends to the distal extension and the offset distal tip portion, and wherein a terminus of the first sidewall forms the distal extension and the offset distal tip portion.

15. The assembly of claim 14, wherein the second sidewall is disposed along the sharp shaft at a second predetermined distance from the offset distal tip portion.

16. The assembly of claim 15, wherein a terminus of the second sidewall is proximal to the terminus of the first sidewall.

17. The assembly of claim 1, wherein the sensor channel extends along an entire length of the sharp shaft.

18. The assembly of claim 1, wherein the distal region of the glucose sensor is proximal to the offset distal tip portion.

19. The assembly of claim 1, wherein the angled portion extends along an axis forming an obtuse angle with an axis of the distal extension portion.

20. The assembly of claim 1, wherein a second sidewall opposite to the first sidewall terminates at the terminus of the U-shaped sensor channel.

21. A glucose monitoring assembly, the assembly comprising:

a sensor control device comprising sensor electronics and a glucose sensor; and an applicator comprising a sharp module comprising a sharp and a hub, wherein the sharp comprises a sharp shaft, a sharp proximal end coupled with a distal end of the hub, and a sharp distal end comprising a distal extension and an offset distal tip portion configured to penetrate a skin surface of a subject, wherein the sharp shaft comprises one or more sidewalls defining a sensor channel with an open side, wherein an edge of a first sidewall of the one or more sidewalls defines an edge of the open side, wherein the distal extension portion is located between a terminus of the sensor channel and the offset distal tip portion, wherein the distal extension portion extends from the first sidewall and has a length between about 1 mm and 8 mm, and wherein the offset distal tip portion comprises an angled portion and a sharp tip portion, wherein at least a portion of the glucose sensor is positioned within the sensor channel, wherein a distal region of the glucose sensor is positioned near the terminus of the sensor channel, and wherein the offset distal tip portion is configured to prevent the glucose sensor from contacting the skin surface during insertion of the offset distal tip portion, wherein the sharp further comprises a metal material and is formed through a coining process, wherein the applicator is configured to advance the sensor control device from a proximal position within the applicator to a distal position on the skin surface, and wherein at least a portion of the glucose sensor is positioned under the skin surface when the sensor control device is in the distal position.

22. The assembly of claim 21, wherein the distal end of the glucose sensor is in a proximal position relative to the offset distal tip portion.

23. The assembly of claim 21, wherein the sensor channel is U-shaped, and wherein the one or more sidewalls further comprises, a second sidewall.

24. The assembly of claim 23, wherein the second sidewall comprises a proximal region height and a distal region height, wherein the proximal region height of the second sidewall is greater than the distal region height of the second sidewall.

25. The assembly of claim 23, wherein the first sidewall comprises a proximal region height and a distal region height, wherein the proximal region height of the first sidewall is greater than the distal region height of the first sidewall.

26. The assembly of claim 21, wherein the offset distal tip portion is coupled with a distal end of the sharp shaft through the distal extension.

27. The assembly of claim 21, wherein the first sidewall extends to the distal extension and the offset distal tip portion, and wherein a terminus of the first sidewall forms the distal extension and the offset distal tip portion.

28. The assembly of claim 21, wherein the angled portion extends along an axis forming an obtuse angle with an axis of the distal extension portion.

* * * * *